(12) United States Patent
Moravcová et al.

(10) Patent No.: US 7,745,450 B2
(45) Date of Patent: Jun. 29, 2010

(54) PYRAZOLO[4,3-D]PYRIMIDINES, PROCESSES FOR THEIR PREPARATION AND METHODS FOR THERAPY

(75) Inventors: Daniela Moravcová, Horazd'ovice (CZ); Libor Havlicek, Prague (CZ); Vladimir Krystof, Ostrava (CZ); René Lenobel, Frydek Mistek (CZ); Miroslav Strnad, Olomouc (CZ)

(73) Assignees: Institute of Experimental Botany, Prague (CZ); Univerzita Palackeho v Olomouci, Olomouc (CZ)

( * ) Notice: Subject to any disclaimer, the term of this patent is extended or adjusted under 35 U.S.C. 154(b) by 1169 days.

(21) Appl. No.: 10/952,087

(22) Filed: Sep. 28, 2004

(65) Prior Publication Data

US 2005/0080097 A1 Apr. 14, 2005

Related U.S. Application Data

(63) Continuation of application No. PCT/EP03/03207, filed on Mar. 27, 2003.

(30) Foreign Application Priority Data

Mar. 28, 2002 (EP) .................. 02007163

(51) Int. Cl.
| | | |
|---|---|---|
| C07D 487/04 | (2006.01) | |
| A61K 31/519 | (2006.01) | |
| A61P 35/04 | (2006.01) | |
| A61P 17/06 | (2006.01) | |
| A61P 17/08 | (2006.01) | |
| A61P 25/28 | (2006.01) | |
| A61P 3/10 | (2006.01) | |
| A61P 37/06 | (2006.01) | |

(52) U.S. Cl. .................. 514/262.1; 544/262
(58) Field of Classification Search .................. 544/262, 544/118; 514/262.1, 234.2
See application file for complete search history.

(56) References Cited

U.S. PATENT DOCUMENTS

| | | | | |
|---|---|---|---|---|
| 3,988,338 A | * | 10/1976 | Skoog et al. | .................. 544/280 |
| 5,723,608 A | * | 3/1998 | Yuan | .................. 544/118 |
| 6,200,980 B1 | | 3/2001 | Piazza et al. | |
| 2003/0195205 A1 | * | 10/2003 | DeNinno et al. | ......... 514/228.5 |

FOREIGN PATENT DOCUMENTS

| | | | |
|---|---|---|---|
| WO | WO 98 29413 A1 | 7/1998 | |
| WO | WO 98 49166 A1 | 11/1998 | |
| WO | WO 99 54333 A1 | 10/1999 | |
| WO | WO 01 19827 A1 | 3/2001 | |

OTHER PUBLICATIONS

Subramanyam et. al., J. Med. Chem., 1995, 38, 587-589.*
Ellames et. al., J. Chem. Soc. Perkin. Trans., 1985, 1(10), 2087-2091.*
Farkas et. al. Collect. Czech. Commun. 1972, 37(8), 2786-2797.*
Long et. al. J. Heterocycl. Chem., 1970, 7(4), 863-869.*
Hernandez et. al., J. Org. Chem., 1981, 46(20), 3941-3945.*
Hecht et. al. (J. of Biol. Chem., 1975, 250(18), 7343-7351).*
Subramanyam et al., "6-(4-Pyridinyl)-1H-1,2,3-triazolo [4, 5-d]-pyrimidine-4(5H)-one: A Structurally Novel Competitive AMPA Receptor Antagonist" J. Med. Chem., vol. 38, No. 4, pp. 587-589 (1995).
Buchanan et al., "C-nucleoside studies. Part 20[538]. Synthesis of some pyrazolo [4,3-d]pyrimidine acyclonucleosides related to (S)-(2,3-dihydroxypropyl)adenine; A direct method for double functionalization of the pyrazole ring", J. Chem. Soc., Perkin Trans., vol. 1, No. 5, pp. 925-930, (1989).

(Continued)

Primary Examiner—Susanna Moore
(74) Attorney, Agent, or Firm—Panitch Schwarze Belisario & Nadel LLP

(57) ABSTRACT

The invention relates to 3-, 5-, 7-trisubstituted pyrazolo[4,3-d]pyrimidines represented by the general formula I

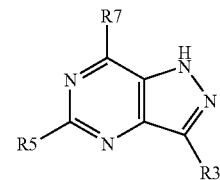

and pharmaceutically acceptable salts thereof, wherein
R3 is an optionally substituted alkyl, cycloalkyl, cycloheteroalkyl, cycloalkyl alkyl, aryl or alkylaryl group;
R5 is halogen, —NHNH$_2$, —NHOH, NHCONH$_2$, guanylo (NH—C(NH)NH$_2$) an optionally substituted C$_1$-C$_6$ alkyl, alkenyl, alkynyl, C$_3$-C$_{15}$ cycloalkyl, R$_f$(C$_3$-C$_{15}$ cycloalkyl), heterocyclyl, heteroalkyl, aryl, heteroaryl, arylalkylene, arylalkenylene, arylalkynylene, cycloheteroalkyl, cycloheteroalkyl alkyl, heteroarylalkylene, heteroarylalkenylene, heteroarylalkynylene group, the group —C(O)—R$_a$, —C(O)NR$_b$R$_c$, —SO$_3$R$_d$, or —NHC(O)R$_e$, wherein R$_a$ and R$_f$ are an optionally substituted C$_1$-C$_6$ alkyl, alkenyl, or alkynyl group, R$_b$, R$_c$, and R$_d$ are independently selected from the group consisting of H, optionally substituted C$_1$-C$_6$ alkyl, alkenyl, or alkynyl group, and R$_e$ is a hydroxy, amino, alkoxy, alkylamino, optionally substituted C$_1$-C$_6$ alkyl, alkenyl or alkynyl group; or the group —X—R$_{5'}$, wherein X is —NH—, —O—, —S— or —N(alkyl)- and R$_{5'}$ is hydrogen, an optionally substituted C$_1$-C$_6$ alkyl, alkenyl, alkynyl, C$_3$-C$_{15}$ cycloalkyl, Rf(C$_3$-C$_{15}$ cycloalkyl), aryl, heterocyclyl, hetero C$_1$-C$_6$ alkyl, arylalkylene, arylalkenylene, arylalkynylene, heteroaryl, cycloheteroalkyl, cycloheteroalkyl alkyl, or heteroarylalkylene, heteroarylalkenylene, heteroarylalkynylene group, the group —C(O)—R$_a$, —C(O)NR$_b$R$_c$, —SO$_3$R$_d$, or —NHC(O)R$_e$, wherein R$_a$, R$_b$, R$_c$, R$_d$, R$_e$ and R$_f$ have the above meaning, and
R7 is halogen, —NHNH$_2$, NHOH, NHCONH$_2$, guanylo (NH—C(NH)NH$_2$) or the group —X—R$_{7'}$, wherein X has the above meaning and the meaning of R$_{7'}$ is as defined for R$_{5'}$.

21 Claims, 18 Drawing Sheets

OTHER PUBLICATIONS

Ellames et al., "The synthesis of acycloformycins and 5-amino-3-(2-hydroxyethoxy)methylpyrazolo [4,3-d]pyrimide in-7(6H)-one, an analog of the antiviral acycloguanosine", *J. Chem. Soc., Perkin Tans.*, vol. 1, No. 10, pp. 2087-2091, (1985).

Neuwels, "Approach to an adenosine pharmacophore by molecular modeling", *J. Pharm. Belg.*, vol. 47, No. 4, pp. 351-363, (1992).

Hecht, et al., Activation of cytokinins, *J. Biol. Chem.*, vol. 250, No. 18, pp. 7343-7351, (1975).

Hernandez et al., A general route for the facile synthesis of 4-Thioxopyrimidin-2-one derivatives via the annulation of cyclic o-aminonitriles using carbonyl sulfide[1], *J. Org. Chem.*, vol. 46, No. 20, pp. 3941-3945, (1981).

Long et al., "Derivatives of the new ring system pyrazolo [4,3-d]-v-triazine and the synthesis of 5,7-disubstituted 3-methylpyrazolo [4,3-d]pyrimidines and 5,7-disubstituted 3-methylpyrazolo [4,3-d]pyrimidines 6-Oxides which are structurally related to the nucleoside antibiotics formycin and formycin B (1)", *J. Heterocycl. Chem.*, vol. 7, No. 4, pp. 863-869, (1970).

Farkas et al., Nucleic acid components and their analogs. CLI. The preparation of 1H-pyrazolo [4,3-d]pyrimidine as an approach to the synthesis of formycin B *Collect. Czech. Chem. Commun.*, vol. 37, No. 8, pp. 2786-2797, (1972).

Sanghvi et al., In vivo antiviral activity of 5-amino-I-methyl-3-beta.-D-ribofuranosylpyrazolo [4,3-d]pyrimidin-7(6H)-one and related guanosine analogs prepared from formycin, vol. 10, No. 6, pp. 1417-1427, (1991).

* cited by examiner

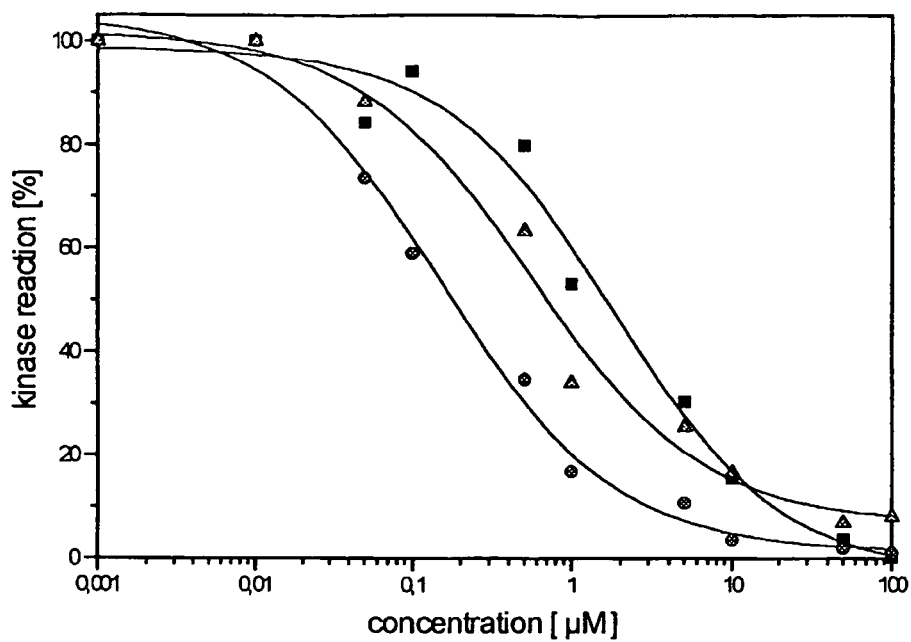
Figure 1: Dose-response curves of CDK1/cyclin B kinase inhibition by 3-isopropyl-5-methyl-7-benzylamino-pyrazolo[4,3-d]pyrimidine (■), 3-isopropyl-5-chloro-7-benzylamino-pyrazolo[4,3-d]pyrimidine (▲), 3-isopropyl-5-(4-hydroxycyclohexylamino)-7-benzylamino-pyrazolo[4,3-d]pyrimidine (●).

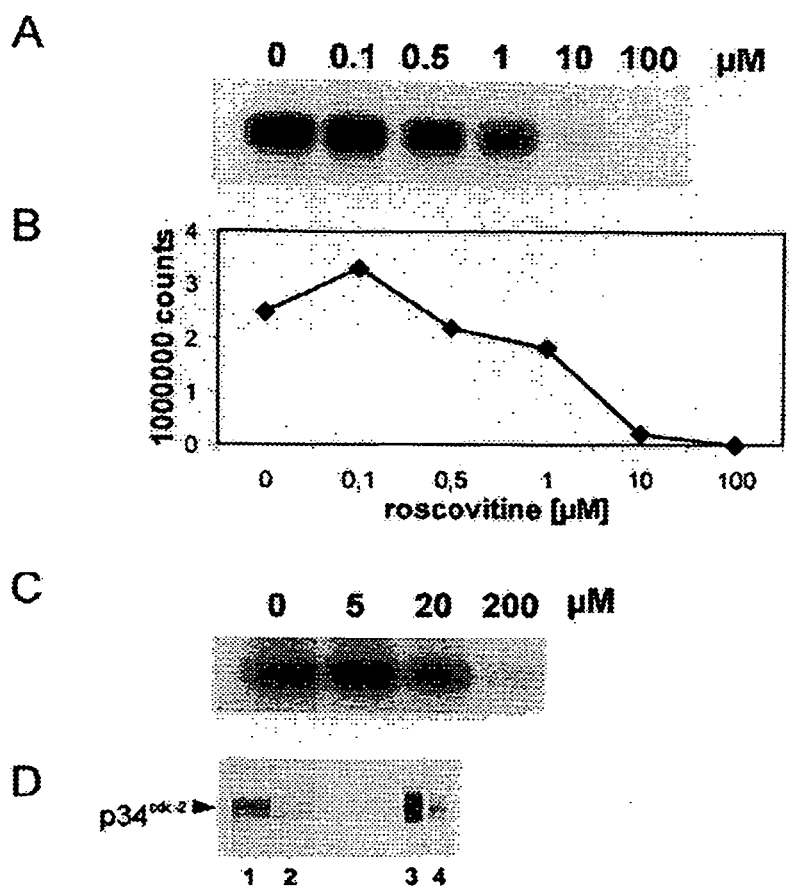

Figure 2: Specific inhibition of cdc2Ms kinase activity by 3-isopropyl-5-(4-aminocyclohexylamino)-7-benzylamino-pyrazolo[4,3-d]pyrimidine (268) in cells of *V. faba*. Enzyme activity measured by phosphorylation of histone H1 substrate protein in presence of various concentration of roscovitine. (A) Phosphoimmager (B) Inhibition of cdc2Ms kinase *in vivo* in cells treated with various concentrations of roscovitine (D). Total cdk protein level as detected by Western blots of whole cell extracts. Control (lane 1), 48h of treatment with 268 (lane 2). W. Blot of suc 1 bound cdks – control (line 3), 48h of 268 treatment

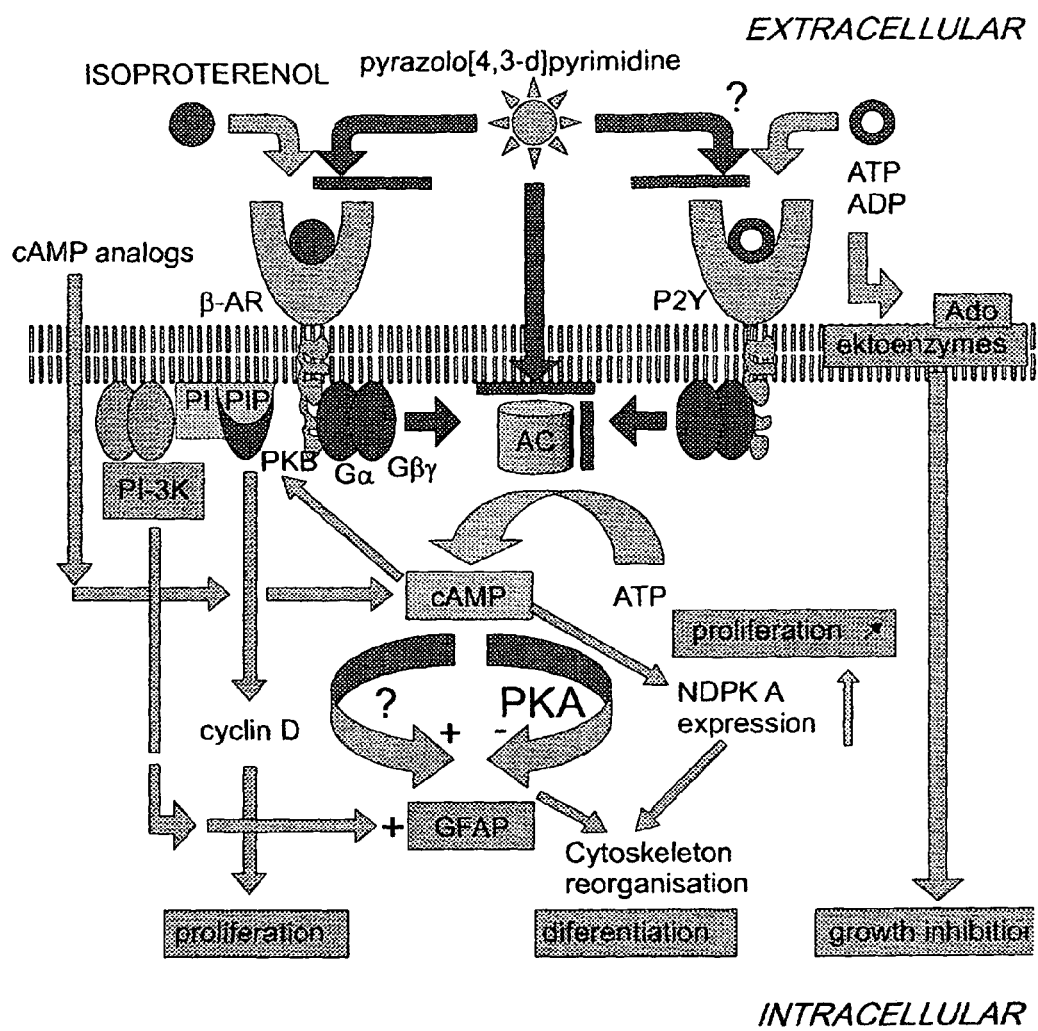
Figure 3: Scheme of signalic pathways induced by agonist or antagonist binding to α- and β-andrenergic and purinogenic receptors. PAK – proteinkinase A, Pi-3K-fosfatidylinositol-3-kinase, Gα, Gβ,γ – protein G subunits, pKB – proteinkinase B, NDPKA- , GFAB - , AC – adenylate kinase, cAMP – cyclic adenosine-5'-monophosphate, P2Y-purinogenic receptors binding adenosin.

A
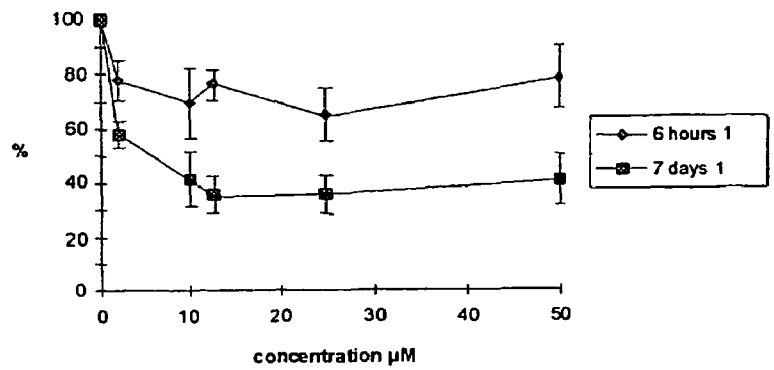
B
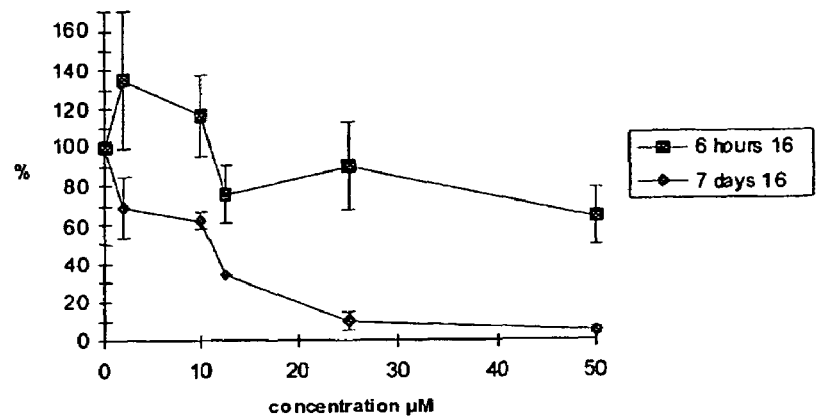
C
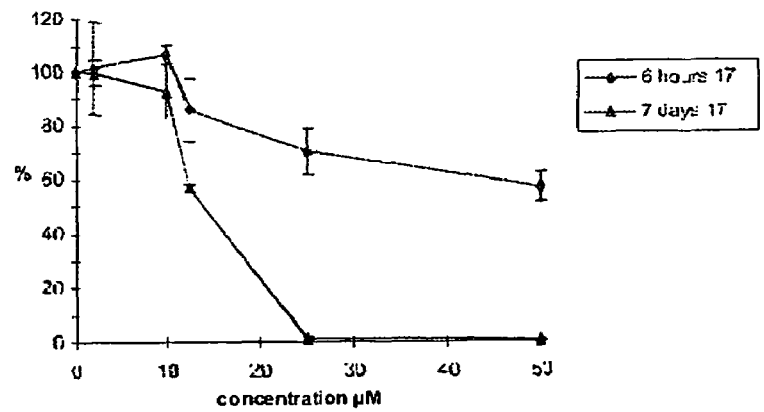
Figure 4: a. Growth curve CEM + 1, b. Growth curve CEM + 172, c. Growth curve CEM + 47

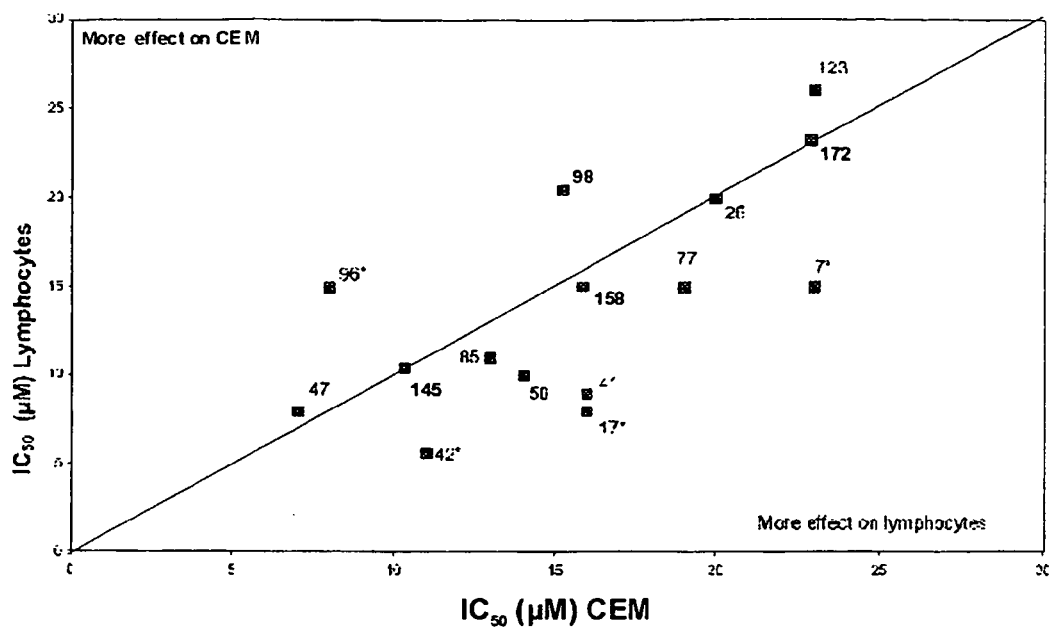
Figure 5: Comparison of IC$_{50}$ of novel purine derivatives on CEM as compared to IC$_{50}$ of lymphocytes. The products indicated by an asterisk are significantly more active in one test system.

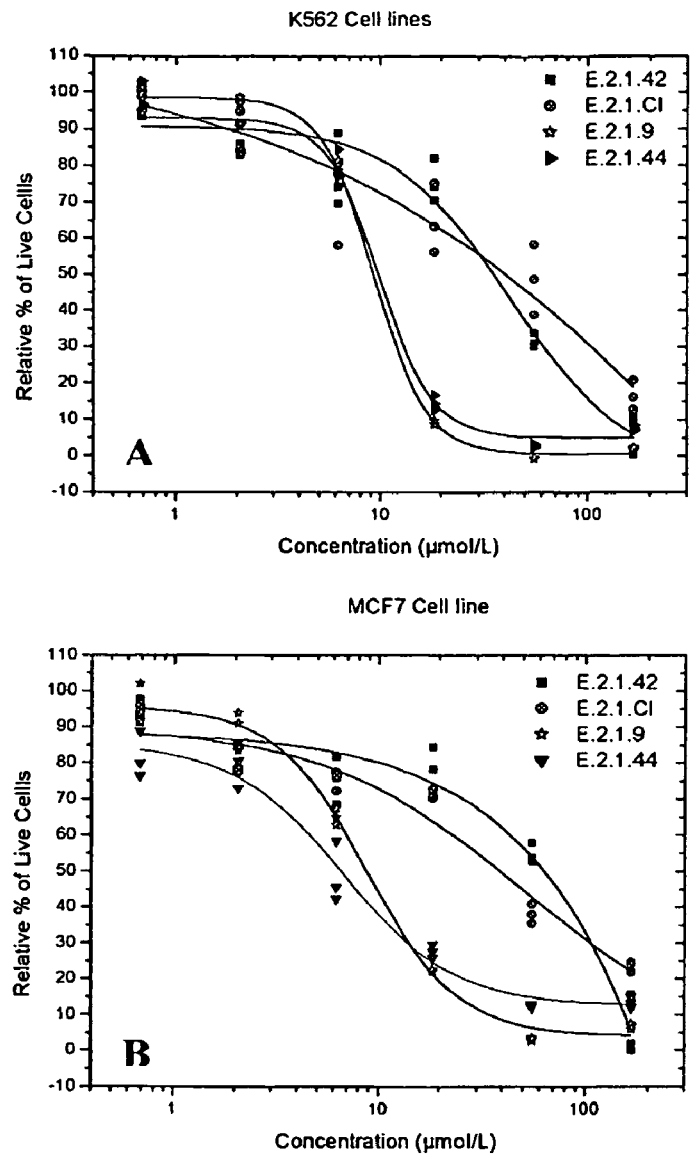

Figure 6: Inhibition of growth of K562 (A) and MCF7 (B) tumour cell lines by different pyrazolo[4,3-d]pyrimidines. Cytotoxicity was determined in the presence of Calceim AM. Activity is presented as percentage of maximal activity (in the absence of inhibitors). E.2.1.Cl: 5-chloro-7-benzylamino-3-isopropylpyrazolo[4,3-d]pyrimidine; E.2.1.9: 269 - 5-( R )-(1-hydroxymethylpropyl)amino-7-benzylamino-3-isopropylpyrazolo[4,3-d]pyrimidine; E.2.1.42: 268 - 5-(4-aminocyclohexyl)amino-7-benzylamino-3-isopropylpyrazolo[4,3-d]pyrimidine; E.2.1.44:5-(4-hydroxycyclohexyl)amino-7-benzylamino-3-isopropylpyrazolo[4,3-d]pyrimidine.

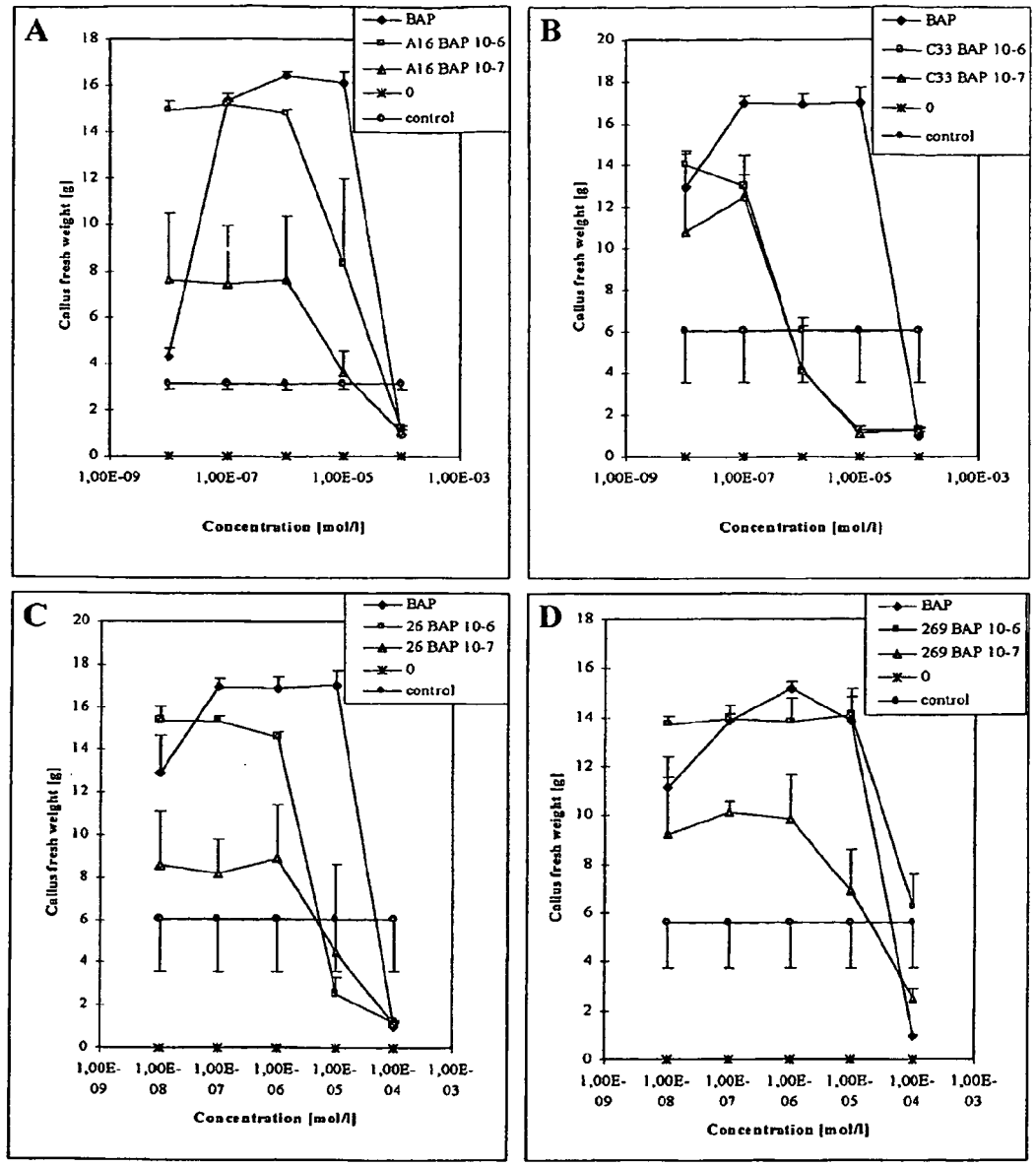
Figure 7: Inhibition of tobacco callus growth by several trisubstituted pyrazolo[4,3-d]pyrimidine derivatives. Inhibitory activity was determined in the presence of $10^{-6}$ and $10^{-7}$ M concentration of cytokinin 6-benzylaminopurine (BAP). Structure of the tested compounds 16, 26, 33, and 269 is present in Table 4.

Figure 8: Immunofluorescence *in situ* detection of DNA double strands breaks in cells of *V. faba*. Cells were stained with: FITC for DNA breaks labeling, chromatin binding dye DAPI. A-B: DNA breaks labeling, B: chromatin binding dye DAPI, A-B: DNA breaks labeling in nuclei after 12h of 2S treatment, chromatin already with apoptotic fragmentation (arrow). C apoptotic nuclei with condensed globular chromatin domains.

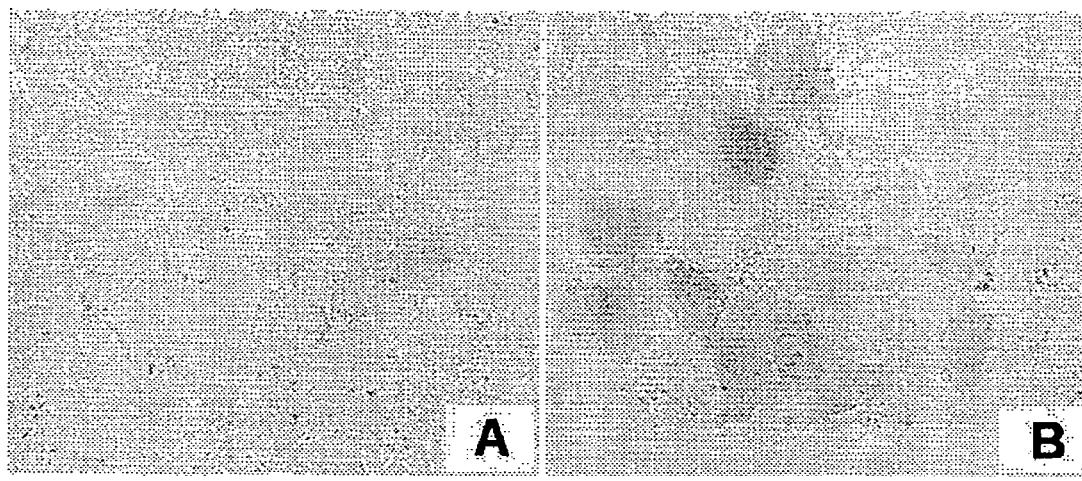
Figure 9: Senescent cells of human fibroblasts (B), but not other cells (A) stained blue due to the action of β-galactosidase on the substrate X-gal (5-bromo-4-chloro-3-indolyl-β-D-galactopyranoside) (1 mg/ml).

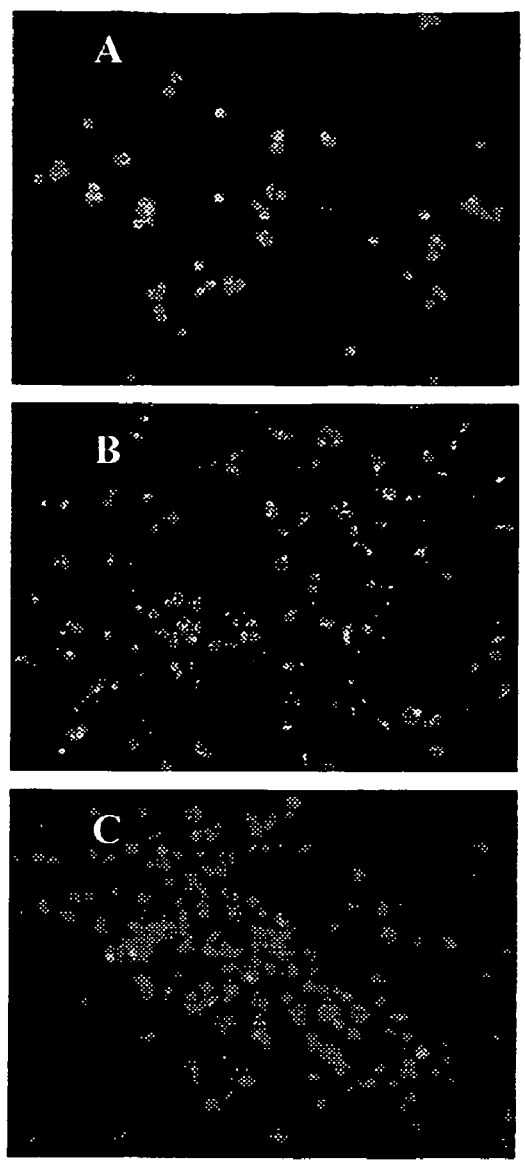
Figure 10: Induction of apoptosis in MCF-7 cells by new pyrazolo[4,3-d]pyrimidine 12. A MCF-7, apoptotic cells: 6 h, 12, 20μM, B MCF-7, secondarily necrotic cell (i.e. necrotic following apoptosis), 12 h, 12, 40 μM; C MCF-7, necrotic cells, 24h, 12, 40μM. Anexin FITC V (Mol. Probes) and propidium iodide labelling: anexin – green, PI – red

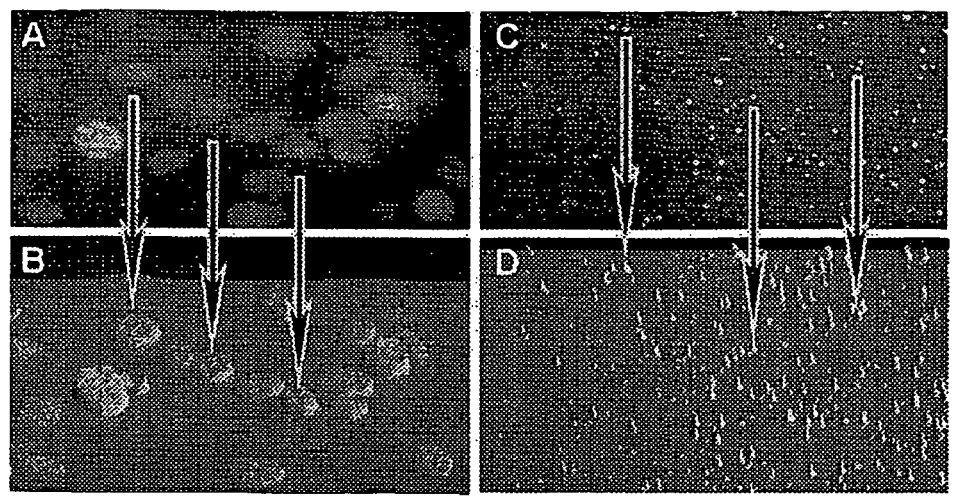
Figure 11: Detection of apoptosis by Anexin (green fluorescence) and Hoechst 33258 (blue fluorescence) labelling as analysed by Olympus image analysis after treatment of MCF-7 cells by new pyrazolo[4,3-d]pyrimidine 14. A,B - control cells without treatment; C,D – apoptotic cells (condensation of chromatin); A,C – fluorescent microscopy; B,D – image analysis of fluorescence.

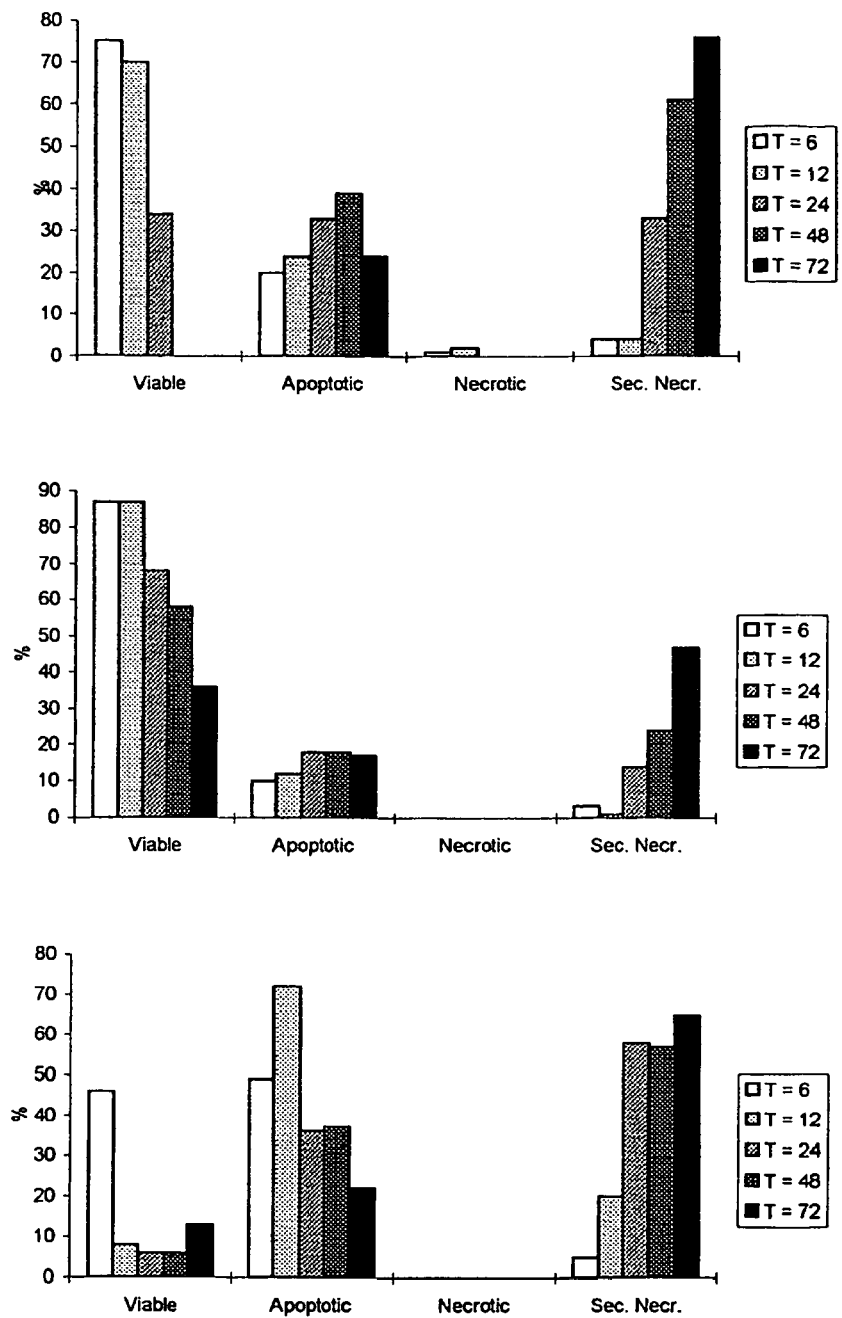
Figure 12: Microscopic detection of viable, apoptotic, necrotic and secondary necrotic cells in CEM cultures incubated with a.98 b.172 c.201 (T: time of incubation with compounds in hours).

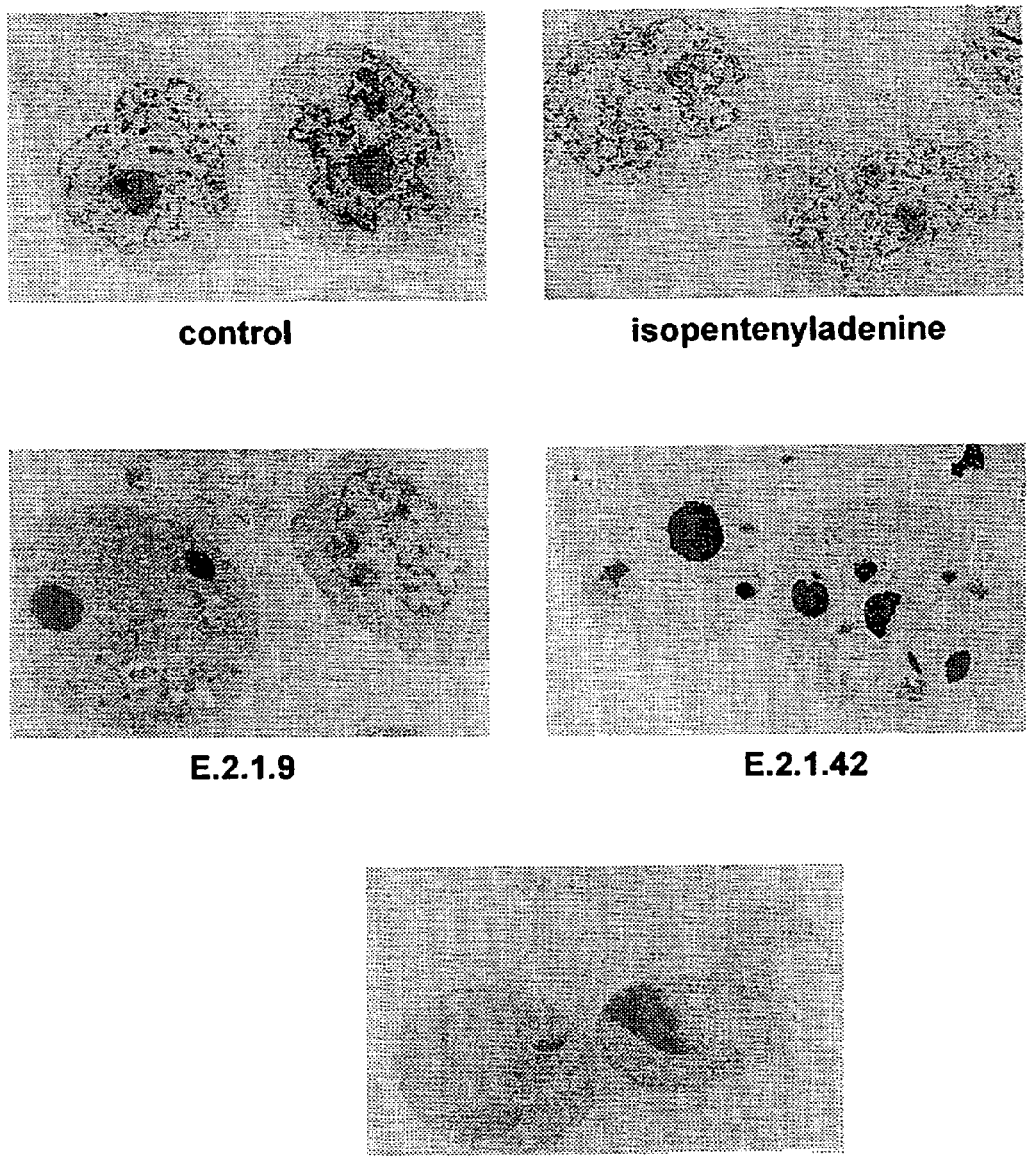
Figure 13: Induction of apoptosis by synthetic CDK inhibitors. Ultrastructural analysis of treated/untreated CEM cells by electron microscopy. E.2.1.Cl: C33, 5-chloro-7-benzylamino-3-isopropylpyrazolo[4,3-d]pyrimidine; E.2.1.9: 269 - 5-( R )-(1-hydroxymethylpropyl)amino-7-benzylamino-3-isopropylpyrazolo[4,3-d]pyrimidine; E.2.1.42: 268 - 5-(4-aminocyclohexyl)amino-7-benzylamino-3-isopropylpyrazolo[4,3-d]pyrimidine.

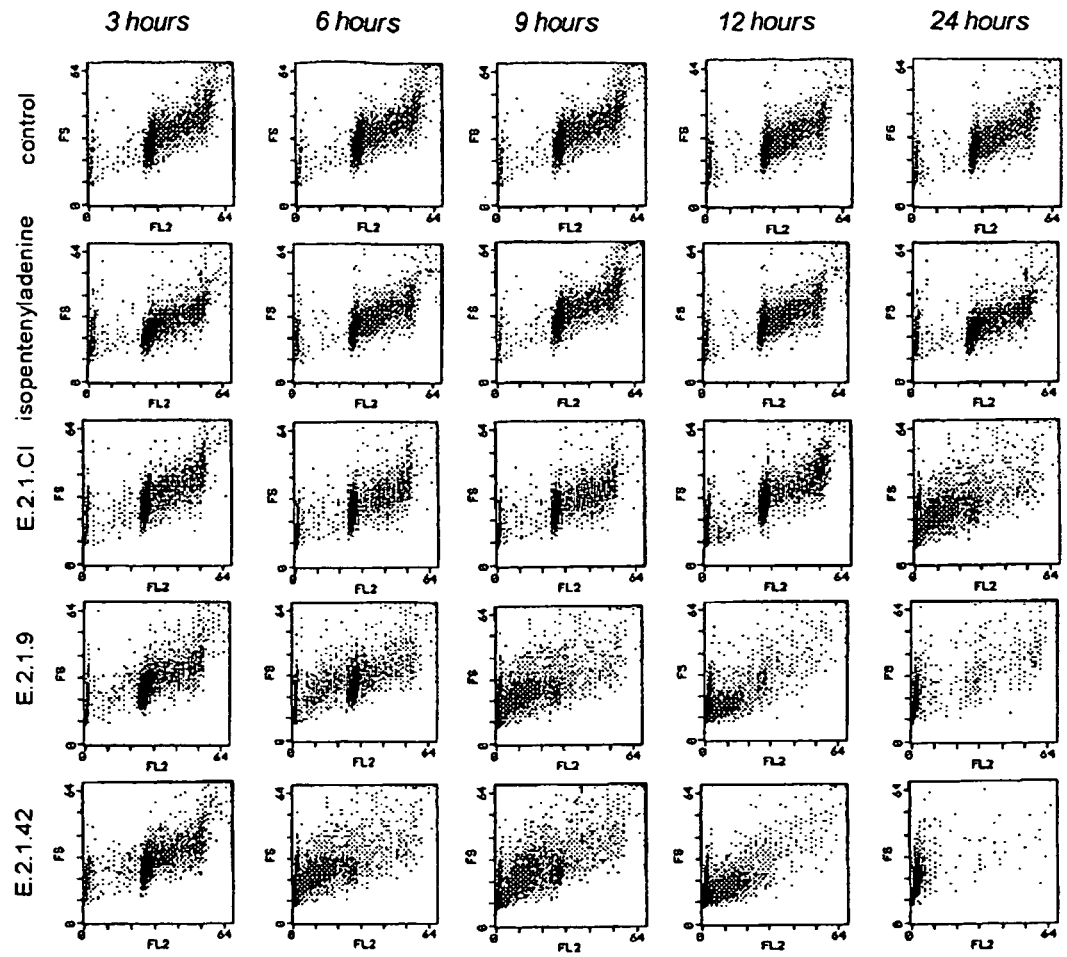
Figure 14: Synthetic CDKIs induce apoptosis in CEM cells – FACS study.
E.2.1.Cl: C33, 5-chloro-7-benzylamino-3-isopropylpyrazolo[4,3-d]pyrimidine;
E.2.1.9: 269 - 5-( R )-(1-hydroxymethylpropyl)amino-7-benzylamino-3-isopropylpyrazolo[4,3-d]pyrimidine;
E.2.1.42: 268 - 5-(4-aminocyclohexyl)amino-7-benzylamino-3-isopropylpyrazolo[4,3-d]pyrimidine.

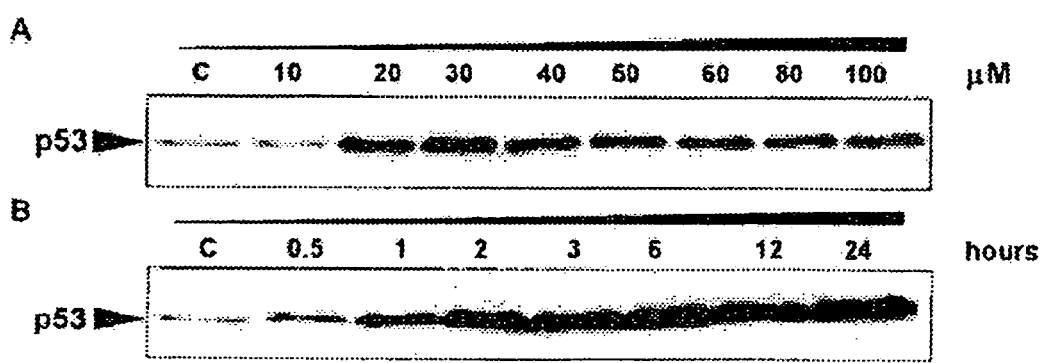

Figure 15: A concentration-dependent induction of p53 protein in MCF-7 cells by 25 after 12 hours treatment. Significant p53 induction is clearly visible at 20 µM concentration of 25 in contrast to the lower concentratins. Another increasing concentrations of 25 don't seem to be of great importance, concerning the induced level of p53 protein. B: time-dependent induction of p53 protein in MCF-7 cells, p53 induction was already visible 30 minutes post treatment, reaching maximum level at 2 hours post treatment. P53 level was kept unchanged following another time periods. Total cell lysates were separated on 10% SDS gel. Immunoblotting was performed with monoclonal anti-53 antibody DO-1.

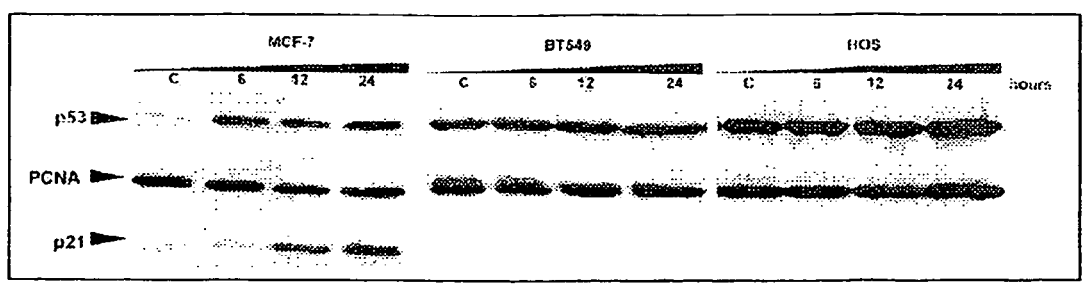

Figure 16: Effect of 25 on p53 and p21$^{WAF1}$ induction in cells expressing either wild-type or mutant p53 protein. Total cell lysates were separated on 12,5% SDS gel. Immunoblotting was performed with monoclonal anti-p53 antibody DO-1,anti-p21 antibody 118 and subsequently with anti-PCNA antibody PC-10, to confirm equal protein loading. Panel A shows, that 20 µM 25 is able to induce p53 protein as well as p21$^{WAF1}$ protein in MCF-7 cells expressing wild-type p53. On the contrary, panels B and C show, that 20 µM 25 failed to induce these proteins in BT549 and HOS cells expressing mutant p53 protein.

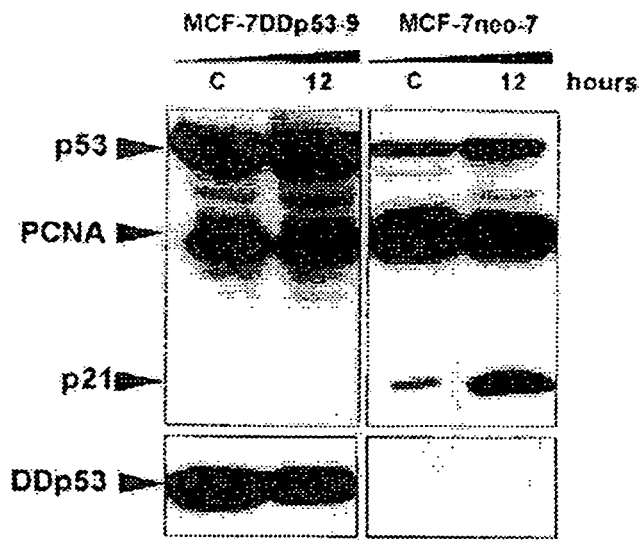

Figure 17: Confirmation of p53-dependent p21$^{WAF1}$ protein induction after 20 μM 25 treatment in MCF-7 cells using transfection of dominant-negative truncated mouse p53 protein (Ddp53), which disrupts p53 transcriptional activity. Total cell lysates were separated on 12,5% SDS gel. Immunoblotting was performed with monoclonal anti-p53 antibodies DO-1, Bp53-10 (for Ddp53 detection), anti-p21 antibody 118 and anti-PCNA antibody PC-10 as a loading control. Left panel shows MCF-7Ddp53-9 clone expressing high level of Ddp53. Treatment with 25 leads to similar effect as observed in cells expressing mutant p53. Right panel shows MCF-7neo-7 control clone without Ddp53. Treatment with 25 induces both p53 and p21$^{WAF1}$ proteins.

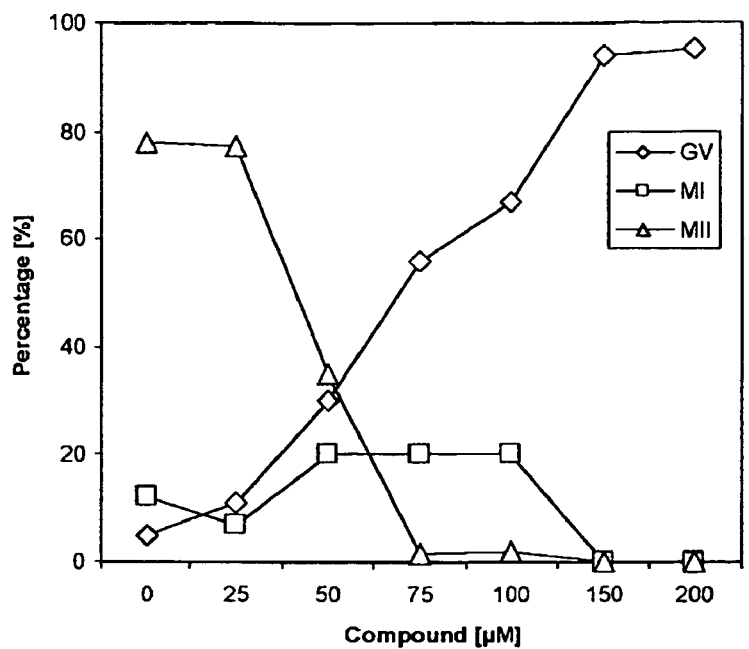
Figure 18: Effect of pyrazolo[4,3-d]pyrimidine 16 on resumption of meiosis in bovine oocytes. Immature cumulus oocyte complexes (COCs, n=341) were cultured fro 24 hr in M199 + 3 mgúml BSA in the absence or presence of 16 (0-200 µM). Two replicates were performed with a total of aproximately 50 COCs per group.

PYRAZOLO[4,3-D]PYRIMIDINES, PROCESSES FOR THEIR PREPARATION AND METHODS FOR THERAPY

This application is a continuation of International Application No. PCT/EP03/03207 filed Mar. 27, 2003, which was published in the English language on Oct. 9, 2003, under International Publication No. WO 03/082872 A1 and the disclosure of which is incorporated herein by reference.

BACKGROUND OF THE INVENTION

This invention relates to new pyrazolo[4,3-d]pyrimidine derivatives and to their use in suitable utilities, especially diagnostic and therapeutic methods.

The cell division cycle is usually regarded as a succession of two phases, the S phase (DNA synthesis) and the M phase (segregation of the synthesized DNA in the two daughter cells) interspaced by two gap periods, $G_1$ and $G_2$. The net result of the cell cycle scenario may not only be growth and differentiation, but also tumor development and apoptosis. This view reflects the evidence accumulated over the last 5 years in mammalian field, that the vast majority and quite likely all tumors have suffered one or more defects that derail the cell cycle machinery. Such defects can either target components of the cell cycle apparatus, including the checkpoint mechanisms that ensure fidelity and orderly progression through the cell cycle phases, thereby protecting genome, or target elements of the upstream signaling cascades, whose effects eventually converge to trigger cell cycle events (Bártek et al. 1999, J. Pathol. 187: 95-99).

Although the concept of cancer as a disease of the cell cycle implies that every tumor is defective in one or more aspects of all cycle control, it clearly does not mean that oncogenesis targets only the cell cycle clock. Development of a tumor appears to require also aberrations in the cell death machinery and cell-cell and/or cell-matrix interactions that co-operate with cell cycle defects. The above concept simply regards cell cycle deregulation as an essential step in the process of multistep tumorigenesis.

In terms of the molecular pathogenesis of tumors, cell cycle defects can either represent the initial, predisposing event, or contribute to tumor progression. Examples of tumor-predisposing alterations include, for instance, germ-line mutations of the CDK inhibitors $p16^{INK4A}$ or $p57^{KIP2}$, while many of the known cell cycle defects result from somatic mutations or even epigenetic changes that may occur during the early or later stages of tumorigenesis (Hunter 1997, Cell 88: 333-346, Fearon 1997, Science 278: 1043-1050).

The importance of cell cycle regulatory proteins, their direct interaction with oncogenes and the tumor suppressor pRb and their frequent deregulation in human tumors has encouraged an active search for low-molecular weight regulators of these proteins. Among them the chemical inhibitors of cyclin-dependent kinases were the first discovered. These inhibitors are anti-mitotic and display very interesting anti-mitotic and anti-tumor activities.

BRIEF SUMMARY OF THE INVENTION

It is an object of this invention to provide anticancer, anti-inflammatory, antiviral, antineurodegenerative, neurodepressive and immunosuppressive compounds having improved selectivity and efficiency index, i.e. that are less toxic yet more efficacious than analogues known heretofore.

It is an object of this invention to provide 3-, 5-, 7-trisubstituted pyrazolo[4,3-d]pyrimidines, which inhibit the cdks, cell proliferation, and/or induce apoptosis.

A further object of the invention is to provide a pharmaceutical composition, which comprises a 3-, 5-, 7-trisubstituted pyrazolo[4,3-d]pyrimidine, and a pharmaceutically acceptable carrier.

A further object of the invention is to provide a method for inhibiting cell proliferation and inflammatory diseases to a mammal in need of an effective amount 3-, 5-, 7-trisubstituted pyrazolo[4,3-d]pyrimidines.

The solution of this object are 3-, 5-, 7-trisubstituted pyrazolo[4,3-d]pyrimidines of the formula I

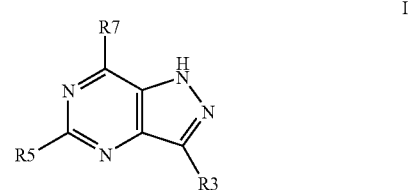

I and the pharmaceutically acceptable salts thereof, wherein

R7 is halogen, hydroxyl, amino, cyano, hydroxylamino or hydrazino R7'—X wherein X is an —NH—, —N(alkyl)-, —O— or —S— moiety;

R7' is H, alkyl, cycloalkyl, aryl, heterocyclyl, heteroaryl, arylalkylene, arylalkenylene, arylalkynylene, cycloheteroalkyl, heteroarylalkylene, heteroarylalkenylene, heteroarylalkenylene, heteroalkyl, cycloalkyl alkylene, cycloalkyl alkenylene, cycloalkyl alkynylene and cycloheteroalkyl alkyl substituted independently at each occurrence with substituents selected from the group halogen, hydroxyl, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

R5 is halogen, hydroxylamino, hydrazino, alkyl, aryl, substituted alkyl, cycloalkyl, substituted cycloalkyl, cycloalkyl alkyl, arylalkylene, arylalkenylene, arylalkynylene, heteroalkyl, heteroarylalkylene, heteroarylalkenylene, heteroarylalkynylene, cycloheteroalkyl alkyl or R5'—X wherein X is an —NH—, —N(alkyl)-, —O— or —S— moiety;

R5' is H, alkyl, acyl, cycloalkyl, aryl, substituted aryl, heterocyclyl, heteroaryl, arylalkylene, arylalkenylene, arylalkynylene, cycloheteroalkyl, heteroarylalkylene, heteroarylalkenylene, heteroarylalkynylene, heteroalkyl, cycloalkyl alkyl, and cycloheteroalkyl alkyl substituted independently at each occurrence with substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

R3 is an alkyl, fluorine or chlorine substituted alkyl, cycloalkyl, fluorine or chlorine substituted cycloalkyl, cycloalkyl alkyl, cycloheteroalkyl alkyl, cycloheteroalkyl, fluorine or chlorine substituted cycloheteroalkyl.

Another solution is a method for inhibiting cdks and cell proliferation and/or for inducing apoptosis in mammals, comprising administering a therapeutically effective amount of a compound of claim 1 to a mammal. The compounds according to claim 1 are cdk inhibiting molecules and are useful for treating disorders, some of them involving cell proliferation, such as cancer, restenosis, rheumatoid arthritis, lupus, type I diabetes, multiple sclerosis, Alzheimer's disease, growth of parasites (animal, protists), graft rejection (host versus graft disease), graft versus host disease, and gout.

Another solution is a method for inhibiting or stimulating α- and β-adrenergic and purinergic receptors in mammals comprising administering a therapeutically effective amount of the composition of claim 1 to the mammal. The inhibiting and stimulating molecules of claim 1 are useful for treating inflammatory diseases and asthma.

Yet another solution is a pharmaceutical composition comprising a compound of claim 1 in an admixture with one or more pharmaceutical excipients. The pharmaceutical composition of the invention is useful for treating fungal infections (fungi) in humans, animal, and in plants.

3-, 5-, 7-trisubstituted pyrazolo[4,3-d]pyrimidines of the invention result in the acquisition of extremely high potency against DNA viruses on the part of the defined compounds.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 shows a dose-response curves of CDK1/cyclin B kinase inhibition by 3-isopropyl-5-methyl-7-benzylamino-pyrazolo[4,3-d]pyrimidine (■), 3-isopropyl-5-chloro-7-benzylamino-pyrazolo[4,3-d]pyrimidine (▲), 3-isopropyl-5-(4-hydroxycyclohexylamino)-7-benzylamino-pyrazolo[4,3-d]pyrimidine (●);

FIG. 2 shows a specific inhibition of cdc2Ms kinase activity by 3-isopropyl-5-(4-aminocyclohexylamino)-7-benzylamino-pyrazolo[4,3-d]pyrimidine (268) in cells of V. faba;

FIG. 3 shows a scheme of signal pathways induced by agonist or antagonist binding to α- and β-andrenergic and purinogenic receptors;

FIG. 4 shows a growth curve CEM+1, b. Growth curve CEM+172, c. Growth curve CEM+47;

FIG. 5 is shows a comparison of $IC_{50}$ of novel purine derivatives on CEM as compared to $IC_{50}$ of lymphocytes;

FIG. 6 shows an inhibition of growth of K562 (A) and MCF7 (B) tumor cell lines by different pyrazolo[4,3-d]pyrimidines. Cytotoxicity was determined in the presence of Calceim AM. Activity is presented as percentage of maximal activity (in the absence of inhibitors);

FIG. 7 shows a inhibition of tobacco callus growth by several trisubstituted pyrazolo[4,3-d]pyrimidine derivatives;

FIG. 8 shows a immunofluorescence in situ detection of DNA double strands breaks in cells of V. faba;

FIG. 9 shows a senescent cells of human fibroblasts (B), but not other cells (A) stained blue due to the action of β-galactosidase on the substrate X-gal (5-bromo-4-chloro-3-indolyl-β-D-galactopyranoside) (1 mg/ml);

FIG. 10 shows an induction of apoptosis in MCF-7 cells by new pyrazolo[4,3-d]pyrimidine 12. A MCF-7, apoptotic cells;

FIG. 11 shows a detection of apoptosis by Anexin (green fluorescence) and Hoechst 33258 (blue fluorescence) labeling as analyzed by Olympus image analysis after treatment of MCF-7 cells by new pyrazolo[4,3-d]pyrimidine 14;

FIG. 12 shows a microscopic detection of viable, apoptotic, necrotic and secondary necrotic cells in CEM cultures incubated with a.98 b.172 c.201 (T: time of incubation with compounds in hours);

FIG. 13 shows an induction of apoptosis by synthetic CDK inhibitors. Ultra structural analysis of treated/untreated CEM cells by electron microscopy;

FIG. 14 shows a synthetic CDKIs induce apoptosis in CEM cells—FACS study;

FIG. 15 shows a concentration-dependent induction of p53 protein in MCF-7 cells by 25 after 12 hours treatment;

FIG. 16 shows an effect of 25 on p53 and $p21^{WAF1}$ induction in cells expressing either wild-type or mutant p53 protein;

FIG. 17 show a confirmation of p53-dependent $p21^{WAF1}$ protein induction after 20 μM 25 treatment in MCF-7 cells using transfection of dominant-negative truncated mouse p53 protein (Ddp53), which disrupts p53 transcriptional activity; and FIG. 18 shows an effect of pyrazolo[4,3-d]pyrimidine 16 on resumption of meiosis in bovine oocytes.

DETAILED DESCRIPTION OF THE INVENTION

As used herein, and unless modified by the immediate context:

"Halogen" refers to one or more atoms of fluorine, bromine, chlorine and iodine atoms.

"Hydroxy" refers to the group —OH.

"Mercapto" refers to group —SH.

"Alkyl", "alkenyl", or "alkynyl", refers to an optionally substituted branched or unbranched $C_1$-$C_6$ chain which is saturated or unsaturated. Such groups as methyl, propyl, isopropyl, tert-butyl, allyl, vinyl, ethynyl, propargyl, hexen-2-yl and the like can exemplify this term.

"Substituted alkyl", "substituted alkenyl", or "substituted alkynyl" refers to alkyl, "alkenyl", or "alkynyl", respectively, as just described including one or more substituents such as hydroxyl, mercapto, alkylmercapto, halogen, alkoxy, acyloxy, amino, acylamino, hydrazino, carbamoyl, amido, carboxyl, sulfo, acyl, guanidino and the like. These groups may be attached to any carbon atom of the alkyl "alkenyl", or "alkynyl" moiety.

"Alkoxy" denotes the group —OR, where R is alkyl, substituted alkyl, aryl, substituted aryl, arylalkylene, arylalkenylene, arylalkynylene, substituted arylalkylene, substituted arylalkenylene, substituted arylalkynylene, cycloalkyl, substituted cycloalkyl, cycloheteroalkyl or substituted cycloheteroalkyl as defined.

"Alkylmercapto" denotes the group —SR, where R is as defined for "alkoxy" group.

"Sulfo" denotes the group —$SO_3R$, where R is H, an optionally substituted alkyl or substituted alkyl.

"Sulfamido" denotes to the group $SO_2NRR"$ where R and R" is H, alkyl or substituted alkyl.

"Acyl" denotes groups —C(O)R, where R is hydrogen, alkyl, substituted alkyl, aryl, substituted aryl, arylalkylene, arylalkenylene, arylalkynylene, substituted arylalkylene, substituted arylalkenylene, substituted arylalkynylene, cycloalkyl, substituted cycloalkyl as defined herein.

"Aryloxy" denotes groups —OAr, where Ar is an aryl, substituted aryl, heteroaryl or substituted heteroaryl group as defined herein.

"Alkylamino" denotes the group —NRR', where R and R' may independently be hydrogen, alkyl, substituted alkyl, aryl, substituted aryl, heteroaryl or substituted heteroaryl as defined herein.

"Amido" denotes the group —C(O)NRR', where R and R' may independently be hydrogen, alkyl, substituted alkyl, aryl, substituted aryl, heteroaryl, substituted heteroaryl as defined herein.

"Carboxyl" denotes the group —C(O)OR, where R is hydrogen, alkyl, substituted alkyl, aryl, substituted aryl, hetaryl or substituted hetaryl as defined herein.

"Acylamino denotes the group —NHCOR, where R may be alkyl, alkenyl, alkynyl, substituted alkyl, substituted alkenyl, substituted alkynyl, heterocyclyl, aryl, substituted aryl, heteroaryl and substituted heteroaryl as defined herein.

Carbamoylamino denotes the group NHCOOR, where R is an optionally substituted alkyl, alkenyl, alkynyl, or aryl.

"Aryl" or "Ar" refers to an optionally substituted aromatic carbocyclic group having at least one aromatic ring (e.g., phenyl or biphenyl) or multiple condensed rings in which at least one ring is aromatic (e.g., 1,2,3,4-tetrahydronaphthyl, naphthyl, anthryl, or phenanthryl).

"Substituted aryl" refers to aryl as just described which is optionally substituted with one or more functional groups such as halogen, alkyl, hydroxy, amino, acylamino, carbamoylamino, hydrazino, mercapto, alkoxy, alkylmercapto, alkylamino, amido, carboxyl, nitro, sulfo and the like.

"Heterocyclyl" refers to an optionally substituted unsaturated or aromatic carbocyclic group having at least one hetero atom, such as N, O or S, within the ring; the ring can be single (e.g. pyranyl, pyridyl or furyl) or multiple condensed (e.g., quinazolinyl, purinyl, quinolinyl or benzofuranyl) which can optionally be unsubstituted or substituted with, e.g., halogen, amino, hydroxy, cyano, nitro, mercapto, alkoxy, alkylamino, acylamino, carbamoylamino, acyloxy, dialkylamino, alkylmercapto, carboxyl, amido, sulfo, sulfamido, and the like.

"Heteroaryl" refers to an optionally substituted heterocyclyl in which at least one heterocyclic ring is aromatic.

"Substituted heteroaryl" refers to a heterocyclyl optionally mono or poly substituted with one or more functional groups, e.g., halogen, amino, hydroxy, cyano, nitro, mercapto, alkoxy, alkylamino, acylamino, carbamoylamino, acyloxy, dialkylamino, alkylmercapto, carboxyl, amido, sulfo, sulfamido, and the like.

"Arylalkylene", "arylalkenylene" or "arylalkynylene", refers to the group —R—Ar where Ar is an optionally substituted aryl group and R is alkyl, alkenyl, or alkynyl, or substituted alkyl, substituted alkenyl, or substituted alkynyl group, respectively. The aryl groups can optionally be unsubstituted or substituted with, e.g., halogen, amino, acylamino, carbamoylamino, hydrazino, acyloxy, alkyl, hydroxyl, alkoxy, alkylmercapto, alkylamino, amido, carboxyl, hydroxy, aryl, nitro, mercapto, sulfo and the like.

"Heteroalkyl", 'heteroalkenyl', or "heteroalkynyl" refers to the group —R-Het where Het is an optionally substituted heterocyclyl group and R is an optionally substituted alkyl, alkenyl, or alkynyl group, respectively. Heteroalkyl groups can optionally be unsubstituted or substituted with e.g., halogen, amino, hydroxy, cyano, nitro, mercapto, alkoxy, alkylamino, acylamino, carbamoylamino, acyloxy, dialkylamino, alkylmercapto, carboxyl, amido, sulfo, sulfamido, and the like.

"Heteroarylalkylene", "heteroarylalkenylene" or "heteroarylalkynylene" refers to the group —R-HetAr where HetAr is an optionally substituted heteroaryl group and R is alkyl, alkenyl, or alkynyl, or substituted alkyl, substituted alkenyl, or substituted alkynyl, respectively. Heteroarylalkylene, heteroarylalkenylene, heteroarylalkynylene groups can optionally be unsubstituted or substituted with, e.g., halogen, alkyl, substituted alkyl, alkoxy, alkylmercapto, nitro, thiol, sulfo and the like.

"Cycloalkyl" refers to an optionally substituted divalent cyclic or polycyclic alkyl group containing 3 to 15 carbon atoms.

"Substituted cycloalkyl" refers to a cycloalkyl group comprising one or more substituents with, e.g., halogen, amino, hydroxy, cyano, nitro, mercapto, alkoxy, alkylamino, acylamino, carbamoylamino, acyloxy, dialkylamino, alkylmercapto, carboxyl, amido, sulfo, sulfamido, and the like.

"Cycloheteroalkyl" refers to an optionally substituted cycloalkyl group wherein one or more of the ring methylene group is replaced with a heteroatom (e.g., NH, O, S)

"Substituted cycloheteroalkyl" refers to a cycloheteroalkyl group as herein defined which contains one or more substituents, such as halogen, amino, hydroxy, cyano, nitro, mercapto, alkoxy, alkylamino, acylamino, carbamoylamino, acyloxy, dialkylamino, alkylmercapto, carboxyl, amido, sulfo, sulfamido and the like.

"Cycloalkyl alkyl" denotes an optionally substituted group —R-cycloalkyl where cycloalkyl is an optionally substituted cycloalkyl group and R is an alkyl or substituted alkyl. Cycloalkyl groups can optionally be unsubstituted or substituted with e.g., halogen, amino, hydroxy, cyano, nitro, mercapto, alkoxy, alkylamino, acylamino, carbamoylamino, acyloxy, dialkylamino, alkylmercapto, carboxyl, amido, sulfo, sulfamido and the like.

"Cycloheteroalkyl alkyl" denotes an optionally substituted group —R-cycloheteroalkyl where R is an alkyl or substituted alkyl. Cycloheteroalkyl groups can optionally be unsubstituted or substituted with e.g. halogen, amino, hydroxy, cyano, nitro, mercapto, alkoxy, alkylamino, acylamino, carbamoylamino, acyloxy, dialkylamino, alkylmercapto, carboxyl, amido, sulfo, sulfamido, and the like.

The invention relates to 3-, 5-, 7-trisubstituted pyrazolo[4,3-d]pyrimidines represented by the general formula I

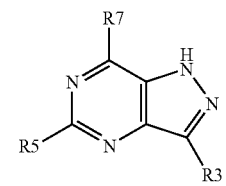

and pharmaceutically acceptable salts thereof, wherein

R3 is an optionally substituted alkyl, cycloalkyl, cycloheteroalkyl, cycloalkyl alkyl, aryl or alkylaryl group;

R5 is halogen, —NHNH$_2$, —NHOH, NHCONH$_2$, guanylo (NH—C(NH)NH$_2$) an optionally substituted $C_1$-$C_6$ alkyl, alkenyl, alkynyl, $C_3$-$C_{15}$ cycloalkyl, $R_f$ ($C_3$-$C_{15}$ cycloalkyl), heterocyclyl, heteroalkyl, aryl, heteroaryl, arylalkylene, arylalkenylene, arylalkynylene, cycloheteroalkyl, cycloheteroalkyl alkyl, heteroarylalkylene, heteroarylalkenylene, or heteroarylalkynylene group, the group C(O)—$R_a$, —C(O)NR$_b$R$_c$, —SO$_3$R$_d$, or —NHC(O)R$_e$, wherein R$_a$ and R$_f$ are an optionally substituted $C_1$-$C_6$ alkyl, alkenyl, or alkynyl group, R$_b$, R$_c$ and R$_d$ are independently selected from the group consisting of H, optionally substituted $C_1$-$C_6$ alkyl, alkenyl, or alkynyl group, and R$_e$ is a hydroxy, amino, alkoxy, alkylamino, optionally substituted $C_1$-$C_6$ alkyl, alkenyl or alkynyl group; or the group —X—R$_5'$, wherein X is —NH—, —O—, —S— or —N(alkyl)- and R$_5'$ is hydrogen, an optionally substituted $C_1$-$C_6$ alkyl, alkenyl, alkynyl, $C_3$-$C_{15}$ cycloalkyl, Rf($C_3$-$C_{15}$ cycloalkyl), aryl, heterocyclyl, hetero $C_1$-$C_6$ alkyl, arylalkylene, arylalkenylene, arylalkynylene, heteroaryl, cycloheteroalkyl, cycloheteroalkyl alkyl, or heteroarylalkylene, heteroarylalkenylene, heteroarylalkynylene group, the group —C(O)—$R_a$, —C(O)$NR_bR_c$, —$SO_3R_d$, or —NHC(O)$R_e$, wherein $R_a$, $R_b$, $R_c$, $R_d$, $R_e$ and $R_f$ have the above meaning, and R7 is halogen, —$NHNH_2$, NHOH, $NHCONH_2$, guanylo (NH—C(NH)$NH_2$) or the group X—$R_{7'}$, wherein X has the above meaning and the meaning of $R_{7'}$ is as defined for $R_{5'}$.

In a preferred embodiment the invention relates to 3-, 5-, 7-trisubstituted pyrazolo[4,3-d]pyrimidines, which inhibit or stimulate the cyclin-dependent kinases and α- and β-adrenergic and purinergic receptors and have formula I

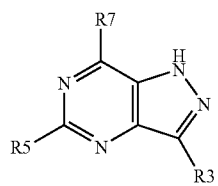

and the pharmaceutically acceptable acid salts thereof, wherein

R7 is
$NHNH_2$,
halogen
R7'—X, wherein X is —NH—, —O—, —S—;
R7'—X, wherein X is preferably N(alkyl)- selected at each occurrence from the group methyl, ethyl, propyl, isopropyl, vinyl, ethynyl, allyl, propargyl, isopentenyl;
R7' is
$C_1$-$C_6$ branched or unbranched alkyl, alkenyl or alkynyl preferentially selected from the group methyl, ethyl, isopropyl, butyl, isobutyl, vinyl, allyl, propenyl, propargyl, propynyl, isopentenyl, and isobutenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;
acyl, —C(O)$R_a$, wherein $R_a$ is $C_1$-$C_6$ branched or unbranched alkyl, alkenyl or alkynyl preferentially selected from the group methyl, ethyl, isopropyl, butyl, isobutyl, vinyl, allyl, propenyl, propargyl, propynyl, isopentenyl, and isobutenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;
amido, —C(O)$NR_bR_c$, wherein $R_b$ and $R_c$ is independently H, $C_1$-$C_6$ branched or unbranched alkyl, alkenyl or alkynyl preferentially selected from the group methyl, ethyl, isopropyl, butyl, isobutyl, vinyl, allyl, propenyl, propargyl, propynyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;
sulfo, —$SO_3R_d$, wherein $R_d$ is H, $C_1$-$C_6$ branched or unbranched alkyl, alkenyl or alkynyl preferentially selected from the group methyl, ethyl, isopropyl, butyl, isobutyl, vinyl, allyl, propenyl, propargyl, propynyl, isopentenyl, and isobutenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;
carbamino, —NHC(O)$R_e$, wherein $R_e$ is hydroxy, amino, alkoxy, alkylamino is $C_1$-$C_6$ alkyl, alkenyl or alkynyl preferentially selected from the group methyl, ethyl, isopropyl, butyl, isobutyl, vinyl, allyl, propenyl, propargyl, propynyl, isopentenyl, and isobutenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;
cycloalkyl is $C_3$-$C_{15}$ cycloalkyl is preferentially selected from the group cyclopropyl, cyclobutyl, cyclopentyl, cyclohexyl, cycloheptyl or adamantyl;
substituted cycloalkyl is $C_3$-$C_{15}$ cycloalkyl is preferentially selected from the group cyclopropyl, cyclobutyl, cyclopentyl, cyclohexyl, cycloheptyl or adamantyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;
cycloalkyl alkylene, cycloalkyl alkenylene, cycloalkyl alkynylene is $R_f$(cycloalkyl), wherein $R_f$ is
$C_1$-$C_6$ alkylene, alkenylene or alkynylene preferentially selected from the group methylene, ethylene, isopropylene, butylene, allylene, propenylene, propargylene, isopentenylene, and isobutenylene, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group,
cycloalkyl is $C_3$-$C_{15}$ cycloalkyl is preferentially selected from the group cyclopropyl, cyclobutyl, cyclopentyl, cyclohexyl, cycloheptyl or adamantyl;
substituted cycloalkyl is $C_3$-$C_{15}$ cycloalkyl is preferentially selected from the group cyclopropyl, cyclobutyl, cyclopentyl, cyclohexyl, cycloheptyl or adamantyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;
aryl is preferentially selected from the group phenyl, biphenyl, naphthyl, tetrahydronaphthyl, fluorenyl, indenyl or phenanthrenyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;
heterocyclyl is preferentially selected from the group thienyl, furyl, pyranyl, pyrrolyl, imidazolyl, pyrazolyl, pyridyl, pyrazinyl, pyrimidinyl, pyridazinyl, isothiazolyl, isoxazyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

heteroalkyl is —$R_g$-Het, wherein $R_g$ is $C_1$-$C_6$ alkylene, alkenylene or alkynylene preferentially selected from the group methylene, ethylene, isopropylene, butylene, vinylene, propynylene, propenylene, ethynylene, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and Het is preferentially selected from the group thienyl, furyl, pyranyl, pyrrolyl, imidazolyl, pyrazolyl, pyridyl, pyrazinyl, pyrimidinyl, pyridazinyl, isothiazolyl, isoxazyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

heteroaryl is —$R_h$-HetAr, wherein $R_h$ is preferentially selected from the group methylene, ethylene, propylene, isopropylene, vinylene, propynylene, propenylene, and HetAr is preferentially selected from the group benzothienyl, naphthothienyl, benzofuranyl, chromenyl, indolyl, isoindolyl, indazolyl, quinolyl, isoquinolyl, phthalazinyl, quinaxalinyl, quinolinyl, quinazolinyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group; arylalkylene, arylalkenylene, or arylalkynylene is —$R_iAr$, wherein $R_i$ is $C_1$-$C_6$ alkylene, alkenylene or alkynylene preferentially selected from the group methylene, ethylene, propylene, isopropylene, vinylene, propynylene, propenylene, ethynylene, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and Ar is preferentially selected from the group phenyl, biphenyl, naphthyl, tetrahydronaphthyl, fluorenyl, indenyl or phenanthrenyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

cycloheteroalkyl is preferentially selected from the group piperidinyl, piperazinyl, morpholinyl, pyrrolidinyl, imidazolidinyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group; cycloheteroalkyl alkyl, —$R_j$(cycloheteroalkyl), wherein $R_j$ is arylalkylene, arylalkenylene, arylalkynylene, —$R_iAr$, wherein $R_i$ is $C_1$-$C_6$ alkylene, alkenylene or alkynylene preferentially selected from the group methylene, ethylene, propylene, isopropylene, vinylene, propynylene, propenylene, ethynylene, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and Ar is preferentially selected from the group phenyl, biphenyl, naphthyl, tetrahydronaphthyl, fluorenyl, indenyl or phenanthrenyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and cycloheteroalkyl is preferentially selected from the group piperidinyl, piperazinyl, morpholinyl, pyrrolidinyl, imidazolidinyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group; heteroarylalkylene, heteroarylalkenylene or heteroarylalkynylene is —$R_k$-HetAr, wherein $R_k$ is $C_1$-$C_6$ alkyl, alkenyl or alkynyl preferentially selected from the group methyl, ethyl, propyl, isopropyl, vinyl, propynyl, propenyl, allyl, propargyl, isopentenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and HetAr is preferentially selected from the group benzothienyl, benzofuranyl, chromenyl, indolyl, isoindolyl, indazolyl, quinolinyl, phthalazinyl, quinoxalinyl, quinazolinyl, carbazolyl, acridinyl, indolinyl, and isoindolinyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

R5 is halogen;

$NHNH_2$;

NHOH;

$C_1$-$C_6$ branched or unbranched alkyl, alkenyl or alkynyl preferentially selected from the group methyl, ethyl, isopropyl, butyl, isobutyl, vinyl, allyl, propenyl, propargyl, propynyl, isopentenyl, and isobutenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

acyl, —C(O)R, wherein $R_a$ is $C_1$-$C_6$ branched or unbranched alkyl, alkenyl or alkynyl preferentially selected from the group methyl, ethyl, isopropyl, butyl, isobutyl, vinyl, allyl, propenyl, propargyl, propynyl, isopentenyl, and isobutenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

amido, —C(O)NR$_b$R$_c$, wherein R$_b$ and R$_c$ is independently H, C$_1$-C$_6$ branched or unbranched alkyl, alkenyl or alkynyl preferentially selected from the group methyl, ethyl, isopropyl, butyl, isobutyl, vinyl, allyl, propenyl, propargyl, propynyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

sulfo, —SO$_3$R$_d$, wherein R$_d$ is H, C$_1$-C$_6$ branched or unbranched alkyl, alkenyl or alkynyl preferentially selected from the group methyl, ethyl, isopropyl, butyl, isobutyl, vinyl, allyl, propenyl, propargyl, propynyl, isopentenyl, and isobutenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

carbamino, —NHC(O)R$_e$, wherein R$_e$ is hydroxy, amino, alkoxy, alkylamino is C$_1$-C$_6$ alkyl, alkenyl or alkynyl preferentially selected from the group methyl, ethyl, isopropyl, butyl, isobutyl, vinyl, allyl, propenyl, propargyl, propynyl, isopentenyl, and isobutenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

cycloalkyl is C$_3$-C$_{15}$ cycloalkyl is preferentially selected from the group cyclopropyl, cyclobutyl, cyclopentyl, cyclohexyl, cycloheptyl or adamantyl;

substituted cycloalkyl is C$_3$-C$_{15}$ cycloalkyl is preferentially selected from the group cyclopropyl, cyclobutyl, cyclopentyl, cyclohexyl, cycloheptyl or adamantyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

cycloalkyl alkylene, cycloalkyl alkenylene, cycloalkyl alkynylene is R$_f$(cycloalkyl), wherein R$_f$ is C$_1$-C$_6$ alkylene, alkenylene or alkynylene preferentially selected from the group methylene, ethylene, isopropylene, butylene, allylene, propenylene, propargylene, isopentenylene, and isobutenylene, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, cycloalkyl is C$_3$-C$_{15}$ cycloalkyl is preferentially selected from the group cyclopropyl, cyclobutyl, cyclopentyl, cyclohexyl, cycloheptyl or adamantyl;

substituted cycloalkyl is C$_3$-C$_{15}$ cycloalkyl is preferentially selected from the group cyclopropyl, cyclobutyl, cyclopentyl, cyclohexyl, cycloheptyl or adamantyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

aryl is preferentially selected from the group phenyl, biphenyl, naphthyl, tetrahydronaphthyl, fluorenyl, indenyl or phenanthrenyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

heterocyclyl is preferentially selected from the group thienyl, furyl, pyranyl, pyrrolyl, imidazolyl, pyrazolyl, pyridyl, pyrazinyl, pyrimidinyl, pyridazinyl, isothiazolyl, isoxazyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

heteroalkyl is —R$_g$-Het, wherein

R$_g$ is C$_1$-C$_6$ alkylene, alkenylene or alkynylene preferentially selected from the group methylene, ethylene, isopropylene, butylene, vinylene, propynylene, propenylene, ethynylene, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and Het is preferentially selected from the group thienyl, furyl, pyranyl, pyrrolyl, imidazolyl, pyrazolyl, pyridyl, pyrazinyl, pyrimidinyl, pyridazinyl, isothiazolyl, isoxazyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

heteroaryl is —R$_h$-HetAr, wherein

R$_h$ is preferentially selected from the group methylene, ethylene, propylene, isopropylene, vinylene, propynylene, propenylene, and HetAr is preferentially selected from the group benzothienyl, naphthothienyl, benzofuranyl, chromenyl, indolyl, isoindolyl, indazolyl, quinolyl, isoquinolyl, phthalazinyl, quinaxalinyl, quinolinyl, quinazolinyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

arylalkylene, arylalkenylene, arylalkenylene is —R$_i$Ar, wherein

R$_i$ is C$_1$-C$_6$ alkylene, alkenylene or alkynylene preferentially selected from the group methylene, ethylene, propylene, isopropylene, vinylene, propynylene, propenylene, ethynylene, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and Ar is preferentially selected from the group phenyl, biphenyl, naphthyl, tetrahydronaphthyl, fluorenyl, indenyl or phenanthrenyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group; cycloheteroalkyl is preferentially selected from the group piperidinyl, piperazinyl, morpholinyl, pyrrolidinyl, imidazolidinyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

cycloheteroalkyl alkyl, —R1(cycloheteroalkyl), wherein $R_j$ is arylalkylene, arylalkenylene, arylalkynylene, —$R_i$Ar, wherein $R_i$ is $C_1$-$C_6$ alkylene, alkenylene or alkynylene preferentially selected from the group methylene, ethylene, propylene, isopropylene, vinylene, propynylene, propenylene, ethynylene, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and Ar is preferentially selected from the group phenyl, biphenyl, naphthyl, tetrahydronaphthyl, fluorenyl, indenyl or phenanthrenyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and cycloheteroalkyl is preferentially selected from the group piperidinyl, piperazinyl, morpholinyl, pyrrolidinyl, imidazolidinyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

heteroarylalkylene, heteroarylalkenylene or heteroarylalkynylene is —$R_k$-HetAr, wherein $R_k$ is $C_1$-$C_6$ alkyl, alkenyl or alkynyl preferentially selected from the group methyl, ethyl, propyl, isopropyl, vinyl, propynyl, propenyl, allyl, propargyl, isopentenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and HetAr is preferentially selected from the group benzothienyl, benzofuranyl, chromenyl, indolyl, isoindolyl, indazolyl, quinolinyl, phthalazinyl, quinoxalinyl, quinazolinyl, carbazolyl, acridinyl, indolinyl, and isoindolinyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

R5'-X, wherein X is —NH—, —O—, —S— moiety;

R5'-X, wherein X is preferably —N(alkyl)- selected at each occurrence from the group methyl, ethyl, propyl, isopropyl, vinyl, ethynyl, allyl, propargyl, isopentenyl;

R5' is

H;

$C_1$-$C_6$ branched or unbranched alkyl, alkenyl or alkynyl preferentially selected from the group methyl, ethyl, isopropyl, butyl, isobutyl, vinyl, allyl, propenyl, propargyl, propynyl, isopentenyl, and isobutenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

acyl, —C(O)R, wherein $R_a$ is $C_1$-$C_6$ branched or unbranched alkyl, alkenyl or alkynyl preferentially selected from the group methyl, ethyl, isopropyl, butyl, isobutyl, vinyl, allyl, propenyl, propargyl, propynyl, isopentenyl, and isobutenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

amido, —C(O)NR$_b$R$_c$, wherein R$_b$ and R$_c$ is independently H, $C_1$-$C_6$ branched or unbranched alkyl, alkenyl or alkynyl preferentially selected from the group methyl, ethyl, isopropyl, butyl, isobutyl, vinyl, allyl, propenyl, propargyl, propynyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

sulfo, —SO$_3$R$_d$, wherein R$_d$ is H, $C_1$-$C_6$ branched or unbranched alkyl, alkenyl or alkynyl preferentially selected from the group methyl, ethyl, isopropyl, butyl, isobutyl, vinyl, allyl, propenyl, propargyl, propynyl, isopentenyl, and isobutenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

carbamino, —NHC(O)R$_e$, wherein R$_e$ is hydroxy, amino, alkoxy, alkylamino is $C_1$-$C_6$ alkyl, alkenyl or alkynyl preferentially selected from the group methyl, ethyl, isopropyl, butyl, isobutyl, vinyl, allyl, propenyl, propargyl, propynyl, isopentenyl, and isobutenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

cycloalkyl is $C_3$-$C_{15}$ cycloalkyl is preferentially selected from the group cyclopropyl, cyclobutyl, cyclopentyl, cyclohexyl, cycloheptyl or adamantyl;

substituted cycloalkyl is $C_3$-$C_{15}$ cycloalkyl is preferentially selected from the group cyclopropyl, cyclobutyl, cyclopentyl, cyclohexyl, cycloheptyl or adamantyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

cycloalkyl alkylene, cycloalkyl alkenylene, cycloalkyl alkynylene is R$_f$(cycloalkyl), wherein R$_f$ is $C_1$-$C_6$ alkylene, alkenylene or alkynylene preferentially selected from the group methylene, ethylene, isopropylene, butylene, allylene, propenylene, propargylene, isopentenylene, and isobutenylene, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, cycloalkyl is $C_3$-$C_{15}$ cycloalkyl is preferentially selected from the group cyclopropyl, cyclobutyl, cyclopentyl, cyclohexyl, cycloheptyl or adamantyl;

substituted cycloalkyl is $C_3$-$C_{15}$ cycloalkyl is preferentially selected from the group cyclopropyl, cyclobutyl, cyclopentyl, cyclohexyl, cycloheptyl or adamantyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

aryl is preferentially selected from the group phenyl, biphenyl, naphthyl, tetrahydronaphthyl, fluorenyl, indenyl or phenanthrenyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

heterocyclyl is preferentially selected from the group thienyl, furyl, pyranyl, pyrrolyl, imidazolyl, pyrazolyl, pyridyl, pyrazinyl, pyrimidinyl, pyridazinyl, isothiazolyl, isoxazyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

heteroalkyl is —$R_g$-Het, wherein $R_g$ is $C_1$-$C_6$ alkylene, alkenylene or alkynylene preferentially selected from the group methylene, ethylene, isopropylene, butylene, vinylene, propynylene, propenylene, ethynylene, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and Het is preferentially selected from the group thienyl, furyl, pyranyl, pyrrolyl, imidazolyl, pyrazolyl, pyridyl, pyrazinyl, pyrimidinyl, pyridazinyl, isothiazolyl, isoxazyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

heteroaryl is —$R_h$-HetAr, wherein $R_h$ is preferentially selected from the group methylene, ethylene, propylene, isopropylene, vinylene, propynylene, propenylene, and HetAr is preferentially selected from the group benzothienyl, naphthothienyl, benzofuranyl, chromenyl, indolyl, isoindolyl, indazolyl, quinolyl, isoquinolyl, phthalazinyl, quinaxalinyl, quinolinyl, quinazolinyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

arylalkylene, arylalkenylene or arylalkynylene is —$R_i$Ar, wherein $R_i$ is $C_1$-$C_6$ alkylene, alkenylene or alkynylene preferentially selected from the group methylene, ethylene, propylene, isopropylene, vinylene, propynylene, propenylene, ethynylene, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and Ar is preferentially selected from the group phenyl, biphenyl, naphthyl, tetrahydronaphthyl, fluorenyl, indenyl or phenanthrenyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group; cycloheteroalkyl is preferentially selected from the group piperidinyl, piperazinyl, morpholinyl, pyrrolidinyl, imidazolidinyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

cycloheteroalkyl alkyl, —$R_j$(cycloheteroalkyl), wherein $R_j$ is arylalkylene, arylalkenylene or arylalkynylene, —$R_i$Ar, wherein $R_i$ is $C_1$-$C_6$ alkylene, alkenylene or alkynylene preferentially selected from the group methylene, ethylene, propylene, isopropylene, vinylene, propynylene, propenylene, ethynylene, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and Ar is preferentially selected from the group phenyl, biphenyl, naphthyl, tetrahydronaphthyl, fluorenyl, indenyl or phenanthrenyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and cycloheteroalkyl is preferentially selected from the group piperidinyl, piperazinyl, morpholinyl, pyrrolidinyl, imidazolidinyl substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

heteroarylalkylene, heteroarylalkenylene or heteroarylalkynylene is —$R_k$HetAr, wherein $R_k$ is $C_1$-$C_6$ alkyl, alkenyl or alkynyl preferentially selected from the group methyl, ethyl, propyl, isopropyl, vinyl, propynyl, propenyl, allyl, propargyl, isopentenyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group, and HetAr is preferentially selected from the group benzothienyl, benzofuranyl, chromenyl, indolyl, isoindolyl, indazolyl, quinolinyl, phthalazinyl, quinoxalinyl, quinazolinyl, carbazolyl, acridinyl, indolinyl, and isoindolinyl, which is substituted independently at each occurrence with 0-5 substituents selected from the group halogen, hydroxy, alkoxy, amino, hydrazo, mercapto, carboxyl, cyano, nitro, amido, sulfo, sulfamido, acylamino, acyloxy, alkylamino, dialkylamino, alkylmercapto and carbamoyl group;

R3 is alkyl, fluorine or chlorine substituted alkyl, fluorine or chlorine substituted cycloalkyl, cycloheteroalkyl, fluorine or chlorine substituted cycloheteroalkyl, cycloalkyl alkyl;

The following derivatives are particularly preferred, namely: 5-[1-(hydroxymethyl)propyl]amino-7-benzylamino-3-isopropyl(methyl,ethyl)pyrazolo[4,3-d]pyrimidine, 5-(R)-(2-hydroxymethylpyrrolidine-1-yl)-7-benzylamino-3-isopropyl(methyl,ethyl)pyrazolo[4,3-d]pyrimidine, 5-(2-aminopropyl)amino-7-benzylamino-3-isopropylpyrazolo[4,3-d]pyrimidine, 5-(2-hydroxypropyl)amino-7-benzylamino-3-isopropyl(methyl,ethyl)pyrazolo[4,3-d]pyrimidine, 5-(R)-[1-isopropyl-2-hydroxyethyl]amino-7-benzylamino-3-isopropyl(methyl,ethyl)pyrazolo[4,3-d]pyrimidine, 5-(4-aminocyclohexyl)amino-7-benzylamino-3-isopropyl(methyl,ethyl)pyrazolo[4,3-d]pyrimidine, 5-(2-aminocyclohexyl)amino-7-benzylamino-3-isopropyl(methyl,ethyl)pyrazolo[4,3-d]pyrimidine, 5-[1-(hydroxymethyl)propyl]amino-7-(3-acetoxybenzyl)amino-3-isopropyl(methyl,ethyl)pyrazolo[4,3-d]pyrimidine, 5-(R)-(2-hydroxymethylpyrrolidine-1-yl)-7-(3-acetoxybenzyl)amino-3-isopropyl(methyl,ethyl)pyrazolo[4,3-d]pyrimidine, 5-(2-aminopropyl)amino-7-(3-acetoxybenzyl)amino-3-isopropyl(methyl,ethyl)pyrazolo[4,3-d]pyrimidine, 5-(2-hydroxypropyl)amino-7-(3-acetoxybenzyl)amino-3-isopropyl(methyl,ethyl)pyrazolo[4,3-d]pyrimidine, 5-(R)-[(1-isopropyl-2-hydroxyethyl]amino-7-(3-acetoxybenzyl)amino)-3-isopropyl(methyl,ethyl)pyrazolo[4,3-d]pyrimidine, 5-(4-aminocyclohexyl)amino-7-(3-acetoxybenzyl)amino-3-isopropyl(methyl,ethyl)pyrazolo[4,3-d]pyrimidine, 5-(2-aminocyclohexyl)amino-7-(3-acetoxybenzyl)amino-3-isopropyl(methyl,ethyl)pyrazolo[4,3-d]pyrimidine, 5-[(1-hydroxymethylpropyl]amino-7-(4-methoxybenzyl)amino-3-isopropyl(methyl,ethyl)pyrazolo[4,3-d]pyrimidine, 5-(R)-(2-hydroxymethylpyrrolidine-1-yl)-7-(4-methoxybenzyl)amino-3-isopropyl(methyl,ethyl)pyrazolo[4,3-d]pyrimidine, 5-(2-aminopropyl)amino-7-(4-methoxybenzyl)amino-3-isopropyl(methyl,ethyl)pyrazolo[4,3-d]pyrimidine, 5-(2-hydroxypropyl)amino-7-(4-methoxybenzyl)amino-3-isopropyl(methyl,ethyl)pyrazolo[4,3-d]pyrimidine, 5-(R)-[1-isopropyl-2-hydroxyethyl]amino-7-(4-methoxybenzyl)amino-3-isopropyl(methyl,ethyl)pyrazolo[4,3-d]pyrimidine, 5-(4-aminocyclohexyl)amino-7-(4-methoxybenzyl)amino-3-isopropyl(methyl,ethyl)pyrazolo[4,3-d]pyrimidine, 5-(2-aminocyclohexyl)amino-7-(4-methoxybenzyl)amino-3-isopropylpyrazolo[4,3-d]pyrimidine, 5-(2-aminocyclohexyl)amino-7-(4-methoxybenzyl)amino-3-isopropylpyrazolo[4,3-d]pyrimidine, 5-(4-methoxybenzyl)amino-7-(4-methoxybenzyl)amino-3-isopropyl(methyl,ethyl)pyrazolo[4,3-d]pyrimidine, 5-(4-methoxybenzyl)amino-7-(4-methoxybenzyl)amino-3-isopropylpyrazolo[4,3-d]pyrimidine, 5-[(1-hydroxymethylpropyl]amino-7-(2-hydroxy-3-methoxybenzyl)amino-3-isopropyl(methyl,ethyl)pyrazolo[4,3-d]pyrimidine, 5-(R)-(2-hydroxymethylpyrrolidine-1-yl)-7-(2-hydroxy-3-methoxybenzyl)amino-3-isopropyl(methyl,ethyl)pyrazolo[4,3-d]pyrimidine, 5-(2-aminopropyl)amino-7-(2-hydroxy-3-methoxybenzyl)amino-3-isopropyl(methyl,ethyl)pyrazolo[4,3-d]pyrimidine, 5-(2-hydroxypropyl)amino-7-(2-hydroxy-3-methoxybenzyl)amino-3-isopropyl(methyl,ethyl)pyrazolo[4,3-d]pyrimidine, 5-(R)-[1-isopropyl-2-hydroxyethyl]amino-7-(2-hydroxy-3-methoxybenzyl)amino-3-isopropyl(methyl,ethyl)pyrazolo[4,3-d]pyrimidine, 5-(4-aminocyclohexyl)amino-7-(2-hydroxy-3-methoxybenzyl)amino-3-isopropyl(methyl,ethyl)pyrazolo[4,3-d]pyrimidine, 5-(2-aminocyclohexyl)amino-7-(2-hydroxy-3-methoxybenzyl)amino-3-isopropylpyrazolo[4,3-d]pyrimidine, 5-[1-(hydroxymethyl)propyl]amino-7-(2,3-dihydroxy-4-methoxybenzyl)amino-3-isopropyl(methyl,ethyl)pyrazolo[4,3-d]pyrimidine, 5-(R)-(2-hydroxymethylpyrrolidine-1-yl)-'7-(2,3-dihydroxy-4-methoxybenzyl)amino-3-isopropyl(methyl,ethyl)pyrazolo[4,3-d]pyrimidine, 5-(2-aminopropyl)amino-7-(2,3-dihydroxy-4-methoxybenzyl)amino-3-isopropyl(methyl,ethyl)pyrazolo[4,3-d]pyrimidine, 5-(2-hydroxypropyl)amino-7-(2,3-dihydroxy-4-methoxybenzyl)amino-3-isopropyl(methyl,ethyl)pyrazolo[4,3-d]pyrimidine, 5-(R)-(1-isopropyl-2-hydroxyethyl)amino-7-(2,3-dihydroxy-4-methoxybenzyl)amino-3-isopropyl(methyl,ethyl)pyrazolo[4,3-d]pyrimidine, 5-(4-aminocyclohexyl)amino-7-(2,3-dihydroxy-4-methoxybenzyl)amino-3-isopropyl(methyl,ethyl)pyrazolo[4,3-d]pyrimidine, 5-(2-aminocyclohexyl)amino-7-(2,3-dihydroxy-4-methoxybenzyl)amino-3-isopropyl(methyl,ethyl)pyrazolo[4,3-d]pyrimidine, 5-(1-hydroxymethylpropyl)amino-7-(2,5-dihydroxy-4-methoxybenzyl)amino-3-isopropyl(methyl,ethyl)pyrazolo[4,3-d]pyrimidine, 5-(R)-(2-hydroxymethylpyrrolidine-1-yl)-7-(2,5-dihydroxy-4-methoxybenzyl)amino-3-isopropyl(methyl,ethyl)pyrazolo[4,3-d]pyrimidine, 5-(2-aminopropyl)amino-7-(2,5-dihydroxy-4-methoxybenzyl)amino-3-isopropyl(methyl,ethyl)pyrazolo[4,3-d]pyrimidine, 5-(2-hydroxypropyl)amino-7-(2,5-dihydroxy-4-methoxybenzyl)amino-3-isopropyl(methyl,ethyl)pyrazolo[4,3-d]pyrimidine, 5-(R)-(1-isopropyl-2-hydroxyethyl)amino-7-(2,5-dihydroxy-4-methoxybenzyl)amino-3-isopropyl(methyl,ethyl)pyrazolo[4,3-d]pyrimidine, 5-(4-aminocyclohexyl)amino-7-(2,5-dihydroxy-4-methoxybenzyl)amino-3-isopropyl(methyl,ethyl)pyrazolo[4,3-d]pyrimidine, 5-(2-aminocyclohexyl)amino-7-(2,5-dihydroxy-4-methoxybenzyl)amino-3-isopropyl(methyl,ethyl)pyrazolo[4,3-d]pyrimidine, 5-[1-(hydroxymethyl)propyl]amino-7-(2,6-dihydroxy-4-methoxybenzyl)amino)-3-isopropyl(methyl,ethyl)pyrazolo[4,3-d]pyrimidine, 5-(R)-(2-hydroxymethylpyrrolidine-1-yl)-7-(2,6-dihydroxy-4-methoxybenzyl)amino-3-isopropyl(methyl,ethyl)pyrazolo[4,3-d]pyrimidine, 5-(2-aminopropyl)amino-7-(2,6-dihydroxy-4-methoxybenzyl)amino-3-isopropyl(methyl,ethyl)pyrazolo[4,3-d]pyrimidine, 5-(2-hydroxypropyl)amino-7-(2,6-dihydroxy-4-methoxybenzyl)amino-3-isopropyl(methyl,ethyl)pyrazolo[4,3-d]pyrimidine, 5-(R)-(1-isopropyl-2-hydroxyethyl)amino-7-(2,6-dihydroxy-4-methoxybenzyl)amino-3-isopropyl(methyl,ethyl)pyrazolo[4,3-d]pyrimidine, 5-(4-aminocyclohexyl)amino-7-(2,6-dihydroxy-4-methoxybenzyl)amino-3-isopropyl(methyl,ethyl)pyrazolo[4,3-d]pyrimidine, 5-(2-aminocyclohexyl)amino-7-(2,6-dihydroxy-4-methoxybenzyl)amino-3-isopropyl(methyl,ethyl)pyrazolo[4,3-d]pyrimidine, 5-[1-(hydroxymethyl)propyl]amino-7-(2,3-dihydroxy-4-chlorobenzyl)amino-3-isopropyl(methyl, ethyl)pyrazolo[4,3-d]pyrimidine, 5-(R)-(2-hydroxymethylpyrrolidine-1-yl)-7-(2,3-dihydroxy-4-chlorobenzyl)amino-3-isopropyl(methyl,ethyl)pyrazolo[4,3-d]pyrimidine, 5-(2-aminopropyl)amino-7-(2,3-dihydroxy-4-chlorobenzyl)amino-3-isopropyl(methyl,ethyl)pyrazolo[4,3-d]pyrimidine, 5-(2-hydroxypropyl)amino-7-(2,3-dihydroxy-4-chlorobenzyl)amino-3-isopropyl(methyl,ethyl)pyrazolo[4,3-d]pyrimidine, 5-(R)-(1-isopropyl-2-hydroxyethyl)amino-7-(2,3-dihydroxy-4-chlorobenzyl)amino-3-isopropyl(methyl,ethyl)pyrazolo[4,3-d]pyrimidine, 5-(4-aminocyclohexyl)amino-7-(2,3-dihydroxy-4-chlorobenzyl)amino-3-isopropyl(methyl,ethyl)pyrazolo[4,3-d]pyrimidine, 5-(2-aminocyclohexyl)amino-7-(2,3-dihydroxy-4-chlorobenzyl)amino-3-isopropyl(methyl,ethyl)pyrazolo[4,3-d]pyrimidine, 5-[1-(hydroxymethyl)propyl]amino-7-(2,5-dihydroxy-4-chlorobenzyl)amino-3-isopropyl(methyl,ethyl)pyrazolo[4,3-d]pyrimidine, 5-(R)-(2-hydroxymethylpyrrolidine-1-yl)-7-(2,5-dihydroxy-4-chlorobenzyl)amino-3-isopropyl(methyl,ethyl)pyrazolo[4,3-d]pyrimidine, 5-(2-aminopropyl)amino-7-(2,5-dihydroxy-4-chlorobenzyl)amino-3-isopropyl(methyl,ethyl)pyrazolo[4,3-d]pyrimidine, 5-(2-hydroxypropyl)amino-7-(2,5-dihydroxy-4-chlorobenzyl)amino-3-isopropyl(methyl,ethyl)pyrazolo[4,3-d]pyrimidine, 5-(R)-(1-isopropyl-2-hydroxyethyl)amino-7-(2,5-dihydroxy-4-chlorobenzyl)amino-3-isopropylpyrazolo[4,3-d]pyrimidine, 5-(4-aminocyclohexyl)amino-7-(2,5-dihydroxy-4-chlorobenzyl)amino-3-isopropyl(methyl,ethyl)pyrazolo[4,3-d]pyrimidine, 5-[1-(hydroxymethyl)propylamino-7-(2,6-dihydroxy-4-chlorobenzyl)amino-3-isopropyl(methyl,ethyl)pyrazolo[4,3-d]pyrimidine, 5-(R)-(2-hydroxymethylpyrrolidine-1-yl)-7-(2,6-dihydroxy-4-chlorobenzyl)amino-3-isopropyl(methyl,ethyl)pyrazolo[4,3-d]pyrimidine, 5-(2-aminopropyl)amino-7-(2,6-dihydroxy-4-chlorobenzyl)amino-3-isopropyl(methyl,ethyl)pyrazolo[4,3-d]pyrimidine, 5-(2-hydroxypropyl)amino-7-(2,6-dihydroxy-4-chlorobenzyl)amino-3-isopropyl(methyl,ethyl)pyrazolo[4,3-d]pyrimidine, 5-(R)-(1-isopropyl-2-hydroxyethyl)amino-7-(2,6-dihydroxy-4-chlorobenzyl)amino-3-isopropylpyrazolo[4,3-d]pyrimidine, 5-(4-aminocyclohexyl)amino-7-(2,6-dihydroxy-4-chlorobenzyl)amino-3-isopropyl(methyl,ethyl)pyrazolo[4,3-d]pyrimidine, 5-(2-aminocyclohexyl)amino-7-(2,6-dihydroxy-4-chlorobenzyl)amino-3-isopropyl(methyl,ethyl)pyrazolo[4,3-d]pyrimidine, 5-[1-(hydroxymethyl)propyl]amino-7-(2-acetoxybenzyl)amino-3-isopropyl(methyl,ethyl)pyrazolo[4,3-d]pyrimidine, 5-(R)-(2-hydroxymethylpyrrolidine-1-yl)-7-(2-acetoxybenzyl)amino-3-isopropyl(methyl,ethyl)pyrazolo[4,3-d]pyrimidine, 5-(2-aminopropyl)amino-7-(2-acetoxybenzyl)amino-3-isopropyl(methyl,ethyl)pyrazolo[4,3-d]pyrimidine, 5-(2-hydroxypropyl)amino-7-(2-acetoxybenzyl)amino-3-isopropyl(methyl,ethyl)pyrazolo[4,3-d]pyrimidine, 5-(R)-(1-isopropyl-2-hydroxyethyl)amino-7-(2-acetoxybenzyl)amino-3-isopropyl(methyl,ethyl)pyrazolo[4,3-d]pyrimidine, 5-(4-aminocyclohexyl)amino-7-(2-acetoxybenzyl)amino-3-isopropyl(methyl,ethyl)pyrazolo[4,3-d]pyrimidine, 5-(2-aminocyclohexyl)amino-7-(2-acetoxybenzyl)amino-3-isopropyl(methyl,ethyl)pyrazolo[4,3-d]pyrimidine, 5-[1-(hydroxymethyl)propyl]amino-7-(2-aminobenzyl)amino-3-isopropyl(methyl,ethyl)pyrazolo[4,3-d]pyrimidine, 5-(R)-(2-hydroxymethylpyrrolidine-1-yl)-7-(2-aminobenzyl)amino-3-isopropyl(methyl,ethyl)pyrazolo[4,3-d]pyrimidine, 5-(2-aminopropyl)amino-7-(2-aminobenzyl)amino-3-isopropyl(methyl,ethyl)pyrazolo[4,3-d]pyrimidine, 5-(2-hydroxypropyl)amino-7-(2-aminobenzyl)amino-3-isopropyl(methyl,ethyl)pyrazolo[4,3-d]pyrimidine, 5-(R)-(1-isopropyl-2-hydroxyethyl)amino-7-(2-aminobenzyl)amino-3-isopropyl(methyl,ethyl)pyrazolo[4,3-d]pyrimidine, 5-(4-aminocyclohexyl)amino-7-(2-aminobenzyl)amino-3-isopropyl(methyl,ethyl)pyrazolo[4,3-d]pyrimidine, 5-(2-aminocyclohexyl)amino-7-(2-aminobenzyl)amino-3-isopropyl(methyl,ethyl)pyrazolo[4,3-d]pyrimidine, 5-[1-(hydroxymethyl)propyl]amino-7-(2-amino-6-chlorobenzyl)amino-3-isopropyl(methyl,ethyl)pyrazolo[4,3-d]pyrimidine, 5-(R)-(2-hydroxymethylpyrrolidine-1-yl)-7-(2-amino-6-chlorobenzyl)amino-3-isopropyl(methyl,ethyl)pyrazolo[4,3-d]pyrimidine, 5-(2-aminopropyl)amino-7-(2-amino-6-chlorobenzyl)amino-3-isopropyl(methyl,ethyl)pyrazolo[4,3-d]pyrimidine, 5-(2-hydroxypropyl)amino-7-(2-amino-6-chlorobenzyl)amino-3-isopropyl(methyl,ethyl)pyrazolo[4,3-d]pyrimidine, 5-(R)-(1-isopropyl-2-hydroxyethyl)amino-7-(2-amino-6-chlorobenzyl)amino-3-isopropyl(methyl,ethyl)pyrazolo[4,3-d]pyrimidine, 5-(4-aminocyclohexyl)amino-7-(2-amino-6-chlorobenzyl)amino-3-isopropyl(methyl,ethyl)pyrazolo[4,3-d]pyrimidine, 5-(2-aminocyclohexyl)amino-7-(2-amino-6-chlorobenzyl)amino-3-isopropyl(methyl,ethyl)pyrazolo[4,3-d]pyrimidine, 5-[1-(hydroxymethyl)propyl]amino-7-(3-amino-4-chlorobenzyl)amino-3-isopropyl(methyl,ethyl)pyrazolo[4,3-d]pyrimidine, 5-(R)-(2-hydroxymethylpyrrolidine-1-yl)-7-(3-amino-4-chlorobenzyl)amino-3-isopropyl(methyl,ethyl)pyrazolo[4,3-d]pyrimidine, 5-(2-aminopropyl)amino-7-(3-amino-4-chlorobenzyl)amino-3-isopropyl(methyl,ethyl)pyrazolo[4,3-d]pyrimidine, 5-(2-hydroxypropyl)amino-7-(3-amino-4-chlorobenzyl)amino-3-isopropyl(methyl,ethyl)pyrazolo[4,3-d]pyrimidine, 5-(R)-(1-isopropyl-2-hydroxyethyl)amino-7-(3-amino-4-chlorobenzyl)amino-3-isopropyl(methyl,ethyl)pyrazolo[4,3-d]pyrimidine, 5-(4-aminocyclohexyl)amino-7-(3-amino-4-chlorobenzyl)amino-3-isopropyl(methyl,ethyl)pyrazolo[4,3-d]pyrimidine, 5-(2-aminocyclohexyl)amino-7-(3-amino-4-chlorobenzyl)amino-3-isopropyl(methyl,ethyl)pyrazolo[4,3-d]pyrimidine, 5-[1-(hydroxymethyl)propyl]amino-7-(3-acetylbenzyl)amino-3-isopropyl(methyl,ethyl)pyrazolo[4,3-d]pyrimidine, 5-(R)-(2-hydroxymethylpyrrolidine-1-yl)-7-(3-acetylbenzyl)amino-3-isopropyl(methyl,ethyl)pyrazolo[4,3-d]pyrimidine, 5-(2-aminopropyl)amino-7-(3-acetylbenzyl)amino-3-isopropyl(methyl,ethyl)pyrazolo[4,3-d]pyrimidine, 5-(2-hydroxypropyl)amino-7-(3-acetylbenzyl)amino-3-isopropyl(methyl,ethyl)pyrazolo[4,3-d]pyrimidine, 5-(R)-(1-isopropyl-2-hydroxyethyl)amino-7-(3-acetylbenzyl)amino-3-isopropyl(methyl,ethyl)pyrazolo[4,3-d]pyrimidine, 5-(4-aminocyclohexyl)amino-7-(3-acetylbenzyl)amino-3-isopropyl(methyl,ethyl)pyrazolo[4,3-d]pyrimidine, 5-(2-aminocyclohexyl)amino-7-(3-acetylbenzyl)amino-3-isopropyl(methyl,ethyl)pyrazolo[4,3-d]pyrimidine, 5-[1-(hydroxymethyl)propyl]amino-7-(2-acetylbenzyl)amino-3-isopropyl(methyl,ethyl)pyrazolo[4,3-d]pyrimidine, 5-(R)-(2-hydroxymethylpyrrolidine-1-yl)-7-(2-acetylbenzyl)amino-3-isopropyl(methyl,ethyl)pyrazolo[4,3-d]pyrimidine, 5-(2-aminopropyl)amino-7-(2-acetylbenzyl)amino-3-isopropyl(methyl,ethyl)pyrazolo[4,3-d]pyrimidine, 5-(2-hydroxypropyl)amino-7-(2-acetylbenzyl)amino-3-isopropyl(methyl,ethyl)pyrazolo[4,3-d]pyrimidine, 5-(R)-(1-isopropyl-2-hydroxyethyl)amino-7-(2-acetylbenzyl)amino-3-isopropyl(methyl,ethyl)pyrazolo[4,3-d]pyrimidine, 5-(4-aminocyclohexyl)amino-7-(2-acetylbenzyl)amino-3-isopropyl(methyl,ethyl)pyrazolo[4,3-d]pyrimidine, 5-(2-aminocyclohexyl)amino-7-(2-acetylbenzyl)amino-3-isopropyl(methyl,ethyl)pyrazolo[4,3-d]pyrimidine, 5-[1-(hydroxymethyl)propyl]amino-7-anilino-3-isopropyl(methyl,ethyl)pyrazolo[4,3-d]pyrimidine, 5-(R)-(2-hydroxymethylpyrrolidine-1-yl)-7-anilino-3-isopropyl(methyl,ethyl)pyrazolo[4,3-d]pyrimidine, 5-(2- aminopropyl)amino-7-anilino-3-isopropyl(methyl,ethyl)pyrazolo[4,3-d]pyrimidine, 5-(2-hydroxypropyl)amino-7-anilino-3-isopropyl(methyl,ethyl)pyrazolo[4,3-d]pyrimidine, 5-(R)-(1-isopropyl-2-hydroxyethyl)amino-7-anilino-3-isopropyl(methyl,ethyl)pyrazolo[4,3-d]pyrimidine, 5-(4-aminocyclohexyl)amino-7-anilino-3-isopropyl(methyl,ethyl)pyrazolo[4,3-d]pyrimidine, 5-(2-aminocyclohexyl)amino-7-anilino-3-isopropyl(methyl,ethyl)pyrazolo[4,3-d]pyrimidine, 5-[1-(hydroxymethyl)propyl]amino-7-(3-chloroanilino)-3-isopropyl(methyl,ethyl)pyrazolo[4,3-d]pyrimidine, 5-(R)-(2-hydroxymethylpyrrolidine-1-yl-7-(3-chloroanilino)-3-isopropyl(methyl,ethyl)pyrazolo[4,3-d]pyrimidine, 5-(2-aminopropyl)amino-7-(3-chloroanilino)-3-isopropyl(methyl,ethyl)pyrazolo[4,3-d]pyrimidine, 5-(2-hydroxypropyl)amino-7-(3-chloroanilino)-3-isopropyl(methyl,ethyl)pyrazolo[4,3-d]pyrimidine, 5-(R)-(1-isopropyl-2-hydroxyethyl)amino-7-(3-chloroanilino)-3-isopropyl(methyl,ethyl)pyrazolo[4,3-d]pyrimidine, 5-(4-aminocyclohexyl)amino-7-(3-chloroanilino)-3-isopropyl(methyl,ethyl)pyrazolo[4,3-d]pyrimidine, 5-(2-aminocyclohexyl)amino-7-(3-chloroanilino)-3-isopropyl(methyl,ethyl)pyrazolo[4,3-d]pyrimidine, 5-[1-hydroxymethylpropyl]amino-7-(4-chloroanilino)-3-isopropyl(methyl,ethyl)pyrazolo[4,3-d]pyrimidine, 5-(R)-(2-hydroxymethylpyrrolidine-1-yl)-7-(4-chloroanilino)-3-isopropyl(methyl,ethyl)pyrazolo[4,3-d]pyrimidine, 5-(2-aminopropyl)amino-7-(4-chloroanilino)-3-isopropyl(methyl,ethyl)pyrazolo[4,3-d]pyrimidine, 5-(2-hydroxypropyl)amino-7-(4-chloroanilino)-3-isopropyl(methyl,ethyl)pyrazolo[4,3-d]pyrimidine, 5-(R)-(1-isopropyl-2-hydroxyethyl)amino-7-(4-chloroanilino)-3-isopropyl(methyl,ethyl)pyrazolo[4,3-d]pyrimidine, 5-(4-aminocyclohexyl)amino-7-(4-chloroanilino)-3-isopropyl(methyl,ethyl)pyrazolo[4,3-d]pyrimidine, 5-(2-aminocyclohexyl)amino-7-(4-chloroanilino)-3-isopropyl(methyl,ethyl)pyrazolo[4,3-d]pyrimidine, 5-[1-(hydroxymethyl)propyl]amino-7-(4-bromoanilino)-3-isopropyl(methyl,ethyl)pyrazolo[4,3-d]pyrimidine, 5-(R)-(2-hydroxymethylpyrrolidine-1-yl)-7-(4-bromoanilino)-3-isopropyl(methyl,ethyl)pyrazolo[4,3-d]pyrimidine, 5-(2-aminopropyl)amino-7-(4-bromoanilino)-3-isopropyl(methyl,ethyl)pyrazolo[4,3-d]pyrimidine, 5-(2-hydroxypropyl)amino-7-(4-bromoanilino)-3-isopropyl(methyl,ethyl)pyrazolo[4,3-d]pyrimidine, 5-(R)-(1-isopropyl-2-hydroxyethyl)amino-7-(4-bromoanilino)-3-isopropyl(methyl,ethyl)pyrazolo[4,3-d]pyrimidine, 5-(4-aminocyclohexyl)amino-7-(4-bromoanilino)-3-isopropyl(methyl,ethyl)pyrazolo[4,3-d]pyrimidine, 5-(2-aminocyclohexyl)amino-7-(4-bromoanilino)-3-isopropyl(methyl,ethyl)pyrazolo[4,3-d]pyrimidine, 5-[1-(hydroxymethyl)propyl]amino-7-(2-aminophenyl)amino-3-isopropyl(methyl,ethyl)pyrazolo[4,3-d]pyrimidine, 5-(R)-(2-hydroxymethylpyrrolidine-1-yl)-7-(2-aminophenyl)amino-3-isopropyl(methyl,ethyl)pyrazolo[4,3-d]pyrimidine, 5-(2-aminopropyl)amino-7-(2-aminophenyl)amino-3-isopropyl(methyl,ethyl)pyrazolo[4,3-d]pyrimidine, 5-(2-hydroxypropyl)amino-7-(2-aminophenyl)amino-3-isopropyl(methyl,ethyl)pyrazolo[4,3-d]pyrimidine, 5-(R)-(1-isopropyl-2-hydroxyethyl)amino-7-(2-aminophenyl)amino-3-isopropyl(methyl,ethyl)pyrazolo[4,3-d]pyrimidine, 5-(4-aminocyclohexyl)amino-7-(2-aminophenyl)amino-3-isopropyl(methyl,ethyl)pyrazolo[4,3-d]pyrimidine, 5-(2-aminocyclohexyl)amino-7-(2-aminophenyl)amino-3-isopropyl(methyl,ethyl)pyrazolo[4,3-d]pyrimidine, 5-[1-(hydroxymethyl)propyl]amino-7-(3-aminophenyl)amino-3-isopropyl(methyl,ethyl)pyrazolo[4,3-d]pyrimidine, 5-(R)-(2-hydroxymethylpyrrolidine-1-yl)-7-(3-aminophenyl)amino-3-isopropyl(methyl,ethyl)pyrazolo[4,3-d]pyrimidine, 5-(2-aminopropyl)amino-7-(3-aminophenyl)amino-3-isopropyl(methyl,ethyl)pyrazolo[4,3-d]pyrimidine, 5-(2-hydroxypropyl)amino-7-(3-aminophenyl)amino-3-isopropyl(methyl,ethyl)pyrazolo[4,3-d]pyrimidine, 5-(R)-(1-isopropyl-2-hydroxyethyl)amino-7-(3-aminophenyl)amino-3-isopropyl(methyl,ethyl)pyrazolo[4,3-d]pyrimidine, 5-(4-aminocyclohexyl)amino-7-(3-aminophenyl)amino-3-isopropyl(methyl,ethyl)pyrazolo[4,3-d]pyrimidine, 5-(2-aminocyclohexyl)amino-7-(3-aminophenyl)amino-3-isopropyl(methyl,ethyl)pyrazolo[4,3-d]pyrimidine, 5-[1-(hydroxymethyl)propyl]amino-7-(4-aminophenyl)amino-3-isopropyl(methyl,ethyl)pyrazolo[4,3-d]pyrimidine, 5-(R)-(2-hydroxymethylpyrrolidine-1-yl)-7-(4-aminophenyl)amino-3-isopropyl(methyl,ethyl)pyrazolo[4,3-d]pyrimidine, 5-(2-aminopropyl)amino-7-(4-aminophenyl)amino-3-isopropyl(methyl,ethyl)pyrazolo[4,3-d]pyrimidine, 5-(2-hydroxypropyl)amino-7-(4-aminophenyl)amino-3-isopropyl(methyl,ethyl)pyrazolo[4,3-d]pyrimidine, 5-(R)-(1-isopropyl-2-hydroxyethyl)amino-7-(4-aminophenyl)amino-3-isopropyl(methyl,ethyl)pyrazolo[4,3-d]pyrimidine, 5-(4-aminocyclohexyl)amino-7-(4-aminophenyl)amino-3-isopropyl(methyl,ethyl)pyrazolo[4,3-d]pyrimidine, 5-(2-aminocyclohexyl)amino-7-(4-aminophenyl)amino-3-isopropyl(methyl,ethyl)pyrazolo[4,3-d]pyrimidine, 5-[1-(hydroxymethyl)propyl]amino-7-(3-chloro-5-aminoanilino)-3-isopropyl(methyl,ethyl)pyrazolo[4,3-d]pyrimidine, 5-(R)-(2-hydroxymethylpyrrolidine-1-yl)-7-(3-chloro-5-aminoanilino)-3-isopropyl(methyl,ethyl)pyrazolo[4,3-d]pyrimidine, 5-(2-aminopropyl)amino-7-(3-chloro-5-aminoanilino)-3-isopropyl(methyl,ethyl)pyrazolo[4,3-d]pyrimidine, 5-(2-hydroxypropyl)amino-7-(3-chloro-5-aminoanilino)-3-isopropyl(methyl,ethyl)pyrazolo[4,3-d]pyrimidine, 5-(R)-(1-isopropyl-2-hydroxyethyl)amino-7-(3-chloro-5-aminoanilino)-3-isopropyl(methyl,ethyl)pyrazolo[4,3-d]pyrimidine, 5-(4-aminocyclohexyl)amino-7-(3-chloro-5-aminoanilino)-3-isopropyl(methyl,ethyl)pyrazolo[4,3-d]pyrimidine, 5-(2-aminocyclohexyl)amino-7-(3-chloro-5-aminoanilino)-3-isopropyl(methyl,ethyl)pyrazolo[4,3-d]pyrimidine, 5-[1-(hydroxymethyl)propyl]amino-7-(3-chloro-4-carboxyanilino)-3-isopropyl(methyl,ethyl)pyrazolo[4,3-d]pyrimidine, 5-(R)-(2-hydroxymethylpyrrolidine-1-yl)-7-(3-chloro-4-carboxyanilino)-3-isopropyl(methyl,ethyl)pyrazolo[4,3-d]pyrimidine, 5-(2-aminopropyl)amino-7-(3-chloro-4-carboxyanilino)-3-isopropyl(methyl,ethyl)pyrazolo[4,3-d]pyrimidine, 5-(2-hydroxypropyl)amino-7-(3-chloro-4-carboxyanilino)-3-isopropyl(methyl,ethyl)pyrazolo[4,3-d]pyrimidine, 5-(R)-(1-isopropyl-2-hydroxyethyl)amino-7-(3-chloro-4-carboxyanilino)-3-isopropyl(methyl,ethyl)pyrazolo[4,3-d]pyrimidine, 5-(4-aminocyclohexyl)amino-7-(3-chloro-4-carboxyanilino)-3-isopropyl(methyl,ethyl)pyrazolo[4,3-d]pyrimidine, 5-(2-aminocyclohexyl)amino-7-(3-chloro-4-carboxyanilino)-3-isopropyl(methyl,ethyl)pyrazolo[4,3-d]pyrimidine, 5-[1-(hydroxymethyl)propyl]amino-7-(3-carboxy-4-chloroanilino)-3-isopropyl(methyl,ethyl)pyrazolo[4,3-d]pyrimidine, 5-(R)-(2-hydroxymethylpyrrolidine-1-yl)-7-(3-carboxy-4-chloroanilino)-3-isopropyl(methyl,ethyl)pyrazolo[4,3-d]pyrimidine, 5-(2-aminopropyl)amino-7-(3-carboxy-4-chloroanilino)-3-isopropyl(methyl,ethyl)pyrazolo[4,3-d]pyrimidine, 5-(2-hydroxypropylamino)-7-(3-carboxy-4-chloroanilino)-3-isopropyl(methyl,ethyl)pyrazolo[4,3-d]pyrimidine, 5-(R)-(1-isopropyl-2-hydroxyethyl)amino-7-(3-carboxy-4-chloroanilino)-3-isopropyl(methyl,ethyl)pyrazolo[4,3-d]pyrimidine, 5-(4-aminocyclohexyl)amino-7-

(3-carboxy-4-chloroanilino)-3-isopropyl(methyl,ethyl)pyrazolo[4,3-d]pyrimidine, 5-(2-aminocyclohexyl)amino-7-(3-carboxy-4-chloroanilino)-3-isopropyl(methyl,ethyl)pyrazolo[4,3-d]pyrimidine, 5-[1-(hydroxymethyl)propyl]amino-7-(3-amino-4-chloroanilino)-3-isopropyl(methyl,ethyl)pyrazolo[4,3-d]pyrimidine, 5-(R)-(2-hydroxymethylpyrrolidine-1-yl)-7-(3-amino-4-chloroanilino)-3-isopropyl(methyl,ethyl)pyrazolo[4,3-d]pyrimidine, 5-(2-aminopropyl)amino-7-(3-amino-4-chloroanilino)-3-isopropyl(methyl,ethyl)pyrazolo[4,3-d]pyrimidine, 5-(2-hydroxypropyl)amino-7-(3-amino-4-chloroanilino)-3-isopropyl(methyl,ethyl)pyrazolo[4,3-d]pyrimidine, 5-(R)-(1-isopropyl-2-hydroxyethyl)amino-7-(3-amino-4-chloroanilino)-3-isopropyl(methyl,ethyl)pyrazolo[4,3-d]pyrimidine, 5-(4-aminocyclohexyl)amino-7-(3-amino-4-chloroanilino)-3-isopropyl(methyl,ethyl)pyrazolo[4,3-d]pyrimidine, 5-(2-aminocyclohexyl)amino-7-(3-amino-4-chloroanilino)-3-isopropyl(methyl,ethyl)pyrazolo[4,3-d]pyrimidine, 5-[1-(hydroxymethyl)propyl]amino-7-(3-chloro-4-aminoanilino)-3-isopropyl(methyl,ethyl)pyrazolo[4,3-d]pyrimidine, 5-(R)-(2-hydroxymethylpyrrolidine-1-yl)-7-(3-chloro-4-aminoanilino)-3-isopropyl(methyl,ethyl)pyrazolo[4,3-d]pyrimidine, 5-(2-aminopropyl)amino-7-(3-chloro-4-aminoanilino)-3-isopropyl(methyl,ethyl)pyrazolo[4,3-d]pyrimidine, 5-(2-hydroxypropyl)amino-7-(3-chloro-4-aminoanilino)-3-isopropyl(methyl,ethyl)pyrazolo[4,3-d]pyrimidine, 5-(R)-(1-isopropyl-2-hydroxyethyl)amino-7-(3-chloro-4-aminoanilino)-3-isopropyl(methyl,ethyl)pyrazolo[4,3-d]pyrimidine, 5-(4-aminocyclohexyl)amino-7-(3-chloro-4-aminoanilino)-3-isopropyl(methyl,ethyl)pyrazolo[4,3-d]pyrimidine, 5-(2-aminocyclohexyl)amino-7-(3-chloro-4-aminoanilino)-3-isopropyl(methyl,ethyl)pyrazolo[4,3-d]pyrimidine, 5-[1-(hydroxymethyl)propyl]amino-7-(3-carboxy-4-hydroxyanilino)-3-isopropyl(methyl,ethyl)pyrazolo[4,3-d]pyrimidine, 5-(R)-(2-hydroxymethylpyrrolidine-1-yl)-7-(3-carboxy-4-hydroxyanilino)-3-isopropyl(methyl,ethyl)pyrazolo[4,3-d]pyrimidine, 5-(2-aminopropyl)amino-7-(3-carboxy-4-hydroxyanilino)-3-isopropyl(methyl,ethyl)pyrazolo[4,3-d]pyrimidine, 5-(2-hydroxypropyl)amino-7-(3-carboxy-4-hydroxyanilino)-3-isopropyl(methyl,ethyl)pyrazolo[4,3-d]pyrimidine, 5-(R)-(1-isopropyl-2-hydroxyethyl)amino-7-(3-carboxy-4-hydroxyanilino)-3-isopropyl(methyl,ethyl)pyrazolo[4,3-d]pyrimidine, 5-(4-aminocyclohexyl)amino-7-(3-carboxy-4-hydroxyanilino)-3-isopropyl(methyl,ethyl)pyrazolo[4,3-d]pyrimidine, 5-(2-aminocyclohexyl)amino-7-(3-carboxy-4-hydroxyanilino)-3-isopropyl(methyl,ethyl)pyrazolo[4,3-d]pyrimidine, 5-(2-hydroxypropyl)amino-7-[N-(3,4-dihydroxybenzyl)-N-methyl]amino-3-isopropyl(methyl,ethyl)pyrazolo[4,3-d]pyrimidine, 2-(R)-(1-isopropyl-2-hydroxyethyl)amino-7-[N-(3,4-dihydroxybenzyl)-N-methyl]amino-3-isopropyl(methyl,ethyl)pyrazolo[4,3-d]pyrimidine, 2-(2-hydroxypropyl)amino-7-[1-(3,4-dihydroxyphenyl)ethyl]amino-3-isopropyl(methyl,ethyl)pyrazolo[4,3-d]pyrimidine 2-(R)-(1-isopropyl-2-hydroxyethyl)amino-7-[1-(3,4-dihydroxyphenyl)ethyl]amino-3-isopropyl(methyl,ethyl)pyrazolo[4,3-d]pyrimidine, 2-(R)-(1-isopropyl-2-hydroxyethyl)amino-6-{N-[2-(3,4-dihydroxyfenyl)ethyl]-N-methyl}amino-7-benzylamino-3-isopropyl(methyl,ethyl)pyrazolo[4,3-d]pyrimidine-3-isopropylpyrazolo[4,3-d]pyrimidine, 2(R)-[1-isopropyl-2-hydroxyethyl]amino-7-(R)-[1-phenyl-2-hydroxyethyl]amino-3-isopropyl(methyl,ethyl)pyrazolo[4,3-d]pyrimidine, 2-(R)-(1-isopropyl-2-hydroxyethyl)amino-7-(R/S)[(1-phenyl-2-hydroxyethyl)amino]-3-isopropyl(methyl,ethyl)pyrazolo[4,3-d]pyrimidine, 5-chloro-6-(R/S)-(1-phenyl-2-hydroxyethyl)amino-3-isopropyl(methyl,ethyl)pyrazolo[4,3-d]pyrimidine, 5-[1-(hydroxymethyl)propyl]amino-7-benzylamino-3-isopropyl(methyl,ethyl)pyrazolo[4,3-d]pyrimidine, 5-(2-aminopropyl)amino-7-benzylamino-3-isopropyl(methyl,ethyl)pyrazolo[4,3-d]pyrimidine, 5-(2-hydroxypropyl)amino-7-benzylamino-3-isopropyl(methyl,ethyl)pyrazolo[4,3-d]pyrimidine, 5-(R)-(1-isopropyl-2-hydroxyethyl)amino-7-(4-methoxybenzyl)amino-3-isopropyl(methyl,ethyl)pyrazolo[4,3-d]pyrimidine, 5-(2-hydroxypropyl)amino-7-(3-chloranilino)-3-isopropyl(methyl,ethyl)pyrazolo[4,3-d]pyrimidine, 5-(2-hydroxypropyl)amino-7-(3-chloro-4-carboxyanilino)-3-isopropyl(methyl,ethyl)pyrazolo[4,3-d]pyrimidine, 5-(R)-(2-hydroxymethylpyrrolidine-1-yl)-7-benzylamino-3-isopropyl(methyl,ethyl)pyrazolo[4,3-d]pyrimidine, 5-(R)-(1-isopropyl-2-hydroxyethyl)amino-6-(3-chloro-4-carboxyanilino)-3-isopropyl(methyl,ethyl)pyrazolo[4,3-d]pyrimidine 5-(R)-(1-isopropyl-2-hydroxyethyl)amino-7-benzylamino-3-isopropyl(methyl,ethyl)pyrazolo[4,3-d]pyrimidine, 5-(R)-(1-isopropyl-2-hydroxyethyl)amino-6-(3-chloranilino)-3-isopropyl(methyl,ethyl)pyrazolo[4,3-d]pyrimidine.

This invention also relates to optical isomers and racemic mixtures of the above-defined derivatives, in particular the (R) or (S) isomers of 5-(R)-(1-isopropyl-2-hydroxyethyl)amino-7-[1-(3,4-dihydroxyphenyl)ethyl]amino-3-isopropyl(methyl,ethyl)pyrazolo[4,3-d]pyrimidine, 5-(R)-(1-isopropyl-2-hydroxyethylamino)-7-(3,4-dihydroxybenzyl)amino-3-isopropyl(methyl,ethyl)pyrazolo[4,3-d]pyrimidine, 5-(R)-[2-hydroxymethylpyrrolidine-1-yl]-7-(3,4-dihydroxybenzyl)amino-3-isopropyl(methyl,ethyl)pyrazolo[4,3-d]pyrimidine, 5-(1R-isopropyl-2-hydroxyethylamino)-7-(1S-phenyl-2-hydroxyethyl)amino-3-isopropyl(methyl,ethyl)pyrazolo[4,3-d]pyrimidine, 5-(1S-isopropyl-2-hydroxyethylamino)-7-(1S-phenyl-2-hydroxyethyl)amino-3-isopropyl(methyl,ethyl)pyrazolo[4,3-d]pyrimidine.

Utilities

The novel compounds of this invention per se or as intermediates in the preparation of novel compound having a wide variety of diagnostic, therapeutic and industrial utilities.

The compounds of this invention are suitable as intermediates for use in the preparation of affinity absorption matrices that harness the chemical properties of the compound's substituent groups. For example, the phosphonate groups in matrix bound form are useful in the chromatographic separation of positively charged molecules. Other immobilized examples of the compounds herein are useful in purifying proteins, e.g., cell cycle enzymes (cdk's), enzymes involved in recognition of the compound of this invention, e.g. transport proteins. Suitable methods of incorporation of the compounds of this invention into polymeric resins will be readily apparent to the skilled artisan, for instance the compounds are incorporated by cross-linking hydroxyl groups of the phosphonate or hydroxymethyl substituents using cross-linking agents heretofore known. Linking through a group other than the heterocyclic base will produce a resin useful in hydrophobic affinity chromatography.

The compounds of the formula I and their pharmaceutically acceptable salts inhibit selectively the enzyme $p34^{cdc2}$/cyclin B kinase and related cdks (cdk2, cdk5, cdk7, cdk9, erk1, erk2).

In another embodiment, this invention relates to a method for inhibiting cdks and cell proliferation and/or for inducing apoptosis in mammals comprising administering a therapeutically effective amount of the composition of claim 1 to the mammal. The cdk inhibiting molecules are useful for treating disorders, some of them involving cell proliferation, such as cancer, restenosis, rheumatoid arthritis, lupus, type I diabetes, multiple sclerosis, Alzheimer's disease, growth of parasites (animal, protists), graft rejection (host versus graft disease), graft versus host disease, and gout.

In still another embodiment, this invention relates to a composition useful for treating fungal infections (fungi) in humans, animals and plants.

Trisubstituted pyrazolo[4,3-d]pyrimidine derivatives of the invention result in the acquisition of extremely high potency against DNA viruses on the part of the defined compounds. Such compounds otherwise have been considered to have little or no activity against DNA viruses. Moreover, surprisingly the chirally enriched or pure (S)-enantiomer is antivirally active. Heretofore, only the (R)-enantiomer was notably antivirally active, and then only against the retroviruses. An important aspect of the present invention is a method for inhibiting proliferation of a DNA virus dependent upon events associated with cell proliferation for replication. The DNA virus includes any of the herpes virus family, and most particularly human cytomegalovirus. The method involves administering a prophylactically or therapeutically effective amount of a cyclin-dependent kinase inhibitor to a patient or animal. The therapeutically effective amount is an amount sufficient to inhibit cellular CDK activity to extent impending viral replication. Other herpes viruses such as herpes simplex, for example, and other cytomegalovirus are also treatable by the procedures of the present invention.

In addition to other cdc2-related kinases, this kinase controls certain steps of cell division cycles, in particular the transition from $G_1$ phase into the S phase and in particular the transition from the $G_2$ phase into the M-phase. The compounds of the formula I and their pharmaceutically acceptable salts can also be used as antimitotic compounds and for treatment of proliferative diseases, such as cancer and restenosis. Thus in very low concentration (micromolar and lower), they are capable of inhibiting cell cycle transitions ($G_1$/S, $G_2$/M, M-phase/metaphase) carried out on the different animal bodies and embryos. Furthermore, the compounds are useful in treating auto-immune diseases, e.g. rheumatoid arthritis, lupus, type I diabetes, multiple sclerosis, etc.; in treating Alzheimer's disease, cardiovascular disease such as restenosis, graft rejection (host vs. graft disease), graft vs. host disease, gout; and in treating cancer, polycystic kidney disease and other proliferative diseases whose pathogenesis involves abnormal cell proliferation.

In addition to proliferative disorders, the treatment of differentiative disorders, which result from, for example, de-differentiation of tissue which may (optionally) be accompanied by abortive reentry into mitosis. Such degenerative disorders include chronic neutrodegenerative diseases of the nervous system, including Alzheimer's disease, Parkinson's disease, Huntington's chorea, amylotrophic lateral sclerosis and the like, as well as spinocerebellar degenerations. Other differentiative disorders include, for example, disorders associated with connective tissue, such as may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors.

In addition to therapeutic applications (e.g., for both human and veterinary uses) the compounds of the invention can be used as a cell culture additive for controlling proliferative and/or differentiation states of cells in vitro, for instance, by controlling the level of activation of a CDK. To illustrate, in vitro neuronal culture systems have proved to be fundamental and indispensable tools for the study of neural development, as well as the identification of neutrophic factors. Once a neuronal cell has become terminally-differentiated, it typically will not change to another terminally differentiated cell-type. However, neuronal cells can nevertheless readily lose their differentiated state. This is commonly observed when they are grown in culture from adult tissue, and when they form a blastema during regeneration. By preventing the activation of a Go/G1 CDK, the subject inhibitors can prevent mitotic progression and hence provide a means for ensuring an adequately restrictive environment in order to maintain neuronal cells at various stages of differentiations, and can be employed, for instance, in cell cultures designed to test the specific activities of trophic factors. Other tissue culture systems, which require maintenance of differentiation, will be readily apparent to those skilled in the art. In this respect, each of the CDK4 inhibitors can be used for ex vivo tissue generation, as for example, to enhance the generation of prosthetic tissue devices for implantation.

Without being bound to this theory, it is likely that inhibition by the compounds of the invention of the catalytic activity of cyclin-dependent kinases is mediated by interaction of the compounds at the ATP-binding site of the enzyme. Such compounds are particularly desirable for reducing excessive cell growth, since they allow inhibition of the kinase activity regardless of the cause underlying the excessive kinase activity leading to excessive cell proliferation. Thus, the compounds of the invention are active in situations in which the excessive kinase activity results from the kinase being a mutated hyperactive, form of the kinase and situations in which the kinase is present at excessive levels. Such compounds can also block excessive kinase activity in situations in which the cyclin regulating the kinase is present at excessive levels or its binding to the kinase is enhanced. Furthermore, compounds which block kinase activity by interacting with the ATP binding site of the enzyme are also useful for inhibiting kinase activity in situations in which a natural inhibitor of cyclin-kinase complexes is mutated.

It will also be apparent that differential screening assays can be used to select for those compounds of the present invention with specificity for non-human CDK enzymes. Thus, compounds, which act specifically on eukaryotic pathogens, e.g., are anti-fungal or anti-parasitic agents, can be selected from the subject pyrazolo-pyrimidines inhibitors. To illustrate inhibitors of the *Candida* CDK kinase, CKS 1 can be used in the treatment of candidiasis- and opportunistic infection that commonly occurs in debilitated and immuno-suppressed patients. CKS 1 inhibitors could be used to treat these infections in patients with leukemias and lymphomas, in people who are receiving immunosuppressive therapy, and in patients with such predisposing factors as diabetes mellitus or AIDS, where fungal infections are a particular problem.

By way of illustration, the assays described in the art can be used to screen for agents which may ultimately be useful for inhibiting at least one fungus implicated in such mycosis as candidiasis, aspergillosis, mucormycosis, blastomycosis, geotrichosis, cryptococcosis, chromoblastomycosis, coccidiodomycosis, conidiosporosis, histoplasmosis, maduromycosis, rhinosporidosis, nocardiosis, paraactinomycosis, penicilliosis, monoliasis, or sporotrichosis. For example, if the mycotic infection to which treatment is desired is candidiasis, an assay as described above or in the appended examples can comprise comparing the relative effectiveness of a test compound on inhibiting a mammalian CDK enzyme with its effectiveness towards a CDK enzyme from yeast, such as selected from the group consisting of *Candida albicans, Candida stellatoidea, Candida tropicalis, Candida parapsilosis, Candida krusei, Candida pseudotropicalis, Candida auillermondii*, or *Candida rugosa. Candida* CDK genes have been described, such as in U.S. Ser. No. 08/463,090.

Likewise, the differential screening assays can be used to identify anti-fungal agents which may have therapeutic value in the treatment of aspergillosis by making use of the CDK genes cloned from yeast such as *Aspergillus fumigatus, Aspergillus flavus, Aspergillus niger, Aspergillus nidulans*, or *Aspergillus terreus*.

Likewise, where the mycotic infection is mucormycosis, the CDK assay can be derived from yeast such as *Rhizopus arrhizus, Rhizopus oryzae, Absidia corymbifera, Absidia ramosa*, or *Mucor pusillus*. Sources of other CDK enzymes include the pathogen *Pneumocystis carinii*.

In addition to such therapeutic uses, anti-fungal agents developed with such differential screening assays can be used, for example, as preservatives in foodstuff, feed supplement for promoting weight gain in livestock, or in disinfectant formulations for treatment of non-living matter, e.g., for decontaminating hospital equipment and rooms.

In similar fashion, side by side comparison of inhibition of a mammalian CDK and an insert CDK, such as the Drosophilia CDK5 gene (Hellmich et al. (1994) *FEBS Lett* 356: 317-21), will permit selection amongst the subject pyrazolo-pyrimidine derivatives of inhibitors which discriminate between the human/mammalian and insect enzymes. Accordingly, the present invention expressly contemplates the use and formulations of the subject benzopyranone in insecticides, such as for use in management of insect like the fruit fly.

In yet another embodiment, certain of the CDK inhibitors of the invention can be selected on the basis of inhibitory specificity for plant CDKs relative to the mammalian enzyme. For example, a plant CDK can be evaluated in a differential screen with one or more of the human enzymes to select those pyrazolo-pyrimidine compounds of greatest selectivity for inhibiting the plant enzyme. Thus, the present invention specifically contemplates formulations of the subject CDK inhibitors for agricultural applications, such as in the form of a defoliant or the like.

This invention also concerns novel compounds that have been discovered to be potent and specific inhibitors of IκB-α kinase which prevents signal induced NF-κB activation and cytokine synthesis in vitro and in vivo. Such inhibitors are expected to inhibit synthesis of cytokines and adhesion proteins whose synthesis is transcriptionally regulated by NF-κB. Pro-inflammatory cytokines such as IL-1, IL-6, TNF and adhesion proteins (e.g. ICAM, VCAM and selections) belong to this class of molecules and have implicated in the pathogenesis of inflammatory diseases. Thus a potent inhibitor of IκB-α kinase is useful in the clinical management of diseases where the NF-κB activation is required for disease induction.

The invention also concerns novel compounds which affect the activation and/or signal transduction of α- and β-adrenergic receptors e.g. phosphatidyl turnover and cyclic AMP synthesis respectively. Activation of β-adrenergic receptors has an anti-inflammatory effect by decreasing the cytokine production of macrophages, astrocytes, and by preventing an increase in vascular permeability (see FIG. 2). On the other hand a decreased β-adrenergic receptor activation is useful in diseases like multiple sclerosis, rheumatoid arthritis. The novel compounds may also affect P2-purinergic receptor activation linked to phosphatidyl turnover and inhibition of activation of cyclic AMP synthesis or P1-purinergic receptor activation positively or negatively coupled to the activation of adenylate cyclase depending on the receptor subtype. Modulation of purinergic receptor signaling may be useful in cerebral ischemia, stroke, treatments of neurodegenerative diseases (e.g. Parkinson's disease), renal failure, treatment of lung dysfunction, and in inhibition of cancer growth.

It also relates to novel compounds activating p53, the mammal cell's own natural brake gene for stopping uncontrolled cell proliferation (cancer), thus being able to switch off the cancer.

p53 as well as retinoblastoma (Rb) are two well characterized tumor suppressors whose inactivation may led to uncontrolled cell proliferation and malignancy. Phosphorylation of these two proteins, which are involved in the cell cycle regulatory mechanisms, is known to modulate their function. Thus, a potent p53 regulators represent a good tool for treatment of cancers due to induction of wild type p53 protein in the selected cancers.

Studies carried out on the derivatives of the invention have demonstrated, in addition, the strong effect on apoptosis of many cancer cell lines. It has been seen that apoptosis can be induced at stage $G_1$ or $G_2$ and following damage of the DNA, some cells stop at stage $G_1$ and p53-dependent apoptotic pathway is then induced. In other situations, it seems that cells stop at $G_2$/M stage in response to damage caused to the DNA, and activation of an independent p53 apoptotic path is observed. This path has proved particularly significant in the therapy of tumors in which a less active p53 is observed. The interest is therefore assessed that by application of the derivatives of the invention, p53-independent apoptosis will be stimulated in cells, which have stopped at stage $G_2$ through damage to the DNA using agents such as mitoxantrone or cis-platinum. The cdk inhibitors of this invention can thus increase the therapeutic potential of the anti-tumor agents currently used.

The compounds of this invention will generally be terminally incorporated into the oligonucleotide. If they contain a nonphosphonyl free hydroxyl group, they optionally are incorporated internally into the sequence of the oligonucleotide. Terminally incorporated diphosphonyl compounds of this invention which contain no free hydroxyl capable of participating in chain elongation also are useful in DNA sequencing in essentially the same manner as deoxyNTPs have been used in the past (see example 8 of U.S. Pat. No. 5,276,143). The nucleotide analogues of the invention (when diphosphorylated) are useful as chain terminators for dideoxynucleotide-type DNA sequencing protocols, provided that the nucleotide analogue lacks a free hydroxyl group suitable for polymerase mediated chain elongation. These compounds will not have R=hydroxymethyl and do not posses a cyclic structure incorporating the phosphorus atom (although compounds having such excluded structures can be intermediates). The nucleotide analogue is included in a kit with other reagents (such as Klenow polymerase or T4 polymerase, dNTPs, etc) needed for DNA sequencing (Otvos et al. "*Nucl. Acids Res.*" 1987; 15: 1763-1777).

If the oligonucleotide-incorporated compound of this invention is binding-competent for its complementary sequence, i.e., if it is capable of base pairing, then this nucleotide monomer will participate in hybridization. It is not necessary, however, that the incorporated nucleotide analogue of this invention base pair or otherwise participates in hybridization. If it is located at the terminus of the oligonucleotide, it will be useful as an immunological recognition site, or haptenic recognition site, to facilitate detection of the oligonucleotide by an antibody capable of binding the compound of this invention.

The compounds of this invention also are useful as linkers or spacers in preparation of affinity absorption matrices (as opposed to functioning as affinity moieties per se as noted above), immobilized enzymes for process control, or immunoassay reagents. The compounds herein contain a multiplicity of functional groups that are suitable as sites for cross-linking desired substances. For example, it is conventional to link affinity reagents such as hormones, peptides, antibodies, drugs, and the like to insoluble substrates. These insolubilised bound reagents are employed in known fashion to absorb binding partners for the affinity reagents from manufactured preparations, diagnostic samples and other impure mixtures. Similarly, immobilized enzymes are used to perform catalytic conversions with easy recovery of enzyme. Bifunctional compounds are commonly used to link analytes to detectable groups in preparing diagnostic reagents.

Many functional groups present in the compounds of this invention are suitable for use in cross-linking. For example, the phosphonic acid is used to form esters with alcohols or amides with amines. The R groups substituted with OH, azido (which is reduced to amino if desired before cross-linking) or vinyl are exemplary suitable sites. Similarly, the amino, halo, acyl and other reactive sites found on group R are suitable. Suitable protection of reactive groups will be used where necessary while assembling the cross-linked reagent. In general, the compounds here are used by linking them through phosphonic acid or amino group to the hydroxyl or amino groups of the linking partner in the same fashion as shown herein, and covalently bound to the other binding partner through an R group. For example a first binding partner such as a steroid hormone is esterified and then this conjugate is cross-linked through hydroxymethyl R to cyanogen bromide activated Sepharose, whereby immobilized steroid is obtained. Other chemistries for conjugation are well known. See for example Maggio, "Enzyme-Immunoassay" (CRC, 1988, pp 71-135) and references cited therein.

The pyrazolo-pyrimidines of this invention are useful for labeling with any conventional detectable label, e.g. a fluorescent moiety such a fluorescein, radioisotopes such as $^{14}C$ or $^{3}H$, stable free radicals, avidin, biotin and the like all of which previously have been used as labels for immunoassays or diagnostic probes. The label will be present on the oligonucleotide or on the residue of an analogue of this invention. Suitable labeling methods are well known and are readily used with reactive groups such as hydroxyl, allyl and the like. A simple method is to label the compound of this invention with $^{3}H$ by proton exchange. The compounds also are biotinylated using conventional methods. See for instance U.S. Pat. No. 5,276,143 for analogous structures. However, the compounds of this invention also are useful directly in diagnostic probe assays without an exogenous detectable label. In one embodiment of this alternative, antibodies are raised against the compounds of this invention. Such antibodies (which in turn are labeled or used in a double antibody configuration) bind to the analogue of this invention and thereby are useful in detecting its presence as label for a protein or oligonucleotide.

The compounds of the invention are useful for treatment of microbial infections, for treatment of tumors or for other indications described below. Microbial infections treatable by the compounds of this invention include viruses, parasites, yeast and fungi, but it is believed that the compounds are most effective against viruses, which constitutes the preferred utility. Exemplary viral infections include infections caused by DNA or RNA viruses including herpes viruses (herpes simplex virus type 1 (HSV-1), HSV-2, varicella zoster virus (VZV), Epstein-Barr virus (EBV), cytomegalovirus (CMV), human herpes virus type 6 (HHV-6), HHV-7, HHV-8, bovine herpes virus type 1, equine herpes virus type 1), papilloma viruses (HPV types 1-55, including carcinogenic HPV), flavi viruses (including yellow fever virus, African swine fever virus and Japanese encephalitis virus), toga viruses (including Venezuelan equine encephalomyelitis virus), influenza viruses (types A-C), retroviruses (HIV-1, HIV-2, HTLV-I, HTLV-II, SIV, FeLV, FIV, MoMSV), adenoviruses (types 1-8), poxviruses (vaccinia virus), enter viruses (poliovirus types 1-3, Coxsackie, hepatitis A virus, and ECHO virus), gastroenteritis viruses (Norwalk viruses, rotaviruses), hantaviruses (Hantaan virus), polyoma virus, papova viruses, rhino viruses, parainfluenza virus types 1-4, rabies virus, respiratory synctial virus (RSV), hepatitis viruses A, B, C and E, and the like.

The antiviral activity of individual compounds is determined by routine assay of antiviral (or other antimicrobial) activity using enzyme inhibition assays, tissue culture assays, animal model assays and the like as will be understood by those skilled in the art.

Protozoan parasite infections are treated using the compounds of the invention. The term protozoa include those members of the subphyla Sarcomastigophora and Sporozoa of the phylum Protozoa. More particularly, the term protozoa as used herein include genera of parasitic protozoa, which are important to man, because they either cause disease in man or in his domestic animals. These genera for the most part are classified in the super class Mastigophora of the subphylum Sarcomastigophora and the class Telesporea of the subphylum Sporozoa in the classification according to Baker (1969). Illustrative genera of these parasitic protozoa include *Histomonas, Pneumocystis, Trypanosoma, Giardia, Trichomonas, Eimeria, Isopora, Leishmania, Entamoeba, Toxoplasma* and *Plasmodium*. Parasitic protozoans include *Plasmodium falciparum, Plasmodium berghei, Plasmodium malariae, Plasmodium vivax, Leishmania braziliensis, Leishmania donovani, Trypanosoma cruzi, Trypanosoma brucei, Trypanosoma rhodesiense, Pneumocystis carinii, Entamoeba histolytica, Trichomonas vaginalis* and the like (de Vries, E. et al., "*Mol. Biochem. Parasitol.*" 1991; 47:43-50) and trypanosomes (Kaminsky et al. "*J. Parasitol.*" 1994; 80(6):1026-1030). The compounds in which R is $CH_2OH$ and B is 3-deazaadenine are particularly interesting in the treatment of malarial parasites.

Compounds of the invention are used to treat yeast or fungal infections caused by *Candida glabrata, Candida tropicalis, Candida albicans*, and other *Candida* species, *Cryptococcus* species including *Cryptococcus neoformans, Blastomyces* species including *Blastomyces dermatitidis, Torulopsis* species including *Torulopsis glabrata, Coccidioides* species including *Coccidioides immitis, Aspergillus* species and the like.

The compounds of the invention can also be (1) applied to tissue culture systems to eliminate or reduce viral spread or growth during the production of biopharmaceutical or other products (such as proteins or vaccines), (2) used to eliminate or reduce viral spread or growth in clinical sample (such as blood), and (3) used to stop growth of tissue culture cells while leaving the cells to carry on with protein production.

The compounds herein have been found to suppress immunostimulation. Accordingly, they can suppress metabolic activities of T-lymphocytes stimulated by diverse agents, e.g. concanavalin A, they principally will find application in the treatment of autoimmune diseases, e.g. arthritis, or in suppression of transplant rejection. Their therapeutically active concentrations are in the range of 1 mg/kg to 50 mg/kg of body weight.

Process for Preparation

The pyrazolo[4,3-d]pyrimidines of the formula I according to the present invention may be prepared via intermediate compounds using the procedures outlined in Reaction Schemes 1-5. The starting pyrazolo compound II is synthesized according to the literature (Baraldi P. G.; Cacciari B.; Recanatini A. L. M.; Roberti M.; Rossi M.: Farmaco 46, 1991: 1351-1363). In the Schemes presented bellow R represents lower alkyl or aryl; X, R3, R5, R7, R5', R7' are as defined for compound of the formula I in the claim 1. Process A is a process step leading to pyrazolo compound nitrated into position 4. This reaction is conducted in oleum (65%) and nitric acid (60%) under heating (104° C.). Process B is a step of commonly used for preparation of amides. Process C is a step to convert the nitro group of intermediate IV to amino group of compound V. This reaction is conducted by hydrogenation over Raney Nickel, Pd° or Pt° in appropriate solvent system or by $Sn^{2+}$ or $S_2O_4^{2-}$. Alternative path for synthesis of compounds V is process D (esterification) succeeded by process E (reduction) and process F (amidation). This way affords lower yield of compound V. A compound of the formula VII may be alternatively obtained by the way depicted in the Scheme 2. Application of known cyclization method using nitriles leads to hydroxy compound XI. Process K is a step for preparing of a 7-chloro derivative XII, which (without isolation) is converted (treatment with nucleophiles as amine, metal alkoxide or metal mercaptide) into 3,5,7-trisubstituted pyrazolo[4,3-d]pyrimidine XIII. The compound V serves as starting material in the synthesis depicted in the Scheme 3, 4, and 5. Process M is a step for preparation of 5,7-dihydroxy derivative of pyrazolo[4,3-d]pyrimidine XIV. Replacement of 5 and 7 hydroxy groups by chlorine is realized by pyrophosphoryl chloride (diphosphoryl dichloride) treatment. Nucleophilic substitution (process O and P) leads to 3,5,7-trisubstituted pyrazolo[4,3-d]pyrimidines. Process Q is a step of preparing a 5-amino-7-hydroxyderivative by means of cyclization with guanidine or with chloroformamidine. 7-Hydroxy group of compound XVIII is then substituted by chlorine (process R, $SOCl_2$, room temperature). Nucleophilic substitution affords 5-amino-3,7-disubstituted pyrazolo[4,3-d]pyrimidines (Scheme 4). The synthesis depicted in the Scheme 5 is alternative path for syntheses of compound XI (Scheme 2).

SCHEME 1:

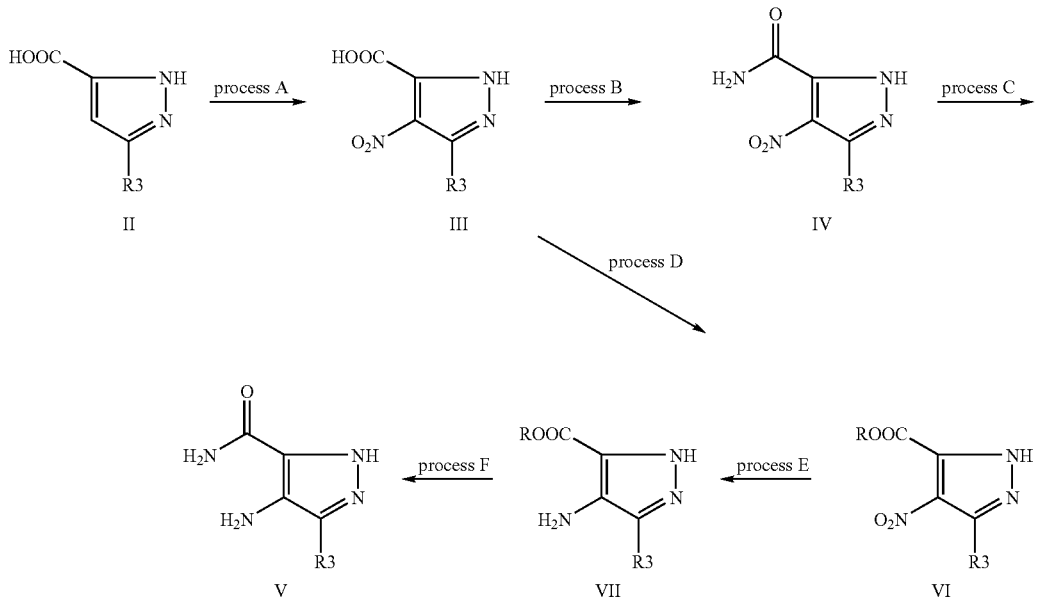

process A: $H_2SO_4/HNO_3$
process B: 1) $SOCl_2$; 2) $NH_4OH$
process C: $H_2$ + Ra Ni/$CH_3OH$ + $H_2O$; $H_2$ + Pd or Pt/$CH_3OH$ + $CH_3COOH$; SnCl; $S_2O_4^{2-}$
process D: ROH/HCl
process E: as the process C
process F: $NH_4OH$

SCHEME 2:

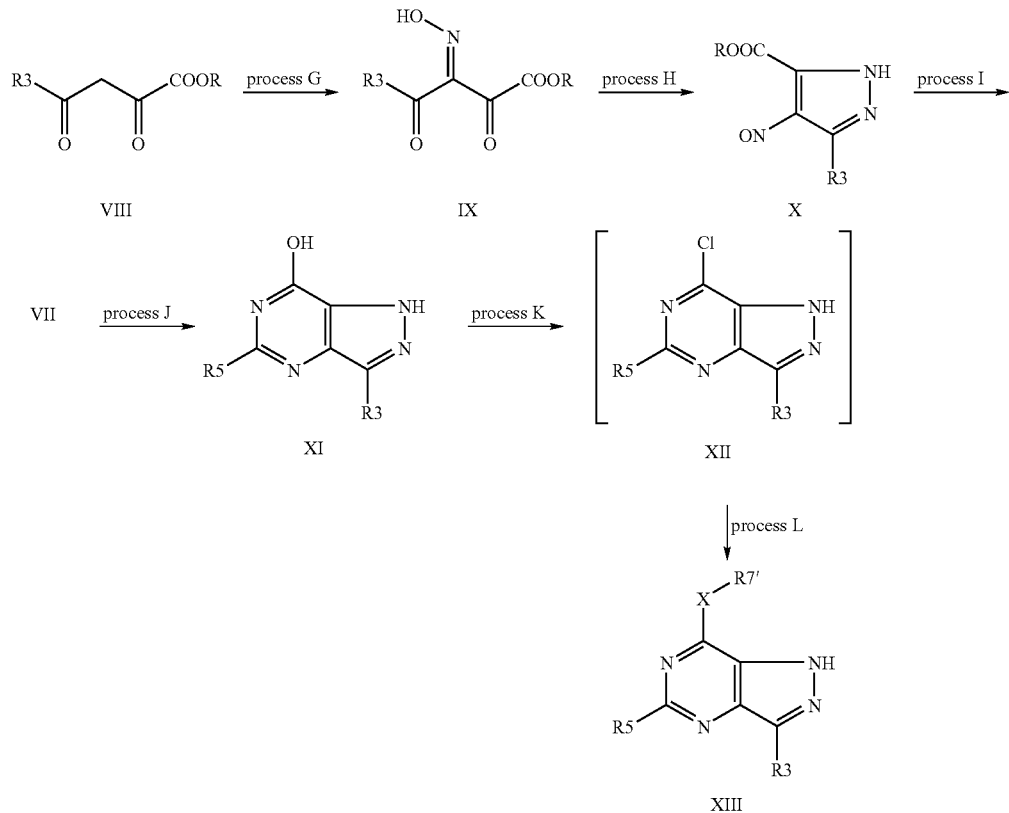

process G: NaNO$_2$/HCl in C$_2$H$_5$OH or N$_2$O$_3$ (g)
process H: N$_2$H$_4$
process I: Na$_2$S$_2$O$_4$/EtOAc + H$_2$O
process J: R$^5$CN
process K: SOCl$_2$/T = 40-100° C. or POCl$_3$ or POCl$_3$ + PCl$_5$
process L: R7'NH$_2$ or R7'ONa (K, Li) or R7'SNa (K, Li)

SCHEME 3:

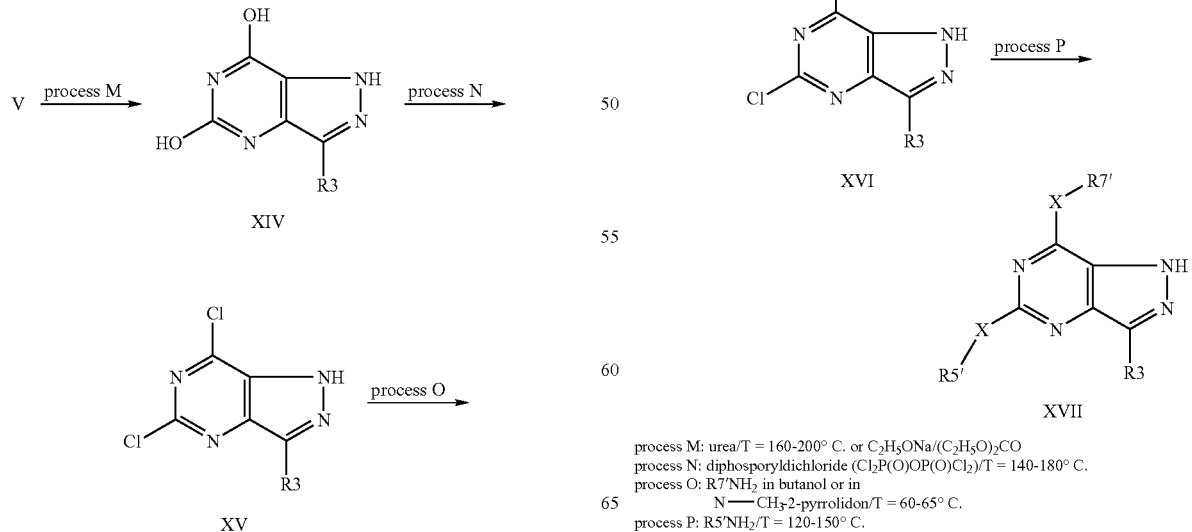

process M: urea/T = 160-200° C. or C$_2$H$_5$ONa/(C$_2$H$_5$O)$_2$CO
process N: diphosporyldichloride (Cl$_2$P(O)OP(O)Cl$_2$)/T = 140-180° C.
process O: R7'NH$_2$ in butanol or in
N—CH$_3$-2-pyrrolidon/T = 60-65° C.
process P: R5'NH$_2$/T = 120-150° C.

SCHEME 4:

-continued

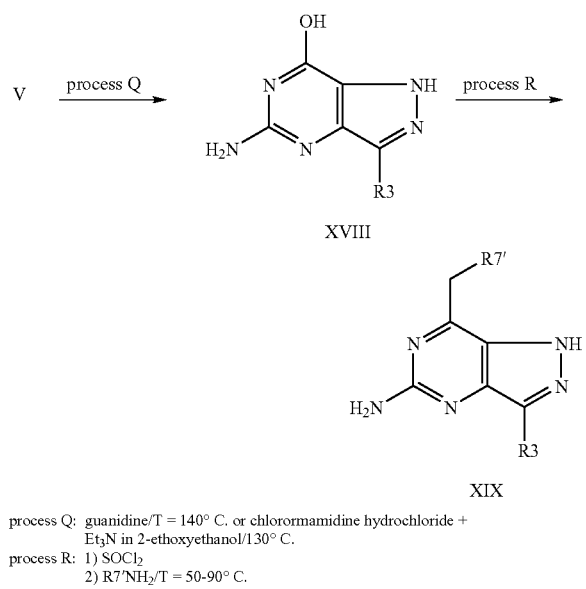

XVIII

XIX process Q: guanidine/T = 140° C. or chlorormamidine hydrochloride + Et₃N in 2-ethoxyethanol/130° C.
process R: 1) SOCl₂
2) R7'NH₂/T = 50-90° C.

SCHEME 5:

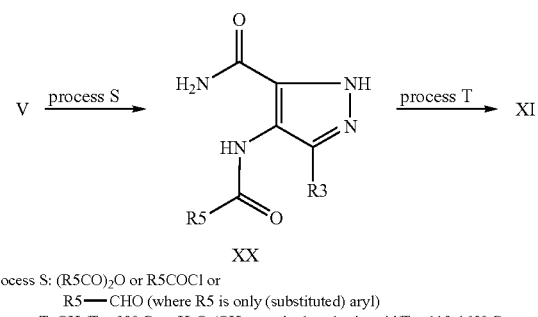

XX process S: (R5CO)₂O or R5COCl or
R5—CHO (where R5 is only (substituted) aryl)
process T: OH⁻/T = 90° C. or H₂O₂/OH⁻ or polyphosphoric acid/T = 110-160° C.

Therapeutic Administration

Suitable routes for administration include oral, rectal, topical (including dermal, ocular, buccal and sublingual), vaginal and parenteral (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

The therapeutic composition comprise about 1% to about 95% of the active ingredient, single-dose forms of administration preferably comprising about 20% to about 90% of the active ingredient and administration forms which are not single-dose preferably comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present invention are prepared in a manner known per se, for example by means of conventional mixing, granulating, coating, dissolving or lyophilizing processes.

Preferably, solutions of the active ingredient, and in addition also suspensions or dispersions, especially isotonic aqueous solutions, dispersions or suspensions, are used, it being possible for these to be prepared before use, for example in the case of lyophilized compositions which comprise the active substance by itself or together with a carrier, for example mannitol. The pharmaceutical compositions can be sterilized and/or comprise excipients, for example preservatives, stabilizers, wetting agents and/or emulsifiers, solubilizing agents, salts for regulating the osmotic pressure and/or buffers, and they are prepared in a manner known per se, for example by means of conventional dissolving or lyophilizing processes. The solutions or suspensions mentioned can comprise viscosity-increasing substances, such as sodium carboxymethylcellulose, carboxymethylcellulose, dextran, polyvinylpyrrolidone or gelatine.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidonic acid, behenic acid or corresponding unsaturated acids, for example oleic acid, elaidic acid, euric acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris) and/or "Miglyol 812" (triglyceride of saturated fatty acids of chain length $C_8$ to $C_{12}$ from Hüls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients. Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidine, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterization of different doses of active ingredient.

Pharmaceutical compositions, which can be used orally, are also hard capsules of gelatine and soft, closed capsules of gelatine and a plasticizer, such as glycerol or sorbitol. The hard capsules can contain the active ingredient in the form of granules, mixed for example with fillers, such as maize starch, binders and/or lubricants, such as talc or magnesium stearate, and stabilizers if appropriate. In soft capsules, the active ingredient is preferably dissolved or suspended in suitable liquid excipients, such as greasy oils, paraffin oil or liquid polyethylene glycol's or fatty acid esters of ethylene glycol or propylene glycol, it being likewise possible to add stabilizers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parental administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate stabilizers. The active ingredient can also be present here in the form of a lyophilized, if appropriate together with excipients, and be dissolved before parenteral administration by addition of suitable solvents. Solutions such as are used, for example, for parental administration can also be used as infusion solutions. Preferred preservatives are, for example antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists, in particular, hydrocarbons, for example vaseline, paraffin oil or hard paraffin's, which preferably comprise suitable hydroxy compounds, such as fatty alcohol's or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also contain emulsifiers and/or additives mentioned in connection with the ointments which increase uptake of water.

Creams are oil-in-water emulsions, which comprise more than 50% of water. Oily bases used are, in particular, fatty alcohols, for example lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding non-ionic emulsifiers, for example fatty acid esters of polyalcohols or ethyleneoxy adducts thereof; such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulphates, for example sodium lauryl sulphate, sodium cetyl sulphate or sodium stearyl sulphate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example titanium oxide or zinc oxide, and furthermore talc and/or aluminium silicates, which have the task of binding the moisture or secretions present.

Foams are administered from pressurized containers and they are liquid oil-in-water emulsions present in aerosol foam. As the propellant gases halogenated hydrocarbons, such as polyhalogenated alkanes, for example dichlorofluoromethane and dichlorotetrafluoroethane, or, preferably, non-halogenated gaseous hydrocarbons air, $N_2O$, or carbon dioxide are used. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with the ethanol, and, if necessary, other excipients and additives, are admixed.

The present invention further provides veterinary compositions comprising at least one active ingredient as above defined together with a veterinary carrier for the active ingredient.

Veterinary carriers are materials for administering the composition and may be solid, liquid or gaseous materials, which are inert or acceptable in the veterinary art and are compatible with the active ingredient. These veterinary compositions may be administered orally, parenterally or by any other desired route.

The invention also relates to a process or method for treatment of the disease states mentioned above. The compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

The following EXAMPLES serve to illustrate the invention without limiting the scope thereof.

Melting points were determined on a Kofler block and are uncorrected. Evaporations were carried out on a rotary evaporator under vacuum at temperatures below 80° C. The $^1$H NMR spectra (d, ppm; J, Hz) were measured on Varian VXR-400 (400 MHz) or on Varian Unity 200 (300 MHz) instruments. All spectra were obtained at 25° C. using tetramethylsilane as on internal standard. Electron impact mass spectra m/z (rel. %, composition, deviation) were measured on a VG 7070E spectrometer (70 eV, 200° C., direct inlet). High-resolution measurements were carried out by the peak-matching method using Ultramark 1600F (PCR Inc., FL, USA) as a standard. Merck silica gel Kieselgel 60 (230-400 mesh) was used for column chromatography. All compounds gave satisfactory elemental analyses (0.4%).

Example 1

5-isopropyl-4-nitropyrazole-3-carboxylic acid III

To an ice-cooled and stirred solution of 2.9 g (18.8 mmol) 5-isopropylpyrazol-3-carboxylic acid II (lit.: Baraldi P. G. et al: *Farmaco*, 46, 1337 (1991); mp=136-140° C.) in fuming sulphuric acid (65%) the nitric acid (65%) was added portion wise. The stirring was continued for 1 h at room temperature and then another 3 h at 104° C. temperature and then poured into ice-water. The white precipitate of product was filtered and crystallized from water; (yield 76%); mp=139-142° C.; $^1$H NMR (300 MHz, DMSO): 1.22 d (6H, 7.1 Hz), 2.94 sept (1H, 7.1 Hz), 3.33 s (1H), 6.45 bs (1H); CHN required: C=42.02%; H=4.56%; N=21.09; found: C=42.41%; H=4.49%; N=21.01%.

Example 2

5-isopropyl-4-nitropyrazol-3-carboxamide IV

5-Isopropyl-4-nitropyrazol-3-carboxylic acid III (10.83 g; 0.054 mol) was suspended in thionyl chloride (19 mL) and heated to dissolve. This mixture was heated under reflux and the product started to precipitate after one hour. The reaction mixture was refluxed two hours and then was evaporated to dryness in vacuo. The residue was (without further purification) dissolved in acetone (10 mL) and added into cold aqueous ammonium hydroxide with stirring. After cooling of the solution at 5° C., the product started to precipitate in a few minutes. The precipitate of the title compound was washed with cold water. Yield 6.9 g (64%); mp=179-180° C.; MS (ES$^+$): 199.1 (100%, M+H$^+$); 221.1 (23%, M+Na). $^1$H NMR (300 MHz, DMSO): 1.28 d (6H, J=6.6 Hz), 3.52 sept (1H, J=6.6 Hz), 7.71 s (1H), 8.00 s (1H).

Example 3

4-amino-5-isopropylpyrazol-3-carboxamide V

To a solution of 5-isopropyl-4-nitropyrazol-3-carboxamide (2.57 g; 12.97 mmol), methanol (20 mL) and water (5 mL) was added 0.7 g Raney Ni (W5). The mixture was stirred under hydrogen atmosphere (760 torr) for four hours. The reaction mixture was filtered, the filtrate was concentrated to dryness in vacuo and the residue was recrystallized from ethyl acetate to yield 1.94 g (89%) of the product. The product was purified by chromatography on silica gel, the mixture of chloroform/methanol (97/3) was used as mobile phase. Yield 95%; mp=178-179° C.; MS (ES$^+$): 169.1 (100%, M+H$^+$). $^1$H NMR (CD$_3$OD; 400 MHz): 1.31 d (6H; J=7.5 Hz), 3.06 sept (1H; J=7.5 Hz), 4.83 s (2H).

Example 4 methyl 5-isopropyl-4-nitropyrazol-3-carboxylate (VI)

5-Isopropyl-4-nitropyrazole-3-carboxylic acid was added to a 4.5M solution of HCl in absolute methanol. The reaction mixture was heated at 60° C. for 7 hours. The title compound was crystallized from ethyl acetate; yield 91%; mp=78-80° C. $^1$H NMR (300 MHz, CDCl$_3$): 1.39 d (6H, J=7.1 Hz); 3.64 sept (1H, J=7.1 Hz), 3.98 s (3H). CHN required: C=45.07%; H=5.20%; N=19.70%; found: C=45.21%; H=5.23%; N=19.65%.

Example 5

Methyl 4-amino-5-isopropylpyrazol-3-carboxylate (VII)

To a solution of methyl-5-isopropyl-4-nitropyrazol-3-carboxylate (7.34 g, 34.4 mmol) in 36 mL n-propanol, 6 mL water and 5.6 mL 10 M HCl was added 0.55 g PtO$_2$. The mixture was stirred under hydrogen atmosphere (760 torr) for 9 hours. The reaction mixture was filtered and the filtrate was concentrated t dryness in vacuo. The desired amine was liberated by treatment of aq. ammonia during extraction into chloroform. The product crystallized after evaporation; yield 95%; mp=122-123. MS (EI, 70 eV, direct inlet): 183 (88; C$_8$H$_{13}$N$_3$O$_2$$^+$; −1.0), 168(59), 152(3), 136(100), 108(8), 80(16), 68(20). $^1$H NMR (400 MHz, CDCl$_3$): 1.31 d (6H; J=6.9 Hz), 2.93 sept (1H), 3.9 s (3H). IR (KBr, cm$^{-1}$): 3399, 3296, 1710, 1626, 1584, 1302.

Example 6

5-methyl-7-hydroxy-3-isopropylpyrazolo[4,3-d]pyrimidine (XI)

The solution of 4-acetamido-5-isopropylpyrazol-3-carboxamide XX (100 mg, 0.40 mmol) in 1 mL of 1 M sodium hydroxide was stirred at 80-90° C. for 3 hours. The product precipitated after cooling and acidifying with glacial acetic acid. Yield 98%; mp>250° C.; MS (ES$^+$): 193.1 (100%, M+H⁺). ¹H NMR (300 MHz; CD₃OD): 1.38 d (6H, J=7.1 Hz); 2.41 s (3H); 3.02 sept (1H, J=7.1 Hz).

Example 7

7-benzylamino-3-isopropyl-5-methylpyrazolo[4,3-d]pyrimidine (XIII)

3-Isopropyl-7-hydroxy-5-methylpyrazolo[4,3-d]pyrimidine (100 mg, 0.52 mmol) XI was dissolved in 0.5 ml of thionyl chloride, 0.1 mL of dimethylformamide and 3 mL of chloroform. This mixture was heated under reflux for 3 hours. The solution was evaporated to dryness in vacuo and the residue was dissolved in chloroform. This solution was extracted twice with water. The chloroform layers were combined and dried over Na₂SO₄. To this solution (after filtration directly used in the subsequent step) was added 2 mL of benzylamine. This mixture was stirred at room temperature overnight and then evaporated to dryness in vacuo. The crude product was purified by chromatography on silica gel the mixture of chloroform/methanol (97/3) was used as mobile phase. Yield 82%; MS (ES⁺): 282.2 (100%, M+H⁺). ¹H NMR (300 MHz, CDCl₃): 1.35 d (6H, J=7.1 Hz); 2.58 s (3H), 3.41 sept (1H, J=7.1 Hz); 4.79 s (2H), 7.22-7.27 m (5H).

Example 8

5,7-dihydroxy-3-isopropylpyrazolo[4,3-d]pyrimidine (XIV)

Mixture of 4-amino-5-isopropylpyrazole-3-carboxamide (770 mg, 4.58 mmol) and urea (1.4 g, 4.58 mmol) was fused at 180° C. for 30 min. After cooling, the solid was dissolved in 2.3 mL of 2 M sodium hydroxide. The boiling solution was acidified with glacial acetic acid and the warm solution was filtered. This solution was cooled to 5° C. and the product started to precipitate after a few minutes. The crude product (1.3 g) was recrystallized twice from a hot water. Yield 78.5%; mp=295-298° C. ¹H NMR (300 MHz, DMSO): 1.21 d (6H, J=6.6 Hz), 3.17 sept (1H, J=6.6 Hz). MS (EI): 194(94; C₈H₁₀N₄O₂); 179(100; C₇H₇N₄O₂); 162(51; C₇H₄N3O₂); 136(15); 123(7); 95(8); 81(13); 54(26); 43(23).

Example 9

5,7-dichloro-3-isopropylpyrazolo[4,3-d]pyrimidine (XV)

5,7-Dihydroxy-3-isopropylpyrazolo[4,3-d]pyrimidine (1.16 g; 5.974 mmol) was dissolved in diphosphoryl dichloride (Cl2(O)POP(O)Cl2, 11.5 mL). This mixture was heated at 160° C. in sealed ampoule for 8 hours. The solution was evaporated in vacuo (bath temperature up to 100° C.) and the residue was cooled and poured (with stirring), on crushed ice. The aqueous solution was extracted with chloroform. The combined chloroform extract was dried over Na₂SO₄ and extract was evaporated to give the crude 5,7-dichloro-3-isopropylpyrazolo[4,3-d]pyrimidine (yield=46%), mp>250° C.; MS (ES⁻): 229.1 (100%, M−H⁺), 231.1 (63%, M−H⁺). ¹NMR (400 MHz, C₆H₆): 1.41 d (6H, J=7.0 Hz), 3.23 sept (1H, J=7.0), 7.15 s (1H).

Example 10

7-benzylamino-5-chloro-3-isopropylpyrazolo[4,3-d]pyrimidine (XVIa)

5,7-Dichloro-3-isopropylpyrazolo[4,3-d]pyrimidine (1.015 mmol; 234.6 mg), 1 mL benzylamine and n-butanol (2 mL) were stirred at 65° C. for 4 hours. The reaction mixture was evaporated to dryness in vacuo. The residue was chromatographed on silica gel eluted with the following solvent system: CHCl₃/MeOH (99/1), to give 7-benzylamino-5-chloro-3-isopropylpyrazolo[4,3-d]pyrimidine. Yield 96%; MS (ES⁺): 302.3 (100%, M+H⁺), 304.3 (32%, M+H⁺). ¹H NMR (CDCl₃; 300 MHz): 1.37 d (6H, J=7.1 Hz); 3.39 sept (1H, J=7.1 Hz), 6.72 s (1H), 4.82 s (2H), 7.28 m (5H).

Example 11

7-(3-chloroanilino)-5-chloro-3-isopropylpyrazolo[4,3-d]pyrimidine (XVIb)

5,7-Dichloro-3-isopropylpyrazolo[4,3-d]pyrimidine (90 mg), 1.2 mL of 3-chloroaniline and 250 μL of diisopropyl ethylamine were stirred at 60° C. for 24 hours. The reaction mixture was evaporated to dryness in vacuo. The residue was chromatographed on silica gel eluted with the following solvent system: CHCl₃/heptane (100/17), to give 7-(3-chloroanilino)-5-chloro-3-isopropylpyrazolo[4,3-d]pyrimidine, yield 16%, mp=257-259° C. MS (ES⁺): 322.3 (100%, M+H⁺), 324.3 (64%, M+H⁺). ¹H NMR (CDCl₃; 300 MHz): 1.54 d (6H, J=7.1 Hz); 3.60 sept (1H, J=7.1 Hz), 7.16 d (1H), 7.34 t (1H), 7.88 d (1H), 8.10 s (1H).

TABLE 1

Compounds Prepared by the Method of Examples 10 and 11

| | pyrazolo[4,3-d]pyrimidine SUBSTITUENT | | | CHN ANALYSES | MS ANALYSES-ZMD | |
|---|---|---|---|---|---|---|
| | C5 | C7 | C3 | [%] | [M − H]⁻ a) | [M + H]⁺ b) |
| A1 | Chloro | 3-chloroanilino | Methyl | C = 49.18; H = 3.00<br>N = 23.61; Cl = 24.21 | 292.0<br>294.0 | |
| A2 | Chloro | anilino | Methyl | C = 55.52; H = 3.90<br>N = 26.95; Cl = 13.63 | 258.1<br>260.1 | |
| A3 | Chloro | 4-carboxy-3-chloroanilino | Methyl | C = 46.18; H = 2.68<br>N = 20.61; Cl = 20.00 | 336.0<br>338.0 | |
| A4 | Chloro | 3-carboxy-4-chloroanilino | Methyl | C = 46.18; H = 2.58<br>N = 20.73; Cl = 20.98 | 336.0<br>338.0 | |
| A5 | Chloro | 4-amino-3-chloroanilino | Methyl | C = 46.62; H = 3.28<br>N = 27.16; Cl = 22.94 | 307.0<br>309.0 | 309.0<br>311.0 |

TABLE 1-continued

Compounds Prepared by the Method of Examples 10 and 11

| | pyrazolo[4,3-d]pyrimidine SUBSTITUENT | | | CHN ANALYSES | MS ANALYSES-ZMD | |
|---|---|---|---|---|---|---|
| | C5 | C7 | C3 | [%] | [M − H]⁻ a) | [M + H]⁺ b) |
| A6 | Chloro | 2-hydroxybenzylamino | Methyl | C = 53.87; H = 4.17<br>N = 24.19; Cl = 12.19 | 288.1<br>290.1 | |
| A7 | Chloro | 2-acetoxybenzylamino | Methyl | C = 55.50; H = 4.60<br>N = 20.28; Cl = 10.23 | 344.1<br>346.1 | |
| A8 | Chloro | 2-hydroxy-3-methoxybenzylamino | Methyl | C = 52.25; H = 4.38<br>N = 21.96; Cl = 11.12 | 318.1<br>320.1 | |
| A9 | Chloro | 2-hydroxy-3-methylbenzylamino | Methyl | C = 55.48; H = 4.65<br>N = 23.01; Cl = 11.65 | 302.1<br>304.1 | |
| A10 | Chloro | 3-chloro-2-hydroxybenzylamino | Methyl | C = 48.07; H = 3.46<br>N = 21.56; Cl = 21.97 | 322.0<br>324.0 | |
| A11 | Chloro | 2,3-dihydroxy-4-methoxybenzylamino | Methyl | C = 50.03; H = 4.25<br>N = 20.82; Cl = 10.58 | 334.1<br>336.1 | |
| A12 | Chloro | 2,6-dihydroxy-4-methoxybenzylamino | Methyl | C = 50.08; H = 4.20<br>N = 20.82; Cl = 10.57 | 334.1<br>336.1 | |
| A13 | Chloro | 2-amino-3-chlorobenzylamine | Methyl | C = 48.21; H = 3.71<br>N = 26.10; Cl = 21.98 | 321.0<br>323.0 | 323.0<br>325.0 |
| A14 | Chloro | 4-chloro-2,3-diaminobenzylamine | Methyl | C = 46.15; H = 4.00<br>N = 28.82; Cl = 21.03 | 336.1<br>338.1 | 338.1<br>340.1 |
| A15 | Chloro | [(R,S)-(2-hydroxyethyl-1-phenyl)amino] | Methyl | C = 55.36; H = 4.68<br>N = 23.11; Cl = 11.65 | 302.1<br>304.1 | |
| A16 | Chloro | benzylamino | Methyl | C = 57.06; H = 4.46<br>N = 25.57; Cl = 12.91 | | 274.1<br>276.1 | a) solution: MeOH p.a. + HCOOH
b) solution: MeOH p.a. + H₂O + NH₃

TABLE 2

Compounds Prepared by the Method of Examples 10 and 11

| | pyrazolo[4,3-d]pyrimidine SUBSTITUENT | | | CHN ANALYSES | MS ANALYSES-ZMD | |
|---|---|---|---|---|---|---|
| | C5 | C7 | C3 | [%] | [M − H]⁻ a) | [M + H]⁺ b) |
| B1 | Chloro | 3-chloroanilino | ethyl | C = 50.65; H = 3.63<br>N = 22.63;<br>Cl = 23.09 | 306.0<br>308.0 | |
| B2 | Chloro | anilino | ethyl | C = 57.04; H = 4.42<br>N = 25.59;<br>Cl = 12.95 | 272.1<br>274.1 | 274.1<br>276.1 |
| B3 | Chloro | 5-amino-3-chloroanilino | ethyl | C = 48.31; H = 3.74<br>N = 26.01;<br>Cl = 21.94 | 321.0<br>323.0 | 323.0<br>325.0 |
| B4 | Chloro | 4-carboxy-3-chloroanilino | ethyl | C = 47.82; H = 3.15<br>N = 19.88;<br>Cl = 20.23 | 350.0<br>352.0 | |
| B5 | Chloro | 3-carboxy-4-chloroanilino | ethyl | C = 47.75; H = 3.17<br>N = 19.82;<br>Cl = 20.14 | 350.0<br>352.0 | |
| B6 | Chloro | 4-bromoanilino | ethyl | C = 44.26; H = 3.14<br>N = 19.85;<br>Cl = 10.15;<br>Br = 22.60 | 350.0<br>352.0<br>354.0 | |
| B7 | Chloro | 4-chloroanilino | ethyl | C = 50.69; H = 3.53<br>N = 22.78;<br>Cl = 23.00 | 306.0<br>308.0 | |
| B8 | Chloro | 3-amino-4-chloroanilino | ethyl | C = 48.24; H = 3.58<br>N = 26.00;<br>Cl = 22.18 | 321.0<br>323.0 | 323.0<br>325.0 |
| B9 | Chloro | 2-hydroxybenzylamino | ethyl | C = 55.39; H = 4.65<br>N = 23.04;<br>Cl = 11.65 | 302.1<br>304.1 | |
| B10 | Chloro | 3-hydroxybenzylamino | ethyl | C = 55.36; H = 4.68<br>N = 23.03;<br>Cl = 11.62 | 302.1<br>304.1 | |
| B11 | Chloro | 2-hydroxy-3-methoxybenzylamino | ethyl | C = 53.95; H = 4.89<br>N = 20.95;<br>Cl = 10.68 | 332.1<br>334.1 | |

TABLE 2-continued

Compounds Prepared by the Method of Examples 10 and 11

| | pyrazolo[4,3-d]pyrimidine SUBSTITUENT | | | CHN ANALYSES | MS ANALYSES-ZMD | |
|---|---|---|---|---|---|---|
| | C5 | C7 | C3 | [%] | [M − H]⁻ a) | [M + H]⁺ b) |
| B12 | Chloro | 2-hydroxy-3-methylbenzylamino | ethyl | C = 56.72; H = 5.05 N = 22.02; Cl = 11.20 | 316.1 318.1 | |
| B13 | Chloro | 3-chloro-2-hydroxybenzylamino | ethyl | C = 49.74; H = 3.85 N = 20.71; Cl = 20.99 | 336.0 338.0 | |
| B14 | Chloro | 4-chloro-2,3-dihydroxybenzylamino | ethyl | C = 47.47; H = 3.76 N = 19.69; Cl = 20.01 | 352.0 354.0 | |
| B15 | Chloro | [(R,S)-(2-hydroxyethyl-1-phenyl)amino] | ethyl | C = 56.73; H = 5.05 N = 22.01; Cl = 11.24 | 316.1 318.1 | |
| B16 | Chloro | [N-(3,4-dihydroxybenzyl)-N-methyl]amino | ethyl | C = 53.95; H = 4.89 N = 20.95; Cl = 10.67 | 332.1 334.1 | |
| B17 | Chloro | benzylamino | ethyl | C = 58.41; H = 4.88 N = 24.36; Cl = 12.44 | | 288.1 290.1 | a) solution: MeOH p.a. + HCOOH
b) solution: MeOH p.a. + H$_2$O + NH$_3$

TABLE 3

Compounds Prepared by the Method of Examples 10 and 11

| | pyrazolo[4,3-d]pyrimidine SUBSTITUENT | | | CHN ANALYSES | MS ANALYSES-ZMD | |
|---|---|---|---|---|---|---|
| | C5 | C7 | C3 | [%] | [M − H]⁻ a) | [M + H]⁺ b) |
| C1 | Chloro | 3,4-dihydroxybenzylamino | isopropyl | C = 53.96; H = 4.80 N = 21.02; Cl = 10.66 | 332.1 334.1 | |
| C2 | Chloro | 3-chloroanilino | isopropyl | C = 52.22; H = 4.04 N = 21.78; Cl = 21.96 | 320.0 322.0 | |
| C3 | Chloro | anilino | isopropyl | C = 58.49; H = 4.85 N = 24.32; Cl = 12.34 | 286.1 288.1 | 288.1 290.1 |
| C4 | Chloro | 5-amino-3-chloroanilino | isopropyl | C = 49.85; H = 4.18 N = 24.90; Cl = 21.07 | 335.1 337.1 | 337.1 339.1 |
| C6 | Chloro | 4-carboxy-3-chloroanilino | isopropyl | C = 49.25; H = 3.54 N = 19.02; Cl = 29.33 | 364.0 366.0 | |
| C7 | Chloro | 3-carboxy-4-chloroanilino | isopropyl | C = 49.20; H = 3.57 N = 19.08; Cl = 19.42 | 364.0 366.0 | |
| C8 | Chloro | 3-carboxy-4-hydroxanilino | isopropyl | C = 51.85; H = 4.02 N = 20.05; Cl = 10.29 | 346.1 348.1 | |
| C9 | Chloro | 4-bromoanilino | isopropyl | C = 45.88; H = 3.52 N = 19.15; Cl = 9.69; Br = 21.76 | 364.0 366.0 368.0 | |
| C10 | Chloro | 4-chloroanilino | isopropyl | C = 52.15; H = 4.03 N = 21.77; Cl = 22.05 | 320.0 322.0 | |
| C11 | Chloro | 3-amino-4-chloroanilino | isopropyl | C = 49.92; H = 4.13 N = 24.87; Cl = 21.08 | 335.1 337.1 | 337.1 339.1 |
| C12 | Chloro | 4-amino-3-chloroanilino | isopropyl | C = 49.87; H = 4.18 N = 24.92; Cl = 21.03 | 335.1 337.1 | 337.1 339.1 |
| C13 | Chloro | 2-hydroxybenzylamino | isopropyl | C = 56.72; H = 5.10 N = 22.08; Cl = 11.18 | 316.1 318.1 | |
| C14 | Chloro | 3-hydroxybenzylamino | isopropyl | C = 56.74; H = 5.06 N = 22.01; Cl = 11.21 | 316.1 318.1 | |

TABLE 3-continued

Compounds Prepared by the Method of Examples 10 and 11

| | pyrazolo[4,3-d]pyrimidine SUBSTITUENT | | | CHN ANALYSES | MS ANALYSES-ZMD | |
|---|---|---|---|---|---|---|
| | C5 | C7 | C3 | [%] | [M − H]⁻ a) | [M + H]⁺ b) |
| C15 | Chloro | 2-acetoxybenzylamino | isopropyl | C = 56.78; H = 5.01<br>N = 19.48; Cl = 9.94 | 358.1<br>360.1 | |
| C16 | Chloro | 3-acetoxybenzylamino | isopropyl | C = 56.75; H = 5.08<br>N = 19.51; Cl = 9.95 | 358.1<br>360.1 | |
| C17 | Chloro | 2-acetylbenzylamino | isopropyl | C = 59.35; H = 5.32<br>N = 20.30;<br>Cl = 10.39 | 342.1<br>344.1 | |
| C18 | Chloro | 3-acetylbenzylamino | isopropyl | C = 59.42; H = 5.33<br>N = 20.34;<br>Cl = 10.29 | 342.1<br>344.1 | |
| C19 | Chloro | 2-hydroxy-3-methoxybenzylamino | isopropyl | C = 55.27; H = 5.33<br>N = 20.12;<br>Cl = 10.09 | 346.1<br>348.1 | |
| C20 | Chloro | 2-hydroxy-3-methylbenzylamino | isopropyl | C = 57.87; H = 5.51<br>N = 21.07;<br>Cl = 10.73 | 330.1<br>332.1 | |
| C21 | Chloro | 3-chloro-2-hydroxybenzylamino | isopropyl | C = 51.11; H = 4.38<br>N = 19.90;<br>Cl = 20.04 | 350.1<br>352.1 | |
| C22 | Chloro | 4-chloro-2,6-dihydroxybenzylamino | isopropyl | C = 48.96; H = 4.15<br>N = 18.95;<br>Cl = 19.20 | 366.1<br>368.1 | |
| C23 | Chloro | 2,3-dihydroxy-4-methoxybenzylamino | isopropyl | C = 52.82; H = 5.08<br>N = 19.21; Cl = 9.70 | 362.1<br>364.1 | |
| C24 | Chloro | 2,5-dihydroxy-4-methoxybenzylamino | isopropyl | C = 52.80; H = 4.98<br>N = 19.21; Cl = 9.85 | 362.1<br>364.1 | |
| C25 | Chloro | 2,6-dihydroxy-4-methoxybenzylamino | isopropyl | C = 52.84; H = 5.03<br>N = 19.28; Cl = 9.68 | 362.1<br>364.1 | |
| C26 | Chloro | 4-chloro-2,3-dihydroxybenzylamino | isopropyl | C = 48.90; H = 4.15<br>N = 18.94;<br>Cl = 19.35 | 366.1<br>368.1 | |
| C27 | Chloro | 4-chloro-2,5-dihydroxybenzylamino | isopropyl | C = 48.85; H = 4.14<br>N = 19.07;<br>Cl = 19.39 | 366.1<br>368.1 | |
| C28 | Chloro | 2-amino-6-chlorobenzylamino | isopropyl | C = 51.35; H = 4.57<br>N = 23.99;<br>Cl = 20.09 | 349.1<br>351.1 | 351.1<br>353.1 |
| C29 | Chloro | 3-amino-4-chlorobenzylamino | isopropyl | C = 51.19; H = 4.54<br>N = 23.98;<br>Cl = 20.29 | 349.1<br>351.1 | 351.1<br>353.1 |
| C30 | Chloro | 4-chloro-2,3-diaminobenzylamino | isopropyl | C = 49.12; H = 4.63<br>N = 26.82;<br>Cl = 19.43 | 364.1<br>366.1 | 366.1<br>368.1 |
| C31 | Chloro | [(R,S)-(2-hydroxyethyl-1-phenyl)amino] | isopropyl | C = 57.94; H = 5.49<br>N = 21.09;<br>Cl = 10.62 | 330.1<br>332.1 | |
| C32 | Chloro | [N-(3,4-dihydroxybenzyl)-N-methyl]amino | isopropyl | C = 55.32; H = 5.20<br>N = 20.17;<br>Cl = 10.16 | 346.1<br>348.1 | |
| C33 | Chloro | benzylamino | isopropyl | C = 59.74; H = 5.37<br>N = 23.18;<br>Cl = 11.71 | | 302.1<br>304.1 | a) solution: MeOH p.a. + HCOOH
b) solution: MeOH p.a. + H₂O + NH₃

Example 12

7-benzylamino-5-[1(R,S)-(hydroxymethyl)propyl]amino-3-isopropylpyrazolo[4,3-d]pyrimidine (XVIIa)

The mixture of 7-benzylamino-5-chloro-3-isopropylpyrazolo[4,3-d]pyrimidine XVI (100 mg, 0.331 mmol) and 2 mL of 1-(R,S)-(hydroxymethyl)propylamine was heated at 120° C. for 3 hours. The reaction mixture was evaporated to dryness in vacuo and then chromatographed on silica gel. The mixture of chloroform/methanol (97/3) was used as a mobile phase. Yield=83.5%; white syrupy; MS (ES⁺): 355.3 (100%, M+H⁺). ¹H-NMR (400 MHz, CDCl₃): 0.96 t (3H, J=7.2 Hz, C$\underline{H}_3$CH₂), 1.299 d (3H, J=7.1 Hz), 1.307 d (3H, J=7.1 Hz), 1.6 m (2H), 3.20 sept (1H, J=7.1 Hz), 3.55-3.80 m (3H), 4.74 bs (2H), 7.22-7.35 m (5H).

Example 13

7-[1 (R,S)-(hydroxymethyl)propyl]amino-5-[1(R,S)-(hydroxymethyl)propyl]amino-3-isopropyl-pyrazolo[4,3-d]pyrimidine (XVIIb)

The mixture of 5,7-dichloro-3-isopropylpyrazolo[4,3-d]pyrimidine (100 mg; 0.331 mmol) and 2 mL 1-(R,S)-(hydroxymethyl)propylamine was heated at 120° C. for 6 hours. The reaction mixture was evaporated to dryness in vacuo. The product was purified by column chromatography on silica gel. The mixture of chloroform/methanol (96/4) was used as a mobile phase. Yield=80%; white syrupy; MS (ES$^+$): 337.4 (100%, M+H$^+$). $^1$H-NMR (300 MHz, CDCl$_3$): 0.90-1.03 m (6H), 1.26 d (6H), 1.50-1.71 m (4H), 2.48 bs (1H), 3.07 m (1H), 3.40 m (1H), 3.59-3.90 m (4H).

Example 14

7-benzylamino-5-(2-aminoethyl)amino-3-isopropylpyrazolo[4,3-d]pyrimidine (XVIIc)

The mixture 138 mg of 7-benzylamino-5-chloro-3-isopropylpyrazolo[4,3-d]pyrimidine (XVI), 0.62 mL of 2-aminoethylamine (20 eq.) and 0.6 mL of N-methyl-2-pyrrolidone was heated at 125° C. for 12 hours. The reaction mixture was evaporated to dryness in vacuo and then chromatographed over silica gel. The mixture of chloroform/methanol/NH$_4$OH (91:9:1) was used as a mobile phase. Yield=56%; mp=145-147° C.; MS (ES$^+$): 326.1 (100%, M+H$^+$). $^1$H-NMR (300 MHz, CD$_3$OD): 1.41 d (6H, J=6.9 Hz), 3.10 t (2H, J=5.8 Hz), 3.35 sept (1H, J=6.9 Hz), 3.73 t (2H, 5.8 Hz), 4.86 s (2H), 7.34 m (5H).

Example 15

7-benzylamino-5-heptylamino-3-isopropylpyrazolo [4,3-d]pyrimidine (XVIId)

The mixture 85.6 mg of 7-benzylamino-5-chloro-3-isopropylpyrazolo[4,3-d]pyrimidine XVI, 0.21 mL of heptyl amine and 1 mL of pentanol was heated at 125° C. for 12 hours. The reaction mixture was evaporated to dryness in vacuo and then chromatographed on silica gel. The mixture of chloroform/acetone/heptane (1:1:1) was used as a mobile phase. Yield=60%; white syrupy; MS (ES$^+$): 381.0 (100%, M+H$^+$). $^1$H-NMR (300 MHz, CDCl$_3$): 0.86 t (3H, J=6.6 Hz), 1.22-1.36 m (12H), 1.56 m (2H), 1.64 m (2H), 3.12 sept (1H, J=7.1 Hz), 3.41 d (2H, J=5.2 Hz), 4.79 bs (2H), 7.19-7.35 m (5H), 7.60 s (1H).

Example 16

7-benzylamino-5-(4-hydroxycyklohexyl)amino-3-isopropylpyrazolo[4,3-d]pyrimidine (XVIIe)

The mixture 180 mg of 7-benzylamino-5-chloro-3-isopropylpyrazolo[4,3-d]pyrimidine XVI, 90.7 mg of 4-aminocyklohexanole hydrochloride (10 eq.), 3 mL of N-methyl-2-pyrrolidone and 1 mL of diisopropyl-ethylamine was heated at 145° C. for 13 hours. The reaction mixture was evaporated to dryness in vacuo and then chromatographed on silica gel. The mixture of chloroform/methanole/NH$_4$OH (95:5:0.5) was used as a mobile phase. Yield=30%; mp=118-119° C.; MS (ES$^+$): 381.1 (100%, M+H$^+$). $^1$H-NMR (300 MHz, DMSO-d$_6$): 1.31 d (6H, J=7.1 Hz), 1.80 m (4H), 1.83 m (4H), 3.16 sept (1H, J=7.1 Hz), 3.60 m (1H), 4.48 m (1H), 4.67 bs (2H), 7.25-7.39 m (5H).

Example 17

5,7-di[(4-methoxybenzyl)amino]-3-isopropylpyrazolo[4,3-d]pyrimidine (XVIIf)

The mixture of 5,7-dichloro-3-isopropylpyrazolo[4,3-d] pyrimidine (156 mg), 1.2 mL of 4-methoxybenzylamine and 0.5 mL of diisopropylethyl amine was heated at 145° C. for 6 hours. The reaction mixture was evaporated to dryness in vacuo. The evaporated residue was extracted from water into ethyl acetate. The combined ethyl acetate extract was chromatographed on silica gel. The mixture of chloroform/methanole/NH$_4$OH (98:2:0.2) was used as a mobile phase. Yield=91%; mp=60-85° C.; MS (ES$^+$): 433.2 (100%, M+H$^+$). $^1$H-NMR (300 MHz, CDCl$_3$): 1.24 d (6H, J=7.1 Hz), 3.02 sept (1H, J=7.1 Hz), 3.71 s (6H), 4.74 s (4H), 6.72-7.15 m (8H), 8.12 s (1H).

TABLE 4

Compounds Prepared by the Method of Examples 12-17

| No | PYRAZOLO[4,3-d]PYRIMIDINE SUBSTITUENT | | | CHN ANALYSES | MS (ZMD)-ANALYSES | |
|---|---|---|---|---|---|---|
| | C5 | C7 | C3 | [%] | [M − H]$^-$ a) | [M + H]$^+$ b) |
| 1 | 2-hydroxyethylamino | 3,4-dihydroxybenzylamino | isopropyl | C = 56.93; H = 6.18 N = 23.47 | 357.2 | |
| 2 | 2-hydroxypropylamino | 3,4-dihydroxybenzylamino | isopropyl | C = 58.02; H = 6.50 N = 22.61 | 371.2 | |
| 3 | 3-hydroxypropylamino | 3,4-dihydroxybenzylamino | isopropyl | C = 58.02; H = 6.50 N = 22.61 | 371.2 | |
| 4 | bis-(2-hydroxyethyl)amino | 3,4-dihydroxybenzylamino | isopropyl | C = 56.72; H = 6.54 N = 20.83 | 401.2 | |
| 5 | 2-aminocyclohexylamino | 3,4-dihydroxybenzylamino | isopropyl | C = 61.31; H = 7.12 N = 23.80 | 410.2 | 412.2 |
| 6 | 4-aminocyclohexylamino | 3,4-dihydroxybenzylamino | isopropyl | C = 61.29; H = 7.15 N = 23.78 | 410.2 | 412.2 |
| 7 | R-(1-hydroxymethyl)propylamino | 3,4-dihydroxybenzylamino | isopropyl | C = 59.15; H = 6.78 N = 21.65 | 385.2 | |
| 8 | R-(1-hydroxymethyl-2-methyl)propylamino | 3,4-dihydroxybenzylamino | isopropyl | C = 59.97; H = 7.06 N = 20.95 | 399.2 | |
| 9 | 3-aminopropylamino | 3,4-dihydroxybenzylamino | isopropyl | C = 58.31; H = 6.76 N = 26.52 | 370.2 | 372.2 |
| 10 | 2-aminoethylamino | 3,4-dihydroxybenzylamino | isopropyl | C = 57.16; H = 6.49 N = 27.26 | 356.2 | 358.2 |
| 11 | 2-hydroxyethylamino | 3-chloroanilino | isopropyl | C = 55.41; H = 5.52 N = 24.23; Cl = 10.22 | 345.1 347.1 | |

TABLE 4-continued

Compounds Prepared by the Method of Examples 12-17

| | PYRAZOLO[4,3-d]PYRIMIDINE SUBSTITUENT | | | CHN ANALYSES | MS (ZMD)-ANALYSES | |
|---|---|---|---|---|---|---|
| No | C5 | C7 | C3 | [%] | [M − H]⁻ a) | [M + H]⁺ b) |
| 12 | 3-hydroxypropylamino | 3-chloroanilino | isopropyl | C = 56.59; H = 5.87<br>N = 23.27; Cl = 9.80 | 359.1<br>361.1 | |
| 13 | bis-(2-hydroxyethyl)amino | 3-chloroanilino | isopropyl | C = 55.34; H = 5.93<br>N = 21.58; Cl = 9.04 | 389.1<br>391.1 | |
| 14 | 2-aminocyclohexylamino | 3-chloroanilino | isopropyl | C = 60.05; H = 6.65<br>N = 24.42; Cl = 8.88 | 398.2<br>400.2 | 400.2<br>402.2 |
| 15 | 4-aminocyclohexylamino | 3-chloroanilino | isopropyl | C = 60.07; H = 6.50<br>N = 24.54; Cl = 8.89 | 398.2<br>400.2 | 400.2<br>402.2 |
| 16 | R-(1-hydroxymethyl)propylamino | 3-chloroanilino | isopropyl | C = 57.77; H = 6.14<br>N = 22.42; Cl = 9.43 | 373.2<br>375.2 | |
| 17 | R-(1-hydroxymethyl-2-methyl)propylamino | 3-chloroanilino | isopropyl | C = 58.65; H = 6.49<br>N = 21.61; Cl = 9.21 | 387.2<br>389.2 | |
| 18 | 3-aminopropylamino | 3-chloroanilino | isopropyl | C = 56.79; H = 6.11<br>N = 27.26; Cl = 9.84 | | 360.2<br>362.2 |
| 19 | 2-aminoethylamino | 3-chloroanilino | isopropyl | C = 55.53; H = 5.83<br>N = 28.35; Cl = 10.29 | | 346.1<br>348.1 |
| 20 | 2-hydroxyethylamino | anilino | isopropyl | C = 61.54; H = 6.45<br>N = 26.98 | | 313.2 |
| 21 | 3-hydroxypropylamino | anilino | isopropyl | C = 62.52; H = 6.85<br>N = 25.71 | | 327.2 |
| 22 | bis-(2-hydroxyethyl)amino | anilino | isopropyl | C = 60.62; H = 6.82<br>N = 23.56 | 355.2 | |
| 23 | 2-aminocyclohexylamino | anilino | isopropyl | C = 65.71; H = 7.47<br>N = 26.82 | | 366.2 |
| 24 | 4-aminocyclohexylamino | anilino | isopropyl | C = 65.75; H = 7.43<br>N = 26.82 | | 366.2 |
| 25 | R-(1-hydroxymethyl)propylamino | anilino | isopropyl | C = 63.58; H = 7.13<br>N = 24.65 | 339.2 | |
| 26 | R-(1-hydroxymethyl-2-methyl)propylamino | anilino | isopropyl | C = 64.38; H = 7.34<br>N = 23.79 | 353.2 | |
| 27 | 3-aminopropylamino | anilino | isopropyl | C = 62.82; H = 7.08<br>N = 30.10 | | 326.2 |
| 28 | 2-aminoethylamino | anilino | isopropyl | C = 61.72; H = 6.88<br>N = 31.40 | | 312.2 |
| 29 | 2-hydroxyethylamino | 4-carboxy-3-chloroanilino | isopropyl | C = 52.20; H = 4.94<br>N = 21.55; Cl = 9.03 | 389.1<br>391.1 | |
| 30 | 3-hydroxypropylamino | 4-carboxy-3-chloroanilino | isopropyl | C = 53.49; H = 5.24<br>N = 20.66; Cl = 8.73 | 403.1<br>405.1 | |
| 31 | bis-(2-hydroxyethyl)amino | 4-carboxy-3-chloroanilino | isopropyl | C = 52.46; H = 5.35<br>N = 19.32; Cl = 8.19 | 433.1<br>435.1 | |
| 32 | 2-aminocyclohexylamino | 4-carboxy-3-chloroanilino | isopropyl | C = 56.86; H = 5.94<br>N = 22.09; Cl = 7.91 | 442.2<br>444.2 | |
| 33 | 4-aminocyclohexylamino | 4-carboxy-3-chloroanilino | isopropyl | C = 56.82; H = 5.95<br>N = 22.09; Cl = 7.94 | 442.2<br>444.2 | |
| 34 | R-(1-hydroxymethyl)propylamino | 4-carboxy-3-chloroanilino | isopropyl | C = 54.44; H = 5.59<br>N = 20.04; Cl = 8.46 | 417.1<br>419.1 | |
| 35 | R-(1-hydroxymethyl-2-methyl)propylamino | 4-carboxy-3-chloroanilino | isopropyl | C = 55.44; H = 5.92<br>N = 19.41; Cl = 8.14 | 431.2<br>433.2 | |
| 36 | 3-aminopropylamino | 4-carboxy-3-chloroanilino | isopropyl | C = 53.58; H = 5.49<br>N = 24.28; Cl = 8.78 | 402.1<br>404.1 | |
| 37 | 2-aminoethylamino | 4-carboxy-3-chloroanilino | isopropyl | C = 52.38; H = 5.02<br>N = 25.15; Cl = 9.19 | 388.1<br>390.1 | |
| 38 | 2-hydroxyethylamino | 3-carboxy-4-chloroanilino | isopropyl | C = 52.14; H = 4.95<br>N = 21.45; Cl = 9.17 | 389.1<br>391.1 | |
| 39 | 3-hydroxypropylamino | 3-carboxy-4-chloroanilino | isopropyl | C = 53.45; H = 5.28<br>N = 20.76; Cl = 8.66 | 403.1<br>405.1 | |
| 40 | bis-(2-hydroxyethyl)amino | 3-carboxy-4-chloroanilino | isopropyl | C = 52.43; H = 5.34<br>N = 19.32; Cl = 8.19 | 433.1<br>435.1 | |
| 41 | 2-aminocyclohexylamino | 3-carboxy-4-chloroanilino | isopropyl | C = 56.80; H = 5.90<br>N = 22.19; Cl = 7.91 | 442.2<br>444.2 | |
| 42 | 4-aminocyclohexylamino | 3-carboxy-4-chloroanilino | isopropyl | C = 56.82; H = 5.96<br>N = 22.01; Cl = 7.94 | 442.2<br>444.2 | |
| 43 | R-(1-hydroxymethyl)propylamino | 3-carboxy-4-chloroanilino | isopropyl | C = 54.41; H = 5.53<br>N = 20.06; Cl = 8.44 | 417.1<br>419.1 | |
| 44 | R-(1-hydroxymethyl-2-methyl)propylamino | 3-carboxy-4-chloroanilino | isopropyl | C = 55.48; H = 5.82<br>N = 19.43; Cl = 8.15 | 431.2<br>433.2 | |
| 45 | 3-aminopropylamino | 3-carboxy-4-chloroanilino | isopropyl | C = 53.53; H = 5.48<br>N = 24.25; Cl = 8.76 | 402.1<br>404.1 | |
| 46 | 2-aminoethylamino | 3-carboxy-4-chloroanilino | isopropyl | C = 52.38; H = 5.19<br>N = 25.15; Cl = 9.07 | 388.1<br>390.1 | |
| 47 | 2-hydroxyethylamino | 3-carboxy-4-hydroxyanilino | isopropyl | C = 54.85; H = 5.48<br>N = 22.54 | 371.1 | |

TABLE 4-continued

Compounds Prepared by the Method of Examples 12-17

| No | PYRAZOLO[4,3-d]PYRIMIDINE SUBSTITUENT | | | CHN ANALYSES | MS (ZMD)-ANALYSES | |
|---|---|---|---|---|---|---|
| | C5 | C7 | C3 | [%] | $[M-H]^-$ a) | $[M+H]^+$ b) |
| 48 | 3-hydroxypropylamino | 3-carboxy-4-hydroxyanilino | isopropyl | C = 55.89; H = 5.76 N = 21.77 | 385.2 | |
| 49 | bis-(2-hydroxyethyl)amino | 3-carboxy-4-hydroxyanilino | isopropyl | C = 54.82; H = 5.88 N = 20.13 | 415.2 | |
| 50 | 2-aminocyclohexylamino | 3-carboxy-4-hydroxyanilino | isopropyl | C = 59.25; H = 6.43 N = 23.07 | 424.2 | |
| 51 | 4-aminocyclohexylamino | 3-carboxy-4-hydroxyanilino | isopropyl | C = 59.24; H = 6.38 N = 23.04 | 424.2 | |
| 52 | R-(1-hydroxymethyl)propylamino | 3-carboxy-4-hydroxyanilino | isopropyl | C = 56.97; H = 6.05 N = 20.94 | 399.2 | |
| 53 | R-(1-hydroxymethyl-2-methyl)propylamino | 3-carboxy-4-hydroxyanilino | isopropyl | C = 57.92; H = 6.35 N = 20.26 | 413.2 | |
| 54 | 3-aminopropylamino | 3-carboxy-4-hydroxyanilino | isopropyl | C = 56.19; H = 6.01 N = 25.34 | 384 | |
| 55 | 2-aminoethylamino | 3-carboxy-4-hydroxyanilino | isopropyl | C = 54.95; H = 5.71 N = 26.46 | 370.2 | |
| 56 | 2-hydroxyethylamino | 4-bromoanilino | isopropyl | C = 49.12; H = 4.86 N = 21.45; Br = 20.47 | 389.1 391.1 | |
| 57 | 3-hydroxypropylamino | 4-bromoanilino | isopropyl | C = 50.34; H = 5.22 N = 20.74; Br = 19.78 | 403.1 405.1 | |
| 58 | bis-(2-hydroxyethyl)amino | 4-bromoanilino | isopropyl | C = 49.61; H = 5.43 N = 19.35; Br = 18.34 | 433.1 435.1 | |
| 59 | 2-aminocyclohexylamino | 4-bromoanilino | isopropyl | C = 54.04; H = 5.90 N = 22.06; Br = 18.00 | | 444.2 446.2 |
| 60 | 4-aminocyclohexylamino | 4-bromoanilino | isopropyl | C = 54.03; H = 5.96 N = 22.06; Br = 17.95 | | 444.2 446.2 |
| 61 | R-(1-hydroxymethyl)propylamino | 4-bromoanilino | isopropyl | C = 51.52; H = 5.55 N = 20.08; Br = 19.04 | 417.1 419.1 | |
| 62 | R-(1-hydroxymethyl-2-methyl)propylamino | 4-bromoanilino | isopropyl | C = 52.66; H = 5.83 N = 19.31; Br = 18.49 | 431.1 433.1 | |
| 63 | 3-aminoproplyamino | 4-bromoanilino | isopropyl | C = 50.54; H = 5.54 N = 24.25; Br = 19.67 | | 404.1 406.1 |
| 64 | 2-aminoethylamino | 4-bromoanilino | isopropyl | C = 49.25; H = 5.14 N = 25.12; Br = 20.49 | | 390.1 392.1 |
| 65 | 2-hydroxyethylamino | 4-chloroanilino | isopropyl | C = 55.41; H = 5.54 N = 24.20; Cl = 10.29 | 345.1 347.1 | |
| 66 | 3-hydroxypropylamino | 4-chloroanilino | isopropyl | C = 56.58; H = 5.85 N = 23.27; Cl = 9.88 | 359.1 361.1 | |
| 67 | bis-(2-hydroxyethyl)amino | 4-chloroanilino | isopropyl | C = 55.35; H = 5.93 N = 21.50; Cl = 9.17 | 389.1 391.1 | |
| 68 | 2-aminocyclohexylamino | 4-chloroanilino | isopropyl | C = 60.05; H = 6.55 N = 24.52; Cl = 8.88 | | 400.2 402.2 |
| 69 | 4-aminocyclohexylamino | 4-chloroanilino | isopropyl | C = 60.07; H = 6.53 N = 24.54; Cl = 8.86 | | 400.2 402.2 |
| 70 | R-(1-hydroxymethyl)propylamino | 4-chloroanilino | isopropyl | C = 57.60; H = 6.15 N = 22.38; Cl = 9.54 | 373.2 375.2 | |
| 71 | R-(1-hydroxymethyl-2-methyl)propylamino | 4-chloroanilino | isopropyl | C = 58.68; H = 6.46 N = 21.58; Cl = 9.16 | 387.2 389.2 | |
| 72 | 3-aminopropylamino | 4-chloroanilino | isopropyl | C = 56.75; H = 6.14 N = 27.15; Cl = 9.96 | | 360.2 362.2 |
| 73 | 2-aminoethylamino | 4-chloroanilino | isopropyl | C = 55.58; H = 5.88 N = 28.30; Cl = 10.24 | | 346.1 348.1 |
| 74 | 2-hydroxyethylamino | 3-amino-4-chloroanilino | isopropyl | C = 53.11; H = 5.59 N = 27.11; Cl = 9.85 | 360.1 362.1 | 362.1 364.1 |
| 75 | 3-hydroxypropylamino | 3-amino-4-chloroanilino | isopropyl | C = 54.33; H = 5.98 N = 26.05; Cl = 9.40 | 374.2 376.2 | 376.2 378.2 |
| 76 | bis-(2-hydroxyethyl)amino | 3-amino-4-chloroanilino | isopropyl | C = 53.24; H = 5.96 N = 24.16; Cl = 8.79 | 404.2 406.2 | |
| 77 | 2-aminocyclohexylamino | 3-amino-4-chloroanilino | isopropyl | C = 57.87; H = 6.55 N = 27.01; Cl = 8.57 | | 415.2 417.2 |
| 78 | 4-aminocyclohexylamino | 3-amino-4-chloroanilino | isopropyl | C = 57.85; H = 6.51 N = 27.05; Cl = 8.59 | | 415.2 417.2 |
| 79 | R-(1-hydroxymethyl)propylamino | 3-amino-4-chloroanilino | isopropyl | C = 55.44; H = 6.20 N = 25.13; Cl = 9.07 | 388.2 390.2 | |
| 80 | R-(1-hydroxymethyl-2-methyl)propylamino | 3-amino-4-chloroanilino | isopropyl | C = 56.56; H = 6.49 N = 24.25; Cl = 8.71 | 402.2 404.2 | |
| 81 | 3-aminopropylamino | 3-amino-4-chloroanilino | isopropyl | C = 54.39; H = 6.18 N = 29.93; Cl = 9.50 | | 375.2 377.2 |
| 82 | 2-aminoethylamino | 3-amino-4-chloroanilino | isopropyl | C = 53.21; H = 5.87 N = 31.05; Cl = 9.87 | | 361.2 363.2 |
| 83 | 2-hydroxyethylamino | 4-amino-3-chloroanilino | isopropyl | C = 53.11; H = 5.57 N = 27.10; Cl = 9.80 | 360.1 362.1 | 362.1 364.1 |

TABLE 4-continued

Compounds Prepared by the Method of Examples 12-17

| | PYRAZOLO[4,3-d]PYRIMIDINE SUBSTITUENT | | | CHN ANALYSES | MS (ZMD)-ANALYSES | |
|---|---|---|---|---|---|---|
| No | C5 | C7 | C3 | [%] | [M − H]⁻ a) | [M + H]⁺ b) |
| 84 | 3-hydroxypropylamino | 4-amino-3-chloroanilino | isopropyl | C = 54.33; H = 5.90<br>N = 26.09; Cl = 9.43 | 374.2<br>376.2 | 376.2<br>378.2 |
| 85 | bis-(2-hydroxyethyl)amino | 4-amino-3-chloroanilino | isopropyl | C = 53.29; H = 5.94<br>N = 24.23; Cl = 8.71 | 404.2<br>406.2 | |
| 86 | 2-aminocyclohexylamino | 4-amino-3-chloroanilino | isopropyl | C = 57.85; H = 6.56<br>N = 27.01; Cl = 8.58 | | 415.2<br>417.2 |
| 87 | 4-aminocyclohexylamino | 4-amino-3-chloroanilino | isopropyl | C = 57.84; H = 6.60<br>N = 27.05; Cl = 8.51 | | 415.2<br>417.2 |
| 88 | R-(1-hydroxymethyl)propylamino | 4-amino-3-chloroanilino | isopropyl | C = 55.45; H = 6.20<br>N = 25.15; Cl = 9.09 | 388.2<br>390.2 | |
| 89 | R-(1-hydroxymethyl-2-methyl)propylamino | 4-amino-3-chloroanilino | isopropyl | C = 56.50; H = 6.49<br>N = 24.27; Cl = 8.78 | 402.2<br>404.2 | |
| 90 | 3-aminopropylamino | 4-amino-3-chloroanilino | isopropyl | C = 54.52; H = 6.18<br>N = 29.89; Cl = 9.41 | | 375.2<br>377.2 |
| 91 | 2-aminoethylamino | 4-amino-3-chloroanilino | isopropyl | C = 53.20; H = 5.87<br>N = 31.05; Cl = 9.88 | | 361.2<br>363.2 |
| 92 | 2-hydroxyethylamino | 2-hydroxybenzylamino | isopropyl | C = 59.63; H = 6.48<br>N = 24.54 | 341.2 | |
| 93 | 3-hydroxypropylamino | 2-hydroxybenzylamino | isopropyl | C = 60.68; H = 6.82<br>N = 23.49 | 355.2 | |
| 94 | bis-(2-hydroxyethyl)amino | 2-hydroxybenzylamino | isopropyl | C = 59.07; H = 6.78<br>N = 21.73 | 385.2 | |
| 95 | 2-aminocyclohexylamino | 2-hydroxybenzylamino | isopropyl | C = 63.75; H = 7.39<br>N = 24.84 | | 396.3 |
| 96 | 4-aminocyclohexylamino | 2-hydroxybenzylamino | isopropyl | C = 63.77; H = 7.39<br>N = 24.79 | | 396.3 |
| 97 | R-(1-hydroxymethyl)propylamino | 2-hydroxybenzylamino | isopropyl | C = 61.63; H = 7.07<br>N = 22.66 | 369.2 | |
| 98 | R-(1-hydroxymethyl-2-methyl)propylamino | 2-hydroxybenzylamino | isopropyl | C = 62.45; H = 7.34<br>N = 21.89 | 383.2 | |
| 99 | 3-aminopropylamino | 2-hydroxybenzylamino | isopropyl | C = 60.81; H = 7.13<br>N = 27.45 | | 356.2 |
| 100 | 2-aminoethylamino | 2-hydroxybenzylamino | isopropyl | C = 59.84; H = 6.79<br>N = 28.76 | | 342.2 |
| 101 | 2-hydroxyethylamino | 3-hydroxybenzylamino | isopropyl | C = 59.65; H = 6.48<br>N = 24.49 | 341.2 | |
| 102 | 3-hydroxypropylamino | 3-hydroxybenzylamino | isopropyl | C = 60.72; H = 6.75<br>N = 23.57 | 355.2 | |
| 103 | bis-(2-hydroxyethyl)amino | 3-hydroxybenzylamino | isopropyl | C = 59.03; H = 6.75<br>N = 21.86 | 385.2 | |
| 104 | 2-aminocyclohexylamino | 3-hydroxybenzylamino | isopropyl | C = 63.74; H = 7.39<br>N = 24.87 | | 396.3 |
| 105 | 4-aminocyclohexylamino | 3-bydroxybenzylamino | isopropyl | C = 63.76; H = 7.37<br>N = 24.74 | | 396.3 |
| 106 | R-(1-hydroxymethyl)propylamino | 3-hydroxybenzylamino | isopropyl | C = 61.66; H = 7.01<br>N = 22.66 | 369.2 | |
| 107 | R-(1-hydroxymethyl-2-methyl)propylamino | 3-hydroxybenzylamino | isopropyl | C = 62.58; H = 7.32<br>N = 21.76 | 383.2 | |
| 108 | 3-aminopropylamino | 3-hydroxybenzylamino | isopropyl | C = 60.84; H = 7.08<br>N = 27.62 | | 356.2 |
| 109 | 2-aminoethylamino | 3-hydroxybenzylamino | isopropyl | C = 59.89; H = 6.76<br>N = 28.70 | | 342.2 |
| 110 | 2-hydroxyethylamino | 2-acetoxybenzylamino | isopropyl | C = 59.26; H = 6.29<br>N = 21.96 | 383.2 | |
| 111 | 3-hydroxypropylamino | 2-acetoxybenzylamino | isopropyl | C = 60.29; H = 6.55<br>N = 21.12 | 397.2 | |
| 112 | bis-(2-hydroxyethyl)amino | 2-acetoxybenzylamino | isopropyl | C = 58.88; H = 6.53<br>N = 19.69 | 427.2 | |
| 113 | 2-aminocyclohexylamino | 2-acetoxybenzylamino | isopropyl | C = 63.21; H = 7.14<br>N = 22.31 | | 438.2 |
| 114 | 4-aminocyclohexylamino | 2-acetoxybenzylamino | isopropyl | C = 63.14; H = 7.18<br>N = 22.36 | | 438.2 |
| 115 | R-(1-hydroxymethyl)propylamino | 2-acetoxybenzylamino | isopropyl | C = 61.17; H = 6.88<br>N = 20.29 | 411.2 | |
| 116 | R-(1-hydroxymethyl-2-methyl)propylamino | 2-acetoxybenzylamino | isopropyl | C = 61.94; H = 7.08<br>N = 19.72 | 425.2 | |
| 117 | 3-aminopropylamino | 2-acetoxybenzylamino | isopropyl | C = 60.47; H = 6.84<br>N = 24.64 | | 398.2 |
| 118 | 2-aminoethylamino | 2-acetoxybenzylamino | isopropyl | C = 59.48; H = 6.59<br>N = 25.64 | | 384.2 |
| 119 | 2-hydroxyethylamino | 3-acetoxybenzylamino | isopropyl | C = 59.35; H = 6.28<br>N = 21.84 | 383.2 | |

TABLE 4-continued

Compounds Prepared by the Method of Examples 12-17

| | PYRAZOLO[4,3-d]PYRIMIDINE SUBSTITUENT | | | CHN ANALYSES | MS (ZMD)-ANALYSES | |
|---|---|---|---|---|---|---|
| No | C5 | C7 | C3 | [%] | [M − H]⁻ a) | [M + H]⁺ b) |
| 120 | 3-hydroxypropylamino | 3-acetoxybenzylamino | isopropyl | C = 60.27; H = 6.63 N = 21.05 | 397.2 | |
| 121 | bis-(2-hydroxyethyl)amino | 3-acetoxybenzylamino | isopropyl | C = 58.85; H = 6.59 N = 19.64 | 427.2 | |
| 122 | 2-aminocyclohexylamino | 3-acetoxybenzylamino | isopropyl | C = 63.17; H = 7.14 N = 22.36 | | 438.2 |
| 123 | 4-aminocyclohexylamino | 3-acetoxybenzylamino | isopropyl | C = 63.14; H = 7.17 N = 22.40 | | 438.2 |
| 124 | R-(1-hydroxymethyl)propylamino | 3-acetoxybenzylamino | isopropyl | C = 61.11; H = 6.84 N = 20.42 | 411.2 | |
| 125 | R-(1-hydroxymethyl-2-methyl)propylamino | 3-acetoxybenzylamino | isopropyl | C = 61.95; H = 7.09 N = 19.70 | 425.2 | |
| 126 | 3-aminopropylamino | 3-acetoxybenzylamino | isopropyl | C = 60.47; H = 6.89 N = 24.61 | | 398.2 |
| 127 | 2-aminoethylamino | 3-acetoxybenzylamino | isopropyl | C = 59.52; H = 6.57 N = 25.54 | | 384.2 |
| 128 | 2-hydroxyethylamino | 2-acetylbenzylamino | isopropyl | C = 61.96; H = 6.55 N = 22.83 | 367.2 | |
| 129 | 3-hydroxypropylamino | 2-acetylbenzylamino | isopropyl | C = 62.81; H = 6.86 N = 21.98 | 381.2 | |
| 130 | bis-(2-hydroxyethyl)amino | 2-acetylbenzylamino | isopropyl | C = 61.14; H = 6.84 N = 20.35 | 411.2 | |
| 131 | 2-aminocyclohexylamino | 2-acetylbenzylamino | isopropyl | C = 65.59; H = 7.41 N = 23.32 | | 422.3 |
| 131 | 4-aminocyclohexylamino | 2-acetylbenzylamino | isopropyl | C = 65.53; H = 7.49 N = 23.21 | | 422.3 |
| 132 | R-(1-hydroxymethyl)propylamino | 2-acetylbenzylamino | isopropyl | C = 63.60; H = 7.10 N = 21.28 | 395.2 | |
| 133 | R-(1-hydroxymethyl-2-methyl)propylamino | 2-acetylbenzylamino | isopropyl | C = 64.39; H = 7.42 N = 20.44 | 409.2 | |
| 134 | 3-aminopropylamino | 2-acetylbenzylamino | isopropyl | C = 62.97; H = 7.09 N = 25.78 | | 382.2 |
| 135 | 2-aminoethylamino | 2-acetylbenzylamino | isopropyl | C = 62.15; H = 6.86 N = 26.64 | | 368.2 |
| 136 | 2-hydroxyethylamino | 3-acetylbenzylamino | isopropyl | C = 61.94; H = 6.63 N = 22.79 | 367.2 | |
| 137 | 3-hydroxypropylamino | 3-acetylbenzylamino | isopropyl | C = 62.87; H = 6.88 N = 21.86 | 381.2 | |
| 138 | bis-(2-hydroxyethyl)amino | 3-acetylbenzylamino | isopropyl | C = 61.14; H = 6.84 N = 20.36 | 411.2 | |
| 139 | 2-aminocyclohexylamino | 3-acetylbenzylamino | isopropyl | C = 65.53; H = 7.55 N = 23.18 | | 422.3 |
| 140 | 4-aminocyclohexylamino | 3-acetylbenzylamino | isopropyl | C = 65.57; H = 7.38 N = 23.29 | | 422.3 |
| 141 | R-(1-hydroxymethyl)propylamino | 3-acetylbenzylamino | isopropyl | C = 63.60; H = 7.12 N = 21.27 | 395.2 | |
| 142 | R-(1-hydroxymethyl-2-methyl)propylamino | 3-acetylbenzylamino | isopropyl | C = 64.42; H = 7.36 N = 20.42 | 409.2 | |
| 143 | 3-aminopropylamino | 3-acetylbenzylamino | isopropyl | C = 62.97; H = 7.18 N = 25.65 | | 382.2 |
| 144 | 2-aminoethylamino | 3-acetylbenzylamino | isopropyl | C = 62.14; H = 6.82 N = 26.75 | | 368.2 |
| 145 | 2-hydroxyethylamino | 2-hydroxy-3-methoxybenzylamino | isopropyl | C = 58.07; H = 6.49 N = 22.47 | 371.2 | |
| 146 | 3-hydroxypropylamino | 2-hydroxy-3-methoxybenzylamino | isopropyl | C = 59.07; H = 6.77 N = 21.69 | 385.2 | |
| 147 | bis-(2-hydroxyethyl)amino | 2-hydroxy-3-methoxybenzylamino | isopropyl | C = 57.75; H = 6.76 N = 20.11 | 415.2 | |
| 148 | 2-aminocyclohexylamino | 2-hydroxy-3-methoxybenzylamino | isopropyl | C = 62.21; H = 7.28 N = 23.01 | 424.3 | 426.3 |
| 149 | 4-aminocyclohexylamino | 2-hydroxy-3-methoxybenzylamino | isopropyl | C = 62.10; H = 7.31 N = 23.07 | 424.3 | 426.3 |
| 150 | R-(1-hydroxymethyl)propylamino | 2-hydroxy-3-methoxybenzylamino | isopropyl | C = 59.84; H = 7.03 N = 21.06 | 399.2 | |
| 151 | R-(1-hydroxymethyl-2-methyl)propylamino | 2-hydroxy-3-methoxybenzylamino | isopropyl | C = 60.84; H = 7.35 N = 20.20 | 413.2 | |
| 152 | 3-aminopropylamino | 2-hydroxy-3-methoxybenzylamino | isopropyl | C = 59.25; H = 7.04 N = 25.48 | | 386.2 |
| 153 | 2-aminoethylamino | 2-hydroxy-3-methoxybenzylamino | isopropyl | C = 58.19; H = 6.75 N = 26.47 | | 372.2 |
| 154 | 2-hydroxyethylamino | 2-hydroxy-3-methylbenzylamino | isopropyl | C = 60.72; H = 6.79 N = 23.50 | 355.2 | |

TABLE 4-continued

Compounds Prepared by the Method of Examples 12-17

| No | PYRAZOLO[4,3-d]PYRIMIDINE SUBSTITUENT | | | CHN ANALYSES | MS (ZMD)-ANALYSES | |
|---|---|---|---|---|---|---|
| | C5 | C7 | C3 | [%] | [M − H]⁻ a) | [M + H]⁺ b) |
| 155 | 3-hydroxypropylamino | 2-hydroxy-3-methylbenzylamino | isopropyl | C = 61.61; H = 7.14 N = 22.56 | 369.2 | |
| 156 | bis-(2-hydroxyethyl)amino | 2-hydroxy-3-methylbenzylamino | isopropyl | C = 59.94; H = 7.01 N = 21.04 | 399.2 | |
| 157 | 2-aminocyclohexylamino | 2-hydroxy-3-methylbenzylamino | isopropyl | C = 64.58; H = 7.62 N = 23.91 | | 410.3 |
| 158 | 4-aminocyclohexylamino | 2-hydroxy-3-methylbenzylamino | isopropyl | C = 64.57; H = 7.60 N = 23.90 | | 410.3 |
| 159 | R-(1-hydroxymethyl)propylamino | 2-hydroxy-3-methylbenzylamino | isopropyl | C = 62.40; H = 7.37 N = 21.93 | 383.2 | |
| 160 | R-(1-hydroxymethyl-2-methyl)propylamino | 2-hydroxy-3-methylbenzylamino | isopropyl | C = 63.25; H = 7.68 N = 21.04 | 397.2 | |
| 161 | 3-aminopropylamino | 2-hydroxy-3-methylbenzylamino | isopropyl | C = 61.76; H = 7.45 N = 26.50 | | 370.2 |
| 162 | 2-aminoethylamino | 2-hydroxy-3-methylbenzylamino | isopropyl | C = 60.80; H = 7.18 N = 27.50 | | 356.2 |
| 163 | 2-hydroxyethylamino | 3-chloro-2-hydroxybenzylamino | isopropyl | C = 54.10; H = 5.62 N = 22.35; Cl = 9.51 | 375.1 377.1 | |
| 164 | 3-hydroxypropylamino | 3-chloro-2-hydroxybenzylamino | isopropyl | C = 55.34; H = 5.94 N = 21.56; Cl = 9.01 | 389.1 391.1 | |
| 165 | bis-(2-hydroxyethyl)amino | 3-chloro-2-hydroxybenzylamino | isopropyl | C = 54.22; H = 5.7 N = 19.90; Cl = 8.49 | 419.2 421.2 | |
| 166 | 2-aminocyclohexylamino | 3-chloro-2-hydroxybenzylamino | isopropyl | C = 58.64; H = 6.56 N = 22.85; Cl = 8.24 | 428.2 230.2 | |
| 167 | 4-aminocyclohexylamino | 3-chloro-2-hydroxybenzylamino | isopropyl | C = 58.65; H = 6.54 N = 22.86; Cl = 8.27 | 428.2 430.2 | |
| 168 | R-(1-hydroxymethyl)propylamino | 3-chloro-2-hydroxybenzylamino | isopropyl | C = 56.36; H = 6.18 N = 20.72; Cl = 8.84 | 403.2 405.2 | |
| 169 | R-(1-hydroxymethyl-2-methyl)propylamino | 3-chloro-2-hydroxybenzylamino | isopropyl | C = 57.34; H = 6.50 N = 20.08; Cl = 8.41 | 417.2 419.2 | |
| 170 | 3-aminopropylamino | 3-chloro-2-hydroxybenzylamino | isopropyl | C = 55.43; H = 6.20 N = 25.14; Cl = 9.15 | 388.2 390.2 | |
| 171 | 2-aminoethylamino | 3-chloro-2-hydroxybenzylamino | isopropyl | C = 54.35; H = 5.90 N = 26.07; Cl = 9.41 | 374.2 376.2 | |
| 172 | 2-hydroxyethylamino | 4-chloro-2,6-dihydroxybenzylamino | isopropyl | C = 51.90; H = 5.38 N = 21.45; Cl = 9.07 | 391.1 393.1 | |
| 173 | 3-hydroxypropylamino | 4-chloro-2,6-dihydroxybenzylamino | isopropyl | C = 53.14; H = 5.72 N = 20.60; Cl = 8.74 | 405.1 407.1 | |
| 174 | bis-(2-hydroxyethyl)amino | 4-chloro-2,6-dihydroxybenzylamino | isopropyl | C = 52.23; H = 5.82 N = 19.18; Cl = 8.15 | 435.2 437.2 | |
| 175 | 2-aminocyclohexylamino | 4-chloro-2,6-dihydroxybenzylamino | isopropyl | C = 56.46; H = 6.44 N = 21.98; Cl = 7.89 | 444.2 446.2 | |
| 176 | 4-aminocyclohexylamino | 4-chloro-2,6-dihydroxybenzylamino | isopropyl | C = 56.54; H = 6.33 N = 21.99; Cl = 7.94 | 444.2 446.2 | |
| 177 | R-(1-hydroxymethyl)propylamino | 4-chloro-2,6-dihydroxybenzylamino | isopropyl | C = 54.18; H = 5.99 N = 19.97; Cl = 8.48 | 419.2 421.2 | |
| 178 | R-(1-hydroxymethyl-2-methyl)propylamino | 4-chloro-2,6-dihydroxybenzylamino | isopropyl | C = 55.13; H = 6.26 N = 19.31; Cl = 8.25 | 433.2 435.2 | |
| 179 | 3-aminopropylamino | 4-chloro-2,6-dihydroxybenzylamino | isopropyl | C = 53.27; H = 5.97 N = 24.12; Cl = 8.77 | 404.2 406.2 | |
| 180 | 2-aminoethylamino | 4-chloro-2,6-dihydroxybenzylamino | isopropyl | C = 52.14; H = 5.62 N = 25.02; Cl = 9.07 | 390.1 392.1 | |
| 181 | 2-hydroxyethylamino | 2,3-dihydroxy-4-methoxybenzylamino | isopropyl | C = 55.61; H = 6.25 N = 21.67 | 387.2 | |
| 182 | 3-hydroxypropylamino | 2,3-dihydroxy-4-methoxybenzylamino | isopropyl | C = 56.71; H = 6.54 N = 20.81 | 401.2 | |
| 183 | bis-(2-hydroxyethyl)amino | 2,3-dihydroxy-4-methoxybenzylamino | isopropyl | C = 55.50; H = 6.59 N = 19.40 | 431.2 | |
| 184 | 2-aminocyclohexylamino | 2,3-dihydroxy-4-methoxybenzylamino | isopropyl | C = 59.80; H = 7.00 N = 22.31 | 440.2 | |
| 185 | 4-aminocyclohexylamino | 2,3-dihydroxy-4-methoxybenzylamino | isopropyl | C = 59.82; H = 7.01 N = 22.25 | 440.2 | |
| 186 | R-(1-hydroxymethyl)propylamino | 2,3-dihydroxy-4-methoxybenzylamino | isopropyl | C = 57.68; H = 6.71 N = 20.12 | 415.2 | |
| 187 | R-(1-hydroxymethyl-2-methyl)propylamino | 2,3-dihydroxy-4-methoxybenzylamino | isopropyl | C = 58.59; H = 7.04 N = 19.54 | 429.2 | |
| 188 | 3-aminopropylamino | 2,3-dihydroxy-4-methoxybenzylamino | isopropyl | C = 56.84; H = 6.71 N = 24.45 | 400.2 | |
| 189 | 2-aminoethylamino | 2,3-dihydroxy-4-methoxybenzylamino | isopropyl | C = 55.84; H = 6.54 N = 25.24 | 386.2 | |
| 190 | 2-hydroxyethylamino | 2,5-dihydroxy-4-methoxybenzylamino | isopropyl | C = 55.61; H = 6.26 N = 21.66 | 387.2 | |

TABLE 4-continued

Compounds Prepared by the Method of Examples 12-17

| | PYRAZOLO[4,3-d]PYRIMIDINE SUBSTITUENT | | | CHN ANALYSES | MS (ZMD)-ANALYSES | |
|---|---|---|---|---|---|---|
| No | C5 | C7 | C3 | [%] | [M − H]⁻ a) | [M + H]⁺ b) |
| 191 | 3-hydroxypropylamino | 2,5-dihydroxy-4-methoxybenzylamino | isopropyl | C = 56.75; H = 6.55 N = 20.84 | 401.2 | |
| 192 | bis-(2-hydroxyethyl)amino | 2,5-dihydroxy-4-methoxybenzylamino | isopropyl | C = 55.55; H = 6.53 N = 19.43 | 431.2 | |
| 193 | 2-aminocyclohexylamino | 2,5-dihydroxy-4-methoxybenzylamino | isopropyl | C = 59.85; H = 7.01 N = 22.28 | 440.2 | |
| 194 | 4-aminocyclohexylamino | 2,5-dihydroxy-4-methoxybenzylamino | isopropyl | C = 59.91; H = 7.06 N = 22.18 | 440.2 | |
| 195 | R-(1-hydroxymethyl)propylamino | 2,5-dihydroxy-4-methoxybenzylamino | isopropyl | C = 57.64; H = 6.74 N = 20.26 | 415.2 | |
| 196 | R-(1-hydroxymethyl-2-methyl)propylamino | 2,5-dihydroxy-4-methoxybenzylamino | isopropyl | C = 58.51; H = 7.14 N = 19.51 | 429.2 | |
| 197 | 3-aminopropylamino | 2,5-dihydroxy-4-methoxybenzylamino | isopropyl | C = 56.86; H = 6.75 N = 24.40 | 400.2 | |
| 198 | 2-aminoethylamino | 2,5-dihydroxy-4-methoxybenzylamino | isopropyl | C = 55.85; H = 6.54 N = 25.23 | 386.2 | |
| 199 | 2-hydroxyethylamino | 2,6-dihydroxy-4-methoxybenzylamino | isopropyl | C = 55.65; H = 6.23 N = 21.62 | 387.2 | |
| 200 | 3-hydroxypropylamino | 2,6-dihydroxy-4-methoxybenzylamino | isopropyl | C = 56.70; H = 6.48 N = 20.85 | 401.2 | |
| 201 | bis-(2-hydroxyethyl)amino | 2,6-dihydroxy-4-methoxybenzylamino | isopropyl | C = 55.55; H = 6.56 N = 19.40 | 431.2 | |
| 202 | 2-aminocyclohexylamino | 2,6-dihydroxy-4-methoxybenzylamino | isopropyl | C = 59.88; H = 7.04 N = 22.20 | 440.2 | |
| 203 | 4-aminocyclohexylamino | 2,6-dihydroxy-4-methoxybenzylamino | isopropyl | C = 59.86; H = 7.09 N = 22.15 | 440.2 | |
| 204 | R-(1-hydroxymethyl)propylamino | 2,6-dihydroxy-4-methoxybenzylamino | isopropyl | C = 57.63; H = 6.73 N = 20.28 | 415.2 | |
| 205 | R-(1-hydroxymethyl-2-methyl)propylamino | 2,6-dihydroxy-4-methoxybenzylamino | isopropyl | C = 58.59; H = 7.02 N = 19.58 | 429.2 | |
| 206 | 3-aminopropylamino | 2,6-dihydroxy-4-methoxybenzylamino | isopropyl | C = 56.84; H = 6.78 N = 24.44 | 400.2 | |
| 207 | 2-aminoethylamino | 2,6-dihydroxy-4-methoxybenzylamino | isopropyl | C = 55.80; H = 6.50 N = 25.31 | 386.2 | |
| 208 | 2-hydroxyethylamino | 4-chloro-2,3-dihydroxybenzylamino | isopropyl | C = 51.91; H = 5.39 N = 21.35; Cl = 9.05 | 391.1 | 393.1 |
| 209 | 3-hydroxypropylamino | 4-chloro-2,3-dihydroxybenzylamino | isopropyl | C = 53.14; H = 5.71 N = 20.62; Cl = 8.72 | 405.1 | 407.1 |
| 210 | bis-(2-hydroxyethyl)amino | 4-chloro-2,3-dihydroxybenzylamino | isopropyl | C = 52.23; H = 5.71 N = 19.23; Cl = 8.16 | 435.2 | 437.2 |
| 211 | 2-aminocyclohexylamino | 4-chloro-2,3-dihydroxybenzylamino | isopropyl | C = 56.55; H = 6.37 N = 21.92; Cl = 7.92 | 444.2 | 446.2 |
| 212 | 4-aminocyclohexylamino | 4-chloro-2,3-dihydroxybenzylamino | isopropyl | C = 56.57; H = 6.38 N = 21.94; Cl = 7.91 | 444.2 | 446.2 |
| 213 | R-(1-hydroxymethyl)propylamino | 4-chloro-2,3-dihydroxybenzylamino | isopropyl | C = 54.23; H = 5.92 N = 19.94; Cl = 8.45 | 419.2 | 421.2 |
| 214 | R-(1-hydroxymethyl-2-methyl)propylamino | 4-chloro-2,3-dihydroxybenzylamino | isopropyl | C = 55.27; H = 6.29 N = 19.30; Cl = 8.12 | 433.2 | 435.2 |
| 215 | 3-aminopropylamino | 4-chloro-2,3-dihydroxybenzylamino | isopropyl | C = 53.30; H = 5.95 N = 24.11; Cl = 8.70 | 404.2 | 406.2 |
| 216 | 2-aminoethylamino | 4-chloro-2,3-dihydroxybenzylamino | isopropyl | C = 52.14; H = 5.61 N = 25.00; Cl = 9.08 | 390.1 | 392.1 |
| 217 | 2-hydroxyethylamino | 4-chloro-2,5-dihydroxybenzylamino | isopropyl | C = 51.98; H = 5.35 N = 21.39; Cl = 9.10 | 391.1 | 393.1 |
| 218 | 3-hydroxypropylamino | 4-chloro-2,5-dihydroxybenzylamino | isopropyl | C = 53.14; H = 5.70 N = 20.61; Cl = 8.75 | 405.1 | 407.1 |
| 219 | bis-(2-hydroxyethyl)amino | 4-chloro-2,5-dihydroxybenzylamino | isopropyl | C = 52.23; H = 5.72 N = 19.24; Cl = 8.15 | 435.2 | 437.2 |
| 220 | 2-aminocyclohexylamino | 4-chloro-2,5-dihydroxybenzylamino | isopropyl | C = 56.54; H = 6.38 N = 21.94; Cl = 7.96 | 444.2 | 446.2 |
| 221 | 4-aminocyclohexylamino | 4-chloro-2,5-dihydroxybenzylamino | isopropyl | C = 56.56; H = 6.37 N = 21.95; Cl = 7.94 | 444.2 | 446.2 |
| 222 | R-(1-hydroxymethyl)propylamino | 4-chloro-2,5-dihydroxybenzylamino | isopropyl | C = 54.20; H = 5.98 N = 19.90; Cl = 8.50 | 419.2 | 421.2 |
| 223 | R-(1-hydroxymethyl-2-methyl)propylamino | 4-chloro-2,5-dihydroxybenzylamino | isopropyl | C = 55.20; H = 6.20 N = 19.32; Cl = 8.25 | 433.2 | 435.2 |
| 224 | 3-aminopropylamino | 4-chloro-2,5-dihydroxybenzylamino | isopropyl | C = 53.37; H = 5.86 N = 24.19; Cl = 8.74 | 404.2 | 406.2 |
| 225 | 2-aminoethylamino | 4-chloro-2,5-dihydroxybenzylamino | isopropyl | C = 52.11; H = 5.46 N = 25.12; Cl = 9.15 | 390.1 | 392.1 |
| 226 | 2-hydroxyethylamino | 2-amino-6-chlorobenzylamino | isopropyl | C = 54.33; H = 5.95 N = 26.04; Cl = 9.43 | 374.2 | 376.1 |

TABLE 4-continued

Compounds Prepared by the Method of Examples 12-17

| | PYRAZOLO[4,3-d]PYRIMIDINE SUBSTITUENT | | | CHN ANALYSES | MS (ZMD)-ANALYSES | |
|---|---|---|---|---|---|---|
| No | C5 | C7 | C3 | [%] | [M − H]⁻ a) | [M + H]⁺ b) |
| 227 | 3-hydroxypropylamino | 2-amino-6-chlorobenzylamino | isopropyl | C = 55.45; H = 6.25<br>N = 25.13; Cl = 9.04 | 388.2<br>390.2 | |
| 228 | bis-(2-hydroxyethyl)amino | 2-amino-6-chlorobenzylamino | isopropyl | C = 54.37; H = 6.26<br>N = 23.35; Cl = 8.40 | 418.2<br>420.2 | |
| 229 | 2-aminocyclohexylamino | 2-amino-6-chlorobenzylamino | isopropyl | C = 58.80; H = 6.81<br>N = 26.15; Cl = 8.24 | | 429.2<br>431.2 |
| 230 | 4-aminocyclohexylamino | 2-amino-6-chlorobenzylamino | isopropyl | C = 58.84; H = 6.82<br>N = 26.10; Cl = 8.24 | | 429.2<br>431.2 |
| 231 | R-(1-hydroxymethyl)propylamino | 2-amino-6-chlorobenzylamino | isopropyl | C = 56.50; H = 6.47<br>N = 24.23; Cl = 8.82 | | 404.2<br>406.2 |
| 232 | R-(1-hydroxymethyl-2-methyl)propylamino | 2-amino-6-chlorobenzylamino | isopropyl | C = 57.48; H = 6.74<br>N = 23.48; Cl = 8.45 | | 418.2<br>420.2 |
| 233 | 3-aminopropylamino | 2-amino-6-chlorobenzylamino | isopropyl | C = 55.57; H = 6.44<br>N = 28.85; Cl = 9.14 | | 389.2<br>391.2 |
| 234 | 2-aminoethylamino | 2-amino-6-chlorobenzylamino | isopropyl | C = 54.49; H = 6.19<br>N = 29.89; Cl = 9.43 | | 375.2<br>377.2 |
| 235 | 2-hydroxyethylamino | 3-amino-4-chlorobenzylamino | isopropyl | C = 54.34; H = 5.81<br>N = 26.13; Cl = 9.53 | 374.2<br>376.1 | |
| 236 | 3-hydroxypropylamino | 3-amino-4-chlorobenzylamino | isopropyl | C = 55.41; H = 6.25<br>N = 25.15; Cl = 9.05 | 388.2<br>390.2 | |
| 237 | bis-(2-hydroxyethyl)amino | 3-amino-4-chlorobenzylamino | isopropyl | C = 54.35; H = 6.23<br>N = 23.34; Cl = 8.50 | 418.2<br>420.2 | |
| 238 | 2-aminocyclohexylamino | 3-amino-4-chlorobenzylamino | isopropyl | C = 58.80; H = 6.82<br>N = 26.15; Cl = 8.23 | | 429.2<br>431.2 |
| 239 | 4-aminocyclohexylamino | 3-amino-4-chlorobenzylamino | isopropyl | C = 58.83; H = 6.84<br>N = 26.09; Cl = 8.24 | | 429.2<br>431.2 |
| 240 | R-(1-hydroxymethyl)propylamino | 3-amino-4-chlorobenzylamino | isopropyl | C = 56.51; H = 6.45<br>N = 24.26; Cl = 8.74 | | 404.2<br>406.2 |
| 241 | R-(1-hydroxymethyl-2-methyl)propylamino | 3-amino-4-chlorobenzylamino | isopropyl | C = 57.41; H = 6.75<br>N = 23.44; Cl = 8.46 | | 418.2<br>420.2 |
| 242 | 3-aminopropylamino | 3-amino-4-chlorobenzylamino | isopropyl | C = 55.59; H = 6.48<br>N = 28.81; Cl = 9.12 | | 389.2<br>391.2 |
| 243 | 2-aminoethylamino | 3-amino-4-chlorobenzylamino | isopropyl | C = 54.47; H = 6.18<br>N = 29.89; Cl = 9.46 | | 375.2<br>377.2 |
| 244 | 2-hydroxyethylamino | 4-chloro-2,3-diaminobenzylamino | isopropyl | C = 52.24; H = 5.93<br>N = 28.67; Cl = 9.07 | | 391.2<br>393.2 |
| 245 | 3-hydroxypropylamino | 4-chloro-2,3-diaminobenzylamino | isopropyl | C = 53.40; H = 6.22<br>N = 27.67; Cl = 8.76 | | 405.2<br>407.2 |
| 246 | bis-(2-hydroxyethyl)amino | 4-chloro-2,3-diaminobenzylamino | isopropyl | C = 52.47; H = 6.26<br>N = 25.76; Cl = 8.15 | | 435.2<br>437.2 |
| 247 | 2-aminocyclohexylamino | 4-chloro-2,3-diaminobenzylamino | isopropyl | C = 56.81; H = 6.81<br>N = 28.39; Cl = 7.99 | | 444.2<br>446.2 |
| 248 | 4-aminocyclohexylamino | 4-chloro-2,3-diaminobenzylamino | isopropyl | C = 56.81; H = 6.81<br>N = 28.39; Cl = 7.99 | | 444.2<br>446.2 |
| 249 | R-(1-hydroxymethyl)propylamino | 4-chloro-2,3-diaminobenzylamino | isopropyl | C = 54.47; H = 6.50<br>N = 26.75; Cl = 8.46 | | 419.2<br>421.2 |
| 250 | R-(1-hydroxymethyl-2-methyl)propylamino | 4-chloro-2,3-diaminobenzylamino | isopropyl | C = 55.48; H = 6.75<br>N = 25.88; Cl = 8.19 | | 433.2<br>435.2 |
| 251 | 3-aminopropylamino | 4-chloro-2,3-diaminobenzylamino | isopropyl | C = 53.53; H = 6.49<br>N = 31.21; Cl = 8.78 | | 404.2<br>406.2 |
| 252 | 2-aminoethylamino | 4-chloro-2,3-diaminobenzylamino | isopropyl | C = 52.37; H = 6.20<br>N = 32.33; Cl = 9.09 | | 404.2<br>406.2 |
| 253 | 2-hydroxyethylamino | [(R,S)-(2-hydroxyethyl-1-phenyl)-amino] | isopropyl | C = 60.68; H = 6.79<br>N = 23.54 | 355.2 | |
| 254 | 3-hydroxypropylamino | [(R,S)-(2-hydroxyethyl-1-phenyl)-amino] | isopropyl | C = 61.60; H = 7.05<br>N = 22.71 | 369.2 | |
| 255 | bis-(2-hydroxyethyl)amino | [(R,S)-(2-hydroxyethyl-1-phenyl)-amino] | isopropyl | C = 60.04; H = 7.01<br>N = 20.95 | 399.2 | |
| 256 | 2-aminocyclohexylamino | [(R,S)-(2-hydroxyethyl-1-phenyl)-amino] | isopropyl | C = 64.54; H = 7.65<br>N = 23.91 | | 410.3 |
| 257 | 4-aminocyclohexylamino | [(R,S)-(2-hydroxyethyl-1-phenyl)-amino] | isopropyl | C = 64.52; H = 7.63<br>N = 23.95 | | 410.3 |
| 258 | R-(1-hydroxymethyl)propylamino | [(R,S)-(2-hydroxyethyl-1-phenyl)-amino] | isopropyl | C = 62.48; H = 7.35<br>N = 21.87 | 383.2 | |
| 259 | R-(1-hydroxymethyl-2-methyl)propylamino | [(R,S)-(2-hydroxyethyl-1-phenyl)-amino] | isopropyl | C = 63.29; H = 7.55<br>N = 21.08 | 397.2 | |
| 260 | 3-aminopropylamino | [(R,S)-(2-hydroxyethyl-1-phenyl)-amino] | isopropyl | C = 61.77; H = 7.35<br>N = 26.56 | | 370.2 |
| 261 | 2-aminoethylamino | [(R,S)-(2-hydroxyethyl-1-phenyl)-amino] | isopropyl | C = 60.83; H = 7.04<br>N = 27.62 | | 356.2 |
| 262 | 2-hydroxyethylamino | benzylamino | isopropyl | C = 62.56; H = 6.79<br>N = 25.75 | | 327.2 |

TABLE 4-continued

Compounds Prepared by the Method of Examples 12-17

| | PYRAZOLO[4,3-d]PYRIMIDINE SUBSTITUENT | | | CHN ANALYSES | MS (ZMD)-ANALYSES | |
|---|---|---|---|---|---|---|
| No | C5 | C7 | C3 | [%] | [M − H]⁻ a) | [M + H]⁺ b) |
| 263 | 3-hydroxypropylamino | benzylamino | isopropyl | C = 63.51; H = 7.11 N = 24.69 | | 345.2 |
| 264 | bis-(2-hydroxyethyl)amino | benzylamino | isopropyl | C = 61.60; H = 7.07 N = 22.69 | 369.2 | |
| 265 | 2-aminocyclohexylamino | benzylamino | isopropyl | C = 66.46; H = 7.70 N = 25.83 | | 380.2 |
| 266 | 4-aminocyclohexylamino | benzylamino | isopropyl | C = 66.46; H = 7.70 N = 25.83 | | 380.2 |
| 267 | R-(1-hydroxymethyl)propylamino | benzylamino | isopropyl | C = 64.38; H = 7.39 N = 23.71 | | 355.2 |
| 268 | R-(1-hydroxymethyl-2-methyl)propylamino | benzylamino | isopropyl | C = 65.19 H = 7.66 N = 22.81 | | 369.2 |
| 269 | 3-aminopropylamino | benzylamino | isopropyl | C = 63.69; H = 7.42 N = 28.8 | | 340.2 |
| 270 | 2-aminoethylamino | benzylamino | isopropyl | C = 62.75; H = 7.12 N = 30.13 | | 326.2 |
| 271 | 2-hydroxyethylamino | [N-(3,4-dihydroxybenzyl)-N-methyl]amino | isopropyl | C = 58.05; H = 6.52 N = 22.59 | 371.2 | |
| 272 | 3-hydroxypropylamino | [N-(3,4-dihydroxybenzyl)-N-methyl]amino | isopropyl | C = 59.02; H = 6.78 N = 21.77 | 385.2 | |
| 273 | bis-(2-hydroxyethyl)amino | [N-(3,4-dihydroxybenzyl)-N-methyl]amino | isopropyl | C = 57.68; H = 6.78 N = 20.18 | 415.2 | |
| 274 | 2-aminocyclohexylamino | [N-(3,4-dihydroxybenzyl)-N-methyl]amino | isopropyl | C = 62.15; H = 7.35 N = 23.01 | 424.2 | |
| 275 | 4-aminocyclohexylamino | [N-(3,4-dihydroxybenzy)l-N-methyl]amino | isopropyl | C = 62.12; H = 7.37 N = 23.02 | 424.2 | |
| 276 | R-(1-hydroxymethyl)propylamino | [N-(3,4-dihydroxybenzyl)-N-methyl]amino | isopropyl | C = 59.93; H = 7.09 N = 20.97 | 399.2 | |
| 277 | R-(1-hydroxymethyl-2-methyl)propylamino | [N-(3,4-dihydroxybenzyl)-N-methyl]amino | isopropyl | C = 60.81; H = 7.37 N = 20.24 | 413.2 | |
| 278 | 3-aminopropylamino | [N-(3,4-dihydroxybenzyl)-N-methyl]amino | isopropyl | C = 59.22; H = 7.08 N = 25.41 | 384.2 | |
| 279 | 2-aminoethylamino | [N-(3,4-dihydroxybenzyl)-N-methyl]amino | isopropyl | C = 58.21; H = 6.76 N = 26.48 | 370.2 | |
| 280 | 2-hydroxyethylamino | [N-(2-(3,4-dihydroxyfenyl)ethyl)-N-methyl]amino | isopropyl | C = 59.05; H = 6.78 N = 21.75 | 385.2 | |
| 281 | 3-hydroxypropylamino | [N-(2-(3,4-dihydroxyfenyl)ethyl)-N-methyl]amino | isopropyl | C = 59.98; H = 7.05 N = 20.98 | 399.2 | |
| 282 | bis-(2-hydroxyethyl)amino | [N-(2-(3,4-dihydroxyfenyl)ethyl)-N-methyl]amino | isopropyl | C = 58.59; H = 7.02 N = 19.52 | 429.2 | |
| 283 | 2-aminocyclohexylamino | [N-(2-(3,4-dihydroxyfenyl)ethyl)-N-methyl]amino | isopropyl | C = 62.85; H = 7.57 N = 22.31 | | 440.3 |
| 284 | 4-aminocyclohexylamino | [N-(2-(3,4-dihydroxyfenyl)ethyl)-N-methyl]amino | isopropyl | C = 62.83; H = 7.57 N = 22.32 | | 440.3 |
| 285 | R-(1-hydroxymethyl)propylamino | [N-(2-(3,4-dihydroxyfenyl)ethyl)-N-methyl]amino | isopropyl | C = 60.85; H = 7.30 N = 20.27 | 413.2 | |
| 286 | R-(1-hydroxymethyl-2-methyl)propylamino | [N-(2-(3,4-dihydroxyfenyl)ethyl)-N-methyl]amino | isopropyl | C = 61.66; H = 7.53 N = 19.61 | 427.2 | |
| 287 | 3-aminopropylamino | [N-(2-(3,4-dihydroxyfenyl)ethyl)-N-methyl]amino | isopropyl | C = 60.13; H = 7.32 N = 24.54 | | 400.2 |
| 288 | 2-aminoethylamino | [N-(2-(3,4-dihydroxyfenyl)ethyl)-N-methyl]amino | isopropyl | C = 59.20; H = 7.06 N = 25.44 | | 386.2 | a) solution: MeOH p.a. + HCOOH b) solution: MeOH p.a. + $H_2O$ + $NH_3$

Trisubstituted pyrazolo[4,3-d]pyrimidines with R5 and R7 defined above in Table 4 and R3 with methyl or ethyl group were also prepared but their characteristics are not precisely characterized.

Example 18

4-acetamido-5-isopropylpyrazol-3-carboxamide (XX)

4-Amino-5-isopropylpyrazolo-3-carboxamide (102 mg, 0.61 mmol) (V) was suspended in 0.8 mL dichloromethane and 60 μl of acetic anhydride was added with stirring. After being stirred 2 hours, the mixture was diluted with 1 mL petroleum ether and filtered to yield 90% of the title compound; mp=162-164° C. MS (ES+): 211.2 (100%, M+H+). $^1$H NMR (300 MHz, DMSO): 1.17 d (6H, J=6.6 Hz); 1.96 s (3H), 2.91 s (1H), 3.44 sept (1H, J=6.60 Hz), 7.09 s (1H), 7.29 s (1H), 8.99 s (1H).

Example 19

Preparation of Affinity Sorbent

Preparation of 5-(2-aminopropylamino)-7-(3-carboxy-4-chloroanilino)-3-isopropylpyrazolo[4,3-d]pyrimidine Epoxy activated Sepharose 6B Affinity Matrix Freeze-dried epoxy activated Sepharose 6B (Pharmacia LKB, Piscataway, N.J.) was chosen for the coupling reaction due to its ability to form an ether bond between a hydroxyl-containing ligand and the epoxide group on the Sepharose. The gel was swollen according to the manufacturer's instructions, (100 mg) of any one of the compound defined in claim 1 and 56 was dissolved in 1 ml coupling solution (1.2:1, v/v, DMF, 0.1N NaOH) and mixed with 0.5 ml of swollen gel at pH 10-11 for 72 h at room temperature with gentle agitation. Excess reactive groups were blocked with 1M ethanolamine for 4 hours at 50° C. and the gel slurry was poured into 1-ml syringe column. The resin was activated with three alternating cycles of twenty column volumes each of pH 4.0 (0.1M acetate, 0.5 M NaCl) and pH 8.0 (0.1M tris-HCl, 0.5 M NaCl) buffers followed by twenty column volumes of reaction buffer (20 mM HEPES, pH 7.3, 10 mM MgCl$_2$, 15 mM glycerophosphate, 0.5 mM sodium orthovanadate, 0.5 mM EGTA). The column was stored at 4° C. in the reaction buffer containing 0.1% sodium azide and regenerated prior to each use with alternating cycles of low and high pH as described above.

The Sf9 insect cell lysate (500 μg protein in 1-ml reaction buffer) was passed over the affinity column matrix sequentially five times and the flow through was saved (unbound material). The matrix was then washed three times with 1 ml reaction buffer (wash 1-3) then three times each reaction buffer containing 0.5M NaCl (eluate 1-3). The coupled proteins were eluted at low pH (pH 4.0, 0.1M acetate, 0.5M NaCl) as described above and aliquots (20 μl from 1 ml) of each sample were assayed for their ability to phosphorylate histone H1 and other substrate proteins as described in Example 15. The presence of CDK complexes was also determined by SDS-PAGE.

Example 20

CDK Inhibition Assays

Selected compounds were tested for cdk1/cyclin B and cdk2/cyclin E inhibitory activity to determine the basic relationships between their interaction energy of docked complex and the inhibitory activity. Cdk2/cyclin E complex was produced in SIP insect cells co-infected with appropriate baculoviral construct. The cells were harvested 70 hours post infection in lysis buffer (50 mM Tris 7.4 pH, 150 mM NaCl, 5 mM EDTA, 20 mM NaF, 1% Tween 20, protease inhibitors) for 30 min on ice and the soluble fraction was recovered by centrifugation at 14.000 g for 10 min. The protein extract was stored at −80° C. until use. The final point test system for kinase activity measurement was used to carry out experiments on the kinetics under linear conditions. The assay mixture contained 1 mg/ml histone (Sigma Type III-S), 15 μM ATP, 0.2 μCi [γ-$^{32}$P] ATP and tested compound in a final volume of 20 μl, all in reaction buffer: 50 mM Hepes 7.4 pH, 10 mM MgCl$_2$, 5 mM EGTA, 10 mM 2-glycerolphosphate, 1 mM NaF, 1 mM DTT and protease inhibitors. After 10 min, the incubations were stopped by adding SDS sample buffer and the proteins were separated using 12.5% SDS-PAGE. The measurement of kinase inhibition employed the digital imaging analyzer BAS 1800. The kinase activity was expressed as a percentage of maximum activity and the IC$_{50}$ value was determined by graphic analysis. The kinase activity is expressed as a percentage of maximum activity, the apparent inhibition constants are determined by graphic analysis from dose-response curves presented on FIG. 1.

TABLE 5

Kinase Inhibitory Activity of Selected 3,5,7-Trisubstituted Pyrazolo[4,3-d]pyrimidine Derivatives

| SUBSTITUENT | | | CDC2 | IκB-α |
|---|---|---|---|---|
| C5 | C7 | C3 | IC$_{50}$ (μM) | IC$_{50}$ (μM) |
| 2-hydroxyethylamino | benzylamino | methyl | 4 | 9.3 |
| 3-hydroxypropylamino | benzylamino | methyl | 0.7 | 1.8 |
| Bis-(2-hydroxyethyl)amino | benzylamino | methyl | 0.9 | 2.1 |
| 2-aminocyclohexylamino | benzylamino | methyl | 0.03 | 0.09 |
| 4-aminocyclohexylamino | benzylamino | methyl | 0.02 | 0.05 |
| R-(1-hydroxymethyl)propylamino | benzylamino | methyl | 0.1 | 0.3 |
| R-(1-hydroxymethyl-2-methyl)propylamino | benzylamino | methyl | 0.01 | 0.02 |
| 3-aminopropylamino | benzylamino | methyl | 0.2 | 0.4 |
| 2-aminoethylamino | benzylamino | methyl | 2 | 5 |
| 2-hydroxyethylamino | 3,4-dihydroxybenzylamino | methyl | 5 | 11 |
| 2-hydroxyethylamino | 3-chloroanilino | methyl | 0.04 | 0.09 |

TABLE 5-continued

Kinase Inhibitory Activity of Selected 3,5,7-Trisubstituted Pyrazolo[4,3-d]pyrimidine Derivatives

| SUBSTITUENT | | | CDC2 | IκB-α |
|---|---|---|---|---|
| C5 | C7 | C3 | IC$_{50}$ (μM) | IC$_{50}$ (μM) |
| 2-hydroxyethylamino | anilino | methyl | 0.09 | 0.21 |
| 2-hydroxyethylamino | 3-chloro-5-aminoanilino | methyl | 0.01 | 0.02 |
| 2-hydroxyethylamino | 3-chloro-4-carboxyanilino | methyl | 0.007 | 0.014 |
| 2-hydroxyethylamino | 3-carboxy-4-chloroanilino | methyl | 0.005 | 0.01 |
| 2-hydroxyethylamino | 3-carboxy-4-hydroxyanilino | methyl | 0.02 | 0.05 |
| 2-hydroxyethylamino | 4-bromoanilino | methyl | 0.008 | 0.02 |
| 2-hydroxyethylamino | 4-chloroanilino | methyl | 0.009 | 0.019 |
| 2-hydroxyethylamino | 3-amino-4-chloroanilino | methyl | 0.009 | 0.023 |
| 2-hydroxyethylamino | 3-chloro-4-aminoanilino | methyl | 0.012 | 0.029 |
| 2-hydroxyethylamino | 2-hydroxybenzylamino | methyl | 0.02 | 0.05 |
| 2-hydroxyethylamino | 3-hydroxybenzylamino | methyl | 0.08 | 0.24 |
| 2-hydroxyethylamino | 2-acetoxybenzylamino | methyl | 0.5 | 1.2 |
| 2-hydroxyethylamino | 3-acetoxybenzylamino | methyl | 0.4 | 1.7 |
| 2-hydroxyethylamino | 2-acetylbenzylamino | methyl | 0.01 | 0.05 |
| 2-hydroxyethylamino | 3-acetylbenzylamino | methyl | 0.04 | 0.09 |
| 2-hydroxyethylamino | 2-hydroxy-3-methoxybenzylamino | methyl | 0.01 | 0.04 |
| 2-hydroxyethylamino | 2-hydroxy-3-methylbenzylamino | methyl | 0.01 | 0.03 |
| 2-hydroxyethylamino | 2-hydroxy-3-chlorobenzylamino | methyl | 0.01 | 0.03 |
| 2-hydroxyethylamino | 2,6-dihydroxy-4-chlorobenzylamino | methyl | 0.005 | 0.012 |
| 2-hydroxyethylamino | 2,3-dihydroxy-4-methoxybenzylamino | methyl | 0.008 | 0.028 |
| 2-hydroxyethylamino | 2,5-dihydroxy-4-methoxybenzylamino | methyl | 0.007 | 0.015 |
| 2-hydroxyethylamino | 2,6-dihydroxy-4-methoxybenzylamino | methyl | 0.004 | 0.009 |
| 2-hydroxyethylamino | 2,3-dihydroxy-4-chlorobenzylamino | methyl | 0.009 | 0.021 |
| 2-hydroxyethylamino | 2,5-dihydroxy-4-chlorobenzylamino | methyl | 0.01 | 0.035 |
| 2-hydroxyethylamino | 2-amino-6-chlorobenzylamine | methyl | 0.04 | 0.08 |
| 2-hydroxyethylamino | 3-amino-4-chlorobenzylamine | methyl | 0.2 | 0.8 |
| 2-hydroxyethylamino | 2,3-diamino-4-chlorobenzylamine | methyl | 0.6 | 0.7 |
| 2-hydroxyethylamino | [(R,S)-(1-phenyl-2-hydroxyethyl)amino] | methyl | 0.2 | 0.4 |
| 2-hydroxyethylamino | [N-(3,4-dihydroxybenzyl-N-methyl]amino | methyl | 0.7 | 0.9 |
| | [(R,S)-(1-phenyl-2-hydroxyethyl)amino] | methyl | 1.2 | 2.5 |
| 2-hydroxyethylamino | benzylamino | isopropyl | 1 | 2.3 |
| 3-hydroxypropylamino | benzylamino | isopropyl | 0.2 | 0.8 |
| Bis-(2-hydroxyethyl)amino | benzylamino | isopropyl | 0.4 | 1.1 |
| 2-aminocyclohexylamino | benzylamino | isopropyl | 0.01 | 0.02 |
| 4-aminocyclohexylamino | benzylamino | isopropyl | 0.005 | 0.02 |
| R-(1-hydroxymethyl)propylamino | benzylamino | isopropyl | 0.01 | 0.03 |
| R-(1-hydroxymethyl-2-methyl)propylamino | benzylamino | isopropyl | 0.004 | 0.01 |
| 3-aminopropylamino | benzylamino | isopropyl | 0.08 | 0.1 |
| 2-aminoethylamino | Benzylamino | isopropyl | 0.4 | 1.2 |
| R-(1-hydroxymethyl)propylamino | 3,4-dihydroxybenzylamino | isopropyl | 0.5 | 1.1 |
| R-(1-hydroxymethyl)propylamino | 3-chloroanilino | isopropyl | 0.004 | 0.009 |
| R-(1-hydroxymethyl)propylamino | anilino | isopropyl | 0.02 | 0.11 |
| R-(1-hydroxymethyl)propylamino | 3-chloro-5-aminoanilino | isopropyl | 0.004 | 0.02 |
| R-(1-hydroxymethyl)propylamino | 3-chloro-4-carboxyanilino | isopropyl | 0.002 | 0.004 |
| R-(1-hydroxymethyl)propylamino | 3-carboxy-4-chloroanilino | isopropyl | 0.001 | 0.002 |
| R-(1-hydroxymethyl)propylamino | 3-carboxy-4-hydroxyanilino | isopropyl | 0.01 | 0.03 |
| R-(1-hydroxymethyl)propylamino | 4-bromoanilino | isopropyl | 0.002 | 0.01 |
| R-(1-hydroxymethyl)propylamino | 4-chloroanilino | isopropyl | 0.003 | 0.009 |
| R-(1-hydroxymethyl)propylamino | 3-amino-4-chloroanilino | isopropyl | 0.004 | 0.013 |
| R-(1-hydroxymethyl)propylamino | 3-chloro-4-aminoanilino | isopropyl | 0.002 | 0.009 |
| R-(1-hydroxymethyl)propylamino | 2-hydroxybenzylamino | isopropyl | 0.008 | 0.012 |
| R-(1-hydroxymethyl)propylamino | 3-hydroxybenzylamino | isopropyl | 0.02 | 0.04 |
| R-(1-hydroxymethyl)propylamino | 2-acetoxybenzylamino | isopropyl | 0.1 | 0.2 |
| R-(1-hydroxymethyl)propylamino | 3-acetoxybenzylamino | isopropyl | 0.07 | 0.4 |
| R-(1-hydroxymethyl)propylamino | 2-acetylbenzylamino | isopropyl | 0.005 | 0.015 |
| R-(1-hydroxymethyl)propylamino | 3-acetylbenzylamino | isopropyl | 0.01 | 0.04 |
| R-(1-hydroxymethyl)propylamino | 2-hydroxy-3-methoxybenzylamino | isopropyl | 0.004 | 0.012 |
| R-(1-hydroxymethyl)propylamino | 2-hydroxy-3-methylbenzylamino | isopropyl | 0.006 | 0.014 |
| R-(1-hydroxymethyl)propylamino | 2-hydroxy-3-chlorobenzylamino | isopropyl | 0.007 | 0.012 |
| R-(1-hydroxymethyl)propylamino | 2,6-dihydroxy-4-chlorobenzylamino | isopropyl | 0.001 | 0.002 |

TABLE 5-continued

Kinase Inhibitory Activity of Selected 3,5,7-Trisubstituted Pyrazolo[4,3-d]pyrimidine Derivatives

| SUBSTITUENT | | | CDC2 | IκB-α |
|---|---|---|---|---|
| C5 | C7 | C3 | IC$_{50}$ (μM) | IC$_{50}$ (μM) |
| R-(1-hydroxymethyl)propylamino | 2,3-dihydroxy-4-methoxybenzylamino | isopropyl | 0.002 | 0.005 |
| R-(1-hydroxymethyl)propylamino | 2,5-dihydroxy-4-methoxybenzylamino | isopropyl | 0.002 | 0.006 |
| R-(1-hydroxymethyl)propylamino | 2,6-dihydroxy-4-methoxybenzylamino | isopropyl | 0.0008 | 0.003 |
| R-(1-hydroxymethyl)propylamino | 2,3-dihydroxy-4-chlorobenzylamino | isopropyl | 0.003 | 0.011 |
| R-(1-hydroxymethyl)propylamino | 2,5-dihydroxy-4-chlorobenzylamino | isopropyl | 0.008 | 0.015 |
| R-(1-hydroxymethyl)propylamino | 2-amino-6-chlorobenzylamine | isopropyl | 0.012 | 0.0035 |
| R-(1-hydroxymethyl)propylamino | 3-amino-4-chlorobenzylamine | isopropyl | 0.08 | 0.024 |
| R-(1-hydroxymethyl)propylamino | 2,3-diamino-4-chlorobenzylamine | isopropyl | 0.2 | 0.4 |
| R-(1-hydroxymethyl)propylamino | [(R,S)-(1-phenyl-2-hydroxyethyl)amino] | isopropyl | 0.09 | 0.21 |
| R-(1-hydroxymethyl)propylamino | [N-(3,4-dihydroxybenzyl-N-methyl]amino | isopropyl | 0.23 | 0.51 |
| R-(1-hydroxymethyl)propylamino | [N-(2-(3,4-dihydroxyfenyl)ethyl)-N-methyl]amino | isopropyl | 0.72 | 1.5 |
| 2-hydroxyethylamino | 3-chloroanilino | isopropyl | 0.11 | 0.28 |
| 3-hydroxypropylamino | 3-chloroanilino | isopropyl | 0.08 | 0.2 |
| Bis-(2-hydroxyethyl)amino | 3-chloroanilino | isopropyl | 0.09 | 0.19 |
| 2-aminocyclohexylamino | 3-chloroanilino | isopropyl | 0.004 | 0.012 |
| 4-aminocyclohexylamino | 3-chloroanilino | isopropyl | 0.001 | 0.012 |
| R-(1-hydroxymethyl)propylamino | 3-chloroanilino | isopropyl | 0.004 | 0.03 |
| R-(1-hydroxymethyl-2-methyl)propylamino | 3-chloroanilino | isopropyl | 0.004 | 0.009 |
| 3-aminopropylamino | 3-chloroanilino | isopropyl | 0.02 | 0.08 |
| 2-aminoethylamino | 3-chloroanilino | isopropyl | 0.14 | 0.25 |
| R-(1-hydroxymethyl-2-methyl)propylamino | 3,4-dihydroxybenzylamino | isopropyl | 0.15 | 0.31 |
| R-(1-hydroxymethyl-2-methyl)propylamino | anilino | isopropyl | 0.001 | 0.003 |
| R-(1-hydroxymethyl-2-methyl)propylamino | 3-chloro-5-aminoanilino | isopropyl | 0.008 | 0.015 |
| R-(1-hydroxymethyl-2-methyl)propylamino | 3-chloro-4-carboxyanilino | isopropyl | 0.0009 | 0.002 |
| R-(1-hydroxymethyl-2-methyl)propylamino | 3-carboxy-4-chloroanilino | isopropyl | 0.001 | 0.002 |
| R-(1-hydroxymethyl-2-methyl)propylamino | 3-carboxy-4-hydroxyanilino | isopropyl | 0.0004 | 0.001 |
| R-(1-hydroxymethyl-2-methyl)propylamino | 4-bromoanilino | isopropyl | 0.002 | 0.003 |
| R-(1-hydroxymethyl-2-methyl)propylamino | 4-chloroanilino | isopropyl | 0.0005 | 0.001 |
| R-(1-hydroxymethyl-2-methyl)propylamino | 3-amino-4-chloroanilino | isopropyl | 0.001 | 0.002 |
| R-(1-hydroxymethyl-2-methyl)propylamino | 3-chloro-4-aminoanilino | isopropyl | 0.002 | 0.003 |
| R-(1-hydroxymethyl-2-methyl)propylamino | 2-hydroxybenzylamino | isopropyl | 0.0005 | 0.001 |
| R-(1-hydroxymethyl-2-methyl)propylamino | 3-hydroxybenzylamino | isopropyl | 0.002 | 0.004 |
| R-(1-hydroxymethyl-2-methyl)propylamino | 2-acetoxybenzylamino | isopropyl | 0.006 | 0.012 |
| R-(1-hydroxymethyl-2-methyl)propylamino | 3-acetoxybenzylamino | isopropyl | 0.02 | 0.06 |
| R-(1-hydroxymethyl-2-methyl)propylamino | 2-acetylbenzylamino | isopropyl | 0.02 | 0.05 |
| R-(1-hydroxymethyl-2-methyl)propylamino | 3-acetylbenzylamino | isopropyl | 0.001 | 0.005 |
| R-(1-hydroxymethyl-2-methyl)propylamino | 2-hydroxy-3-methoxybenzylamino | isopropyl | 0.006 | 0.015 |
| R-(1-hydroxymethyl-2-methyl)propylamino | 2-hydroxy-3-methylbenzylamino | isopropyl | 0.001 | 0.002 |
| R-(1-hydroxymethyl-2-methyl)propylamino | 2-hydroxy-3-chlorobenzylamino | isopropyl | 0.002 | 0.004 |
| R-(1-hydroxymethyl-2-methyl)propylamino | 2,6-dihydroxy-4-chlorobenzylamino | isopropyl | 0.001 | 0.002 |
| R-(1-hydroxymethyl-2-methyl)propylamino | 2,3-dihydroxy-4-methoxybenzylamino | isopropyl | 0.0004 | 0.0012 |

TABLE 5-continued

Kinase Inhibitory Activity of Selected 3,5,7-Trisubstituted Pyrazolo[4,3-d]pyrimidine Derivatives

| SUBSTITUENT | | | CDC2 | IκB-α |
|---|---|---|---|---|
| C5 | C7 | C3 | IC$_{50}$ (μM) | IC$_{50}$ (μM) |
| R-(1-hydroxymethyl-2-methyl)propylamino | 2,5-dihydroxy-4-methoxybenzylamino | isopropyl | 0.0006 | 0.0015 |
| R-(1-hydroxymethyl-2-methyl)propylamino | 2,6-dihydroxy-4-methoxybenzylamino | isopropyl | 0.0007 | 0.0016 |
| R-(1-hydroxymethyl-2-methyl)propylamino | 2,3-dihydroxy-4-chlorobenzylamino | isopropyl | 0.0002 | 0.001 |
| R-(1-hydroxymethyl-2-methyl)propylamino | 2,5-dihydroxy-4-chlorobenzylamino | isopropyl | 0.0008 | 0.001 |
| R-(1-hydroxymethyl-2-methyl)propylamino | 2-amino-6-chlorobenzylamine | isopropyl | 0.0009 | 0.002 |
| R-(1-hydroxymethyl-2-methyl)propylamino | 3-amino-4-chlorobenzylamine | isopropyl | 0.002 | 0.003 |
| R-(1-hydroxymethyl-2-methyl)propylamino | 2,3-diamino-4-chlorobenzylamine | isopropyl | 0.02 | 0.04 |
| R-(1-hydroxymethyl-2-methyl)propylamino | [(R,S)-(1-phenyl-2-hydroxyethyl)amino] | isopropyl | 0.06 | 0.15 |
| R-(1-hydroxymethyl-2-methyl)propylamino | [N-(3,4-dihydroxybenzyl-N-methyl]amino | isopropyl | 0.03 | 0.11 |
| R-(1-hydroxymethyl-2-methyl)propylamino | [N-(2-(3,4-dihydroxyfenyl)ethyl)-N-methyl]amino | isopropyl | 0.09 | 0.15 |

Table 5 shows the results of inhibitory activity of novel compounds against CDC2 and IκB-α in comparison with the data on the prototype compounds (trisubstituted purines olomoucine, roscovitine and purvalanol A). Most of the 3,5,7-trisubstituted pyrazolo[4,3-d]pyrimidine derivatives showed marked inhibitory activity in in vitro kinase assays. Modification of the purine ring to pyrazolo[4,3-d]pyrimidine ring led usually to increase in cdk inhibitory activity of the tested compound.

Example 21

CDK Inhibitory Activity on Plant Kinases

Protein extraction and purification of pant CDK by binding to p13$^{suc1}$-beads or immunopurification with an antibody specific to the cdc2a-MS protein was carried out as described previously (Bögre et al. 1997, Plant Physiol. 113, 1997, 841-852). The MMK1 protein kinase was purified with a specific antibody from *Vicia faba* extracts as described by Bögre et al. 1997a, Plant Cell 9, 75-83). Protein kinase activity was measures as described above in Example 20. The quantification of radioactivity incorporated into histone H1 or myelin basic protein was undertaken using phosphoimager (FIG. 2).

TABLE 6

Kinase Inhibitory Activity of Selected 3,5,7-Trisubstituted Pyrazolo[4,3-d]pyrimidine Derivatives

| SUBSTITUENT | | | Cdc2a | MMK1 |
|---|---|---|---|---|
| C5 | C7 | C3 | IC$_{50}$ (μM) | IC$_{50}$ (μM) |
| 2-hydroxyethylamino | benzylamino | methyl | 12 | 29.3 |
| 3-hydroxypropylamino | benzylamino | methyl | 7.5 | 5.8 |
| Bis-(2-hydroxyethyl)amino | benzylamino | methyl | 8.9 | 8.1 |
| 2-aminocyclohexylamino | benzylamino | methyl | 0.5 | 0.9 |
| 4-aminocyclohexylamino | benzylamino | methyl | 0.2 | 0.6 |
| R-(1-hydroxymethyl)propylamino | benzylamino | methyl | 1.5 | 1.3 |
| R-(1-hydroxymethyl-2-methyl)propylamino | benzylamino | methyl | 0.2 | 0.4 |
| 3-aminopropylamino | benzylamino | methyl | 1.2 | 1.4 |
| 2-aminoethylamino | benzylamino | methyl | 12 | 15 |
| 2-hydroxyethylamino | 3,4-dihydroxybenzylamino | methyl | 18 | 24 |
| 2-hydroxyethylamino | 3-chloroanilino | methyl | 0.4 | 0.9 |
| 2-hydroxyethylamino | anilino | methyl | 0.9 | 2.5 |
| 2-hydroxyethylamino | 3-chloro-5-aminoanilino | methyl | 0.1 | 0.3 |
| 2-hydroxyethylamino | 3-chloro-4-carboxyanilino | methyl | 0.09 | 0.16 |
| 2-hydroxyethylamino | 3-carboxy-4-chloroanilino | methyl | 0.08 | 0.3 |
| 2-hydroxyethylamino | 3-carboxy-4-hydroxyanilino | methyl | 0.4 | 0.7 |
| 2-hydroxyethylamino | 4-bromoanilino | methyl | 0.08 | 0.15 |

TABLE 6-continued

Kinase Inhibitory Activity of Selected 3,5,7-Trisubstituted Pyrazolo[4,3-d]pyrimidine Derivatives

| SUBSTITUENT | | | Cdc2a | MMK1 |
|---|---|---|---|---|
| C5 | C7 | C3 | IC$_{50}$ (µM) | IC$_{50}$ (µM) |
| 2-hydroxyethylamino | 4-chloroanilino | methyl | 0.09 | 0.18 |
| 2-hydroxyethylamino | 3-amino-4-chloroanilino | methyl | 0.09 | 0.24 |
| 2-hydroxyethylamino | 3-chloro-4-aminoanilino | methyl | 0.13 | 0.25 |
| 2-hydroxyethylamino | 2-hydroxybenzylamino | methyl | 0.25 | 0.41 |
| 2-hydroxyethylamino | 3-hydroxybenzylamino | methyl | 0.6 | 0.84 |
| 2-hydroxyethylamino | 2-acetoxybenzylamino | methyl | 1.5 | 3.3 |
| 2-hydroxyethylamino | 3-acetoxybenzylamino | methyl | 1.4 | 3.4 |
| 2-hydroxyethylamino | 2-acetylbenzylamino | methyl | 0.12 | 0.4 |
| 2-hydroxyethylamino | 3-acetylbenzylamino | methyl | 0.4 | 0.9 |
| 2-hydroxyethylamino | 2-hydroxy-3-methoxybenzylamino | methyl | 0.12 | 0.45 |
| 2-hydroxyethylamino | 2-hydroxy-3-methylbenzylamino | methyl | 0.15 | 0.34 |
| 2-hydroxyethylamino | 2-hydroxy-3-chlorobenzylamino | methyl | 0.16 | 0.38 |
| 2-hydroxyethylamino | 2,6-dihydroxy-4-chlorobenzylamino | methyl | 0.06 | 0.16 |
| 2-hydroxyethylamino | 2,3-dihydroxy-4-methoxybenzylamino | methyl | 0.08 | 0.29 |
| 2-hydroxyethylamino | 2,5-dihydroxy-4-methoxybenzylamino | methyl | 0.07 | 0.16 |
| 2-hydroxyethylamino | 2,6-dihydroxy-4-methoxybenzylamino | methyl | 0.05 | 0.09 |
| 2-hydroxyethylamino | 2,3-dihydroxy-4-chlorobenzylamino | methyl | 0.09 | 0.22 |
| 2-hydroxyethylamino | 2,5-dihydroxy-4-chlorobenzylamino | methyl | 0.15 | 0.38 |
| 2-hydroxyethylamino | 2-amino-6-chlorobenzylamine | methyl | 0.45 | 0.86 |
| 2-hydroxyethylamino | 3-amino-4-chlorobenzylamine | methyl | 2.4 | 1.8 |
| 2-hydroxyethylamino | 2,3-diamino-4-chlorobenzylamine | methyl | 1.6 | 2.8 |
| 2-hydroxyethylamino | [(R,S)-(1-phenyl-2-hydroxyethyl)amino] | methyl | 1.3 | 1.6 |
| 2-hydroxyethylamino | [N-(3,4-dihydroxybenzyl-N-methyl]amino | methyl | 1.8 | 1.95 |
| | [(R,S)-(1-phenyl-2-hydroxyethyl)amino] | methyl | 2.4 | 4.6 |
| 2-hydroxyethylamino | benzylamino | isopropyl | 1 | 2.3 |
| 3-hydroxypropylamino | benzylamino | isopropyl | 0.2 | 0.8 |
| Bis-(2-hydroxyethyl)amino | benzylamino | isopropyl | 0.4 | 1.1 |
| 2-aminocyclohexylamino | benzylamino | isopropyl | 0.01 | 0.02 |
| 4-aminocyclohexylamino | benzylamino | isopropyl | 0.005 | 0.02 |
| R-(1-hydroxymethyl)propylamino | benzylamino | isopropyl | 0.01 | 0.03 |
| R-(1-hydroxymethyl-2-methyl)propylamino | benzylamino | isopropyl | 0.004 | 0.01 |
| 3-aminopropylamino | benzylamino | isopropyl | 0.08 | 0.1 |
| 2-aminoethylamino | Benzylamino | isopropyl | 0.4 | 1.2 |
| R-(1-hydroxymethyl)propylamino | 3,4-dihydroxybenzylamino | isopropyl | 0.5 | 1.1 |
| R-(1-hydroxymethyl)propylamino | 3-chloroanilino | isopropyl | 0.004 | 0.009 |
| R-(1-hydroxymethyl)propylamino | anilino | isopropyl | 0.02 | 0.11 |
| R-(1-hydroxymethyl)propylamino | 3-chloro-5-aminoanilino | isopropyl | 0.004 | 0.02 |
| R-(1-hydroxymethyl)propylamino | 3-chloro-4-carboxyanilino | isopropyl | 0.002 | 0.004 |
| R-(1-hydroxymethyl)propylamino | 3-carboxy-4-chloroanilino | isopropyl | 0.001 | 0.002 |
| R-(1-hydroxymethyl)propylamino | 3-carboxy-4-hydroxyanilino | isopropyl | 0.01 | 0.03 |
| R-(1-hydroxymethyl)propylamino | 4-bromoanilino | isopropyl | 0.002 | 0.01 |
| R-(1-hydroxymethyl)propylamino | 4-chloroanilino | isopropyl | 0.003 | 0.009 |
| R-(1-hydroxymethyl)propylamino | 3-amino-4-chloroanilino | isopropyl | 0.004 | 0.013 |
| R-(1-hydroxymethyl)propylamino | 3-chloro-4-aminoanilino | isopropyl | 0.002 | 0.009 |
| R-(1-hydroxymethyl)propylamino | 2-hydroxybenzylamino | isopropyl | 0.008 | 0.012 |
| R-(1-hydroxymethyl)propylamino | 3-hydroxybenzylamino | isopropyl | 0.02 | 0.04 |
| R-(1-hydroxymethyl)propylamino | 2-acetoxybenzylamino | isopropyl | 0.1 | 0.2 |
| R-(1-hydroxymethyl)propylamino | 3-acetoxybenzylamino | isopropyl | 0.07 | 0.4 |
| R-(1-hydroxymethyl)propylamino | 2-acetylbenzylamino | isopropyl | 0.005 | 0.015 |
| R-(1-hydroxymethyl)propylamino | 3-acetylbenzylamino | isopropyl | 0.01 | 0.04 |
| R-(1-hydroxymethyl)propylamino | 2-hydroxy-3-methoxybenzylamino | isopropyl | 0.004 | 0.012 |
| R-(1-hydroxymethyl)propylamino | 2-hydroxy-3-methylbenzylamino | isopropyl | 0.006 | 0.014 |
| R-(1-hydroxymethyl)propylamino | 2-hydroxy-3-chlorobenzylamino | isopropyl | 0.007 | 0.012 |
| R-(1-hydroxymethyl)propylamino | 2,6-dihydroxy-4-chlorobenzylamino | isopropyl | 0.001 | 0.002 |
| R-(1-hydroxymethyl)propylamino | 2,3-dihydroxy-4-methoxybenzylamino | isopropyl | 0.002 | 0.005 |
| R-(1-hydroxymethyl)propylamino | 2,5-dihydroxy-4-methoxybenzylamino | isopropyl | 0.002 | 0.006 |
| R-(1-hydroxymethyl)propylamino | 2,6-dihydroxy-4-methoxybenzylamino | isopropyl | 0.0008 | 0.003 |

TABLE 6-continued

Kinase Inhibitory Activity of Selected 3,5,7-Trisubstituted Pyrazolo[4,3-d]pyrimidine Derivatives

| SUBSTITUENT | | | Cdc2a | MMK1 |
|---|---|---|---|---|
| C5 | C7 | C3 | IC$_{50}$ (μM) | IC$_{50}$ (μM) |
| R-(1-hydroxymethyl)propylamino | 2,3-dihydroxy-4-chlorobenzylamino | isopropyl | 0.003 | 0.011 |
| R-(1-hydroxymethyl)propylamino | 2,5-dihydroxy-4-chlorobenzylamino | isopropyl | 0.008 | 0.015 |
| R-(1-hydroxymethyl)propylamino | 2-amino-6-chlorobenzylamine | isopropyl | 0.012 | 0.0035 |
| R-(1-hydroxymethyl)propylamino | 3-amino-4-chlorobenzylamine | isopropyl | 0.08 | 0.024 |
| R-(1-hydroxymethyl)propylamino | 2,3-diamino-4-chlorobenzylamine | isopropyl | 0.2 | 0.4 |
| R-(1-hydroxymethyl)propylamino | [(R,S)-(1-phenyl-2-hydroxyethyl)amino] | isopropyl | 0.09 | 0.21 |
| R-(1-hydroxymethyl)propylamino | [N-(3,4-dihydroxybenzyl-N-methyl]amino | isopropyl | 0.23 | 0.51 |
| R-(1-hydroxymethyl)propylamino | [N-(2-(3,4-dihydroxyfenyl)ethyl)-N-methyl]amino | isopropyl | 0.72 | 1.5 |
| 2-hydroxyethylamino | 3-chloroanilino | isopropyl | 0.11 | 0.28 |
| 3-hydroxypropylamino | 3-chloroanilino | isopropyl | 0.08 | 0.2 |
| Bis-(2-hydroxyethyl)amino | 3-chloroanilino | isopropyl | 0.09 | 0.19 |
| 2-aminocyclohexylamino | 3-chloroanilino | isopropyl | 0.004 | 0.012 |
| 4-aminocyclohexylamino | 3-chloroanilino | isopropyl | 0.001 | 0.012 |
| R-(1-hydroxymethyl)propylamino | 3-chloroanilino | isopropyl | 0.004 | 0.03 |
| R-(1-hydroxymethyl-2-methyl)propylamino | 3-chloroanilino | isopropyl | 0.004 | 0.009 |
| 3-aminopropylamino | 3-chloroanilino | isopropyl | 0.02 | 0.08 |
| 2-aminoethylamino | 3-chloroanilino | isopropyl | 0.14 | 0.25 |
| R-(1-hydroxymethyl-2-methyl)propylamino | 3,4-dihydroxybenzylamino | isopropyl | 0.15 | 0.31 |
| R-(1-hydroxymethyl-2-methyl)propylamino | anilino | isopropyl | 0.001 | 0.003 |
| R-(1-hydroxymethyl-2-methyl)propylamino | 3-chloro-5-aminoanilino | isopropyl | 0.008 | 0.015 |
| R-(1-hydroxymethyl-2-methyl)propylamino | 3-chloro-4-carboxyanilino | isopropyl | 0.0009 | 0.002 |
| R-(1-hydroxymethyl-2-methyl)propylamino | 3-carboxy-4-chloroanilino | isopropyl | 0.001 | 0.002 |
| R-(1-hydroxymethyl-2-methyl)propylamino | 3-carboxy-4-hydroxyanilino | isopropyl | 0.0004 | 0.001 |
| R-(1-hydroxymethyl-2-methyl)propylamino | 4-bromoanilino | isopropyl | 0.002 | 0.003 |
| R-(1-hydroxymethyl-2-methyl)propylamino | 4-chloroanilino | isopropyl | 0.0005 | 0.001 |
| R-(1-hydroxymethyl-2-methyl)propylamino | 3-amino-4-chloroanilino | isopropyl | 0.001 | 0.002 |
| R-(1-hydroxymethyl-2-methyl)propylamino | 3-chloro-4-aminoanilino | isopropyl | 0.002 | 0.003 |
| R-(1-hydroxymethyl-2-methyl)propylamino | 2-hydroxybenzylamino | isopropyl | 0.0005 | 0.001 |
| R-(1-hydroxymethyl-2-methyl)propylamino | 3-hydroxybenzylamino | isopropyl | 0.002 | 0.004 |
| R-(1-hydroxymethyl-2-methyl)propylamino | 2-acetoxybenzylamino | isopropyl | 0.006 | 0.012 |
| R-(1-hydroxymethyl-2-methyl)propylamino | 3-acetoxybenzylamino | isopropyl | 0.02 | 0.06 |
| R-(1-hydroxymethyl-2-methyl)propylamino | 2-acetylbenzylamino | isopropyl | 0.02 | 0.05 |
| R-(1-hydroxymethyl-2-methyl)propylamino | 3-acetylbenzylamino | isopropyl | 0.001 | 0.005 |
| R-(1-hydroxymethyl-2-methyl)propylamino | 2-hydroxy-3-methoxybenzylamino | isopropyl | 0.006 | 0.015 |
| R-(1-hydroxymethyl-2-methyl)propylamino | 2-hydroxy-3-methylbenzylamino | isopropyl | 0.001 | 0.002 |
| R-(1-hydroxymethyl-2-methyl)propylamino | 2-hydroxy-3-chlorobenzylamino | isopropyl | 0.002 | 0.004 |
| R-(1-hydroxymethyl-2-methyl)propylamino | 2,6-dihydroxy-4-chlorobenzylamino | isopropyl | 0.001 | 0.002 |
| R-(1-hydroxymethyl-2-methyl)propylamino | 2,3-dihydroxy-4-methoxybenzylamino | isopropyl | 0.0004 | 0.0012 |
| R-(1-hydroxymethyl-2-methyl)propylamino | 2,5-dihydroxy-4-methoxybenzylamino | isopropyl | 0.0006 | 0.0015 |
| R-(1-hydroxymethyl-2-methyl)propylamino | 2,6-dihydroxy-4-methoxybenzylamino | isopropyl | 0.0007 | 0.0016 |
| R-(1-hydroxymethyl-2-methyl)propylamino | 2,3-dihydroxy-4-chlorobenzylamino | isopropyl | 0.0002 | 0.001 |

TABLE 6-continued

Kinase Inhibitory Activity of Selected 3,5,7-Trisubstituted Pyrazolo[4,3-d]pyrimidine Derivatives

| SUBSTITUENT | | | Cdc2a | MMK1 |
|---|---|---|---|---|
| C5 | C7 | C3 | $IC_{50}$ (µM) | $IC_{50}$ (µM) |
| R-(1-hydroxymethyl-2-methyl)propylamino | 2,5-dihydroxy-4-chlorobenzylamino | isopropyl | 0.0008 | 0.001 |
| R-(1-hydroxymethyl-2-methyl)propylamino | 2-amino-6-chlorobenzylamine | isopropyl | 0.0009 | 0.002 |
| R-(1-hydroxymethyl-2-methyl)propylamino | 3-amino-4-chlorobenzylamine | isopropyl | 0.002 | 0.003 |
| R-(1-hydroxymethyl-2-methyl)propylamino | 2,3-diamino-4-chlorobenzylamine | isopropyl | 0.02 | 0.04 |
| R-(1-hydroxymethyl-2-methyl)propylamino | [(R,S)-(1-phenyl-2-hydroxyethyl)amino] | isopropyl | 0.06 | 0.15 |
| R-(1-hydroxymethyl-2-methyl)propylamino | [N-(3,4-dihydroxybenzyl-N-methyl]amino | isopropyl | 0.03 | 0.11 |
| R-(1-hydroxymethyl-2-methyl)propylamino | [N-(2-(3,4-dihydroxyfenyl)ethyl)-N-methyl]amino | isopropyl | 0.09 | 0.15 |

Table 6 shows the results of inhibitory activity of novel compounds against plant cdk. Most of the 3,5,7-trisubstituted pyrazolo[4,3-d]pyrimidine derivatives showed marked inhibitory activity in in vitro plant kinase assays. Modification of the purine ring to pyrazolo[4,3-d]pyrimidine ring led usually to increase in plant CDK inhibitory activity of the tested compound.

Example 22

Modulation of the Activity of β-Adrenergic Receptors

Mechanism of action of novel compounds is presented on FIG. 3. Rat C6 glioma (ATCC N° CCL107) was cultivated in monolayer in serum-free chemically defined medium containing Ham's F10/minimal essential medium (1:1 vol/vol), 2 mM L-glutamine, 1% (vol/vol) minimal essential medium vitamins (100×), 1% (vol/vol) minimal essential medium nonessential amino acids (100×), 100 U/ml penicillin, 100 µg/ml streptomycin and 30 nM sodium selenide. Incubation was at 37° C. in a humidified atmosphere. Assays were performed in the logarithmic growth phase at a density of 2.5× $10^5$ cells/$cm^2$. Intracellular cAMP synthesis was induced by addition of 5 µM (−) isoproterenol. After 30 min incubation at 37° C. the medium was removed and the cellular amount of cAMP determined using the cAMP-enzyme immunoassay kit of Amersham. The $I_{50}$ is determined from a dose-response curve in duplicate.

The effect of seven purine-analogs was measured after simultaneous addition with isoproterenol.

TABLE 7

Modulation of the activity of β-adrenergic receptors by 3,5,7-trisubstituted pyrazolo[4,3-d]pyrimidines

| R5 | R7 | R3 | Effect | $I_{50}$(µM) |
|---|---|---|---|---|
| Hexylamino | (R,S)-(1-phenyl-2-hydroxyethyl)amino | Isopropyl | inhibition | 8 ± 1 |
| 3-aminopropylamino | Benzylamino | Isopropyl | inhibition | 25 ± 2 |
| (1-hydroxymethyl-2-methyl)propylamino | Benzylamino | Isopropyl | inhibition | 25 ± 2 |
| (R)-(1-hydroxymethyl)propylamino | 4-hydroxybenzyl amino | Isopropyl | 1.8-fold activation | |
| (R)-(1-hydroxymethyl)propylamino | 3-hydroxybenzyl amino | Isopropyl | 1.7-fold activation | |
| 2-aminoethylamino | Benzylamino | Isopropyl | 1.3-fold activation | |
| (S)-(1-hydroxymethyl)propylamino | (R)-hydroxy-1-phenylethylamino | Isopropyl | inactive | |
| 2-hydroxypropylamino | (R)-hydroxy-1-phenylethylamino | Isopropyl | inactive | |

As P2Y$_1$-like and A2 purinergic receptors, negatively and positively coupled to adenylate cyclase respectively, are present on rat C6 glioma it as to be determined if the modulation of the synthesis of cAMP is due to inhibition of the activation of β-adrenergic receptors by isoproterenol are due to activation of purinergic receptors.

Example 23

Effect of Novel Compounds on Proliferation of Hematopoietic Cells

Cell Separation and Cell Cultures

Cell lines: Human leukemic cell lines were obtained from the American Type Culture Collection (ATCC, Rockville, Md., USA). They were cultured in Iscove's Modified Dulbecco's Medium (IMDM) supplemented with 10% heat inactivated fetal calf serum (FCS), 200 U/ml penicillin, 200 µg/ml streptomycin and 1 µg/ml amphotericin B. Cells were cultured in a 5% $CO_2$-95% air fully humidified incubator. For effects on clonogenic output, 1000 cells/well were plated in duplicate in methylcellulose (0.9%), supplemented with 20% FCS for 14 days.

Peripheral blood mononuclear cells (PBMC): Human peripheral blood mononuclear cells were isolated by density gradient (Ficoll-Hypaque) (LSM, ICN Biomedicals Inc.). PBMC were stimulated with 5 µg/ml phytohemaglutinin A (PHA) (Sigma) during 24-48 hours in IMDM supplemented with 10% FCS at 37° C. After washing off the PHA, PBMC were incubated with interleukin-2 (IL-2) (10 U/ml) (Genzyme).

Adult Bone Marrow Cells (ABM): Bone marrow samples were obtained by sternal puncture from hematologically normal donors undergoing cardiac surgery, after obtaining informed consent according to the ethical regulations of the University of Antwerp. Cells were collected in IMDM supplemented with 10% FCS and 100 U/ml heparin and separated by density gradient as mentioned for PBMC. After washing, cells were resuspended in IMDM 10% FCS and were sorted on a FACStar (Becton Dickinson, Erembodegem, Belgium).

Cell sorting: ABM cells ($10^7$ cells/ml) were incubated with 43A1 hybridoma supernatant at a 1/10 dilution for 20 minutes at 4° C. The supernatant of the 43A1 hybridoma (immunoglobulin IgG3) was kindly donated by Dr. H. J. Bühring (University of Tübingen, Germany) and was used as a source of anti-CD34 antibodies. After washing twice in IMDM, the cells were incubated with FITC-conjugated rabbit anti-mouse IgG (1/40 dilution) for 20 min at 4° C. After washing twice cells were incubated for 10 minutes with 5 µg mouse Ig and for 15 minutes with anti-CD38-PE (20 µl/$10^6$ cells). After washing twice in IMDM, the cells were sorted on a FACStar-Plus cell sorter equipped with an water-cooled argon ion laser (INNOVA Enterprise Ion Laser) with multiple wave length outputs including UV (488 nm). Cells with low-to-medium forward and low side scatter, highly positive green (CD34) fluorescence, and an orange (CD38) fluorescence signal lower than the mean fluorescence of cells labeled with an irrelevant isotype-matched control antibody were retained as CD34$^+$CD38$^-$ cells; cells with an orange fluorescence above this threshold were retained as CD34$^+$CD38$^+$ cells.

Myeloid Colony-forming unit (CFU) assays: Direct myeloid colony formation of CD34$^+$CD38$^+$ cells was assessed in a CFU assay. These assays were initiated with 500 cells per well and plated in duplicate in methylcellulose (0.9%) supplemented with 20% FCS, 1% bovine serum albumin (BSA), $10^{-5}$ M mercaptoethanol and 10 vol. % 5637 conditioned medium of the 5637 bladder carcinoma cell line (containing G-CSF and GM-CSF), 2 U/ml erythropoietin and 30 U/ml interleukine-3 (IL-3). After 14 days of culture at 37° C. in 7.5% $O_2$ and 5% $CO_2$ in a fully humidified incubator, these cultures were scored with the microscope for colony formation. The following colony types were scored: myeloid colonies: macrophage (CFU-M), granulocyte (CFU-G), and granulocyte-macrophage (CFU-GM); erythroid colonies (BFU-E (burst-forming units, erythroid) and CFU-E); and mixed erythroid-myeloid colonies (CFU-Mix).

Pre-CFU: Pre-CFU assays were initiated by performing liquid cultures of CD34$^+$CD38$^-$ in duplicate in 96-well flat-bottomed plates in IMDM/10% FCS, 1% bovine serum albumin (BSA), and different combinations of the following cytokines: 100 U/ml IL-1, 200 U/ml IL-6, 30 U/ml IL-3 and 100 ng/ml stel cell factor (SCF). Pre-CFU cultures were initiated with 500 CD34$^+$CD38$^-$ cells/well (200 µl). After 14 days of culture at 37° C. in 7.5% O2 and 5% CO2 in a fully humidified incubator, the number of cells in each well was counted. Following this the cells were harvested, washed three times in IMDM/10% FCS, and plated in duplicate at 500 cells/well (1000 µl) in secondary methylcellulose CFU cultures as described for CFU assays.

Effect of New Compounds on Cell Proliferation

Cells were plated at 10000 per well in 200 µl IMDM medium and incubated with 0-50 µM of the novel compounds (Tab 8), by addition of drug directly to the culture medium and incubated at 37° C. for 96 hours (Tab 8). Absolute cell number was determined by addition of a known concentration Fluoresbrite microspheres (FITC) (Polysciences, Inc.). The absolute number of cells/well was calculated as: {(total number of beads added/well)/(number of beads measured)×(number of measured cells in the gate of interest)}. All analyses were performed with a FACScan (BD), using CELLQuest software (Becton Dickinson).

Response of the myeloid leukemia KG1 and T-lymphocyte leukemia Molt3 cell lines to the cytostatic effect of the novel compounds was determined using the above-mentioned standardized bead suspension that was used to determine the absolute cell number by flow cytometric (FCM) measurement. Cells were grown in the presence of increasing concentration of the novel compounds. After 96 hours of culture the concentration at which cell growth was inhibited by 50%—the 50% inhibitory concentration or IC$_{50}$—was calculated from dose-response curves (FIG. 4) and are presented in Table 8.

TABLE 8

Tested novel compounds: Structural names and IC$_{50}$ values on the different cell culture systems (lymphocytes, KG1, Molt3, CFU and pre-CFU) and on CDC2 activity in cell free system.

| Structural name | NR. | Lymphocytes IC$_{50}$ (µM) | KG1 IC$_{50}$ (µM) | Molt3 IC$_{50}$ (µM) | CFU IC$_{50}$ (µM) | Pre-CFU IC$_{50}$ (µM) | CDC2 IC$_{50}$ (µM) |
|---|---|---|---|---|---|---|---|
| 5-(3-hydroxypropylamino)-7-benzylamino-3-isopropylpyrazolo[4,3-d]pyrimidine | 7 | 9 ± 0.2 | 25 ± 4.4 | 24 ± 2.2 | | | 1 |
| 5-(3-aminopropylamino)-7-benzylamino-3-isopropylpyrazolo[4,3-d]pyrimidine | 17 | 4 ± 0.2 | 6 ± 1.0 | 9.3 ± 0.3 | 17 | 10 | 11 |
| 5-(methylthio)-7-[N-(3,4-dihydroxybenzyl-N-methyl]amino-3-isopropylpyrazolo[4,3-d]pyrimidine | 26 | 16.5 ± 0.8 | 13 ± 0.2 | 17 ± 2.9 | >50 | 86 | >100 |
| 5-(hexylamino)-7-[N-(3,4-dihydroxybenzyl-N-methyl]amino-isopropylpyrazolo[4,3-d]pyrimidine | 41 | 10 ± 2.0 | 15.3 ± 2.4 | 14 ± 3.2 | | | 1 |
| 5-(3-hydroxypropylamino)-7-[N-(3,4-dihydroxybenzyl-N-methyl]amino-isopropylpyrazolo[4,3-d]pyrimidine | 42 | 5.9 ± 2.9 | 10.7 ± 0.3 | 13 ± 2.1 | | | 2.6 |
| 5-(1-ethyl-2-hydroxyethylamino)-7-(3,4-dihydroxybenzyl)amino-3-isopropylpyrazolo[4,3-d]pyrimidine | 47 | 3 ± 1.2 | 8 ± 1.0 | 10 ± 1 | | | 1.2 |
| 5-(3-hydroxypropylamino)-7[N-(3,4-dihydroxybenzyl-N-methyl]amino-3-isopropylpyrazolo[4,3-d]pyrimidine | 50 | 15 ± 7.3 | 21 | 21 | | | |
| 5-(morpholino)-7-(1-phenyl-2-hydroxyethylamino)-3-isopropylpyrazolo[4,3-d]pyrimidine | 85 | 20 ± 7.7 | 28 ± 1.5 | 20 ± 1.3 | | | 5.5 |
| 5-(2-hydroxyethylthio)-671-phenyl-2-hydroxyethylamino-3-isopropylpyrazolo[4,3-d]pyrimidine | 96 | 8 ± 0.5 | 9 ± 0.4 | 10 ± 1.2 | | | 5.8 |
| 5-(hexylamino)-7-(1-phenyl-2-hydroxyethylamino)-3-isopropylpyrazolo[4,3-d]pyrimidine | 98 | 18 ± 1 | 5 ± 0.3 | 8 ± 0.4 | 5.4 ± 0.4 | >25 | 30 |
| 5-(5-cyanopentyl)-7-[(R,S)-(1-phenyl-2-hydroxyethyl)amino]-9-isopropylpurine | 123 | 33 ± 4.4 | 42 ± 4.8 | 42.5 ± 6 | | | 33 |
| 5-(3-hydroxypropylamino)-7-benzylthio-3-isopropylpyrazolo[4,3-d]pyrimidine | 145 | 18 ± 1.6 | 42 ± 5 | 19 ± 2 | | | >50 |
| 5-(2,3-dihydroxypropylamino)-7-[(R,S)-(1-phenyl-2-hydroxyethyl)amino]-3-isopropylpyrazolo[4,3-d]pyrimidine | 158 | 10 ± 1 | 12 ± 1 | 13.4 ± 1.4 | | | >50 |
| 5-(3-hydroxypropylamino)-7-[(R,S)-(1-phenyl-2-hydroxyethyl)amino-3-isopropylpyrazolo[4,3-d]pyrimidine | 172 | 4 ± 0.5 | 3 ± 1 | 8 ± 1.5 | >20 | >25 | >50 |
| 5-(3-aminoethylamino)-7-(3,4-dihydroxybenzyl)amino-3-isopropylpyrazolo[4,3-d]pyrimidine | 201 | 8 ± 2.2 | 12 ± 1.3 | 12 ± 1.8 | 4.5 | 1.5 | 0.5 |
| 2-(1-ethyl-2-hydroxyethylamino)-6(3,4-dihydroxybenzylamino)-9-isopropylpurine | 243 | 9 ± 6.6 | 16.5 ± 1 | 9 ± 1.2 | | | 10 |

Different response patterns were seen for the novel compounds tested, with IC$_{50}$ ranging from 3 µM to >50 µM for KG1 and from 5 µM to >50 µM for Molt3.

Clonogenic output of KG1 was tested in methylcellulose with 25 µM of some of the novel compounds. Colony output vs. control cultures without novel compound, was 16% for 26, 19% for 98.8% for 172 and 0% for 201.

PHA-stimulated lymphocytes (PBMC) were tested for their cytotoxicity as one of the normal counterparts of the cell lines. Cells were grown for 96 hours in the presence of IL-2 and different concentrations of the novel compounds and cell number was counted on the flow cytometer. The IC$_{50}$ values are shown in Table 8. Comparison between normal PHA-stimulated lymphocytes and hematopoietic cell lines shows that lymphocytes are often more sensitive to the novel compounds than cell lines, with the exception of 96, that was significantly more effective on KG1 than on normal PBMC (FIG. 5).

To determine reversibility of the effects of the novel compounds, cells were plated at 10000 per well and exposed to 0-50 µM of the compounds for the time indicated, followed by washing in phosphate-buffered saline (PBS) (Life Technologies) and reseeded into drug-free medium for 7 additional days. An identical set of cells was plated and exposed to the drugs for 7 additional days. After 7 days (168 hours), the relative cell number was assayed by flow cytometry. When KG1 cells were exposed continuously to compounds 17, 172 and 201 the IC$_{50}$ were respectively 16±1.7 µM; 7±2 µM and 16±1.3 µM (Tab. 8). However, if cells were washed free of novel compounds after 6 hours of exposure to 17, 172 and 201, there was substantial recovery of cell number as compared to control without novel.

CD34+CD38+ hematopoietic progenitors (HPC) from adult bone marrow were isolated and investigated for response to novel compounds. CD34+CD38+ cells were grown in a methylcellulose system in the presence of increasing concentrations of compounds. After 14 days, colonies were microscopically scored and $IC_{50}$ concentrations were calculated from the dose-response patterns of total colony output (Tab. 8). 26, 98, 172 were further investigated for their effect on growth of (primitive) hematopoietic progenitors. 96 and 201 were chosen as potent control. 26, 98 and 158 have low or no inhibitory activity on progenitors with $IC_{50}$>50 µM. 201 has potent inhibitory activity with an $IC_{50}$ of 8.5 µM, 201 has intermediate effect with an $IC_{50}$ of 37 µM.

Clonogenic output of CD34+CD38+HPC was also scored differentially. 26 caused no significant difference in the output of the different types of myeloid colonies. Culture with 17, 98, 172 and 201 resulted in significantly lower colony output for CFU-E, CFU-G and CFU-M, with an exception for P27 where CFU-M were not significantly decreased. No significant difference was seen for CFU-GM and CFU-MIX for tested compounds. Control semi-solid cultures with DMSO were not significantly different from the control cultures.

Pre-CFU were cultured starting from adult bone marrow CD34+CD38− cells, that had been isolated using the FCM cell sorter. Novel compounds were added at different concentrations to the primary 14-day liquid culture. $IC_{50}$ was calculated from dose-response curves from total clonogenic output after secondary methylcellulose culture (Tab. 8). Effects were in a range similar to those on CFU with an exception for 26 that was more active on pre-CFU than on CFU.

Example 24

Antimitotic Activities of CDK Inhibitors

Metaphase-arrested *Xenopus* egg extracts were prepared as described previously by Blow "*J. Cell Biol.*" 1993; 122:993 and stored in liquid nitrogen. Demembranated *Xenopus* sperm nuclei were prepared as described. by Blow & Laskey "*Cell*" 1986; 47:577. After thawing, extracts were supplemented with 25 mM phosphocreatine, 5 µg/ml creatine phosphokinase, 250 µg/ml cycloheximide, [α-$^{32}$P]dATP (for DNA synthesis assays). Demembranated sperm nuclei were added to a final sperm concentration of 3 ng/µl DNA extract and CDK inhibitor tested was then added at different concentrations. M-phase promoting factor inhibition by different CDK inhibitors was monitored 1.5 h after addition by assessing the amount of sperm nuclei that had been assembled into interphase nuclei, possessing a complete phase-dense nuclear envelope. DNA synthesis was assessed by releasing extract into interphase by the addition of 0.3 mM $CaCl_2$ and measuring the total amount of [α-$^{32}$P]dATP incorporation after 3 h by TCA co-precipitation.

At concentrations of CDK inhibitors (see Table 9) ranging from 0.1-2 µM, chromosomes remained highly condensed and no nuclear envelope was visible. At 4-6 µM and higher concentrations, interphase nuclei appeared with partially decondensed chromatin and an intact nuclear envelope. Replication was significantly inhibited at 1-5 µM CDK inhibitors tested. For the inhibition effect to become detectable, the first 15-min incubation of the interphase extract is probably sufficient.

TABLE 9

Antimitotic Activities of 3,5,7-Trisubstituted Pyrazolo[4,3-d]pyrimidine Derivatives

| SUBSTITUENT | | | Inhibition of MPF activity | Inhibition of DNA synthesis |
|---|---|---|---|---|
| R5 | R7 | R3 | $IC_{50}$ (µM) | $IC_{50}$ (µM) |
| 3-hydroxypropylamino | benzylamino | isopropyl | 1.4 | 4.2 |
| 3-hydroxypropylamino | 3-amino-4-chloroanilino | isopropyl | 0.5 | 0.4 |
| 3-hydroxypropylamino | 2-hydroxy-3-chlorobenzylamino | isopropyl | 2.6 | 3.7 |
| (R)-1-(hydroxyethyl)propylamino | 2-hydroxybenzylamino | isopropyl | 1.8 | 1.5 |
| (R)-1-(hydroxyethyl)propylamino | 2-hydroxy-3-methylabenzylamino | isopropyl | 0.5 | 0.65 |
| (R)-1-(hydroxymethyl)propylamino | 2,3-diamino-4-chlorobenzylamino | isopropyl | 0.22 | 0.3 |

Example 25

In Vitro Cytotoxic Activity of Novel Compounds

We have been using the following cell lines: HELA (human cervical carcinoma), MCF7 (human breast adenocarcinoma), NIH 3T3 (mouse fibroblasts), HOS (human osteogenic sarcoma), HL 60 (human promyelocytic leukemia), G 361 (human malignant melanoma), K562 (human erythroleukemia), CEM (human lymphoblastoid leukemia). Tested drugs were added to the cell cultures in six different concentration and kept at 37° C. and 5% $CO_2$ for three days. All cell lines were grown in DMEM medium (Gibco BRL) supplemented with 10% (v/v) fetal bovine serum and L-glutamine and maintained at 37° C. in a humidified atmosphere with 5% $CO_2$. $10^4$ cells were seeded into each well of 96 well plate, allowed to stabilize for at least 2 h and then tested compounds were added at various concentrations ranging from 200 to 0.2 µM in triplicates. Three days after drug addition Calcein AM solution (Molecular Probes) was added and let to enter the cells for 1 hour. Fluorescence of viable cells was quantified employing Fluoroskan Ascent (Microsystems). The $GI_{50}$ value, the drug concentration lethal to 50% of the tumor cells, was calculated from the obtained dose response curves (FIG. 6).

Cytotoxicity of novel compounds was tested on panel of cell lines of different histogenetic and species origin (Tab. 10). Higher activities were found in all tumor cell lines tested. Notably, the higher effectiveness of novel derivatives was also found in cell lines bearing various mutations or deletions in cell cycle associated proteins, e.g. HL-60, BT549, Hela, U2OS, MDA-MB231, and Saos2. It indicates that these substances should be equally effective in tumors with various alterations of tumor suppressor genes, namely p53, Rb, etc. Importantly, this observation distinguishes the novel compounds from flavopiridol and related compounds, as their biological activity is dependent on p53 status.

TABLE 10

Cytotoxicity of Novel Compounds for Different Cancer Cells

| SUBSTITUENT | | | CEM | B16 |
|---|---|---|---|---|
| R5 | R7 | R3 | $GI_{50}$ (μM) | $GI_{50}$ (μM) |
| 2-hydroxyethylamino | benzylamino | methyl | 45 | 47 |
| 3-hydroxypropylamino | benzylamino | methyl | 40 | 41 |
| Bis-(2-hydroxyethyl)amino | benzylamino | methyl | 35 | 40 |
| 2-aminocyclohexylamino | benzylamino | methyl | 2.3 | 3.2 |
| 4-aminocyclohexylamino | benzylamino | methyl | 1.7 | 2.5 |
| R-(1-hydroxymethyl)propylamino | benzylamino | methyl | 3.4 | 4.2 |
| R-(1-hydroxymethyl-2-methyl)propylamino | benzylamino | methyl | 2.8 | 4.3 |
| 3-aminopropylamino | benzylamino | methyl | 32 | 38 |
| 2-aminoethylamino | benzylamino | methyl | 35 | 41 |
| 2-hydroxyethylamino | 3,4-dihydroxybenzylamino | methyl | 15.5 | 18.7 |
| 2-hydroxyethylamino | 3-chloroanilino | methyl | 8.9 | 9.8 |
| 2-hydroxyethylamino | anilino | methyl | 10.2 | 12.4 |
| 2-hydroxyethylamino | 3-chloro-5-aminoanilino | methyl | 13.4 | 14.5 |
| 2-hydroxyethylamino | 3-chloro-4-carboxyanilino | methyl | 8.9 | 9.2 |
| 2-hydroxyethylamino | 3-carboxy-4-chloroanilino | methyl | 6.5 | 7.2 |
| 2-hydroxyethylamino | 3-carboxy-4-hydroxyanilino | methyl | 12.4 | 15.8 |
| 2-hydroxyethylamino | 4-bromoanilino | methyl | 8.5 | 8.6 |
| 2-hydroxyethylamino | 4-chloroanilino | methyl | 7.6 | 8.4 |
| 2-hydroxyethylamino | 3-amino-4-chloroanilino | methyl | 5.7 | 6.4 |
| 2-hydroxyethylamino | 3-chloro-4-aminoanilino | methyl | 16.2 | 17.5 |
| 2-hydroxyethylamino | 2-hydroxybenzylamino | methyl | 5.6 | 8.2 |
| 2-hydroxyethylamino | 3-hydroxybenzylamino | methyl | 9.4 | 10.2 |
| 2-hydroxyethylamino | 2-acetoxybenzylamino | methyl | 14.5 | 16.2 |
| 2-hydroxyethylamino | 3-acetoxybenzylamino | methyl | 15.4 | 16.7 |
| 2-hydroxyethylamino | 2-acetylbenzylamino | methyl | 10.8 | 9.3 |
| 2-hydroxyethylamino | 3-acetylbenzylamino | methyl | 13.5 | 14.2 |
| 2-hydroxyethylamino | 2-hydroxy-3-methoxybenzylamino | methyl | 3.5 | 4.2 |
| 2-hydroxyethylamino | 2-hydroxy-3-methylbenzylamino | methyl | 2.8 | 3.1 |
| 2-hydroxyethylamino | 2-hydroxy-3-chlorobenzylamino | methyl | 1.5 | 2.1 |
| 2-hydroxyethylamino | 2,6-dihydroxy-4-chlorobenzylamino | methyl | 1.8 | 2.5 |
| 2-hydroxyethylamino | 2,3-dihydroxy-4-methoxybenzylamino | methyl | 3.5 | 4.2 |
| 2-hydroxyethylamino | 2,5-dihydroxy-4-methoxybenzylamino | methyl | 4.2 | 3.7 |
| 2-hydroxyethylamino | 2,6-dihydroxy-4-methoxybenzylamino | methyl | 2.8 | 4.7 |
| 2-hydroxyethylamino | 2,3-dihydroxy-4-chlorobenzylamino | methyl | 2.1 | 3.2 |
| 2-hydroxyethylamino | 2,5-dihydroxy-4-chlorobenzylamino | methyl | 1.5 | 2.8 |
| 2-hydroxyethylamino | 2-amino-6-chlorobenzylamine | methyl | 5.8 | 7.2 |
| 2-hydroxyethylamino | 3-amino-4-chlorobenzylamine | methyl | 12.4 | 13.5 |
| 2-hydroxyethylamino | 2,3-diamino-4-chlorobenzylamine | methyl | 5.6 | 6.5 |
| 2-hydroxyethylamino | [(R,S)-(1-phenyl-2-hydroxyethyl)amino] | methyl | 8.9 | 9.4 |
| 2-hydroxyethylamino | [N-(3,4-dihydroxybenzyl-N-methyl]amino | methyl | 10.3 | 11.5 |
| 2-hydroxyethylamino | [(R,S-(1-phenyl-2-hydroxyethyl)amino] | methyl | 12.4 | 14.2 |
| 2-hydroxyethylamino | benzylamino | isopropyl | 25 | 37 |
| 3-hydroxypropylamino | benzylamino | isopropyl | 21 | 32 |
| Bis-(2-hydroxyethyl)amino | benzylamino | isopropyl | 25 | 38 |
| 2-aminocyclohexylamino | benzylamino | isopropyl | 14 | 28 |
| 4-aminocyclohexylamino | benzylamino | isopropyl | 1.5 | 2.3 |
| R-(1-hydroxymethyl)propylamino | benzylamino | isopropyl | 2.4 | 3.2 |
| R-(1-hydroxymethyl-2-methyl)propylamino | benzylamino | isopropyl | 2.2 | 2.3 |
| 3-aminopropylamino | benzylamino | isopropyl | 24 | 28 |
| 2-aminoethylamino | Benzylamino | isopropyl | 26 | 42 |

TABLE 10-continued

Cytotoxicity of Novel Compounds for Different Cancer Cells

| SUBSTITUENT | | | CEM | B16 |
|---|---|---|---|---|
| R5 | R7 | R3 | GI$_{50}$ (μM) | GI$_{50}$ (μM) |
| R-(1-hydroxymethyl)propylamino | 3,4-dihydroxybenzylamino | isopropyl | 9.2 | 15.7 |
| R-(1-hydroxymethyl)propylamino | 3-chloroanilino | isopropyl | 8.5 | 12.8 |
| R-(1-hydroxymethyl)propylamino | anilino | isopropyl | 13.2 | 18.4 |
| R-(1-hydroxymethyl)propylamino | 3-chloro-5-aminoanilino | isopropyl | 9.4 | 16.5 |
| R-(1-hydroxymethyl)propylamino | 3-chloro-4-carboxyanilino | isopropyl | 7.9 | 11.2 |
| R-(1-hydroxymethyl)propylamino | 3-carboxy-4-chloroanilino | isopropyl | 4.5 | 5.2 |
| R-(1-hydroxymethyl)propylamino | 3-carboxy-4-hydroxyanilino | isopropyl | 18.4 | 25.8 |
| R-(1-hydroxymethyl)propylamino | 4-bromoanilino | isopropyl | 6.5 | 9.8 |
| R-(1-hydroxymethyl)propylamino | 4-chloroanilino | isopropyl | 6.7 | 9.5 |
| R-(1-hydroxymethyl)propylamino | 3-amino-4-chloroanilino | isopropyl | 4.7 | 7.5 |
| R-(1-hydroxymethyl)propylamino | 3-chloro-4-aminoanilino | isopropyl | 12.2 | 19.6 |
| R-(1-hydroxymethyl)propylamino | 2-hydroxybenzylamino | isopropyl | 7.8 | 9.3 |
| R-(1-hydroxymethyl)propylamino | 3-hydroxybenzylamino | isopropyl | 10.5 | 12.4 |
| R-(1-hydroxymethyl)propylamino | 2-acetoxybenzylamino | isopropyl | 13.8 | 19.3 |
| R-(1-hydroxymethyl)propylamino | 3-acetoxybenzylamino | isopropyl | 18.5 | 23.7 |
| R-(1-hydroxymethyl)propylamino | 2-acetylbenzylamino | isopropyl | 11.9 | 16.3 |
| R-(1-hydroxymethyl)propylamino | 3-acetylbenzylamino | isopropyl | 11.5 | 19.1 |
| R-(1-hydroxymethyl)propylamino | 2-hydroxy-3-methoxybenzylamino | isopropyl | 3.1 | 6.2 |
| R-(1-hydroxymethyl)propylamino | 2-hydroxy-3-methylbenzylamino | isopropyl | 1.9 | 2.1 |
| R-(1-hydroxymethyl)propylamino | 2-hydroxy-3-chlorobenzylamino | isopropyl | 1.2 | 2.4 |
| R-(1-hydroxymethyl)propylamino | 2,6-dihydroxy-4-chlorobenzylamino | isopropyl | 1.6 | 2.9 |
| R-(1-hydroxymethyl)propylamino | 2,3-dihydroxy-4-methoxybenzylamino | isopropyl | 4.7 | 6.2 |
| R-(1-hydroxymethyl)propylamino | 2,5-dihydroxy-4-methoxybenzylamino | isopropyl | 3.5 | 5.7 |
| R-(1-hydroxymethyl)propylamino | 2,6-dihydroxy-4-methoxybenzylamino | isopropyl | 1.8 | 3.4 |
| R-(1-hydroxymethyl)propylamino | 2,3-dihydroxy-4-chlorobenzylamino | isopropyl | 3.1 | 5.6 |
| R-(1-hydroxymethyl)propylamino | 2,5-dihydroxy-4-chlorobenzylamino | isopropyl | 2.5 | 4.8 |
| R-(1-hydroxymethyl)propylamino | 2-amino-6-chlorobenzylamine | isopropyl | 4.6 | 8.3 |
| R-(1-hydroxymethyl)propylamino | 3-amino-4-chlorobenzylamine | isopropyl | 11.4 | 18.7 |
| R-(1-hydroxymethyl)propylamino | 2,3-diamino-4-chlorobenzylamine | isopropyl | 4.6 | 9.9 |
| R-(1-hydroxymethyl)propylamino | [(R,S)-(1-phenyl-2-hydroxyethyl)amino] | isopropyl | 7.9 | 13.7 |
| R-(1-hydroxymethyl)propylamino | [N-(3,4-dihydroxybenzyl-N-methyl]amino | isopropyl | 11.6 | 19.4 |
| R-(1-hydroxymethyl)propylamino | [N-(2-(3,4-dihydroxyfenyl)ethyl)-N-methyl]amino | isopropyl | 13.1 | 18.6 |
| 2-hydroxyethylamino | 3-chloroanilino | isopropyl | 18 | 29 |
| 3-hydroxypropylamino | 3-chloroanilino | isopropyl | 15 | 33 |
| Bis-(2-hydroxyethyl)amino | 3-chloroanilino | isopropyl | 21 | 34 |
| 2-aminocyclohexylamino | 3-chloroanilino | isopropyl | 14 | 28 |
| 4-aminocyclohexylamino | 3-chloroanilino | isopropyl | 0.5 | 1.3 |
| R-(1-hydroxymethyl)propylamino | 3-chloroanilino | isopropyl | 1.4 | 2.8 |
| R-(1-hydroxymethyl-2-methyl)propylamino | 3-chloroanilino | isopropyl | 1.2 | 1.7 |
| 3-aminopropylamino | 3-chloroanilino | isopropyl | 15 | 18 |
| 2-aminoethylamino | 3-chloroanilino | isopropyl | 16 | 22 |
| R-(1-hydroxymethyl-2-methyl)propylamino | 3,4-dihydroxybenzylamino | isopropyl | 4.2 | 5.8 |
| R-(1-hydroxymethyl-2-methyl)propylamino | anilino | isopropyl | 2.5 | 3.6 |
| R-(1-hydroxymethyl-2-methyl)propylamino | 3-chloro-5-aminoanilino | isopropyl | 9.5 | 14.5 |
| R-(1-hydroxymethyl-2-methyl)propylamino | 3-chloro-4-carboxyanilino | isopropyl | 7.6 | 12.4 |
| R-(1-hydroxymethyl-2-methyl)propylamino | 3-carboxy-4-chloroanilino | isopropyl | 5.8 | 9.1 |
| R-(1-hydroxymethyl-2-methyl)propylamino | 3-carboxy-4-hydroxyanilino | isopropyl | 2.7 | 4.2 |
| R-(1-hydroxymethyl-2-methyl)propylamino | 4-bromoanilino | isopropyl | 5.8 | 11.4 |
| R-(1-hydroxymethyl-2-methyl)propylamino | 4-chloroanilino | isopropyl | 4.1 | 5.7 |
| R-(1-hydroxymethyl-2-methyl)propylamino | 3-amino-4-chloroanilino | isopropyl | 2.9 | 4.4 |

TABLE 10-continued

Cytotoxicity of Novel Compounds for Different Cancer Cells

| SUBSTITUENT | | | CEM | B16 |
|---|---|---|---|---|
| R5 | R7 | R3 | $GI_{50}$ (μM) | $GI_{50}$ (μM) |
| R-(1-hydroxymethyl-2-methyl)propylamino | 3-chloro-4-aminoanilino | isopropyl | 2.5 | 4.8 |
| R-(1-hydroxymethyl-2-methyl)propylamino | 2-hydroxybenzylamino | isopropyl | 6.7 | 9.8 |
| R-(1-hydroxymethyl-2-methyl)propylamino | 3-hydroxybenzylamino | isopropyl | 4.9 | 8.5 |
| R-(1-hydroxymethyl-2-methyl)propylamino | 2-acetoxybenzylamino | isopropyl | 8.7 | 10.9 |
| R-(1-hydroxymethyl-2-methyl)propylamino | 3-acetoxybenzylamino | isopropyl | 12.5 | 14.6 |
| R-(1-hydroxymethyl-2-methyl)propylamino | 2-acetylbenzylamino | isopropyl | 14.5 | 18.2 |
| R-(1-hydroxymethyl-2-methyl)propylamino | 3-acetylbenzylamino | isopropyl | 8.6 | 9.4 |
| R-(1-hydroxymethyl-2-methyl)propylamino | 2-hydroxy-3-methoxybenzylamino | isopropyl | 9.7 | 9.1 |
| R-(1-hydroxymethyl-2-methyl)propylamino | 2-hydroxy-3-methylbenzylamino | isopropyl | 1.2 | 3.5 |
| R-(1-hydroxymethyl-2-methyl)propylamino | 2-hydroxy-3-chlorobenzylamino | isopropyl | 0.7 | 1.1 |
| R-(1-hydroxymethyl-2-methyl)propylamino | 2,6-dihydroxy-4-chlorobenzylamino | isopropyl | 0.4 | 1.2 |
| R-(1-hydroxymethyl-2-methyl)propylamino | 2,3-dihydroxy-4-methoxybenzylamino | isopropyl | 0.6 | 2.5 |
| R-(1-hydroxymethyl-2-methyl)propylamino | 2,5-dihydroxy-4-methoxybenzylamino | isopropyl | 1.7 | 2.5 |
| R-(1-hydroxymethyl-2-methyl)propylamino | 2,6-dihydroxy-4-methoxybenzylamino | isopropyl | 1.2 | 2.7 |
| R-(1-hydroxymethyl-2-methyl)propylamino | 2,3-dihydroxy-4-chlorobenzylamino | isopropyl | 0.9 | 1.4 |
| R-(1-hydroxymethyl-2-methyl)propylamino | 2,5-dihydroxy-4-chlorobenzylamino | isopropyl | 1.3 | 2.7 |
| R-(1-hydroxymethyl-2-methyl)propylamino | 2-amino-6-chlorobenzylamine | isopropyl | 1.5 | 2.5 |
| R-(1-hydroxymethyl-2-methyl)propylamino | 3-amino-4-chlorobenzylamine | isopropyl | 2.6 | 4.4 |
| R-(1-hydroxymethyl-2-methyl)propylamino | 2,3-diamino-4-chlorobenzylamine | isopropyl | 8.2 | 12.4 |
| R-(1-hydroxymethyl-2-methyl)propylamino | [(R,S)-(1-phenyl-2-hydroxyethyl)amino] | isopropyl | 2.6 | 4.8 |
| R-(1-hydroxymethyl-2-methyl)propylamino | [N-(3,4-dihydroxybenzyl-N-methyl]amino | isopropyl | 3.5 | 4.8 |
| R-(1-hydroxymethyl-2-methyl)propylamino | [N-(2-(3,4-dihydroxyfenyl)ethyl)-N-methyl]amino | isopropyl | 8.4 | 9.7 |

Example 26

Novel Compounds have Cytotoxic Effects for Plant Cells and Induce their Apoptosis The novel compounds have also been tested in tobacco callus bioassay for cytotoxicity (herbicidal activity) and induction of cell death. The compounds to be tested were dissolved in dimethylsulfoxide (DMSO) and the solution brought up to $10^{-3}$ M with distilled water. This tock solution was further diluted in the respective media used for the tobacco bioassay to concentration ranging from $10^{-8}$ M to $10^{-4}$ M. The final concentration of DMSO in the media did not exceed 0.2%, and therefore did not affect biological activity in the assay system used. Cytokinin-dependent tobacco callus Nicotiana tabacum L. cv. Wisconsins 38 Murashige-Skoog medium, containing per 1 liter: 4 μmol nicotinic acid, 2.4 μmol pyridoxine hydrochloride, 1.2 μmol thiamine, 26.6 μmol glycine, 1.37 μmol glutamine, 1.8 μmol myo.inositol, 30 g of sucrose, 8 g of agar, 5.37 mmol α-naphthylacetic acid and 0.5 μmol 6-benzylaminopurine. Sub cultivation was carried out every three weeks. Fourteen days before the bioassay, the callus tissue was transferred to the media without 6-benzylaminopurine. Compounds were tested with two different concentrations of 6-benzylaminopurine ($10^{-5}$ M and $10^{-6}$ M). Inhibitory growth activity was determined from the increase in fresh callus weight after four weeks of cultivation. Five replicates were prepared for each concentration tested and the entire test was repeated at least twice. Inhibitory activity was compared with growth response curve of 6-benzylaminopurine in the range from $10^{-8}$ M to $10^{-4}$ M and $IC_{50}$ was calculated for each compound for $10^{-5}$M and $10^{-6}$M of 6-benzylaminopurine (FIG. 7). FIG. 7 shows an inhibitory effect of a compound 17.

TABLE 11

Cytotoxicity of Novel Compounds for Tobacco Plant Cells Cultivated in vitro

| SUBSTITUENT | | | $10^{-5}$ M BAP | $10^{-6}$ M BAP |
|---|---|---|---|---|
| R5 | R7 | R3 | $IC_{50}$ (μM) | $IC_{50}$ (μM) |
| 2-aminocyclohexylamino | benzylamino | methyl | >50 | 48 |
| 4-aminocyclohexylamino | benzylamino | methyl | >50 | 43 |
| R-(1-hydroxymethyl)propylamino | benzylamino | methyl | >50 | 37 |
| R-(1-hydroxymethyl-2-methyl)propylamino | benzylamino | methyl | >50 | 28 |
| 3-aminopropylamino | benzylamino | methyl | >50 | 45 |
| 2-aminoethylamino | benzylamino | methyl | >50 | >50 |
| 2-aminocyclohexylamino | benzylamino | isopropyl | >50 | 36 |
| 4-aminocyclohexylamino | benzylamino | isopropyl | >50 | 32 |
| R-(1-hydroxymethyl)propylamino | benzylamino | isopropyl | >50 | 28 |
| R-(1-hydroxymethyl-2-methyl)propylamino | benzylamino | isopropyl | >50 | 14 |
| 3-aminopropylamino | benzylamino | isopropyl | >50 | 48 |
| 2-aminoethylamino | benzylamino | isopropyl | >50 | >50 |
| R-(1-hydroxymethyl)propylamino | 3-chloroanilino | isopropyl | 45 | 5.8 |
| R-(1-hydroxymethyl)propylamino | anilino | isopropyl | 48 | 6.2 |
| R-(1-hydroxymethyl)propylamino | 3-chloro-5-aminoanilino | isopropyl | 36 | 2.8 |
| R-(1-hydroxymethyl)propylamino | 3-chloro-4-carboxyanilino | isopropyl | >50 | 12.8 |
| R-(1-hydroxymethyl)propylamino | 3-carboxy-4-chloroanilino | isopropyl | 28 | 1.5 |
| R-(1-hydroxymethyl)propylamino | 3-carboxy-4-hydroxyanilino | isopropyl | >50 | >50 |
| R-(1-hydroxymethyl)propylamino | 4-bromoanilino | isopropyl | 38 | 4.3 |
| R-(1-hydroxymethyl)propylamino | 4-chloroanilino | isopropyl | 35 | 3.9 |
| R-(1-hydroxymethyl)propylamino | 3-amino-4-chloroanilino | isopropyl | 26 | 1.5 |
| R-(1-hydroxymethyl)propylamino | 3-chloro-4-aminoanilino | isopropyl | 48 | 8.7 |
| R-(1-hydroxymethyl)propylamino | 2-acetoxybenzylamino | isopropyl | 45 | 12.4 |
| R-(1-hydroxymethyl)propylamino | 3-acetoxybenzylamino | isopropyl | >50 | 28.7 |
| R-(1-hydroxymethyl)propylamino | 2-hydroxy-3-methoxybenzylamino | isopropyl | >50 | 14.8 |
| R-(1-hydroxymethyl)propylamino | 2-hydroxy-3-methylbenzylamino | isopropyl | >50 | 12.3 |
| R-(1-hydroxymethyl)propylamino | 2-hydroxy-3-chlorobenzylamino | isopropyl | 46 | 6.7 |
| R-(1-hydroxymethyl)propylamino | 2-amino-6-chlorobenzylamine | isopropyl | >50 | 29.7 |
| R-(1-hydroxymethyl)propylamino | 3-amino-4-chlorobenzylamine | isopropyl | 25.7 | 1.3 |
| R-(1-hydroxymethyl)propylamino | 2,3-diamino-4-chlorobenzylamine | isopropyl | 49 | 8.3 |
| 2-aminocyclohexylamino | 3-chloroanilino | isopropyl | >50 | 28 |
| 4-aminocyclohexylamino | 3-chloroanilino | isopropyl | >50 | 25 |
| R-(1-hydroxymethyl)propylamino | 3-chloroanilino | isopropyl | >50 | 23 |
| R-(1-hydroxymethyl-2-methyl)propylamino | 3-chloroanilino | isopropyl | >50 | 11 |
| 3-aminopropylamino | 3-chloroanilino | isopropyl | >50 | 45 |
| 2-aminoethylamino | 3-chloroanilino | isopropyl | >50 | 48 |
| R-(1-hydroxymethyl-2-methyl)propylamino | anilino | isopropyl | 42 | 4.8 |
| R-(1-hydroxymethyl-2-methyl)propylamino | 3-chloro-5-aminoanilino | isopropyl | 38 | 4.2 |
| R-(1-hydroxymethyl-2-methyl)propylamino | 3-chloro-4-carboxyanilino | isopropyl | 26 | 1.4 |
| R-(1-hydroxymethyl-2-methyl)propylamino | 3-carboxy-4-chloroanilino | isopropyl | >50 | 9.6 |
| R-(1-hydroxymethyl-2-methyl)propylamino | 3-carboxy-4-hydroxyanilino | isopropyl | 18 | 1.2 |
| R-(1-hydroxymethyl-2-methyl)propylamino | 4-bromoanilino | isopropyl | >50 | >50 |
| R-(1-hydroxymethyl-2-methyl)propylamino | 4-chloroanilino | isopropyl | 24 | 2.3 |
| R-(1-hydroxymethyl-2-methyl)propylamino | 3-amino-4-chloroanilino | isopropyl | 25 | 1.8 |
| R-(1-hydroxymethyl-2-methyl)propylamino | 3-chloro-4-aminoanilino | isopropyl | 16 | 0.9 |
| R-(1-hydroxymethyl-2-methyl)propylamino | 2-acetoxybenzylamino | isopropyl | 38 | 4.2 |
| R-(1-hydroxymethyl-2-methyl)propylamino | 3-acetoxybenzylamino | isopropyl | 36 | 8.5 |
| R-(1-hydroxymethyl-2-methyl)propylamino | 2-hydroxy-3-methoxybenzylamino | isopropyl | >50 | 21.6 |
| R-(1-hydroxymethyl-2-methyl)propylamino | 2-hydroxy-3-methylbenzylamino | isopropyl | >50 | 10.7 |
| R-(1-hydroxymethyl-2-methyl)propylamino | 2-hydroxy-3-chlorobenzylamino | isopropyl | >50 | 9.4 |
| R-(1-hydroxymethyl-2-methyl)propylamino | 2-amino-6-chlorobenzylamine | isopropyl | 38 | 3.7 |

TABLE 11-continued

Cytotoxicity of Novel Compounds for Tobacco Plant Cells Cultivated in vitro

| | SUBSTITUENT | | $10^{-5}$ M BAP | $10^{-6}$ M BAP |
|---|---|---|---|---|
| R5 | R7 | R3 | IC$_{50}$ (µM) | IC$_{50}$ (µM) |
| R-(1-hydroxymethyl-2-methyl)propylamino | 3-amino-4-chlorobenzylamine | isopropyl | >50 | 19.4 |
| R-(1-hydroxymethyl-2-methyl)propylamino | 2,3-diamino-4-chlorobenzylamine | isopropyl | 15.6 | 0.4 |

Table 11 shows the results of inhibitory activity of novel compounds on growth of tobacco cells cultivated in vitro. Most of the 3,5,7-trisubstituted pyrazolo[4,3-d]pyrimidine derivatives showed marked inhibitory activity on in vitro growth. Furthermore, these compounds are able to induce apoptosis in plants cells (are able to kill plant cells) and induce strong antimitotic activities (see FIG. 8). The results presented here clearly show that the novel compounds exhibit herbicidal activity.

Example 27

Induction of Apoptosis by Novel Compounds in Plant Cells

Seeds of field bean (*Vicia faba* L.) were germinated at 25° C. in Hoagland solution. Seedlings with about 2-cm long main roots were treated with new cdk inhibitors at concentration from 20-300 µM for various time periods of 2, 6, 12, 24, and 48 h.

Antibodies

CDC-2 was detected with rabbit polyclonal Ab prepared against to a peptide (RITARGALEHEYFKDIK) corresponding to the last 16 amino acids of cdc2Ms (Hirt et al., 1991) as described in Bögre et al., (1997). Monoclonal antibody MPM-2 against phosphorylated epitope in mitotic cells was kindly provided by Dr. P. Rao (University of Texas, Texas Medical Center, Houston). Microtubular structures were detected with mouse monoclonal antibody DmlA (Sigma) against α-tubulin, or with rabbit affinity purified antibody against α,β-tubulin heterodimer. The γ-tubulin was detected with mouse monoclonal antibody TU-31, or with affinity purified rabbit polyclonal antibody (Nováková et al.: Cell Motil. Cytoskel. 33, 1996: 38-51). Fluorescein isothiocyanate (FITC) and indocarbocyanate (Cy3)-conjugated anti-mouse and anti-rabbit antibodies were from Jackson Immunoresearch Laboratories (West Grove, Pa., USA). Anti-mouse antibody conjugated with alkaline phosphatase was from Promega Biotec (Madison, Va., USA).

Immunofluorescence Staining

Root tips were fixed in 3.7% paraformaldehyde in microtubule stabilizing buffer (MTSB; 100 mM PIPES, 1 mM MgSO$_4$, 2.0 mM EGTA, pH 6.9) for 1 hr. After washing in MTSB root tips were digested for 30 min in 1% Cellulysin (Calbiochem) in MTSB with protease inhibitors (0.3 mM leupeptin, 1.0 mM phenylmethyl sulphonyl fluoride). After washing, root tips were squashed on poly-L-lysine coated slides. Cells were thereafter fixed for 10 min in 100% methanol at −20° C. followed by 30 min extraction with 1% Triton X-100 in MTSB at room temperature. After washing in PBS slides were incubated with primary antibodies for 1 h at room temperature or overnight at 4° C. All antibody dilutions were made with 2% BSA in PBS. Antibody TU-31, was used as undiluted supernatant, antibodies DMA1 and MPM-2 were used at dilution 1:500. Polyclonal antibodies against α,β-tubulin heterodimer and g tubulin were at dilution 1:5. After washing in PBS slides were incubated for 45 mM at root temperature with secondary fluorochrome conjugated antibodies diluted 1:200. After washing out of secondary antibody samples were stained for 10 min with 4,6-diamidino-2-phenylindol (DAPI) in PBS (1 um/mg). Slides were mounted in MOWIOL 4-88 (Calbiochem, Lucerne, Switzerland) and examined with Olympus BX 60 microscope equipped with a 100×1.4 standard objective, epi-illumination and a 35 mm camera.

Labeling of DNA Strand Breaks with BrdUTP

Fixation, digestion with enzymes, squashing to poly-L lysine slides and postfixation with methanol were the same as described for immunofluorescence. Then reaction containing bromo deoxyuridine triphosphate (Sigma) and terminal deoxynucleotidyl transferase (Boehringer) was applied to slides and enzyme reaction proceeded 40 min at 37° C. After washing in PBS buffer slides were incubated with anti-BrdU MoAb solution (Amersham, Buskinhamshire, UK) and with secondary anti-mouse FITS conjugated Ab (Sigma). For double labeling, after incubation with anti-Brdu Ab slides were incubated with primary Ab Against cdc-2 or anti-£-tubulin mo Ab. Slides were stained for DNA in DAPI, mounted and observed as described for immunofluorescence.

DNA Extraction and Electrophoresis.

Root tips were homogenized in liquid nitrogen and incubated in CTAB lysis buffer (2% CTAB w/v, 0.1 M Tris, 20 mM EDTA, pH 8.0, 0.2% β-mercaptoethanol) at 65° C. for 5 minutes. The samples were then extracted chloroform: isoamyl alcohol, and aqueous phase precipitated with ethanol. The DNA samples were resuspended in TE buffer, electrophoresis was run 40 min at voltage 2 V/cm.

Observations

Novel derivatives were used, to study the role on CDKs in cell cycle progression and microtubule organization in *Vicia faba* root tip cells. The tested drugs inhibited the activity of immunopurified *Vicia faba* and alfalfa cdc2-kinase. The transcript levels of an A- and B-type cyclin, as well as of the cdc2 genes, declined in treated root tips, while the mRNA level of a D-type cyclin gene was not affected. An observed transient arrest at the G1/S and G2/M regulatory points indicated that inhibition of the cdc2-kinase had an effect on both transitions. In contrast to the regular bipolar spindle in untreated cells, in drug treated metaphase cells abnormally short and dense kinetochore microtubule fibers were observed. These microtubules were randomly arranged in the vicinity of the kinetochores and connected the chromosomes. Thus, the chromosomes were not aligned on the metaphase plate but were arranged in a circle, with kinetochores pointing inwards and chromosome arms pointing outwards. γ-Tubulin, which plays a role in microtubule nucleation, also localized to the centre on the monopolar spindle. The observed abnormalities in mitosis, after inhibition of CDC2-kinase by specific CDK drugs, suggest a role for this enzyme in regulating some of the steps leading to a bipolar spindle structure. These compounds also induce apoptosis of different plant cells in vivo (FIG. 8).

Example 28

Inhibition of Senescence by Novel Compounds

In this example, human diploid fibroblasts (HCA cells of various passage levels: passage 25—designated HCA25; passage 45—designated HCA45; passage 80—designated HCA80) were stained for β-galactosidase activity. The medium present on cultured cells was removed, the cells were washed twice in PNS, and fixed in 2-3 ml of fixing solution comprised of a 2% formaldehyde and 0.2% glutaraldehyde in PBS. The cells were incubated at room temperature for 5 minutes, then washed twice with PBS. The cells were then incubated at 37° C. (without $CO_2$) for 1 to 16 hours in 2-3 ml of a solution comprising potassium ferricyanide (5 mM), potassium ferrocyanide (5 mM), $MgCl_2$ (2 mM), X-gal (5-bromo-4-chloro-3-indolyl-β-D-galactopyranoside) (1 mg/ml), in citric/phosphate buffer, pH 6.0) Following this incubation period, the cell samples were observed in order to detect the presence of blue cells, indicating that X-gal had been cleaved (positively senescent cells). In this experiment, senescent cells, but not other cells were stained blue due to the action of β-galactosidase on the substrate (FIG. 9).

TABLE 12

Efect of Novel Compound. on Number of Senescent Cells in Culture of Human Fibroblasts

| SUBSTITUENT | | | SENESCENT CELLS (%) | | |
|---|---|---|---|---|---|
| R5 | R7 | R3 | HCA25 | HCA45 | HCA80 |
| CONTROL | | | 3 | 3 | 36 |
| 2-hydroxyethylamino | 3-chloroanilino | isopropyl | 4 | 4 | 38 |
| 4-aminocyclohexylamino | 3-chloroanilino | isopropyl | 4 | 5 | 35 |
| chloro | 3-chloroanilino | isopropyl | 3 | 4 | 33 |
| H | 3-chloroanilino | isopropyl | 5 | 3 | 31 |
| H | 3-chloroanilino | H | 5 | 5 | 24 |
| H | 3,4-dihydroxybenzylamino | H | 4 | 6 | 29 |
| H | anilino | H | 5 | 6 | 25 |
| H | 3-chloro-5-aminoanilino | H | 3 | 4 | 26 |
| H | 3-chloro-4-carboxyanilino | H | 2 | 5 | 26 |
| H | 3-carboxy-4-chloroanilino | H | 2 | 4 | 21 |
| H | 3-carboxy-4-hydroxyanilino | H | 3 | 5 | 29 |
| H | 4-bromoanilino | H | 4 | 4 | 28 |
| H | 4-chloroanilino | H | 3 | 6 | 27 |
| H | 3-amino-4-chloroanilino | H | 3 | 3 | 21 |
| H | 3-chloro-4-aminoanilino | H | 4 | 3 | 26 |
| H | 2-hydroxybenzylamino | H | 3 | 3 | 18 |
| H | 3-hydroxybenzylamino | H | 4 | 3 | 28 |
| H | 2-acetoxybenzylamino | H | 5 | 6 | 31 |
| H | 3-acetoxybenzylamino | H | 4 | 5 | 28 |
| H | 2-acetylbenzylamino | H | 3 | 5 | 28 |
| H | 3-acetylbenzylamino | H | 3 | 6 | 29 |
| H | 2-hydroxy-3-methoxybenzylamino | H | 3 | 3 | 20 |
| H | 2-hydroxy-3-methylbenzylamino | H | 2 | 3 | 17 |
| H | 2-hydroxy-3-chlorobenzylamino | H | 3 | 3 | 18 |
| H | 2,6-dihydroxy-4-chlorobenzylamino | H | 2 | 3 | 21 |
| H | 2,3-dihydroxy-4-methoxybenzylamino | H | 3 | 4 | 23 |
| H | 2,5-dihydroxy-4-methoxybenzylamino | H | 4 | 5 | 23 |
| H | 2,6-dihydroxy-4-methoxybenzylamino | H | 2 | 2 | 18 |
| H | 2,3-dihydroxy-4-chlorobenzylamino | H | 3 | 3 | 21 |
| H | 2,5-dihydroxy-4-chlorobenzylamino | H | 4 | 3 | 21 |
| H | 2-amino-6-chlorobenzylamine | H | 3 | 3 | 16 |
| H | 3-amino-4-chlorobenzylamine | H | 4 | 5 | 21 |
| H | 2,3-diamino-4-chlorobenzylamine | H | 3 | 3 | 18 |
| H | [(R,S)-(1-phenyl-2-hydroxyethyl)amino] | H | 4 | 5 | 23 |
| H | [N-(3,4-dihydroxybenzyl-N-methyl]amino | H | 4 | 4 | 22 |
| H | [N-(2-(3,4-dihydroxyfenyl)ethyl)-N-methyl]amino | H | 3 | 5 | 24 |

As shown in Table 12 with increasing numbers of passages, the staining became darker. For the oldest cells, there were only blue cells ranging from a bright blue to an almost opaque color. Trisubstituted pyrazolo[4,3-d]pyrimidines were not active in delaying senescence and from this reason the results are not presented in detail. On the other hand mono- and disubstituted pyrazolo[4,3-d]pyrimidine derivatives were very affective retaining much lower level of senescent cells after 80 passages. Substitution at R7 was the most effective from all possible substitutions of the pyrazolo[4,3-d]pyrimidine ring.

Example 29

Novel Compounds Induce Apoptosis in Tumor Cells

For detection of apoptotic versus necrotic mode of cell death, two independent methods were employed: assessment of morphology by fluorescence microscopy and analysis of DNA fragmentation by flow cytometry using the TUNEL technique.

Determination of Apoptosis and Cell Cycle Distribution

Microscopy: Nuclear morphology of the cells was analyzed with the fluorochromes Hoechst 33342 ($\lambda_{Ex}$ max 346 nm; $\lambda_{Em}$ max 460 nm) (Sigma) prepared in phosphate-buffered saline (PBS at 0.1 mg/ml, added to the culture medium at a final concentration of 2 µg/ml and ethidium homodimer (EB) ($\lambda_{Ex}$ max 540 nm; $\lambda_{Em}$ max 625 nm) (Sigma) prepared in PBS at 100 µg/ml and added to the culture medium at a final concentration of 2 µg/ml (Lizard, 1995). Hundred cells were counted for each sample and percentage of apoptosis was determined.

TdT-mediated dUTP nick end labeling (TUNEL): Control and novel compound-treated cell cultures were washed with PBS and fixed in 1% buffered formaldehyde (pH 7.4) for 15 minutes on ice. After washing in PBS, cells were permeabilized in 70% cold (−20° C.) ethanol and transferred to 4° C. for at least 1 hour. After rehydratation in PBS, cells were labeled with 50 µl/well TUNEL reaction mixture (Boehringer Mannheim). Cells were incubated in this solution at 37° C. for 40 minutes, washed in PBS and resuspended in 500 µl PBS containing 5 µg/ml EB and 0.1% RNAse. After 30 minutes of incubation at 4° C., green (FITC-dUTP) and red (EB-DNA) fluorescence of individual cells was measured on a FACscan flow cytometer (Gorczyca, 1993). Negative control (fixed and permeabilized cells incubated with 50 µl label solution per well without terminal transferase, instead of TUNEL reaction mixture) and positive control (fixed and permeabilized cells incubated with DNase I (100 µg/ml) that induces DNA strand breaks) were included in each experimental set-up.

Apoptosis and cell cycle analysis by FACS: Cells ($1.10^6$/ml) were cultured in 6-well plates with or without 70 µM concentration of OC derivatives at 37° C. and 5% $CO_2$ for 3-24 hours. Following the incubation cells were pelleted, washed in Hank's buffered salt solution and fixed in 96% ethanol overnight at ±20° C. Low molecular weight apoptotic DNA was extracted in citrate buffer and RNA was cleaved by RNA-se (50 µg/ml). The DNA was stained by ethidium bromide and the cells were analyzed by flow-cytometry using a 488 nm single beam laser (Becton Dickinson).

Pro-Apoptotic Effect of New Compounds

Fluorescence microscopy analysis of apoptosis and necrosis: Cell cultures treated with different doses of novel compounds were examined microscopically for apoptosis. Apoptotic cells exhibit a very bright Hoechst 33342 fluorescence, while viable cells display a very faint fluorescence. Late apoptotic cells or secondarily necrotic cells display a fragmented nucleus with bright red ethidium bromide fluorescence. Primary necrotic cells show a red fluorescence and do not have fragmented nuclei. An illustration of these different features can be found in FIG. 9 (MCF-7-cell line incubated with compound 98).

FIG. 10 shows the result of microscopic examination of KG1 cells incubated with 98, 172 and 201. Viable, apoptotic, necrotic (=primary necrosis, not following apoptosis) and secondarily necrotic cells (=late apoptosis, evolving to necrosis) were scored differentially after 6, 12, 24, 48 and 72 hours of exposure to novel compounds. For the three products a different apoptosis-inducing pattern could be observed. Apoptosis induction occurs fast after incubation with 172 and 201 but slower after incubation with 98.

low cytometric detection of apoptosis and cell cycle analysis: The induction of apoptotic death of MCF-7 cells by the novel compounds was confirmed using the TUNEL reaction technique (FIG. 9). Initial phase contrast microscopy examinations indicated that the CDKIs treated MCF-7 line exhibit typical morphological features of apoptotic cells and this was later confirmed by electron microscopy on CEM cells (FIG. 10). Corresponding results were obtained from flow cytometric analysis of the DNA content in CEM cells treated with various cytokinin derivatives (FIG. 11). Extensive apoptosis of tumor cells, measured as a percentage of sub-Go/G1, was initiated in the treated cells as early as 6 hours after the treatment. The distribution of cells within the cell cycle showed an early disappearance of G2/M and S-phase cells in the treated cells (FIG. 11). Further experiments were designed to manipulate the apoptotic process in order to elucidate the mechanisms of cell death. These results indicates that inhibition of DNA transcription/protein translation, by the specific inhibitors actinomycin D and cycloheximide respectively, does not influence synthetic CDKIs induced apoptosis. However, both the inactivation of serine/threonine phosphatases by ocadaic acid or the inhibition of caspases by specific peptide YVAD, inhibited CDK inhibitor triggered apoptosis. Nonetheless the down regulation of poly(ADP-ribose) polymerase (PARP) activity by specific inhibitor, 3-aminobenzamide, did not influence the apoptotic process. Apoptosis triggered by synthetic CDKIs was accompanied by the dephosphorylation of the Rb protein (110 kDa) and the appearance of the hypocoincident form of Rb (105 kDa), which was later cleaved to a 40 kDa immunoreactive Rb fragment and rapidly degraded (not shown). Since the cleavage of lamin B and PARP was also detected we assume that activated caspases digested those proteins.

Exposure to 201 demonstrates apoptosis detected already after 6 hours of incubation. After 6 and 12 hours of incubation the apoptotic population seems mainly to evolve from S phase. Apoptotic cells in $G_0$-G1 phase increase with time after 24 hours. No significant difference was detected between control and the non-apoptotic population in the incubated culture.

Example 30

Immunosuppressive Activity

One of the most important parameters of specific cellular immunity is proliferative response of lymphocytes to antigens or polyclonal mitogens. The majority of normal mammalian peripheral lymphocytes comprise resting cells. Antigens or nonspecific polyclonal mitogens have the capacity to activate lymphoid cells and this is accompanied by dramatic changes of intracellular metabolism (mitochondrial activity, protein synthesis, nucleic acids synthesis, formation of blastic cells and cellular proliferation). Compounds with ability to selectively inhibit lymphocyte proliferation are potent immunosuppressants. Variety of in vitro assays was developed to measure proliferative response of lymphocytes. The most commonly used is $^3$H-thymidine incorporation method.

During cell proliferation, DNA has to be replicated before the cell is divided into two daughter cells. This close association between cell doublings and DNA synthesis is very attractive for assessing cell proliferation. If labeled DNA precursors are added to the cell culture, cells that are about to divide incorporate the labeled nucleotide into their DNA. Traditionally, those assays usually involve the use of radio labeled nucleosides, particularly tritiated thymidine ([$^3$H]-TdR). The amount of [$^3$H]-TdR incorporated into the cellular DNA is quantified by liquid scintillation counting.

Human heparinized peripheral blood was obtained from healthy volunteers by cubital vein punction. The blood was diluted in PBS (1:3) and mononuclear cells were separated by centrifugation in Ficoll-Hypaque density gradient (Pharmacia, 1.077 g/ml) at 2200 rpm for 30 minutes. Following centrifugation, lymphocytes were washed in PBS and resuspended in cell culture medium (RMPI 1640, 2 mM glutamine, 100 U/ml penicillin, 100 µg/ml streptomycin, 10% fetal calf serum and sodium bicarbonate).

The cells were diluted at target density of 1.100.000 cells/ml were added by pipette (180 µl) into 96/well microtiter plates. Four-fold dilutions of the intended test concentration were added at time zero in 20 µl aliquots to the microtiter plate wells. Usually, test compound was evaluated at six 4-fold dilutions. In routine testing, the highest well concentration was 266.7 µM. All drug concentrations were examined in duplicates. All wells with exception of unstimulated controls were activated with 50 µl of concanavalin A (25 µg/ml). Incubations of cells with test compounds lasted for 72 hours at 37° C., in 5% $CO_2$ atmosphere and 100% humidity. At the end of incubation period, the cells were assayed by using the [$^3$H]-TdR:

Cell cultures were incubated with 0.5 µCi (20 µl of stock solution 500 µCi/ml) per well for 6 hours at 37° C. and 5% $CO_2$. The automated cell harvester was used to lyse cells in water and adsorb the DNA onto glass-fiber filters in the format of microtiter plate. The DNA incorporated [$^3$H]-TdR was retained on the filter while unincorporated material passes through. The filters were dried at room temperature overnight, sealed into a sample bag with 10-12 ml of scintillant. The amount of [$^3$H]-TdR present in each filter (in cpm) was determined by scintillation counting in a Betaplate liquid scintillation counter. The effective dose of immunosuppressant (ED) was calculated using the following equation: ED= ($CCPM_{drug\ exposed\ well}$/mean $CCPM_{control\ wells}$)×100%. The $ED_{50}$ value, the drug concentration inhibiting proliferation of 50% of lymphocytes, was calculated from the obtained dose response curves.

To evaluate immunosuppressive activity of substituted adenines, their ability to inhibit polyclonal mitogen induced proliferation of normal human lymphocytes was analyzed (Tab. 13). Our data demonstrate that these compounds have only marginal activity on $^3$H-thymidine incorporation, nonetheless, they efficiently inhibit proliferation of activated lymphocytes. Effective immunosuppressive dose of new derivatives under in vitro conditions was close to 1-20 µM.

TABLE 13

Immunosupressive activity of novel derivatives

| SUBSTITUENT | | | Human lymphocytes |
|---|---|---|---|
| R5 | R7 | R3 | $ED_{50}$ (µM) |
| 2-hydroxyethylamino | benzylamino | methyl | 34 |
| 3-hydroxypropylamino | benzylamino | methyl | 28 |
| Bis-(2-hydroxyethyl)amino | benzylamino | methyl | 25 |
| 2-aminocyclohexylamino | benzylamino | methyl | 1.2 |
| 4-aminocyclohexylamino | benzylamino | methyl | 1.5 |
| R-(1-hydroxymethyl)propylamino | benzylamino | methyl | 9.5 |
| R-(1-hydroxymethyl-2-methyl)propylamino | benzylamino | methyl | 6.5 |
| 3-aminopropylamino | benzylamino | methyl | 12.4 |
| 2-aminoethylamino | benzylamino | methyl | 14.7 |
| 2-hydroxyethylamino | benzylamino | isopropyl | 27 |
| 3-hydroxypropylamino | benzylamino | isopropyl | 21 |
| Bis-(2-hydroxyethyl)amino | benzylamino | isopropyl | 16 |
| 2-aminocyclohexylamino | benzylamino | isopropyl | 0.8 |
| 4-aminocyclohexylamino | benzylamino | isopropyl | 1.1 |
| R-(1-hydroxymethyl)propylamino | benzylamino | isopropyl | 4.5 |
| R-(1-hydroxymethyl-2-methyl)propylamino | benzylamino | isopropyl | 6.5 |
| 3-aminopropylamino | benzylamino | isopropyl | 9.8 |
| 2-aminoethylamino | Benzylamino | isopropyl | 11.5 |
| 2-hydroxyethylamino | 3-chloroanilino | isopropyl | 17 |
| 3-hydroxypropylamino | 3-chloroanilino | isopropyl | 12 |
| Bis-(2-hydroxyethyl)amino | 3-chloroanilino | isopropyl | 7 |
| 2-aminocyclohexylamino | 3-chloroanilino | isopropyl | 0.2 |
| 4-aminocyclohexylamino | 3-chloroanilino | isopropyl | 0.5 |
| R-(1-hydroxymethyl)propylamino | 3-chloroanilino | isopropyl | 1.8 |
| R-(1-hydroxymethyl-2-methyl)propylamino | 3-chloroanilino | isopropyl | 3.2 |
| 3-aminopropylamino | 3-chloroanilino | isopropyl | 4.5 |
| 2-aminoethylamino | 3-chloroanilino | isopropyl | 6.7 |

Example 31

Antiviral Activity

The activity of the compounds against HIV-1- and HIV-2-induced cytopathicity was examined in human lymphocyte MT-4 cells. The cells (300 000 cells/ml) were infected with 100 $CCID_{50}$ (1 $CCID_{50}$ is a virus quantity which causes cytopathicity effect in 50% of the cells under the experimental conditions) of HIV-1 or HIV-2 and added to 200 µl wells of a microtiter plate containing different dilutions of the tested compounds. The infected cell cultures were incubated at 37° C. for 5 days in a humidified $CO_2$ incubator. The cytopathicity of the virus was examined by determination of MT-4 cell viability by trypan blue dye staining. The results are summarized in Tab. 14 with comparison on the prototype compounds.

Table 14 also shows the results of activity testing of novel compounds against MSV-induced transformation in murine embryo fibroblast C3H/3T3 cells. The cells were seeded in 1-ml-wells of 48-well plates and exposed to 80 PFU (plaque forming units) for 60-90 min. The virus was subsequently removed and culture medium containing appropriate concentrations of the tested compounds was added (1 ml per well). At day 6-post infection, MSV-induced transformation of the cell culture was examined microscopically. The results are summarized in Table 14 in comparison with the data on the prototype compounds.

TABLE 14

Anti-retroviral Activity of Novel Compounds Substituted at R9 by PMP (N-(2-phosphonomethoxypropyl)group) or PME (N-(2-phosphonomethoxyethyl)derivative) (μg/ml) (R2 = $NH_2$). IC50 values (μg/ml).

|  | HIV-1 | | | HIV-2 | |
|---|---|---|---|---|---|
| R3 | MSV | MT-4 | CEM | MT-4 | CEM |
| PME-derivatives | | | | | |
| Amino | 0.6 | 2.67 | 6.9 | ND | ND |
| Cyclohexylamino | 0.26 | 5.7 | >20 | 4.8 | >20 |
| Cyclobutylamino | 1.5 | 50 | >20 | 49 | >20 |
| Cyclopentylamino | 1.3 | 47 | >20 | 45 | >20 |
| 3-chloroanilino | 1.8 | 56 | >20 | 57 | >20 |
| 3-carboxy-4-chloroanilino | 0.9 | 45 | >20 | 32 | >20 |
| PMP-derivatives | | | | | |
| Cyclobutylamino | 3.78 | 3.4 | 4.5 | 5.8 | 8.5 |
| Cyclopentylamino | 2.54 | 3.2 | 4.1 | 4.6 | 8.3 |
| 3-chloroanilino | 6.32 | 10.1 | >20 | 11.2 | >20 |
| 3-carboxy-4-chloroanilino | 1.37 | 2.1 | 5.2 | 3.2 | 7.8 |

Most of the PMP (N-(2-phosphonomethoxypropyl)derivative) and PME (N-(2-phosphonomethoxyethyl)derivative) compounds of the formula I showed marked anti-HIV activity in vitro. HIV-1 and HIV-2 did not differ in their sensitivity to the test compounds. (R)-PMP compounds were markedly inhibitory to retroviruses at 2-3 μg/ml and not toxic to the cells at 100 μg/ml. Its selectivity index (ratio cytotoxic dose/antivirally active dose) proved superior over that of the prototype compound PME. The (S)-enantiomer of PME was devoid of marked anti-retroviral activity. (R) —PMPD were exquisitely inhibitory to retrovirus replication (EC50 0.01-0.1 μg/ml) and not toxic to the cells at 100 μg/ml. It proved superior over PMEA and other prototype compounds in terms of both antiviral activity and lack of toxicity. It selectivity index was higher than 2000 for HIV-1 and HIV-2.

Example 32

Induction of Tumor Suppressor p53 in Cancer Cells

Cell Cultures and Treatment

Cell lines established from the human cervical carcinoma (HeLa), human breast carcinoma (MCF-7, BT549 and BR474), human osteosarcoma (HOS), human colon carcinoma (HT29), murine fibroblasts (T221acZ) and the human melanoma (Arn8) cell lines were cultured in Dubecco's Modified Eagle Medium (DMEM) supplemented with 10% fetal bovine serum. Tested compounds were added from 50 mM stock solution in dimethyl-sulphoxide (DMSO) into the culture medium at final concentration 20 μM. Control cells received an equivalent volume of DMSO.

Analysis of p53-Dependent Transcriptional Activity

β-galactosidase activity of human melanoma cell line Arn8 and murine fibroblasts cell line Arn8 and murine fibroblasts cell line T221acZ (both stabile transfected with a p53-responsive reporter construct pRGCΔfoslacZ) (Frebung et al., Cancer Res., 52, 1992-6976) was determined. For the determination of total β-galactosidase activity, cells were lysed by 3 freeze-thaw cycles in 0.25 M Tris pH 7.5, and lysates were assayed as described by Sambrook et al., Mol. cloning, New York, 1989.

Antibodies

DO-1, DO-2 and 1801 monoclonal antibodies recognize the N-terminal region of p53 protein, monoclonal antibodies DO-11 and DO-12 recognize different epitopes in the core domain of p53 protein, monoclonal antibodies Bp53-10 and Pab421 recognize the C-terminal region of p53 protein.

Monoclonal antibody 118 recognizes $p21^{WAF1}$.

Polyacrylamide Gel Electrophoresis and Immunoblotting

For direct immunoblotting, total cellular protein lysates were prepared by harvesting cells in hot Laemmli electrophoresis sample buffer. Proteins were then separated by SDS-polyacrylamide gel electrophoresis (SDS-PAGE) on 10% gel and transferred onto a nitrocellulose membrane in Bio. Rad Mini Trans-Blott Electrophoretic Transfer Cell for 2 hrs at 4° C. applying 150 mA in transfer buffer (240 mM Tris, 190 mM glycine and 20% methanol). Prestained molecular weight markers (Bio-Rad) were run in parallel. The blotted membranes were blocked in 5% milk and 0.1% Tween 20 in PBS for 2 hrs and probed overnight with monoclonal antibodies. After washing 3 times in PBS plus 0.1% Tween 20, peroxidase conjugated rabbit anti-mouse immunoglobulin antiserum (Dako, Denmark) diluted 1:1000 was used as the secondary antibody. To visualize peroxidase activity, ECL reagents from AMERSHAM were used according to the manufacturer instructions.

Transfection Experiment

MCF7-DDp53 cell line was derived from MCF-7 parental cell line by stable transaction with plasmid pCMV-neonDDp53 coding for dominant negative truncated mouse p53 protein including amino acid residues 1-14 and 302-390 under the control of at the CMV promoter (37). The control cell line MCF-7neo was derived by transfecting MCF-7 cells with pCMVneo vector. Transfections were performed using the Effectene transfection reagent (QIAGEN, Germany) as recommended by the supplier. Stable transfectants were selected at 2 mg/ml G418 sulphate (Life Technologies). The expression of Ddp53 miniprotein in MCF-7Ddp53 cell line has been examined by immunoblotting with Bp53-10 monoclonal antibody. Independently isolated MCF-7Dp53 clones 9, 12 and 14 expressing high levels of Ddp53 miniprotein and MCF-7-neo clones 3, 4 and 7 were used.

25 Induces Wild-Type, but not Mutant, p53 Protein

First, we determined appropriate concentration 25 for our experiments. The MCF-7 (wt p53) cells were treated for 12 hrs with increasing concentrations of ranging from 1 to 100 μM and analyzed for p53 protein expression using monoclonal antibody DO-1 (FIG. 15). The concentration of 25 20-100 μM has been shown to affect the level of p53 protein in these cells. As shown at FIG. 15 the level of protein expression induced by 20 μM 25 was not substantially different from expression induced by 100 μM 25, so that 20 μM concentration was selected for further experiments. Second, the periods of time 6, 12 and 24 hrs were chosen, since the level of protein expression reached a steady state. FIG. 15 shows a time-dependent increase of p53 after 20 μM treatment with 25.

We analyzed the expression of p53 protein in MCF-7 (wt p53), BT549 (mut p53) and BT474 (mut p53) breast cancer cell lines, in HT 29 (mut p53) colorectal cancer cell line and in osteosarcoma cell line HOS (mut p53). Treatment of MCF-7 cells for 6, 12 and 24 hrs with 20 μM 25 results in significant accumulation of wild-type p53 (FIG. 16). No induction of p53 was observed following exposure of BT549 and HOS cell lines, expressing mutant p53, to 20 μM 25 for 6, 12 and 24 hrs (FIG. 16). No correlation was observed between the sensitivity of cell lines to 25 ant the presence of wild type or mutant p53.

25-Induced Wt p53 is Transcriptionally Active and Responsible for Induction of $p21^{WAF1}$ Effect of 25 and related compounds on activation of p53 protein was also analyzed in human melanoma cell line Arn8 and murine fibroblast cell line T22LacZ expressing β-galactosidase under control of p53 responsive promoter. Induction of wt p53 in these cells treated with 20 μM 25 (6, 12 and 24 hrs) leads to activation of responsive promoter and consequently to expression of β-galactosidase. Arn8 and T221acZ cells treated with 25 were fixed and examined microscopically for β-galactosidase activity using X-gal substrate leading to about 25% blue-colored cells compared to less than 1%

Following compounds had comparable effects but the concentrations of the tested compound inducing maximum of 3-galactosidase activity differed from each to another. These results are presented in Table. 15 as concentration inducing maximum of β-galactosidase activity. It seems that trisubstituted pyrazolo[4,3-d]pyrimidines with hydrophobic substituents at R3, R5, and R7 are powerful inducers of wt p53 expression.

TABLE 15

The effect of selected trisubstituted pyrazolo[4,3-d]pyrimidines on induction of p53 protein as well as p21$^{WAF1}$ protein in MCF-7 cells expressing wild-type p53.

| SUBSTITUENT | | | Max β-Gal. Activtity |
|---|---|---|---|
| R5 | R7 | R3 | Conc. (μM) |
| 4-methoxybenzylamino | benzylamino | methyl | 34 |
| petnylamino | benzylamino | methyl | 28 |
| octylamino | benzylamino | methyl | 25 |
| cyclopentylamino | benzylamino | methyl | 1.2 |
| cyclohexylamino | benzylamino | methyl | 1.5 |
| R-(1-hydroxymethyl)propylamino | benzylamino | methyl | 9.5 |
| R-(1-hydroxymethyl-2-methyl)propylamino | benzylamino | methyl | 6.5 |
| 4-methoxybenzylamino | 4-methoxybenzylaminbo | Isopropyl | 12.4 |
| petnylamino | 4-methoxybenzylaminbo | isopropyl | 14.7 |
| octylamino | 4-methoxybenzylaminbo | isopropyl | 27 |
| cyclopentylamino | 4-methoxybenzylaminbo | isopropyl | 21 |
| cyclohexylamino | 4-methoxybenzylaminbo | isopropyl | 16 |
| R-(1-hydroxymethyl)propylamino | 4-methoxybenzylaminbo | isopropyl | 0.8 |
| R-(1-hydroxymethyl-2-methyl)propylamino | 4-methoxybenzylaminbo | isopropyl | 1.1 |
| 4-methoxybenzylamino | 3-chloroanilino | isopropyl | 4.5 |
| petnylamino | 3-chloroanilino | isopropyl | 6.5 |
| octylamino | 3-chloroanilino | isopropyl | 9.8 |
| cyclopentylamino | 3-chloroanilino | isopropyl | 11.5 |
| cyclohexylamino | 3-chloroanilino | isopropyl | 17 |
| R-(1-hydroxymethyl)propylamino | 3-chloroanilino | isopropyl | 12 |
| R-(1-hydroxymethyl-2-methyl)propylamino | 3-chloroanilino | isopropyl | 7 | of blue-colored cells in DMSO-treated control cells (data not shown). The total β-galactosidase activity in Arn8 cells was also assessed using colorimetric assay. The results show strong activity of β-galactosidase at periods of time 12 and 24 hours after treatment giving evidence of transcriptionally active p53 protein in comparison with control cells treated with DMSO.

This transcription activity was also proved by analyzing p21$^{WAF1}$ expression in MCF-7 cells. The induction of p53 protein was apparent in 4 hrs but enhanced level of p21$^{WAF1}$ protein was observed in only 12 hrs after treatment with 25 (FIG. 16). Only cells expressing wt p53 responded to 25 with p21 induction. To confirm, that p21$^{WAF1}$ induction is p53-responsive, a series of stable transfected MCF-7 clones expressing high levels of a dominant-negative Ddp53 miniprotein was established. This protein, consisting of amino acids 1-14 and 302-390 of mouse p53 sequence, has been shown to bind to the C-terminus of wt p53 and abrogate the p53-dependent transcription. The control MCF-7neo clones were also established by stable transfection of MCF-7 cells with the backbone vector pCMVneo without insert. Clones expressing high level of Ddp53 as well as the control clones were treated with 25 and assayed for p21$^{WAF1}$ expression using immunoblotting with p21$^{WAF1}$ specific monoclonal antibody 118. As a result of Ddp53 expression, disrupting p53 transcriptional activity, no p21$^{WAF1}$ induction could be detected in MCF-7Ddp53 clones (FIG. 17).

Example 33

Bovine Oocyte and Embryo Development Following Meiotic Inhibition with Selected Trisubstituted Pyrazolo[4,3-d]pyrimidine During final oocyte maturation, immature oocytes progress from prophase I, the germinal vesicle (GV) stage, to metaphase II at which stage they are arrested again until insemination or parthenogenetic activation. Despite much research in the area of in vitro embryo production over the past decade, only 30-40% of bovine oocytes develop to the blastocyst stage following in vitro maturation, fertilization, and culture. While suboptimal culture conditions undoubtedly contribute to this poor development, the intrinsic quality of the oocyte itself is the key limiting factor.

New approaches towards improving oocyte development are examining the "prematuration" of the oocyte i.e., holding the oocyte at GV stage in vitro before submission to normal in vitro maturation. It is hypothesized that if oocytes are cultured in vitro under conditions that maintain arrest at the GV stage, then they may have the opportunity to acquire greater developmental competence.

Oocyte Collection and In Vitro Maturation (IVM)

Chemicals were purchased from Sigma Chemical Co (St. Louis, Mo.) unless otherwise indicated. A stock solution of 10 μg/ml epidermal growth factor (EGF) was prepared, aliquoted and stored at −20° C. until use.

Cumulus oocyte complexes (COCs) were obtained by aspiration of 2-8 mm Follicles of ovaries from slaughtered cows. Following four washes in modified phosphate-buffered saline (PBS, supplemented with 36 µg/ml pyruvate, 50 µg/ml gentamycin, and 0.5 mg/ml bovine serum albumin, Sigma fraction V, cat #A-9647), groups of approximately 50 COCs were placed in 500 µl of maturation medium in 4-well dishes (Nunc, Roskilde, Denmark) for 24 hr culture at 39° C. under an atmosphere of 5% $CO_2$ in air with maximum humidity. The maturation medium was Medium 199 supplemented with 10 ng/ml EGF and 10% (v/v) fetal calf serum (FCS).

Sperm Preparation and In Vitro Fertilization (IVF)

For IVF, COCs were washed four times in PBS and then in fertilization medium before being transferred in groups of 50 into four-well plates containing 250 µl of fertilization medium (Tyrode's medium with 25 mM bicarbonate, 22 mM Na-lactate, 1M Na-pyruvate, 6 mg/ml fatty acid-free BSA, and 10 µg/ml heparin-sodium salt-184 U/mg, Calbiochem, San Diego, Calif.) per well. Motile spermatozoa were obtained by centrifugation of frozen-thawed spermatozoa (Dairygold A.I. Station, Mallow, Ireland) on a Percoll (Pharmacia, Uppsala, Sweden) discontinuous density gradient (2.5 ml 45% Percoll over 2.5 ml 90% Percoll) for 20 min at 700 g at room temperature. Viable spermatozoa, collected at the bottom of the 90% fraction, were washed in HEPES-buffered Tyrode's and pelleted by centrifugation at 100 g for 10 min. Spermatozoa were counted in a haemocytometer and diluted in the appropriate volume of TALP to give a concentration of $2 \times 10^6$ spermatozoa/ml, a 250 µl aliquot of this suspension was added to each fertilization well to obtain a final concentration of $1 \times 10^6$ spermatozoa/ml. Plates were incubated for 24 hr in 5% $CO_2$ in humidified air at 39° C.

In Vitro Culture (IVC)

Embryo culture was carried out in modified synthetic oviduct fluid medium (SOF) under mineral oil in a humidified atmosphere of 5% $CO_2$, 5% $O_2$, 90% $N_2$ at 39° C. (Carolan et al., 1995). Twenty-four hours after insemination, presumptive zygotes were denuded of cumulus cells by vortexing for 2 min in 2 ml of PBS. The zygotes were then washed four times in PBS and then in SOF before being transferred to 25 µl culture droplets. Fetal calf serum was added to the droplets (10%, v/v) 24 hr after placement in culture (i.e., 48 hr post-insemination, hpi). Blastocyst rates were recorded at days 6-8 post-insemination. For estimation of blastocyst cell numbers, blastocysts were placed on a slide, air-dried, and fixed in 100% ethanol overnight. They were subsequently stained using Hoechst 33342 (10 mg/ml in 2.3% (w/v) sodium citrate) and visualized with an epifluorescence microscope.

Oocyte Vitrification

Matured oocytes were vitrified using the methods described by Dinnyés at al. (2000). Matured COCs were partially denuded by a short exposure to 0.1% hyaluonidase and subsequent pipetting. Oocytes were washed three times in TCM 199 supplemented with 20% FCS and then suspended in an equilibration medium consisting of 4% (v/v) ethylene glycol in TCM 199+20% FCS at 39° C. for 12-15 min. Following equilibration, groups of 5-10 oocytes were rinsed three times in small drops of vitrification solution consisting of 25% ethylene glycol, 5% polyvinyl pyrrolidone, 0.4 M trehalose in TCM 199+20% FCS, for 25-30 sec, and dropped onto the surface of a steel cube which was covered with aluminum foil and cooled down to between −150 and −180° C. by partial immersion in $LN_2$.

Vitrified droplets were thawed by dropping them into a 0.3 M trehalose solution for 3 min. Oocyte survival was then evaluated based on the integrity of the oocyte membrane and the zona pellucida. The surviving vitrified-thawed oocytes were parthenogenetically activated and cultured as described above.

Oocyte Activation

For parthenogenetic activation, following IVM, oocytes were fully denuded of cumulus and activated by a 5 min exposure to Ca-ionophore A23187 at room temperature followed by culture in 2.5 mM 6-dimethylaminopurine for 3.5 hr (Liu et al., 1998). The oocytes were then placed in culture as described above.

Results

In this study we have shown that 16, a potent inhibitor of cyclin-dependent kinases, inhibits meiotic resumption in bovine oocytes by blocking germinal vesicle breakdown in dose-dependent manner (FIG. 18). A concentration 30 µM blocked over 60% of oocytes, while 100 µM inhibited almost all oocytes compared to the control in which over 85% resumed meiosis. Following a second 24 hr culture under conditions permissive to normal maturation, almost all (90%) of blocked oocytes resumed meiosis and progressed to metaphase II. In terms of developmental competence, oocytes maintained in meiotic arrest for 24 hr with 80 µM exhibited a similar capacity to develop to the blastocyst stage as non-blocked control oocytes following maturation, fertilization, and culture in vitro. Cryopreservation was employed as a tool to detect differences in the oocyte viability between blocked and control oocytes. Cleavage of oocytes was significantly reduced following vitrification and activation both in BL-1 treated (40.2% vs. 71.9%, P<0.05) and the control groups (45.6% vs. 81.7%, P<0.05). However, BL-1 treated oocytes were less likely to develop into blastocysts following vitrification (20.0% from vitrified vs 42.5% from non-vitrified cleaved oocytes, P<0.05, based on cleaved oocytes) compared to non-treated oocytes (34.0% from vitrified vs. 42.9% from non-vitrified oocytes, P<0.05). These results demonstrate the feasibility of maintaining bovine oocytes in artificial meiotic arrest without compromising their subsequent developmental competence and may represent a tool for improving the development of less competent oocytes (Table 16 and 17).

TABLE 16

Effect of Inhibition of Meiotic Resumption in Bovine Oocytes Using Pyrazolo[4,3-d]pyrimidine 16 on Subsequent Development Blastocyst rate

| Treatment | n | Cleavege rate n | % | 5-8 celss N | % | Day 6 n | % | Day 8 n | % | Hatching n | % |
|---|---|---|---|---|---|---|---|---|---|---|---|
| Control | 211 | 167 | 79 | 89 | 42.1[a] | 29 | 13.7 | 57 | 27[a] | 28 | 49.1 |
| BL1-50[2] | 225 | 198 | 88 | 83 | 36.9[ab] | 35 | 15.6 | 64 | 28.4[a] | 24 | 37.5 |
| BL1-100[2] | 243 | 213 | 87 | 82 | 33.7[a] | 28 | 11.5 | 58 | 22.2[b] | 17 | 29.3 |

[1]Control oocytes were cultured for 24 hr in M199 + 105 FCS + 10 mg/ml EGF.
[2]Treatment with 16 was followed by 24 hr of maturATION UNDER CONTROL CONDITIONS.
[3]Values in the same column with different superscripts differ significantly (P < 0.05, $\chi^2$ test).

TABLE 17

Effects of Vitrification on Activation of Bovine
Oocytes Following Inhibition of Meiotic Resumption
by Pyrazolo[4,3-d]pyrimidine 16
Blastocyst rate

| Treatment | n | Cleavege rate n | % | 5-8 cells N | % | Day 6 n | % | Day 8 n | % | Hatching n | % | Cell number Mean ± SEM(n) |
|---|---|---|---|---|---|---|---|---|---|---|---|---|
| Control | 176 | 142 | 80.7a | 60 | 34.1 | 33 | 18.7a | 61 | 34.6a | 7 | 11.5 | 76.6 ± 5.8 (54) |
| Vitrified | 103 | 47 | 45.6a | 12 | 11.6 | 5 | 4.8b | 16 | 15.5b | 0 | — | 82.7 ± 8.1 (13) |
| BL1[2] | 121 | 87 | 71.9a | 22 | 18.2 | 20 | 16.5a | 37 | 30.6a | 10 | 27.0 | 70.3 ± 7.2 (26) |
| Vitrified | 87 | 35 | 40.2b | 7 | 8.0 | 4 | 4.6b | 7 | 8.0b | 1 | 14.2 | 75.0 ± 11.7 (5) |

Example 34

Dry Capsules 5000 capsules, each of which contain 0.25 g of one of the compounds of the formula I, mentioned in the preceding or following Examples as active ingredient, are prepared as follows:
Composition
Active ingredient 1250 g
Talc 180 g
Wheat starch 120 g
Magnesium stearate 80 g
Lactose 20 g
Preparation process: The powdered substances mentioned are pressed through a sieve of mesh width 0.6 mm. Portions of 0.33 g of the mixture are transferred to gelatine capsules with the aid of a capsule-filling machine.

Example 35

Soft Capsules 5000 soft gelatine capsules, each of which contain 0.05 g of one of the compounds of the formula I:
Composition
Active ingredient 250 g
Lauroglycol 2 liters
Preparation process: The powdered active ingredient is suspended in Lauroglykol® (propylene glycol laurate, Gattefossé S.A., Saint Priest, France) and ground in a wet-pulveriser to a particle size of about 1 to 3 µm. Portions of in each case 0.419 g of the mixture are then transferred to soft gelatine capsules by means of a capsule-filling machine.

Example 36

Soft Capsules 5000 soft gelatine capsules, each of which contain 0.05 g of one of the compounds of the formula I, mentioned in the preceding or following Examples as active ingredient, are prepared as follows:
Composition
Active ingredient 250 g
PEG 400 1 liter
Tween 80 1 liter
Preparation process: The powdered active ingredient is suspended in PEG 400 (polyethylene glycol of Mr between 380 and about 420, Sigma, Fluka, Aldrich, USA) and Tween® 80 (polyoxyethylene sorbitan monolaurate, Atlas Chem. Inc., Inc., USA, supplied by Sigma, Fluka, Aldrich, USA) and ground in a wet-pulveriser to a particle size of about 1 to 3 mm. Portions of in each case 0.43 g of the mixture are then transferred to soft gelatine capsules by means of a capsule-filling machine.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A 3-, 5-, 7-trisubstituted pyrazolo[4,3-d]pyrimidine compound represented by the formula I

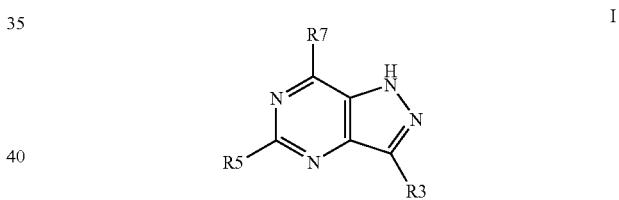

and a pharmaceutically acceptable salt thereof, wherein
R3 is selected from the group consisting of a $C_1$-$C_6$ alkyl, $C_2$-$C_6$ alkenyl, $C_2$-$C_6$ alkynyl, cycloalkyl, cycloalkenyl, cycloheteroalkyl, cycloheteroalkenyl, cycloalkyl alkylene, cycloalkyl alkenylene, cycloalkyl alkynylene, aryl, arylalkylene, arylalkenylene, and arylalkynylene group;
$R_5$ is selected from the group consisting of halogen, —NHNH$_2$, —NHOH, NHCONH$_2$, guanylo (NH—C(NH)NH$_2$), —SO$_3$R$_d$, —NHC(O)R$_e$, and —X—R$_{5'}$, wherein
R$_d$ is H, a $C_1$-$C_6$ alkyl, $C_2$-$C_6$ alkenyl, or $C_2$-$C_6$ alkynyl group, and
R$_e$ is hydroxy, amino, alkoxy, alkylamino, a $C_1$-$C_6$ alkyl, $C_2$-$C_6$ alkenyl or $C_2$-$C_6$ alkynyl group;
X is —NH—, —O—, —N($C_1$-$C_6$ alkyl)-, —N($C_2$-$C_6$ alkenyl)-, or —N($C_2$-$C_6$ alkynyl)- and
$R_{5'}$ is a $C_1$-$C_6$ alkyl, $C_2$-$C_6$ alkenyl, $C_2$-$C_6$ alkynyl, $C_3$-$C_{15}$ cycloalkyl, $C_3$-$C_{15}$ cycloalkenyl, R$_f$($C_3$-$C_{15}$ cycloalkyl), R$_f$($C_3$-$C_{15}$ cycloalkenyl), aryl, heterocyclyl, hetero $C_1$-$C_6$ alkyl, hetero $C_2$-$C_6$ alkenyl, hetero $C_2$-$C_6$ alkynyl, heteroaryl, arylalkylene, arylalkenylene, arylalkynylene, cycloheteroalkyl, cycloheteroalkenyl, cycloheteroalkyl alkylene, cycloheteroalkyl alkenylene, cycloheteroalkyl alkynylene, heteroarylalkylene, heteroarylalkenylene, heteroarylalkynylene, —C(O)—$R_a$, —C(O)$NR_bR_c$, —$SO_3R_d$, or —NHC(O)$R_e$, wherein $R_a$ is a $C_1$-$C_6$ alkyl, $C_2$-$C_6$ alkenyl, or $C_2$-$C_6$ alkynyl group, $R_f$ is a $C_1$-$C_6$ alkylene, $C_2$-$C_6$ alkenylene, or $C_2$-$C_6$ alkynylene group, $R_b$, $R_c$, and $R_d$ are independently H, a $C_1$-$C_6$ alkyl, $C_2$-$C_6$ alkenyl, or $C_2$-$C_6$ alkynyl group, $R_e$ has independently the meaning as defined above, $R_7$ is selected from the group consisting of halogen, —$NHNH_2$, NHOH, $NHCONH_2$, guanylo (NH—C(NH)$NH_2$) and —X'—$R_7$, wherein X' is —NH—, —O—, —S—, —N($C_1$-$C_6$ alkyl)-, —N($C_2$-$C_6$ alkenyl)-, or —N($C_2$-$C_6$ alkynyl), and $R_7$, has independently the same meaning as $R_5$, as defined above;

wherein in R5 and R7, each of the $C_1$-$C_6$ alkyl, $C_2$-$C_6$alkenyl, $C_2$-$C_6$alkynyl, $C_3$-$C_{15}$ cycloalkyl, $C_3$-$C_{15}$ cycloalkenyl, $R_f$($C_3$-$C_{15}$ cycloalkyl), $R_f$($C_3$-$C_{15}$ cycloalkenyl), aryl, heterocyclyl, hetero $C_1$-$C_6$ alkyl, hetero $C_2$-$C_6$alkenyl, hetero $C_2$-$C_6$alkynyl, heteroaryl, arylalkylene, arylalkenylene, arylalkynylene, cycloheteroalkyl, cycloheteroalkenyl, cycloheteroalkyl alkylene, cycloheteroalkyl alkenylene, cycloheteroalkyl alkynylene, heteroarylalkylene, heteroarylalkenylene, heteroarylalkynylene, $C_1$-$C_6$ alkylene, $C_2$-$C_6$ alkenylene, and $C_2$-$C_6$ alkynylene is independently optionally substituted with one or more substituents selected from the group consisting of halogen, hydroxy, alkoxy, amino, hydrazo, mercapto, carboxyl, cyano, nitro, amido, sulfo, sulfamido, acylamino, acyloxy, alkylamino, dialkylamino, and alkylmercapto and carbamoyl group; and wherein in R3, each of the alkyl, alkenyl, alkynyl, alkylene, alkenylene, and alkynylene is independently optionally substituted with one or more substituents selected from the group consisting of hydroxyl, mercapto, alkylmercapto, halogen, alkoxy, acyloxy, amino, acylamino, hydrazino, carbamoyl, amido, carboxyl, sulfo, acyl and guanidine; the aryl is optionally substituted with one or more substituents selected from the group consisting of halogen, alkyl, hydroxy, amino, acylamino, carbamoylamino, hydrazino, mercapto, alkoxy, alkylmercapto, alkylamino, amido, carboxyl, nitro and sulfo; the cycloalkyl is optionally substituted with one or more substituents selected from the group consisting of halogen, amino, hydroxy, cyano, nitro, mercapto, alkoxy, alkylamino, acylamino, carbamoylamino, acyloxy, dialkylamino, alkylmercapto, carboxyl, amido, sulfo and sulfamido; and the cycloheteroalkyl is optionally substituted or unsubstituted with one or more substituents selected from the group consisting of halogen, amino, hydroxy, cyano, nitro, mercapto, alkoxy, alkylamino, acylamino, carbamoylamino, acyloxy, dialkylamino, alkylmercapto, carboxyl, amido, sulfo and sulfamido.

2. The 3-, 5-, 7-trisubstituted pyrazolo[4,3-d]pyrimidine compound according to claim 1, wherein R3 is an unsubstituted alkyl, unsubstituted alkenyl, unsubstituted alkynyl, fluorine or chlorine substituted alkyl, fluorine or chlorine substituted alkenyl, fluorine or chlorine substituted alkynyl, fluorine or chlorine substituted cycloalkyl, fluorine or chlorine substituted cycloalkenyl, unsubstituted cycloheteroalkyl, unsubstituted cycloheteroalkenyl, fluorine or chlorine substituted cycloheteroalkyl, fluorine or chlorine substituted cycloheteroalkenyl, unsubstituted cycloalkyl alkylene, unsubstituted cycloalkyl alkenylene, unsubstituted cycloalkyl alkynylene, fluorine or chlorine substituted cycloalkyl alkylene, fluorine or chlorine substituted cycloalkyl alkenylene, fluorine or chlorine substituted cycloalkyl alkynylene, unsubstituted aryl, fluorine or chlorine substituted aryl, unsubstituted arylalkylene, unsubstituted arylalkenylene, unsubstituted arylalkynylene, fluorine or chlorine substituted arylalkylene, fluorine or chlorine substituted arylalkenylene, or fluorine or chlorine substituted arylalkynylene;

R5 is

—$SO_3R_d$, wherein $R_d$ is $C_1$-$C_6$ alkyl, $C_2$-$C_6$ alkenyl or $C_2$-$C_6$ alkynyl, selected from the group consisting of methyl, ethyl, isopropyl, butyl, isobutyl, vinyl, allyl, propenyl, propargyl, propynyl, isopentenyl, and isobutenyl, substituted independently at each occurrence with 0-5 substituents selected from the group consisting of halogen, hydroxy, alkoxy, amino, hydrazo, mercapto, carboxyl, cyano, nitro, amido, sulfo, sulfamido, acylamino, acyloxy, alkylamino, dialkylamino, alkylthio and carbamoyl group;

—NHC(O)$R_e$, wherein $R_e$ is alkoxy, alkylamino, $C_1$-$C_6$ alkyl, $C_2$-$C_6$ alkenyl or $C_2$-$C_6$ alkynyl, the $C_1$-$C_6$ alkyl, $C_2$-$C_6$ alkenyl or $C_2$-$C_6$ alkynyl being independently selected from the group defined above for $SO_3R_d$; or —X—$R_5$, wherein X is —N($C_1$-$C_6$ alkyl)-, —N($C_2$-$C_6$ alkenyl)-, or —N($C_2$-$C_6$alkynyl)-, each $C_1$-$C_6$ alkyl, $C_2$-$C_6$ alkenyl or $C_2$-$C_6$ alkynyl being selected from the group consisting of methyl, ethyl, propyl, isopropyl, vinyl, ethynyl, allyl, propargyl, and isopentenyl; and $R_5$, is a $C_1$-$C_6$ alkyl, $C_2$-$C_6$ alkenyl, $C_2$-$C_6$ alkynyl, $C_3$-$C_{15}$ cycloalkyl, $C_3$-$C_{15}$ cycloalkenyl, $R_f$($C_3$-$C_{15}$ cycloalkyl), aryl, heterocyclyl, hetero $C_1$-$C_6$ alkyl, hetero $C_2$-$C_6$ alkenyl, or hetero $C_2$-$C_6$ alkynyl, heteroaryl, arylalkylene, arylalkenylene, arylalkynylene, cycloheteroalkyl, cycloheteroalkyl alkylene, cycloheteroalkyl alkenylene, cycloheteroalkyl alkynylene, heteroarylalkylene, heteroarylalkenylene, heteroarylalkynylene, —C(O)$R_a$, —C(O)$NR_bR_c$, —$SO_3R_d$, or —NHC(O)$R_e$, wherein the $C_1$-$C_6$ alkyl, $C_2$-$C_6$ alkenyl or $C_2$-$C_6$ alkynyl is independently selected from the group defined above for $SO_3R_d$;

the $C_3$-$C_{15}$ cycloalkyl or $C_3$-$C_{15}$ cycloalkenyl is selected from the group consisting of cyclopropyl, cyclobutyl, cyclopentyl, cyclohexyl, cycloheptyl and adamantyl, substituted independently at each occurrence with 0-5 substituents selected from the group defined above for $SO_3R_d$;

the $R_f$ is a $C_1$-$C_6$ alkylene, $C_2$-$C_6$ alkenylene or $C_2$-$C_6$ alkynylene, independently selected from the group defined above for $SO_3R_d$;

the aryl is selected from the group consisting of phenyl, biphenyl, naphthyl, tetrahydronaphthyl, fluorenyl, indenyl and phenanthrenyl, substituted independently at each occurrence with 0-5 substituents selected from the group defined above for $SO_3R_d$;

the heterocyclyl is selected from the group consisting of thienyl, furyl, pyranyl, pyrrolyl, imidazolyl, pyrazolyl, pyridyl, pyrazinyl, pyrimidinyl, pyridazinyl, isothiazolyl, and isoxazolyl, substituted independently at each occurrence with 0-5 substituents selected from the group defined above for $SO_3R_d$;

the hetero $C_1$-$C_6$ alkyl, hetero $C_2$-$C_6$ alkenyl, or hetero $C_2$-$C_6$ alkynyl, is —$R_g$-Het, wherein the $R_g$ is a $C_1$-$C_6$ alkylene, $C_2$-$C_6$ alkenylene or $C_2$-$C_6$ alkynylene, independently selected from the group defined above for $SO_3R_d$, and the Het is heterocyclyl as defined above;

the heteroaryl is —$R_h$-HetAr, wherein the $R_h$ is selected from the group consisting of methylene, ethylene, propylene, isopropylene, vinylene, propynylene, and propenylene, and the HetAr is selected from the group consisting of benzothienyl, naphthothienyl, benzofuranyl, chromenyl, indolyl, isoindolyl, indazolyl, quinolyl, isoquinolyl, phthalazinyl, quinoxalinyl, quinolinyl, and quinazolinyl, substituted independently at each occurrence with 0-5 substituents selected from the group defined above for $SO_3R_d$;

the arylalkyl, arylalkenyl, or arylalkynyl is —$R_iAr$, wherein the $R_i$ is a $C_1$-$C_6$ alkylene, $C_2$-$C_6$ alkenylene or $C_2$-$C_6$ alkynylene independently selected from the group defined above for $SO_3R_d$, and Ar is aryl as defined above;

the cycloheteroalkyl is selected from the group consisting of piperidinyl, piperazinyl, morpholinyl, pyrrolidinyl, imidazolidinyl, substituted independently at each occurrence with 0-5 substituents selected from the group defined above for $SO_3R_d$;

the cycloheteroalkyl alkylene, cycloheteroalkyl alkenylene, or cycloheteroalkyl alkynylene, is —$R_j$(cycloheteroalkyl), wherein the $R_j$ is $R_iAr$, wherein $R_i$ is a $C_1$-$C_6$ alkylene, $C_2$-$C_6$ alkenylene or $C_2$-$C_6$ alkynylene independently selected from the group defined above for $SO_3R_d$, Ar is aryl as defined above, and the cycloheteroalkyl is selected from the group consisting of piperidinyl, piperazinyl, morpholinyl, pyrrolidinyl, imidazolidinyl, substituted independently at each occurrence with 0-5 substituents selected from the group defined above for $SO_3R_d$;

the heteroarylalkylene, heteroarylalkenylene, or heteroarylalkynylene is —$R_k$-HetAr, wherein the $R_k$ is a $C_1$-$C_6$ alkylene, $C_2$-$C_6$ alkenylene or $C_2$-$C_6$ alkynylene independently selected from the group defined above for $SO_3R_d$, and the HetAr is heteroaryl group as defined above;

R7 is —X'—$R_{7'}$, wherein

X' is —N($C_1$-$C_6$ alkyl)-, —N($C_2$-$C_6$ alkenyl)-, or —N($C_2$-$C_6$ alkynyl), each $C_1$-$C_6$ alkyl, $C_2$-$C_6$ alkenyl or $C_2$-$C_6$ alkynyl being selected from the group consisting of methyl, ethyl, propyl, isopropyl, vinyl, ethynyl, allyl, propargyl, and isopentenyl; and $R_{7'}$ has independently the same meaning as $R_{5'}$ as defined above.

3. The 3-, 5-, 7-trisubstituted pyrazolo[4,3-d]pyrimidine compound according to claim 1, which has independent occurrence of (R) or (S) configuration in R3, R5, or R7.

4. A method of preparing a 3, 5, 7-trisubstituted pyrazolo[4,3-d]pyrimidine compound of claim 1, comprising chlorination of a 3,5-disubstituted-7-hydroxypyrazolo[4,3-d]pyrimidine compound with a chlorination agent wherein the chlorination agent comprises $SOCl_2$, dimethylformamide, and chloroform; or the chlorination agent comprises $POCl_3$ and dimethylformamide; or the chlorination agent comprises $POCl_3$, $PCl_5$, and dimethylformamide; or the chlorination agent comprises $Cl_2P(O)OP(O)Cl_2$, to obtain a 3,5-disubstituted-7-chloropyrazolo[4,3-d]pyrimidine compound.

5. The method according to claim 4, further comprising substituting, by a nucleophilic substitution, the chlorine atom at position 7 of the 3,5-disubstituted-7-chloropyrazolo[4,3-d]pyrimidine compound with the substituent —X'$R_{7'}$.

6. A method of preparing a 3, 5, 7-trisubstituted pyrazolo[4,3-d]pyrimidine compound of claim 1, comprising chlorination of a 5,7-dihydroxy-3-substituted-pyrazolo[4,3-d]pyrimidine compound with diphosphoryldichloride ($Cl_2P(O)OP(O)Cl_2$) to obtain a 5,7-dichloro-3-substituted-pyrazolo[4,3-d]pyrimidine compound, and isolating the 5,7-dichloro-3-substituted pyrazolo[4,3-d]pyrimidine compound by extraction and subsequent crystallization.

7. The method according to claim 6, further comprising substituting, by a nucleophilic substitution, at least one of the chlorine atoms at positions 5 and 7 of the 5,7-dichloro-3-substituted pyrazolo[4,3-d]pyrimidine compound with the substituents —X—$R_{5'}$ and —X'$R_{7'}$, respectively.

8. A method of preparing a 3,7-substituted-5-aminopyrazolo[4,3-d]pyrimidine compound of claim 1, comprising chlorination of a 5-amino-7-hydroxy-3-substituted-pyrazolo[4,3-d]pyrimidine compound with $SOCl_2$, and substituting, by a nucleophilic substitution, the chlorine atom at position 7 of the chlorinated compound with the —X'$R_{7'}$ substituent as defined in claims 1.

9. A method of treating a hyperproliferative skin disease in a human subject comprising administering to the human subject a therapeutically effective amount of a 3-, 5-, 7-trisubstituted pyrazolo[4,3-d]pyrimidine compound according to claim 1 or a pharmaceutically acceptable salt thereof, together with a pharmaceutical carrier.

10. The method according to claim 9, wherein the hyperproliferative skin disease is selected from the group consisting of actinic keratosis, Bowen's disease, papilloma, seborrheic keratosis, toxic eczema, atopic dermatitis and ichthyosis.

11. A method of maintaining a mammalian oocyte at the germinal vesicle stage comprising administering to the mammalian oocyte an effective amount of a 3-, 5-, 7-trisubstituted pyrazolo[4,3-d]pyrimidine compound according to claim 1 or a pharmaceutically acceptable salt thereof.

12. The method of claim 11, wherein the mammalian oocyte is used in an in vitro fertilization process.

13. A pharmaceutical composition comprising a 3-, 5-, 7-trisubstituted pyrazolo[4,3-d]pyrimidine compound according to claim 1 or a pharmaceutically acceptable salt thereof and a pharmaceutical carrier.

14. A method of treating a mammal that suffers from a disease or disorder selected from the group consisting of human cervical carcinoma, human breast carcinoma, human osteosarcoma, human colon carcinoma, murine fibroblast tumor, human melanoma, comprising administering to the mammal an effective amount of a 3-, 5-, 7-trisubstituted pyrazolo[4,3-d]pyrimidine compound according to claim 1 or a pharmaceutically acceptable salt thereof together with a pharmaceutical carrier.

15. A method of treating a mammal that suffers from psoriasis comprising administering to the mammal an effective amount of a 3-, 5-, 7-trisubstituted pyrazolo[4,3-d]pyrimidine compound according to claim 1 or a pharmaceutically acceptable salt thereof together with a pharmaceutical carrier.

16. The 3-, 5-, 7-trisubstituted pyrazolo[4,3-d]pyrimidine compound according to claim 1, wherein R3 is an isopropyl group.

17. The 3-, 5-, 7-trisubstituted pyrazolo[4,3-d]pyrimidine compound according to claim 1, wherein R5 is an aminocyclohexylamino group or an optionally substituted benzylamino group.

18. The 3-, 5-, 7-trisubstituted pyrazolo[4,3-d]pyrimidine compound according to claim 17, being selected from the group consisting of:

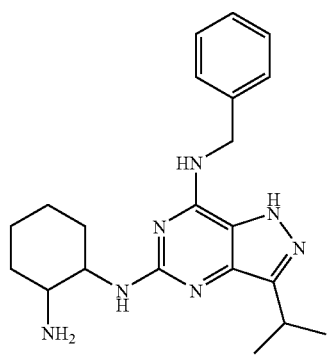

1406

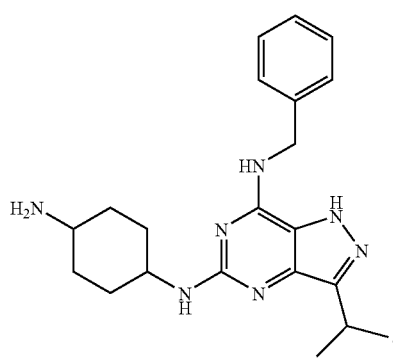

1407

19. The 3-, 5-, 7-trisubstituted pyrazolo[4,3-d]pyrimidine compound according to claim 1, wherein R7 is an optionally substituted benzylamino group.

20. The 3-, 5-, 7-trisubstituted pyrazolo[4,3-d]pyrimidine compound according to claim 19, wherein R7 is an optionally substituted methoxybenzylamino group.

21. The 3-, 5-, 7-trisubstituted pyrazolo[4,3-d]pyrimidine compound according to claim 20, being selected from the group consisting of:

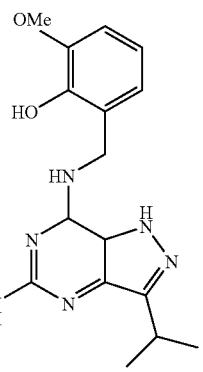

E2PP41

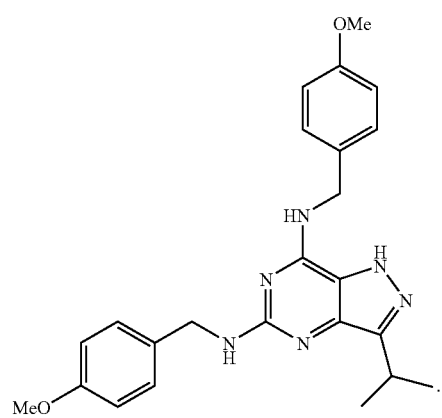

Compound 670

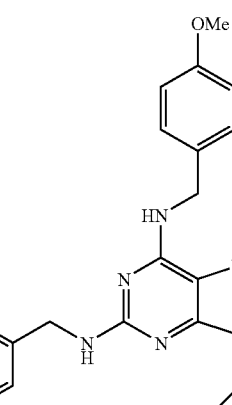

* * * * *